(12) United States Patent
Galan et al.

(10) Patent No.: US 10,335,477 B2
(45) Date of Patent: Jul. 2, 2019

(54) COMPOSITIONS AND METHODS FOR DIAGNOSING, PREVENTING AND TREATING SALMONELLA TYPHI AND SALMONELLA PARATYPHI INFECTION

(71) Applicant: Yale University, New Haven, CT (US)

(72) Inventors: Jorge E. Galan, New Haven, CT (US); Jeongmin Song, Hamden, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/892,237

(22) PCT Filed: May 20, 2014

(86) PCT No.: PCT/US2014/038805
§ 371 (c)(1),
(2) Date: Nov. 19, 2015

(87) PCT Pub. No.: WO2014/189942
PCT Pub. Date: Nov. 27, 2014

(65) Prior Publication Data
US 2016/0144013 A1  May 26, 2016

Related U.S. Application Data

(60) Provisional application No. 61/825,375, filed on May 20, 2013.

(51) Int. Cl.
*A61K 39/112* (2006.01)
*A61K 39/39* (2006.01)
(Continued)

(52) U.S. Cl.
CPC .......... *A61K 39/0275* (2013.01); *A61K 39/39* (2013.01); *A61K 39/3955* (2013.01);
(Continued)

(58) Field of Classification Search
CPC .... C07K 14/22; C07K 14/255; C07K 14/315; C07K 14/36; C07K 14/205; C07K 16/12; C12N 15/31; C12N 15/09; C12N 1/15; C12N 1/19; C12N 1/21; C12N 5/10; A61K 38/00; A61K 39/00; A61K 39/108; A61K 39/02; A61K 39/07; A61K 39/106;
(Continued)

(56) References Cited

U.S. PATENT DOCUMENTS

2009/0202592 A1*  8/2009  Shenker ............... A61K 38/164
424/241.1

FOREIGN PATENT DOCUMENTS

| WO | 02079242 A2 | 10/2002 | | |
|---|---|---|---|---|
| WO | WO 2002/079242 | * | 10/2002 | ............. C07K 14/22 |
| WO | WO 2011060431 | * | 5/2011 | ............. A61K 39/08 |

OTHER PUBLICATIONS

Spano et al..(Delivery of a Salmonella Typhi exotoxin from a host intracellular compartment. Cell Host Microbe. Jan. 17, 2008, vol. 3, No. 1, pp. 30-38).*

(Continued)

*Primary Examiner* — Jana A Hines
(74) *Attorney, Agent, or Firm* — Riverside Law LLP

(57) ABSTRACT

The invention provides compositions and methods for preventing, treating and diagnosing infection by *Salmonella enterica* serovar *typhi* (*S. typhi*) and/or *S. paratyphi*, i.e., typhoid fever.

6 Claims, 65 Drawing Sheets

Specification includes a Sequence Listing.

(51) Int. Cl.
  A61K 39/395 (2006.01)
  C07H 15/12 (2006.01)
  C07K 16/40 (2006.01)
  C12Q 1/689 (2018.01)
  G01N 33/569 (2006.01)
  A61K 39/00 (2006.01)

(52) U.S. Cl.
  CPC ............ *C07H 15/12* (2013.01); *C07K 16/40* (2013.01); *C12Q 1/689* (2013.01); *G01N 33/56916* (2013.01); *A61K 2039/505* (2013.01); *A61K 2039/55583* (2013.01); *G01N 2333/255* (2013.01); *G01N 2333/916* (2013.01); *G01N 2333/91142* (2013.01); *Y02A 50/484* (2018.01)

(58) Field of Classification Search
  CPC ......... C12P 21/02; C12Q 1/68; G01N 33/569; A61P 35/00
  USPC ............................................ 424/241.1, 236.1
  See application file for complete search history.

(56) References Cited

OTHER PUBLICATIONS

Haghjoo et al., (PNAS. Mar. 2004. vol. 101. No. 13:4614-4619).*
Spano, et al., "Delivery of a Salmonella Typhi exotoxin from a host intracellular compartment". Cell Host Microbe. Jan. 17, 2008. 3(1):30-38.
Song, et al., "Conferring Virulence: STructure and Function of the chimeric A2B5 Typhoid Toxin". Nature. Jul. 18, 2013. 499(7458):350-354.
Haghjoo and Galan, "Salmonella typhi encodes a functional cytolethal distending toxin that is delivered into host cells by a bacterial-internalization pathway". 2004, Proc. Natl. Acad. Sci. USA 101(13):4614-4619.
Spano and Galan, "A novel pathway for exotoxin delivery by an intracellular pathogen". 2008, Curr. Opin. Microbiol. 11 (1):15-20.
Beddoe et al., "Structure, Biological Functions and Applications of the AB5 Toxins". 2010, Trends Biochem. Sci. 35 (7):411-418.
Merritt and Hol, "AB5 toxins". 1995, Curr. Opin. Struct. Biol. 5:165-171.
Lara-Tejero and Galan, "A Bacterial Toxin That Controls Cell Cycle Progression as a Deoxyribonucleic I-like Protein". 2000, Science. 290:354-357.
Lara-Tejero and Galan, "Cytolethal distending toxin: limited damage as a strategy to modulate cellular functions". 2002, Trends in Microbiology 10(3):147-152.
Yu et al., "A Bipartite Signal Regulates the Faithful Delivery of Apical Domain Marker Podocalyxin/Gp135". 2007, Mol. Biol. Cell. 18:1710-1722.
Hermiston et al., "CD45, CD148, and Lyp/Pep: Critical Phosphatases Regulating Src Family Kinase Signaling Networks in Immune Cells". 2009, Immunol. Rev. 228(1):288-311.
Yu et al., "Structures, biosynthesis, and functions of gangliosides—An overview". 2011, J. Oleo Sci. 60(10):537-544.
Stein et al., "Structure of a pertussis toxin-sugar complex as a model for receptor binding". 1994, Nature Struc. Biol., vol. 1(9):591-596.
Millen et al., "Identification and Characterization of the Carbohydrate Ligands Recognized by Pertussis Toxin through Glycan Microarray and Surface Plasmon Resonance". 2010, Biochemistry. 49(28):5954-5967.
Byres et al., "Incorporation of a non-human glycan mediates human susceptibility to a bacterial toxin". 2008, Nature 456(7222):648-652.
Nesić et al., "Assembly and functoin of a bacterial genotoxin". 2004, Nature 429:429-433.
Locht et al., "The ins and outs of pertussis toxin". 2011, FEBS Journal 278:4668-4682.
Saitoh et al., "The artAB genes encode a putative ADP-ribosyltransferase toxin homologue associated with Salmonella enterica serovar Typhimurium DT104". 2005, Microbiology 151:3089-3096.
Deng et al., "Host Adaptation of a Bacterial Toxin from the Human Pathogen Salmonella Typhi," Cell, 2014, 159:1290-1299.
EBI accession No. EPOP:AX663604. Mar. 21, 2003. Sequence 5 from Patent WO02079242.
EBI accession No. EPOP:AX663605. Mar. 21, 2003. Sequence 6 from Patent WO02079242.

* cited by examiner

```
   1 MYLWLKLLAF GFAFLDTEVF VTGQSPTPSP TGLTTAKMPS VPLSSDPLPT
  51 HTTAFSPAST FERENDFSET TTSLSPDNTS TQVSPDSLDN ASAFNTTGVS
 101 SVQTPHLPTH ADSQTPSAGT DTQTFSGSAA NAKLNPTPGS NAISDVPGER
 151 STASTFPTDP VSPLTTTLSL AHSSAALPA RTSNTTITAN TSDAYLNASE
 201 TTTLSPSGSA VISTTTIATT PSKPTCDEKY ANITVDYLYN KETKLFTAKL
 251 NVNENVECGN NTCTNNEVHN LTECKNASVS ISHNSCTAPD K QCGNMIFDNK
 301                      ADTTIC LKWKNIETFT CDTQNITYRF
 351 EIK        BEYK CDSEIL YNNHKFTNAS KIIK
 401 TK         SFHNF TLCYIKETEK DCLNLDENLI KYDLQNLKPY
 451              S APPSQVWNMT VSMTSDNSMH
 501 VKCRPPRDRN GFHERYHLEV EAGNTLVRNE SKKNCDFRVK DLQYSTDYTF
 551 KAYFHNGDYP GEFFILHHST SYNSKALIAF LAPLIIVTSI ALIVLYKIY
 601 DLHKR         QLMNVEP IHADILLETY KRKIADEGN
 651                             MIWE QKATVIVMVT
 701                       INQHF LRRR
 751 RCEEGNRNK       GYVVKLRRQR CLMVQVEAQY
 801 EKATGR         VPLKHELE LP
 851         TGT YIGIDAMLEG LEAAENK     MSKESEHDSD
 901 ILIHQALVEY NQFGETEVNL SELHPYLHNM      IAAQGPLR    IGDPNQMLFQ
 951 SYRSWR     N     IMSYWKPEVM QI        KGDLEVDLKD  VDK  SSTYTLR
1001 ESSDDDSDSE EPSKYINASF R                           QKLPQKN
1051 RKVKVIVMLT ELK
1101 VEELRHSKRK DSR
1151 SSENKBHK      DG SQQTGIFCAL LNLLESAETE EVVDIFQVVK
1201 ALRKARPGMV STFEQQFLY DVIASTYPAQ NGQVKKHHQ EDRLEFINSV
1251 DFVF
1301
```

(Jurkat, Ramos, THP1)    (SEQ ID NO: 21)

Figure 8 a

| Subunit | Mw (kDa) | Stoichiometry (yielding observed 116 kDa complex) | | | |
|---|---|---|---|---|---|
| | | Complex 1 | Complex 2 | Complex 3 | Complex 4 |
| CdtB | 29.835 | 1 | 2 | 2 | 1 |
| PltA | 25.094 | 1 | 2 | 1 | 2 |
| PltB | 12.553 | 5 | 1 | 3 | 3 |
| Predicted Mw | | 117.694 | 122.411 | 122.423 | 117.682 |
| Predicted 0.1% extinction coefficient | | 1.65 | 1.26 | 1.47 | 1.43 | b

| Complex | Observed UV/RI ratio | Predicted UV/RI ratio | Difference (%) ((Predicted-Observed)/Predicted) | Observed Mw | Predicted Mw | Difference (%) ((Predicted-Observed)/Predicted) |
|---|---|---|---|---|---|---|
| Complex 1 | 8388.94 | 8604.094 | 3% | 116 | 117.694 | 1% |
| Complex 2 | 8388.94 | 6585.783 | -21% | 116 | 122.411 | 6% |
| Complex 3 | 8388.94 | 7701.642 | -9% | 116 | 122.423 | 6% |
| Complex 4 | 8388.94 | 7443.486 | -11% | 116 | 117.682 | 1% | c

| Subunit | Amino acid composition analysis | |
|---|---|---|
| | nmole (analyzed) | Stoichiometry |
| CdtB | 0.0444 | 1 |
| PltA | 0.0505 | 1 |
| PltB | 0.2402 | 5 |

Group 1: Sialo-N-glycans

| Glycan Number | Glycan structure | Average RFU | StDev | % CV |
|---|---|---|---|---|
| 461 | NeuSAcα2-3Galb1-4GlcNAcb1-6(NeuSAcα2-3Galb1-4(NeuSAcα2-3Galb1-4GlcNAcb1-2Manα1-3)Manb1-4GlcNAcb1-4GlcNAcb-Sp21 | 12301 | 2330 | 19 |
| 483 | NeuSAcα2-3Galb1-4(NeuSAcα2-3Galb1-6)GlcNAcb1-2Manα1-3)Manb1-4GlcNAcb1-4(Fucα1-6)GlcNAcb-Sp24 | 3626 | 162 | 4 |
| 459 | NeuSAcα2-3Galb1-4GlcNAcb1-4(NeuSAcα2-3Galb1-4GlcNAcb1-2Manα1-6)(NeuSAcα2-3Galb1-4GlcNAcb1-2Manα1-3)Manb1-4GlcNAcb-Sp21 | 1940 | 286 | 15 |
| 474 | NeuSAcα2-3Galb1-3GlcNAcb1-6(NeuSAcα2-3Galb1-2Manα1-6)(NeuSAcα2-3Galb1-3GlcNAcb1-2Manα1-3)Manb1-4GlcNAcb1-4GlcNAcb-Sp19 | 1079 | 48 | 4 |
| 57 | NeuSAcα2-6Galb1-4GlcNAcb1-2Manα1-6(NeuSAcα2-6Galb1-4GlcNAcb1-2Manα1-3)Manb1-4GlcNAcb1-4GlcNAcb-Sp24 | 492 | 134 | 27 |
| 318 | NeuSAcα2-6Galb1-4GlcNAcb1-2Manα1-6(NeuSAcα2-6Galb1-4GlcNAcb1-2Manα1-3)Manb1-4GlcNAcb1-4GlcNAcb-Sp12 | 467 | 92 | 20 |
| 301 | NeuSAcα2-6Galb1-4GlcNAcb1-2Manα1-6(NeuSAcα2-6Galb1-4GlcNAcb1-2Manα1-3)Manb1-4GlcNAcb1-4GlcNAcb-Sp12 | 254 | 49 | 19 |
| 482 | NeuSAcα2-6Galb1-4GlcNAcb1-2Manα1-6(NeuSAcα2-6Galb1-4GlcNAcb1-2Manα1-3)Manb1-4GlcNAcb1-4(Fucα1-6)GlcNAcb-Sp24 | 228 | 13 | 6 |
| 463 | NeuSAcα2-6Galb1-4GlcNAcb-Sp21 | 209 | 17 | 8 |
| 543 | NeuSGcα2-3Galb1-4GlcNAcb1-2Manα1-6(NeuSGcα2-3Galb1-4GlcNAcb1-2Manα1-3)Manb1-4GlcNAcb1-4GlcNAcb-Sp24 | 146 | 18 | 12 |
| Average RFU for the group | | 2074 | | |

Figure 20A

Group 2: Asialo-N-glycans

| Glycan Number | Glycan structure | Average RFU | StDev | % CV |
|---|---|---|---|---|
| 544 | Fucα1-2Galβ1-4GlcNAcβ1-3Galβ1-4GlcNAcβ1-2Manα1-6(Fucα1-2Galβ1-4GlcNAcβ1-2Manα1-3)Manβ1-4GlcNAcβ1-4GlcNAcb-Sp24 | 4738 | 1361 | 29 |
| 588 | Galβ1-4GlcNAcβ1-3Galβ1-4GlcNAcβ1-3Galβ1-4GlcNAcβ1-2Manα1-6(Galβ1-4GlcNAcβ1-3Galβ1-4GlcNAcβ1-3Galβ1-4GlcNAcβ1-2Manα1-3)Manβ1-4GlcNAcβ1-4(Fucα1-6)GlcNAcb-Sp24 | 2248 | 390 | 17 |
| 584 | Galβ1-4GlcNAcβ1-3Galβ1-4GlcNAcβ1-6(Galβ1-4GlcNAcβ1-3Galβ1-4GlcNAcβ1-2Manα1-6(Galβ1-4GlcNAcβ1-3Galβ1-4GlcNAcβ1-3Galβ1-4GlcNAcβ1-4(Fucα1-6)GlcNAcb-Sp24 | 1902 | 82 | 4 |
| 550 | Galβ1-4GlcNAcβ1-3Galβ1-4GlcNAcβ1-3Galβ1-4GlcNAcβ1-2Manα1-6(Galβ1-4GlcNAcβ1-3Galβ1-4GlcNAcβ1-2Manα1-3)Manβ1-4GlcNAcβ1-4GlcNAcb-Sp25 | 1258 | 303 | 24 |
| 542 | Galβ1-4GlcNAcβ1-3Galβ1-4GlcNAcβ1-2Manα1-6(Galβ1-4GlcNAcβ1-2Manα1-3)Manβ1-4GlcNAcβ1-4GlcNAcb-Sp24 | 606 | 156 | 26 |
| 548 | Galβ1-4GlcNAcβ1-3Galβ1-4GlcNAcβ1-2Manα1-6(Galβ1-4GlcNAcβ1-2Manα1-3)Manβ1-4GlcNAcβ1-4GlcNAcb-Sp24 | 281 | 23 | 8 |
| 579 | Galβ1-4GlcNAcβ1-3Galβ1-4GlcNAcβ1-3Galβ1-4GlcNAcβ1-2Manα1-6(Fucα1-2Galβ1-4GlcNAcβ1-3Galβ1-4GlcNAcβ1-4(Fucα1-6)GlcNAcb-Sp24 | 250 | 26 | 10 |
| 445 | Fucα1-2Galβ1-4 GlcNAcβ1-2(Fucα1-2Galβ1-4GlcNAcβ1-4)Manα1-6(Fucα1-2Galβ1-4GlcNAcβ1-2Manα1-3)Manβ1-4GlcNAcβ1-4GlcNAcb-Sp12 | 188 | 36 | 19 |
| Average RFU for the group | | 1434 | | |

Figure 20B

Group 3: Sialo-glycolipids

| Glycan Number | Glycan structure | Average RFU | StDev | % CV |
|---|---|---|---|---|
| 228 | GalNAcb1-4(NeuSAca2-8NeuSAca2-3)Galb1-4Glcb-Sp0 | 9582 | 1645 | 17 |
| 276 | Neu5Aca2-8Neu5Aca2-3Galb1-4Glcb-Sp0 | 3702 | 464 | 13 |
| 573 | Neu5Aca2-8Neu5Aca2-3Galb1-3GalNAcb1-4(Neu5Aca2-3)Galb1-4Glc-Sp21 | 3255 | 503 | 15 |
| 226 | GalNAcb1-4(Neu5Aca2-8Neu5Aca2-3)Galb1-4Glcb-Sp0 | 1726 | 136 | 8 |
| 411 | Galb1-3GalNAcb1-4(Neu5Aca2-8Neu5Aca2-3)Galb1-4Glcb-Sp0 | 827 | 107 | 13 |
| 456 | Neu5Aca2-6Galb1-4GlcNAcb1-6(Fuca1-2Galb1-3GlcNAcb1-3)Galb1-4Glc-Sp21 | 467 | 79 | 17 |
| | Average RFU for the group | 3260 | | |

Group 4: Sialo-O-glycans

| Glycan Number | Glycan structure | Average RFU | StDev | % CV |
|---|---|---|---|---|
| 243 | Neu5Aca2-6(Neu5Aca2-3Galb1-3)GalNAca-Sp8 | 1656 | 219 | 13 |
| 266 | Neu5Aca2-8Galb1-4GlcNAcb-Sp0 | 1100 | 147 | 13 |
| 267 | Neu5Aca2-6Galb1-4(6S)GlcNAcb-Sp8 | 419 | 93 | 22 |
| 295 | Neu5Aca2-3Galb1-4GlcNAcb1-3GalNAcb1-3GlcNAcb-Sp0 | 358 | 72 | 20 |
| 268 | Neu5Aca2-6Galb1-4GlcNAcb-Sp0 | 311 | 33 | 11 |
| 332 | Neu5Aca2-6Galb1-4GlcNAcb1-3Galb1-4GlcNAcb-Sp0 | 228 | 32 | 14 |
| | Average RFU for the group | 679 | | |

Figure 20C

| Glycan number | Glycan structure | Average RFU | StDev | % CV |
|---|---|---|---|---|
| 461 | Neu5Aca2-3Galb1-4GlcNAcb1-6(Neu5Aca2-3Galb1-4GlcNAcb1-2)Mana1-6(GlcNAcb1-4)(Neu5Aca2-3Galb1-4GlcNAcb1-2Mana1-3)Manb1-4GlcNAcb1-4GlcNAcb-Sp21 | 12301 | 2330 | 19 |
| 539 | Galb1-3GlcNAcb1-3Galb1-4GlcNAcb1-3Galb1-4GlcNAcb-Sp0 | 9582 | 1645 | 17 |
| 509 | Galb1-3GlcNAcb1-3Galb1-4GlcNAcb-Sp8 | 8373 | 585 | 7 |
| 460 | Neu5Aca2-3Galb1-4GlcNAcb1-4Mana1-6(Neu5Aca2-3Galb1-4GlcNAcb1-4(Neu5Aca2-3Galb1-4GlcNAcb1-2)Mana1-3)Manb1-4GlcNAcb1-4GlcNAcb-Sp21 | 7186 | 4337 | 60 |
| 544 | Fuca1-2Galb1-3GlcNAcb1-3Galb1-4(Fuca1-3)GlcNAcb1-3Galb1-4(Fuca1-3)GlcNAcb1-2Mana1-3)Mana1-3)Manb1-3)Mana1-3)Manb1 | 4738 | 1381 | 29 |
| 276 | Galb1-3GlcNAcb1-3Galb1-4GlcNAcb-Sp0 | 3702 | 464 | 13 |
| 483 | Neu5Aca2-3Galb1-4GlcNAcb1-2Mana1-6(Neu5Aca2-3Galb1-4GlcNAcb1-2Mana1-3)Manb1-4GlcNAcb1-4(Fuca1-6)GlcNAcb-Sp24 | 3626 | 162 | 4 |
| 575 | Galb1-3GlcNAcb1-3Galb1-3GlcNAcb1-3Galb1-4GlcNAcb-Sp0 | 3255 | 503 | 15 |
| 74 | Fuca1-2Galb1-4GlcNAcb1-3Galb1-4GlcNAcb-Sp0 | 2999 | 963 | 32 |
| 595 | GalNAca1-3(Fuca1-2)Galb1-4GlcNAcb1-3Galb1-4GlcNAcb-Sp0 | 2690 | 186 | 7 |
| 462 | Neu5Aca2-3Galb1-4GlcNAcb1-2Mana1-6(Neu5Aca2-3Galb1-4GlcNAcb-Sp21 | 2574 | 2879 | 112 |
| 588 | Galb1-4GlcNAcb1-4(Galb1-4GlcNAcb1-2)Mana1-6(Galb1-4GlcNAcb1-2Mana1-3)Manb1-4GlcNAcb1-4GlcNAcb1-3(Galb1-4GlcNAcb1-2Mana1-3)Manb1-4GlcNAcb1-4GlcNAcb-Sp24 | 2248 | 390 | 17 |
| 73 | Fuca1-2Galb1-4GlcNAcb-Sp8 | 2217 | 746 | 34 |
| 586 | Galb1-4GlcNAcb1-3Galb1-4GlcNAcb1-6(Galb1-4GlcNAcb1-3Galb1-4GlcNAcb1-2Mana1-6(Galb1-4GlcNAcb1-3Galb1-4GlcNAcb1-2Mana1-3)Manb1-4GlcNAcb1-4GlcNAcb-Sp24 | 2115 | 801 | 38 |
| 459 | Galb1-4GlcNAcb1-6(GlcNAcb1-2)Mana1-6(Galb1-4GlcNAcb1-2Mana1-3)Manb1-4GlcNAcb1-4GlcNAcb-Sp21 | 1940 | 286 | 15 |
| 584 | Galb1-4GlcNAcb1-3Galb1-4GlcNAcb1-4(Fuca1-3)GlcNAcb1-4(Fuca1-3)GlcNAcb-Sp24 | 1902 | 82 | 4 |
| 598 | Galb1-4(Fuca1-3)GlcNAcb1-3Galb1-4(Fuca1-3)GlcNAcb-Sp0 | 1726 | 136 | 8 |
| 243 | Neu5Aca2-6GalNAca1-3Galb1-3)GalNAca-Sp8 | 1656 | 219 | 13 |
| 326 | Neu5Aca2-3Galb1-4GlcNAcb1-2Mana1-3)Mana1-4GlcNAcb-Sp12 | 1636 | 1545 | 94 |
| 336 | Galb1-4Neu5Aca2-3Galb1-3GalNAca-Sp0 | 1326 | 355 | 27 |
| 550 | Galb1-4GlcNAcb1-6(Galb1-4GlcNAcb1-2Mana1-3)Mana1-8(Neu5Aca2-3Galb1-4GlcNAcb1-3Galb1-4GlcNAcb-Sp25 | 1258 | 303 | 24 |
| 266 | Neu5Aca2-6Galb1-4GlcNAcb-Sp0 | 1100 | 147 | 13 |
| 474 | Neu5Aca2-6(Neu5Aca2-3Galb1-3)GalNAca-Sp0 | 1079 | 48 | 4 |
| 411 | Galb1-4GlcNAcb1-3Galb1-4GlcNAcb-Sp0 | 827 | 107 | 13 |
| 542 | Galb1-4GlcNAcb1-3Galb1-4GlcNAcb1-2Mana1-3)GlcNAcb1-4(Neu5Aca2-3Galb1-4GlcNAcb1-2Mana1-3)Manb1-4GlcNAcb1-4GlcNAcb-Sp24 | 606 | 156 | 26 |

| Glycan number | Glycan structure | Average RFU | StDev | %CV |
|---|---|---|---|---|
| 67 | Fuca1-2Galb1-3GlcNAcb-Sp0 | 78 | 42 | 54 |
| 439 | Galb1-4Galb-Sp10 | 78 | 27 | 34 |
| 541 | Galb1-4GlcNAcb1-3Galb1-4GlcNAcb1-2Mana1-6(Galb1-3Galb1-4GlcNAcb1-2Mana1-3)Manb1-4GlcNAcb1-4GlcNAc-Sp12 | 77 | 98 | 127 |
| | | 77 | 62 | 81 |
| 241 | NeuAca2-3Galb1-4(NeuAca2-3Galb1-3)GlcNAcb-Sp0 | 76 | 33 | 44 |
| 606 | NeuAca2-6Galb1-4GlcNAcb1-3Galb1-4GlcNAcb1-2Mana1-3(NeuAca2-6Galb1-4GlcNAcb1-3Galb1-4GlcNAcb1-2Mana1-6)Manb1-4GlcNAcb1-4GlcNAcb-Sp12 | 76 | 35 | 46 |
| 361 | Fuca1-2Galb1-4GlcNAcb1-2Mana1-6(Mana1-3)Manb1-4GlcNAc-Sp8 | 76 | 34 | 45 |
| 557 | NeuAca2-3NeuAca2-3Galb1-4GlcNAcb-Sp8 | 75 | 23 | 30 |
| 577 | Galb1-4GlcNAcb1-6(Fuca1-4(Fuca1-2Galb1-3)GlcNAcb1-3)Galb1-4GlcNAcb1-3Galb1-4GlcNAcb1-2Mana1-6(Gala1-3(Fuca1-2)Galb1-4GlcNAcb1-3Galb1-4GlcNAcb1-2Mana1-3)Manb1-4GlcNAcb1-4GlcNAcb-Sp24 | 71 | 18 | 25 |
| 91 | GalNAca1-3GalNAcb-Sp8 | 66 | 50 | 76 |
| 658 | GlcNAcb1-4GlcNAcb1-4(GlcNAcb1-6)GlcNAcb1-4GlcNAcb1-4GlcNAcb1-4GlcNAcb1-2Mana a1-3)Manb1- | 61 | 24 | 39 |
| 244 | NeuGca2-6(NeuAca2-3)Galb1-3GalNAca-Sp14 | 60 | 39 | 65 |
| 49 | Neu5,9Ac2a2-6Galb1-4GlcNAc-Sp8 | 59 | 33 | 55 |
| 252 | NeuAca2-3Galb1-4(Fuca1-3)(6S)GlcNAcb-Sp0 | 59 | 25 | 42 |
| | | 58 | 11 | 19 |
| 227 | | 57 | 41 | 72 |
| 44 | (6S)Galb1-4GlcNAcb-Sp8 | 56 | 29 | 52 |
| 530 | GlcNAcb1-2 Mana1-6(GlcNAcb1-4)(GlcNAcb1-2Mana1-3)Manb1-4GlcNAcb1-4(Fuca1-6)GlcNAc-Sp21 | 54 | 104 | 192 |
| 362 | Fuca1-2Galb1-4GlcNAcb1-3Galb1-4GlcNAcb1-2Mana1-6(Fuca1-2Galb1-4(Fuca1-3)GlcNAcb1-2Mana1-3)Manb1-4GlcNAcb1-4GlcNAc-Sp20 | 50 | 64 | 126 |
| 553 | NeuAca2-8NeuAca2-3Galb1-3GalNAca-Sp8 | 50 | 21 | 42 |
| 487 | NeuAca2-8NeuAca2-8Galb1-4(Fuca1-3)GlcNAcb1-3Galb1-4GlcNAc-Sp21 | 50 | 71 | 144 |
| 440 | Galb1-4GlcNAcb1-2Mana-Sp0 | 49 | 22 | 44 |
| 136 | NeuAca2-8(6S)Galb1-3)GalNAca-Sp14 | 49 | 50 | 103 |
| 562 | NeuGca2-8NeuGca2-3Galb1-4GlcNAc-Sp0 | 49 | 31 | 64 |
| 69 | Fuca1-2Galb1-4(Fuca1-3)Galb1-4(Fuca1-3)GlcNAcb-Sp0 | 49 | 21 | 43 |
| 46 | NeuGca2-3(6S)Galb1-4GlcNAc-Sp8 | 49 | 11 | 23 |
| 364 | Galb1-4GlcNAcb1-2Mana1-6(NeuAca2-3Galb1-3)Mana1-3)Manb-Sp12 | 49 | 23 | 48 |
| 317 | NeuAca2-3Galb1-4GlcNAcb1-6(NeuAca2-3Galb1-3)GalNAca-Sp14 | 48 | 32 | 66 |
| 546 | GlcNAcb1-3Galb1-4GlcNAcb1-6(Galb1-3)GlcNAcb1-4(Gala1-3(Fuca1-2)Galb1-4GlcNAcb1-3)Mana1-6(GlcNAcb1-2Mana1-3)Manb1-4GlcNAcb1-4GlcNAcb-Sp25 | 46 | 53 | 111 |
| 572 | Galb1-3)Mana1-4)GlcNAcb1-4(Fuca1-6)GlcNAcb-Sp24 | 47 | 45 | 97 |

Figure 21C

| Glycan number | Glycan structure | Average RFU | StDev | %CV |
|---|---|---|---|---|
| 247 | Neu5Aca2-3Galb1-3GlcNAcb1-3Galb1-4GlcNAcb-Sp0 | 46 | 48 | 103 |
| 6 | Fuca-Sp8 | 46 | 15 | 33 |
| 531 | Galb1-4GlcNAcb1-2Mana1-6(GlcNAcb1-4)(Galb1-4GlcNAcb1-2Manb1-3)Manb1-4GlcNAcb1-4(Fuca1-6)GlcNAc-Sp21 | 46 | 22 | 47 |
| 197 | GlcNAcb1-6(GlcNAcb1-4)GalNAca-Sp8 | 45 | 31 | 68 |
| 270 | Neu5Aca2-6Galb1-4GlcNAcb1-3Galb1-4(Fuca1-3)GlcNAcb1-3Galb1-4(Fuca1-3)GlcNAcb-Sp0 | 45 | 11 | 25 |
| 141 | Galb1-3GalNAca-Sp16 | 45 | 62 | 138 |
| 418 | | 44 | 24 | 55 |
| 291 | Neu5Gca2-3Galb1-3GlcNAcb-Sp0 | 43 | 33 | 76 |
| 376 | Neu5Aca2-3Galb1-4GlcNAcb1-3GalNAca-Sp14 | 43 | 22 | 52 |
| 559 | Galb1-4GlcNAcb1-3Galb1-4GlcNAcb1-6(Galb1-4GlcNAcb1-3)Galb1-4GlcNAcb1-2Mana1-6((Galb1-4GlcNAcb1-3Galb1-4GlcNAcb1-2Mana1-3)Manb1-4GlcNAc-Sp24 | 43 | 22 | 52 |
| 388 | 2Mana1-3)Manb1-4GlcNAcb1-4)GlcNAcb1-2Mana1-3)Manb1-4GlcNAcb-Sp12 | 42 | 25 | 59 |
| 54 | Galb1-4GlcNAcb1-2Mana1-6(GlcNAcb1-2Mana1-3)Manb1-4GlcNAcb-Sp0 | 42 | 22 | 53 |
| 102 | Galb1-3(Fuca1-2)Galb1-3)GlcNAcb-Sp0 | 42 | 23 | 54 |
| 324 | Neu5Aca2-3(Fuca1-2)Galb1-3GlcNAcb1-2Mana1-3)Manb1-4GlcNAcb-Sp19 | 42 | 28 | 68 |
| 424 | Neu5Aca2-3Galb1-3GlcNAcb1-3GalNAca-Sp14 | 41 | 9 | 21 |
| 399 | Neu5Aca2-3Galb1-3(6S)GalNAca-Sp8 | 40 | 23 | 57 |
| 242 | Galb1-3(6S)GalNAca-Sp8 | 40 | 13 | 32 |
| 563 | GalNAcb1-4GlcNAcb1-3GalNAcb1-4GlcNAcb-Sp0 | 40 | 18 | 45 |
| 275 | Neu5Aca2-8Neu5Aca-Sp8 | 39 | 15 | 39 |
| 93 | Galb1-3(Fuca1-4)GlcNAcb-Sp8 | 39 | 20 | 50 |
| 147 | Galb1-3GlcNAcb1-3Galb1-4GlcNAcb-Sp0 | 39 | 24 | 61 |
| 86 | Galb1-3(Fuca1-2)Galb1-4GlcNAcb-Sp0 | 39 | 15 | 39 |
| 125 | Galb1-2Galb-Sp8 | 39 | 18 | 46 |
| 423 | Galb1-3(Fuca1-2)Galb1-3GalNAcb1-3Galb1-4GlcNAcb-Sp0 | 38 | 26 | 68 |
| 369 | Galb1-4GlcNAcb1-2Mana1-6(Galb1-4GlcNAcb1-2Mana1-3)Manb1-4GlcNAcb1-4GlcNAc-Sp21 | 38 | 16 | 43 |
| 30 | (3S)Galb1-3GalNAca-Sp8 | 38 | 15 | 41 |
| 118 | Gala1-3Galb-Sp8 | 37 | 29 | 79 |
| 85 | Galb1-3(Fuca1-2)Galb1-4GlcNAcb-Sp0 | 37 | 24 | 64 |
| 2 | Glca-Sp8 | 36 | 13 | 35 |
| 320 | GlcNAcb1-2Mana1-6(Neu5Aca2-6Galb1-4GlcNAcb1-2Mana1-3)Manb1-4GlcNAcb1-4GlcNAcb-Sp12 | 36 | 32 | 89 |
| 269 | Neu5Aca2-6Galb1-4GlcNAcb-Sp8 | 35 | 18 | 51 |
| 297 | Neu5Aca2-3Galb1-4(Fuca1-3)GlcNAcb1-6(GalNAca-Sp14 | 34 | 26 | 76 |
| 58 | (6S)Galb1-4(6S)GlcNAcb-Sp0 | 34 | 30 | 89 |
| 34 | (3S)Galb1-3(Fuca1-4)GlcNAcb-Sp8 | 34 | 28 | 83 |
| 291 | GalNAcb1-4(Neu5Aca2-3)Galb1-4)GlcNAcb-Sp0 | 34 | 19 | 57 |
| 395 | Galb1-3Galb1-3(Fuca1-4)GlcNAca1-2Mana1-3(Fuca1-4)GlcNAcb1-2Mana1-3(Fuca1-4)GlcNAcb1-2Mana1-3)Manb1-4GlcNAcb-Sp19 | 33 | 17 | 50 |
| 251 | Neu5Aca2-3Galb1-4(6S)GlcNAcb-Sp8 | 33 | 5 | 17 |
| 360 | Neu5Aca2-3Galb1-4GlcNAcb-Sp8 | 33 | 7 | 22 |

Figure 21D

| Glycan number | Glycan structure | Average RFU | StDev | % CV |
|---|---|---|---|---|
| 446 | Fuca1-2Galb1-4(Fuca1-3)GlcNAcb1-2Mana1-6(Fuca1-2Galb1-4(Fuca1-3)GlcNAcb1-4(Fuca1-2Galb1-4(Fuca1-3)GlcNAcb1-2)Mana1-3)Mana1- | 33 | 15 | 45 |
| 117 | | 32 | 35 | 110 |
| 490 | Galb1-3Fuca1-4)GlcNAcb1-6GalNAca-Sp14 | 32 | 25 | 77 |
| 5 | GalNAca-Sp15 | 32 | 20 | 64 |
| 257 | Neu5Aca2-3(Galb1-4(Fuca1-3)GlcNAcb1-3)Galb1-4GlcNAcb-Sp0 | 32 | 21 | 66 |
| 345 | Neu5Aca2-6Galb1-4(Fuca1-3)Mana1-6(Mana1-3)Manb1-4GlcNAcb1-4GlcNAc-Sp12 | 31 | 7 | 22 |
| 76 | Fuca1-2Galb1-4GlcNAcb-Sp8 | 31 | 11 | 37 |
| 587 | GlcNAcb1-3Galb1-4GlcNAcb1-3Galb1-4GlcNAcb1-3Galb1-4GlcNAcb1-3Galb1-4GlcNAcb1-6(GlcNAcb1-3)Galb1-4GlcNAcb1-6(Galb1-3)GalNAc-Sp14 | 31 | 2 | 6 |
| 476 | Galb1-3GlcNAcb1-2Mana1-6(GlcNAcb1-4)(GlcNAcb1-2Mana1-3)Manb1-4GlcNAcb-Sp21 | 31 | 10 | 34 |
| 354 | Neu5Aca2-3Galb1-3GlcNAcb1-4GlcNAcb-Sp0 | 31 | 11 | 36 |
| 608 | Neu5Aca2-6Galb1-4GlcNAcb1-3Galb1-4GlcNAcb1-3Galb1-4GlcNAcb1-2Mana1-6(Neu5Aca2-6Galb1-4GlcNAcb1-2Mana1-3)Manb1-4GlcNAcb-Sp12 | 31 | 21 | 69 |
| 56 | Neu5Aca2-6Galb1-4GlcNAcb-Sp8 | 31 | 16 | 51 |
| 348 | Neu5Aca2-6Galb1-4(Fuca1-3)GlcNAcb1-3Galb1-4(Fuca1-3)GlcNAcb-Sp12 | 31 | 32 | 106 |
| 3 | Mana-Sp8 | 30 | 13 | 43 |
| 341 | | 29 | 18 | 61 |
| 259 | Neu5Aca1-3Galb1-4GlcNAcb-Sp0 | 29 | 30 | 103 |
| 472 | Fuca1-2Galb1-3(Fuca1-4)GlcNAcb1-2Mana1-6(Fuca1-2Galb1-3(Fuca1-4)GlcNAcb1-2Mana1-3)Manb1-4(Fuca1- | 29 | 11 | 37 |
| 157 | 6)GlcNAcb-Sp24 | 29 | 16 | 54 |
| 444 | Galb1-4GalNAca2-6)GlcNAc-Sp0 | 29 | 21 | 72 |
| 104 | (6S)Galb1-3(6S)GlcNAc-Sp0 | 28 | 6 | 21 |
| 377 | Galb1-3(Fuca1-2)Galb1-4(Fuca1-3)GlcNAcb-Sp8 | 28 | 9 | 33 |
| 428 | Neu5Aca2-6)Galb1-4)GlcNAcb-Sp14 | 28 | 11 | 41 |
| 305 | Fuca1-2Galb1-3GlcNAcb1-2Mana1-6(Fuca1-2Galb1-3GlcNAcb1-2Mana1-3)Manb1-4GlcNAcb1-4(Fuca1-6)GlcNAcb-Sp22 | 28 | 25 | 88 |
| 378 | | 28 | 34 | 123 |
| 328 | Neu5Aca2-3(6S)Galb1-3GlcNAc-Sp14 | 28 | 22 | 78 |
| 510 | Neu5,9Ac2a2-3Galb1-4GlcNAcb-Sp0 | 28 | 21 | 74 |
| 127 | Galb1-3(6S)GlcNAc-Sp0 | 28 | 32 | 116 |
| 20 | Galb1-3GlcNAcb1-4Fuca1-3)GlcNAcb-Sp0 | 28 | 11 | 41 |
| 72 | Galb1-4GlcNAcb1-6(Galb1-3)GalNAc-Sp14 | 28 | 14 | 52 |
| 205 | Fuca1-2Galb1-4(Fuca1-3)GlcNAcb-Sp8 | 28 | 2 | 9 |
| 343 | KDNa2-3Galb-Sp0 | 27 | 10 | 36 |
| 1 | GlcNAcb1-4Galb1-4(Fuca1-3)GlcNAcb1-3Galb1-4(Fuca1-3)GlcNAcb-Sp0 | 27 | 17 | 62 |
| | Gala-Sp8 | 27 | 26 | 96 |

Figure 21E

| Glycan number | Glycan structure | Average RFU | StDev | % CV |
|---|---|---|---|---|
| 152 | Galb1-4(Fuca1-3)GlcNAcb-Sp8 | 27 | 17 | 60 |
| 603 | Neu5Aca2-3Galb1-4GlcNAcb1-3Galb1-4GlcNAcb1-2Mana1-6(Neu5Aca2-3Galb1-4GlcNAcb1-3Galb1-4GlcNAcb1-2Mana1-3)Manb1-4GlcNAcb-Sp12 | 27 | 20 | 73 |
| 237 | Neu5Aca2-3galbNAcb1-4GlcNAcb-Sp0 | 27 | 3 | 12 |
| 304 | Galb1-4GlcNAcb1-6GalNAcb1-4GlcNAcb-Sp0 | 27 | 26 | 96 |
| 375 | Fuca1-4(Fuca1-2Galb1-3)GlcNAcb1-2Mana1-6(Fuca1-4(Fuca1-2Galb1-3)GlcNAcb1-2Mana1-3)Manb1-4GlcNAcb-Sp19 | 26 | 4 | 14 |
| 443 | (6S)Galb1-3GlcNAca-Sp8 | 26 | 13 | 51 |
| 249 | Neu5Aca2-3Galb1-3GlcNAcb-Sp0 | 26 | 18 | 67 |
| 138 | Neu5Aca2-8(Galb1-3)Galb1-3)GlcNAcb1-4Glcb-Sp10 | 26 | 18 | 70 |
| 16 | GlcNAcb-Sp0 | 26 | 18 | 69 |
| 400 | Fuca1-2Galb1-4GlcNAcb1-3GalNAca-Sp14 | 26 | 23 | 89 |
| 271 | Neu5Aca2-3Galb1-3GalNAcb1-3Galb1-4GlcNAcb-Sp0 | 26 | 26 | 101 |
| 566 | Neu5Aca2-3Galb1-3GalNAcb1-3Galb1-4GlcNAcb1-6(Neu5Aca2-3Galb1-4GlcNAcb1-3)GalNAca-Sp14 | 25 | 14 | 57 |
| 13 | Glcb-Sp0 | 25 | 1 | 5 |
| 527 | Galb1-3GalNAcb1-3(GlcNAcb1-2Mana-Sp0 | 25 | 17 | 70 |
| 176 | GlcNAcb1-6(GlcNAcb1-3)Galb1-4GlcNAcb-Sp8 | 25 | 15 | 59 |
| 324 | | 25 | 13 | 54 |
| 31 | (3S)Galb1-3GlcNAcb-Sp0 | 25 | 12 | 49 |
| 344 | GlcNAcb1-4Galb1-3GalNAc-Sp14 | 24 | 17 | 69 |
| 324 | | 24 | 9 | 36 |
| 471 | Neu5Aca2-3Galb1-4GlcNAcb1-6(Neu5Aca2-3Galb1-3)GalNAca-Sp14 | 24 | 10 | 43 |
| 495 | Galb1-3Galb1-4GlcNAcb1-3GalNAca-Sp14 | 24 | 12 | 46 |
| 349 | Galb1-4GlcNAcb1-3Mana1-3Manb1-4GlcNAc-Sp0 | 24 | 4 | 16 |
| 303 | GlcNAcb1-6(Galb1-3)GalNAca1-4GlcNAcb1-3Galb1-4GlcNAcb-Sp0 | 24 | 11 | 49 |
| 294 | Neu5Aca2-3Galb1-3GalNAcb1-3Galb1-4GlcNAcb-Sp0 | 23 | 46 | 202 |
| 274 | Neu5Aca2-6GalNAca-Sp0 | 23 | 18 | 77 |
| 457 | GalNAca1-3(Fuca1-2)Galb1-3GlcNAcb1-3Mana1-6)GalNAca1-3(Fuca1-2)Galb1... | 23 | 20 | 86 |
| 347 | 6)GlcNAca-Sp22 | 23 | 12 | 52 |
| 32 | (3S)Galb1-4(Fuca1-3)GlcNAc-Sp0 | 23 | 25 | 112 |
| 437 | Galb1-4GlcNAcb1-6(Galb1-4GlcNAcb1-2)Mana1-6(GlcNAcb1-4)(Galb1-4GlcNAcb1-2Mana1-3)Manb1-4GlcNAcb-Sp13 | 23 | 16 | 73 |
| 51 | Mana1-6(Mana1-3)Manb1-4GlcNAcb1-4GlcNAcb-Sp0 | 22 | 22 | 98 |
| 319 | Galb1-4GlcNAcb1-2Mana1-6(Neu5Aca2-6Galb1-4GlcNAcb1-2Mana1-3)Manb1-4GlcNAcb1-4GlcNAc-Sp12 | 22 | 11 | 49 |
| 501 | Galb1-4GlcNAcb1-3Galb1-4GlcNAcb1-6(Galb1-4GlcNAcb1-3)GalNAca-Sp14 | 22 | 14 | 61 |
| 224 | | 22 | 14 | 65 |
| 47 | (6S)GlcNAcb-Sp8 | 22 | 22 | 100 |
| 412 | | 22 | 14 | 64 |

Figure 21F

| Glycan number | Glycan structure | Average RFU | StDev | % CV |
|---|---|---|---|---|
| 346 | Mana1-6(NeuSAca2-6Galb1-4GlcNAcb1-2Mana1-3)Manb1-4GlcNAcb1-4GlcNAc-Sp12 | 22 | 6 | 30 |
| 318 | Mana1-6(Mana1-3)Mana1-6(Mana1-3)Mana1-6(Mana1-3)Mana1-3Mana-Sp9 | 22 | 9 | 43 |
| 396 | NeuSAca2-3Galb1-3GlcNAcb1-3Galb1-3GlcNAcb1-2Mana1-6(NeuSAca2-3Galb1-4GlcNAc-Sp19 | 21 | 7 | 31 |
| 255 | NeuSAca2-3Galb1-4Fuca1-3)GlcNAcb-Sp8 | 21 | 29 | 135 |
| 40 | | 21 | 8 | 39 |
| 360 | Fuca1-2Galb1-3GlcNAcb1-3Galb1-4(Fuca1-3)GlcNAcb1-3Galb1-4(Fuca1-3)GlcNAcb-Sp0 | 21 | 18 | 83 |
| 78 | Fuca1-2Galb-Sp8 | 21 | 11 | 51 |
| 6 | Rhaa-Sp8 | 21 | 22 | 103 |
| 475 | GlcNAcb1-6(GlcNAcb1-2)Mana1-6(GlcNAcb1-4(GlcNAcb1-2)Mana1-3)Manb1-4GlcNAcb1-4(Fuca1-6)GlcNAcb-Sp24 | 21 | 10 | 50 |
| 146 | Galb1-3GlcNAcb-Sp8 | 21 | 15 | 70 |
| 185 | | 21 | 14 | 67 |
| 119 | Gaba1-4(Fuca1-2)Galb1-4)GlcNAcb-Sp8 | 21 | 4 | 19 |
| 221 | Fuca1-2(4S)Galb1-4(6S)GlcNAcb-Sp8 | 21 | 24 | 115 |
| 413 | Gala1-3(Fuca1-2)Galb1-4GlcNAcb1-3GalNAca-Sp14 | 21 | 9 | 44 |
| 522 | Gala1-3(Fuca1-2)Galb1-4GlcNAcb1-4GalNAca-Sp8 | 21 | 6 | 29 |
| 198 | Glcb1-4Glcb-Sp8 | 20 | 8 | 38 |
| 464 | Mana1-6(Mana1-3)Manb1-4GlcNAcb1-4(Fuca1-6)GlcNAcb-Sp19 | 20 | 5 | 24 |
| 560 | Gala1-3Galb1-4GlcNAcb1-2Mana1-6(Gala1-3Galb1-4GlcNAcb1-2Mana1-3)Manb1-4GlcNAc-Sp24 | 20 | 8 | 39 |
| 149 | Galb1-3(6S)GlcNAcb-Sp8 | 20 | 6 | 28 |
| 477 | | 20 | 22 | 110 |
| 486 | Galb1-4(Fuca1-3)GlcNAcb1-3(6S)GlcNAcb-Sp0 | 20 | 15 | 77 |
| 501 | Fuca1-2(6S)Galb1-3(6S)GlcNAcb-Sp8 | 20 | 7 | 34 |
| 583 | GlcNAcb1-3Galb1-4GlcNAcb1-3Galb1-4GlcNAcb1-6(GlcNAcb1-3)Galb1-4(Fuca1-3)GlcNAcb1-3Galb1-4GlcNAcb1-6)GlcNAc-Sp24 | 19 | 8 | 44 |
| 585 | GlcNAcb1-3Galb1-4GlcNAcb1-6(GlcNAcb1-3Galb1-4GlcNAcb1-3)Galb1-4GlcNAcb1-2Mana1-6(GlcNAcb1-3Galb1-4GlcNAcb1-2Mana1-3)Manb1-4GlcNAcb1-4(Fuca1-6)GlcNAcb-Sp0 | 19 | 8 | 40 |
| 109 | Gala1-4(Gala1-3)Galb1-4GlcNAcb-Sp8 | 19 | 12 | 65 |
| 601 | NeuSAca2-6Galb1-4GlcNAcb1-3Galb1-4(Fuca1-3)GlcNAcb1-6(Galb1-3)GalNAca-Sp14 | 19 | 13 | 67 |
| 455 | Galb1-3(Fuca1-2)Galb1-3)Galb1-4GlcNAcb1-2Mana1-6(Galb1-3)Galb1-3GlcNAcb1-2Mana1-3)Manb1-4GlcNAcb1-4(Fuca1-6)GlcNAcb-Sp22 | 19 | 15 | 81 |
| 184 | | 19 | 12 | 64 |
| 420 | | 19 | 12 | 63 |
| 90 | GalNAca1-3Fuca1-2Galb-Sp16 | 19 | 9 | 46 |
| 461 | NeuSAca2-6Galb1-4 GlcNAcb1-6(NeuSAca2-6Galb1-4GlcNAcb1-3)GalNAca-Sp14 | 19 | 15 | 82 |
| 351 | Mana1-6Galb1-4GlcNAcb1-2Mana1-3Manb1-4GlcNAcb1-4GlcNAcb-Sp12 | 19 | 14 | 72 |
| 174 | GlcNAcb1-6Galb1-4GlcNAcb-Sp8 | 18 | 9 | 50 |
| 598 | (6P)Galb1-4GlcNAcb-SP0 | 18 | 9 | 49 |

Figure 21G

| Glycan number | Glycan structure | Average RFU | StDev | % CV |
|---|---|---|---|---|
| 545 | GlcNAcb1-3(GlcNAcb1-4)Galb1-4GlcNAcb1-3(GlcNAcb1-2Mana1-6(GlcNAcb1-3Galb1-4GlcNAcb1-2Mana1-3)Manb1-4GlcNAcb1-4GlcNAcb-Sp12 | 18 | 12 | 65 |
| 101 | Gala1-3(Fuca1-2)Galb1-3GlcNAcb-Sp0 | 18 | 6 | 34 |
| 548 | GlcNAcb1-3(GlcNAcb1-4)Galb1-4GlcNAcb1-2Mana1-3(Manb1-6(GlcNAcb1-2Mana1-6(GlcNAcb1-3Galb1-4GlcNAcb1-3(GlcNAcb1-4GlcNAcb-Sp25 | | 8 | 45 |
| 4 | 3(Galb1-4GlcNAcb1-2Mana1-3)Mana1-6(Manb1-4GlcNAcb1-4GlcNAcb-Sp25 | 18 | 15 | 82 |
| 4 | GalNAca-Sp8 | 18 | 15 | 82 |
| 98 | GalNAcb1-4GlcNAcb-Sp0 | 18 | 12 | 67 |
| 153 | Galb1-4(Fuca1-3)GlcNAcb1-3Galb1-4(Fuca1-3)GlcNAcb-Sp0 | 18 | 15 | 84 |
| 282 | Neu5Fuca2-3Galb1-4Fuca1-3GlcNAcb-Sp0 | 18 | 9 | 53 |
| 602 | Neu5Aca2-6Galb1-4GlcNAcb1-6(Galb1-3)GalNAca-Sp14 | 18 | 8 | 45 |
| | | 18 | 5 | 30 |
| 240 | Neu5Aca2-3Galb1-3(Fuca1-4)GlcNAcb1-3Galb1-4Fuca1-3)GlcNAcb-Sp0 | 18 | 11 | 63 |
| 208 | Mana1-2Mana1-6(Mana1-2Mana1-3)Mana-Sp9 | 17 | 11 | 63 |
| 478 | Neu5Aca2-3Galb1-4GlcNAcb1-2Mana-Sp0 | 17 | 3 | 19 |
| 7 | Fuca3-Sp8 | 17 | 11 | 61 |
| 497 | Fuca1-2(6S)Galb1-3GlcNAcb-Sp0 | 17 | 22 | 130 |
| 370 | GalNAca1-3(Fuca1-2)Galb1-4(Fuca1-3)GlcNAcb1-2Mana1-6(GalNAca1-3(Fuca1-2)Galb1-4(Fuca1-3)GlcNAcb1-2Mana1-3)Manb1-4GlcNAcb1-4GlcNAcb-Sp20 | 17 | 4 | 25 |
| | | 17 | 9 | 53 |
| | | 17 | 16 | 91 |
| 89 | GalNAcb1-3(Fuca1-2)Galb-Sp8 | 17 | 3 | 19 |
| 60 | Fuca1-2Galb1-3(Fuca1-4)GlcNAcb-Sp8 | 17 | 8 | 46 |
| 605 | Neu5Aca2-6Galb1-4GlcNAcb1-3Galb1-4GlcNAcb1-6(Neu5Aca2-6Galb1-4GlcNAcb1-3)GalNAca-Sp14 | 17 | 16 | 95 |
| 352 | GlcNAcb1-2Mana1-6(GlcNAcb1-4)(Fuca1-6)GlcNAcb-Sp12 | 17 | 6 | 33 |
| 467 | Gala1-3(Fuca1-2)Galb1-3GalNAca-Sp8 | 17 | 4 | 26 |
| | | 17 | 29 | 172 |
| 392 | GalNAcb1-4(Neu5Aca2-3)Galb1-4GlcNAcb1-3GalNAca-Sp14 | 17 | 4 | 26 |
| 484 | Neu5Aca2-6Galb1-4GlcNAcb1-4Mana1-6(GlcNAcb1-4Mana1-3)Manb1-4GlcNAcb1-4(Fuca1-6)GlcNAcb-Sp21 | 17 | 14 | 84 |
| 131 | Gala1-4Galb1-4GlcNAcb-Sp0 | 17 | 10 | 60 |
| 547 | GalNAcb1-4GlcNAcb1-3Galb1-4GlcNAcb1-3(GlcNAcb1-4)Galb1-4GlcNAcb1-2Mana1-6(Galb1-4GlcNAcb1-2Mana1-3)Manb1-4GlcNAcb1-4GlcNAcb-Sp12 | 17 | 8 | 48 |
| 99 | GalNAcb1-4GlcNAcb-Sp0 | 16 | 5 | 29 |
| 110 | Gala1-3GalNAca-Sp8 | 16 | 4 | 22 |
| 494 | Fuca1-2Galb1-4GlcNAcb1-6GalNAca-Sp14 | 16 | 5 | 34 |
| 535 | GlcNAcb1-3Galb1-4GlcNAcb1-6(Galb1-3)GalNAc-Sp0 | 16 | 12 | 75 |
| 564 | Neu5Aca2-8Neu5Aca2-3Galb1-4GlcNAc-Sp0 | 16 | 9 | 53 |
| | | 16 | 10 | 62 |

Figure 21H

| Glycan number | Glycan structure | Average RFU | StDev | % CV |
|---|---|---|---|---|
| 391 | Galb1-3GlcNAcb1-3GalNAca-Sp14 | 16 | 8 | 49 |
| 62 | Fuca1-2Galb1-3GalNAca-Sp14 | 16 | 7 | 45 |
| 521 | Gala1-3Galb1-4GlcNAcb1-2Mana-Sp0 | 16 | 4 | 25 |
| 353 | Galb1-4GlcNAcb1-2Mana1-6(Galb1-4GlcNAcb1-4Fuca1-6)GlcNAcb-Sp22 | 16 | 10 | 63 |
| 524 | Galb1-3GlcNAcb1-2Mana-Sp0 | 16 | 3 | 20 |
| 568 | Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3GlcNAcb1-2Mana1-3)Mana1-4GlcNAcb1-4GlcNAcb-Sp25 | 16 | 14 | 89 |
| 219 | (3S)Galb1-4(Fuca1-3)6S)GlcNAcb-Sp8 | 16 | 10 | 65 |
| 188 | Galb1-4-MDPLys | 16 | 12 | 79 |
| 507 | GlcNAcb1-3(GlcNAcb1-2Mana1-6)Mana1-3)Manb1-4GlcNAcb1-4(Fuca1-6)GlcNAc-Sp21 | 16 | 13 | 83 |
| 88 | GlcNAca1-3Galb1-3GalNAca-Sp8 | 16 | 12 | 75 |
|  |  | 15 | 12 | 78 |
| 126 | GlcNAcb1-3(Fuca1-4)Galb1-4(Fuca1-3)GlcNAcb-Sp0 | 15 | 12 | 80 |
| 372 | Gala1-3Galb1-4(Fuca1-3)GlcNAcb1-2Mana1-6(Galb1-4GlcNAcb1-2Mana1-3)Manb1-4GlcNAcb1-4GlcNAc-Sp20 | 15 | 9 | 58 |
| 18 | GlcNAcb-Sp8 | 15 | 10 | 66 |
| 574 | GlcNAcb1-3(Fuca1-3)Galb1-4(Fuca1-3)GlcNAcb1-2Mana1-6(Galb1-4GlcNAcb1-2Mana1-3)Manb1-4GlcNAcb1-4(Fuca1-6)GlcNAc-Sp24 | 15 | 2 | 11 |
| 607 | Neu5Aca2-3Galb1-3Galb1-4GlcNAcb1-2Mana1-3(Neu5Aca2-3Galb1-4GlcNAcb1-3Galb1-4GlcNAcb1-2Mana1-6)GlcNAca-Sp12 | 15 | 6 | 41 |
| 179 | GlcNAcb1-3GalNAca-Sp8 | 15 | 11 | 71 |
| 600 | Neu5Aca2-3Galb1-4GlcNAcb1-3Galb1-4GlcNAca-Sp0 | 15 | 7 | 47 |
| 55 | Neu5Aca2-3Galb1-4(6S)GlcNAcb-Sp8 | 15 | 7 | 46 |
| 199 | Galb1-6Galb-Sp8 | 15 | 5 | 34 |
| 280 | Galb1-4Fuca1-3(6S)GlcNAcb-Sp8 | 15 | 5 | 34 |
| 146 | Galb1-3GlcNAcb1-4(Fuca1-3)GlcNAcb-Sp10 | 15 | 9 | 62 |
| 504 | Fuca1-2Galb1-4(Fuca1-3)GlcNAcb1-3GalNAca-Sp8 | 14 | 18 | 125 |
| 514 | GalNAcb1-4(6S)GlcNAc-Sp8 | 14 | 11 | 76 |
| 70 | Fuca1-2Galb1-4(Fuca1-3)GlcNAcb1-3GlcNAcb1-4GlcNAc-Sp0 | 14 | 8 | 54 |
| 34 | (3S)Galb1-4(6S)GlcNAcb-Sp8 | 14 | 4 | 28 |
| 37 | (3S)Galb1-4GlcNAcb-Sp8 | 14 | 8 | 53 |
| 350 | Galb1-3GlcNAcb1-2Mana1-6Mana1-4GlcNAcb-Sp12 | 14 | 3 | 21 |
| 416 | Fuca1-2Galb1-4Fuca1-3(3SGalb1-4)GlcNAcb-Sp8 | 14 | 15 | 103 |
| 569 | Galb1-4GlcNAcb1-4(Fuca1-3)GalNAca-Sp8 | 14 | 17 | 119 |
| 431 | GlcNAcb1-2Mana1-6(Galb1-4GlcNAcb1-2Mana1-3)Manb1-4GlcNAcb1-4GlcNAc-Sp21 | 14 | 9 | 63 |
|  |  | 14 | 9 | 64 |
| 306 | KDNa2-3Galb1-4GlcNAcb-Sp0 | 14 | 5 | 34 |
| 564 | GlcNAcb1-4(Galb1-4GlcNAcb1-3Galb1-4GlcNAcb1-3Galb1-4GlcNAcb1-3Galb1-4GlcNAcb1-6)GalNAcb1-2Mana1-6(Galb1-4GlcNAcb1-2Mana1-3)Manb1-4GlcNAcb1-4GlcNAc-Sp25 | 14 | 3 | 25 |

Figure 21I

| Glycan number | Glycan structure | Average RFU | StDev | % CV |
|---|---|---|---|---|
| 129 | Galb1-3(Fuca1-4)GlcNAc-Sp8 | 14 | 15 | 104 |
| 177 | GlcNAcb1-6(GlcNAcb1-3)GalNAca-Sp14 | 14 | 8 | 54 |
| 29 | (3S)Galb1-3GalNAca-Sp3 | 14 | 8 | 56 |
| 61 | Fuca1-2Galb1-3GalNAca-Sp8 | 14 | 6 | 46 |
| 224 | Neu5Aca2-3Galb1-3GalNAca-Sp14 | 14 | 10 | 69 |
| 96 | GalNAcb1-3(Fuca1-2)Galb-Sp8 | 14 | 2 | 16 |
| 473 | Fuca1-2Galb1-3(Fuca1-4)GlcNAcb1-2Mana1-6(Fuca1-2Galb1-3(Fuca1-4)GlcNAcb1-2Mana1-3)Manb1-4GlcNAcb1-4(Fuca1-6)GlcNAcb1-4GlcNAc-Sp19 | 14 | 11 | 79 |
| 151 | Galb1-4(Fuca1-3)GlcNAc-Sp8 | 14 | 5 | 36 |
| 52 | GlcNAcb1-2Mana1-6(GlcNAcb1-2Mana1-3)Manb1-4GlcNAcb-Sp12 | 13 | 9 | 67 |
| 534 | Neu5Aca2-3Galb1-4(Fuca1-3)GlcNAcb1-2Mana-Sp0 | 13 | 5 | 38 |
| 384 | Galα1-2Galb1-3GalNAcα1-2Mana1-6(Galα1-3GalNAcα1-3Manα1-3)Manb1-4GlcNAc-Sp19 | 13 | 17 | 126 |
| 203 | GlcAb1-3Galb-Sp8 | 13 | 8 | 63 |
| 404 | Galα1-4Galb1-4GlcNAcb1-2Mana1-6(Galα1-4Galb1-4GlcNAcb1-2Manα1-3)Manb1-4GlcNAc-Sp20 | 13 | 10 | 76 |
| 330 | Neu5Acα2-8Galb1-4GlcNAcb1-2Mana-Sp0 | 13 | 14 | 103 |
| 53 | GlcNAcb1-2Mana1-3Galb1-4GlcNAcb1-2Mana-Sp0 | 13 | 2 | 15 |
| 570 | (3S)Galb1-4(Fuca1-3)GlcNAcb-Sp8 | 13 | 11 | 80 |
| 97 | Fuca1-2Galb1-3GlcNAcb-Sp8 | 13 | 1 | 6 |
| 88 | Fuca1-2Galb1-3GlcNAcb-Sp0 | 13 | 6 | 43 |
| 97 | Galb1-4(Fuca1-3)GlcNAcb-Sp8 | 13 | 10 | 79 |
| 338 | GlcNAcb1-4GlcNAcb-Sp10 | 13 | 9 | 65 |
| 567 | Galb1-4GlcNAcb1-3)Galb1-4(Fuca1-3)GlcNAcb1-3GlcNAcα1-4Gc-Sp21 | 13 | 9 | 70 |
| 364 | Galb1-4GlcNAcb1-6(Fuca1-4Galb1-2Galb1-3)GlcNAcb1-3)Galb1-4Gc-Sp21 | 13 | 4 | 29 |
| 329 | Neu5,9Ac2α2-3Galb1-4GlcNAc-Sp0 | 13 | 11 | 67 |
| 120 | Galb1-4Galb1-4GlcNAcb-Sp0 | 13 | 13 | 99 |
| 401 | Galb1-4(Fuca1-3)GlcNAcb1-3GalNAcα-Sp14 | 13 | 9 | 70 |
|  |  | 13 | 4 | 32 |
|  |  | 13 | 7 | 52 |
| 33 | (3S)Galb1-4(Fuca1-3)GlcNAcb-Sp8 | 13 | 10 | 82 |
| 554 | Neu5Gcα2-8Neu5Gcα2-3Galb1-4GlcNAc-Sp14 | 13 | 10 | 84 |
| 9 | Neu5Acα-Sp8 | 13 | 5 | 39 |
| 134 | GlcNAcα1-6(Galb1-3)GalNAca-Sp14 | 12 | 15 | 121 |
|  |  | 12 | 12 | 99 |
|  |  | 12 | 28 | 222 |
| 427 | Galb1-3(Fuca1-2)Galb1-4GlcNAcb1-2Mana1-6(Galα1-3(Fuca1-2)Galb1-4GlcNAcb1-2Manα1-3)Manb1-4GlcNAcb1-4(Fuca1-6)GlcNAcb-Sp22 | 12 | 5 | 39 |
|  | 6)GlcNAcb-Sp22 | 12 | 8 | 65 |

Figure 21J

| Glycan number | Glycan structure | Average RFU | StDev | % CV |
|---|---|---|---|---|
| 506 | GalNAcα1-3Fucα1-2Galβ1-3GlcNAcβ1-6GalNAcα-Sp14 | 12 | 34 | 270 |
| 212 | Manα1-2Manα1-6(Manα1-2Manα1-3)Manβ1-4GlcNAcβ1-4GlcNAc-Sp12 | 12 | 13 | 101 |
| 173 | GlcNAcα1-3Galβ1-4GlcNAcβ-Sp8 | 12 | 7 | 58 |
| 168 | GlcNAcβ1-3GalNAcα-Sp14 | 12 | 14 | 117 |
| 428 | Galβ1-3GlcNAcβ1-6(Galβ1-3GlcNAcβ1-3)Galβ1-4GlcNAcβ1-6(Galβ1-3GlcNAcβ1-3)Galβ1-4GlcNAc-Sp19 | 12 | 5 | 38 |
| 511 | (6S)(4S)GalNAcβ1-4GlcNAc-Sp8 | 12 | 7 | 53 |
| 583 | Galβ1-4GlcNAcβ1-3Galβ1-4(GlcNAcβ1-6)Galβ1-4GlcNAcβ1-3Galβ1-4(GlcNAcβ1-6)Galβ1-4GlcNAcβ1-2Manα1-3)Manβ1-4GlcNAcβ1-4(Fucα1-6)GlcNAc-Sp24 | 12 | 12 | 101 |
| 343 | GlcNAcα1-4Galβ1-4GlcNAcβ1-3Galβ1-4GlcNAc-Sp8 | 12 | 21 | 170 |
| 71 | Fucα1-2Galβ1-3Fucα1-3GlcNAc-Sp0 | 12 | 11 | 94 |
| 417 | Galα1-3(Fucα1-2)Galβ1-4(Fucα1-3)GlcNAc-Sp14 | 12 | 5 | 44 |
| 510 | [shaded] | 12 | 6 | 49 |
| 158 | Galβ1-3GlcNAc-Sp8 | 12 | 9 | 73 |
| 39 | (6S)(4S)Galβ1-4GlcNAcβ-Sp8 | 12 | 5 | 40 |
| 38 | (3S)(6S)Galβ-Sp8 | 12 | 9 | 72 |
| 137 | Neu5Acα2-6(Manα1-3)Galβ1-3GlcNAcβ-Sp8 | 12 | 9 | 79 |
| 210 | Manα1-6(Manα1-3)Manα1-6(Manα1-3)Manβ1-4GlcNAcβ1-4GlcNAcβ-Sp12 | 12 | 6 | 52 |
| 218 | Neu5Acα2-3Galβ1-4GlcNAcβ1-6GalNAcα-Sp14 | 12 | 7 | 60 |
| 488 | Galβ1-3GlcNAcβ1-3Manα-Sp8 | 11 | 5 | 41 |
| 160 | Galα1-2Galβ-Sp8 | 11 | 8 | 70 |
| 447 | Galβ1-4(Fucα1-3)GlcNAcβ1-6GalNAcα-Sp14 | 11 | 15 | 134 |
| 215 | Manα1-6(Manα1-3)Manα1-6(Manα1-2Manα1-3)Manβ1-4GlcNAcβ1-4GlcNAcβ-Sp12 | 11 | 7 | 62 |
| 304 | [shaded] | 11 | 8 | 74 |
| 96 | GalNAcβ1-3Galα1-4Galβ1-4GlcNAcβ-Sp0 | 11 | 7 | 60 |
| 486 | Neu5Acα2-3Galβ1-3GlcNAcβ1-6(GlcNAcβ1-4)(Neu5Acα2-3Galβ1-3GlcNAcβ1-2Manα1-3)Manβ1-4GlcNAcβ1-4GlcNAc-Sp21 | 11 | 6 | 57 |
| 314 | Manα1-6(Manα1-3)Galβ1-4GlcNAcβ-Sp8 | 11 | 7 | 61 |
| 105 | Galα1-3Galβ1-4GlcNAcβ-Sp8 | 11 | 6 | 59 |
| 371 | Galα1-3(Fucα1-2)Galβ1-4GlcNAcβ1-2Manα1-6(Galα1-3(Fucα1-2)Galβ1-4GlcNAcβ1-2Manα1-3)Manβ1-4GlcNAcβ1-4GlcNAc-Sp20 | 11 | 7 | 60 |
| 209 | Manα1-2Manα1-3Manα-Sp9 | 11 | 8 | 70 |
| 189 | GlcNAcβ1-4GlcNAcβ1-4GlcNAcβ1-4GlcNAcβ-Sp8 | 11 | 12 | 110 |
| 374 | Galβ1-3(Fucα1-2)Galβ1-4GlcNAcβ1-2Manα1-6(Galβ1-3(Fucα1-2)Galβ1-4GlcNAcβ1-2Manα1-3)Manβ1-4GlcNAcβ1-4GlcNAc-Sp20 | 11 | 12 | 107 |
| 469 | Glcα1-4Glcα1-6Glcα1-Sp10 | 11 | 3 | 25 |
| 292 | Galβ1-4(Fucα1-3)GlcNAcβ1-3Galβ1-3(Fucα1-4)GlcNAcβ-Sp0 | 11 | 7 | 69 |
| 556 | GlcNAcβ1-3Galβ1-4GlcNAcβ1-6GalNAc-Sp14 | 11 | 10 | 95 |
| 466 | Neu5Acα2-6Galβ1-4GlcNAcβ1-6(Neu5Acα2-6Galβ1-4GlcNAcβ1-2Manα1-6)(Neu5Acα2-6Galβ1-4GlcNAcβ1-4)(Neu5Acα2-6Galβ1-4GlcNAcβ1-2Manα1-3)Manβ1-4GlcNAcβ1-4GlcNAc-Sp21 | 11 | 6 | 57 |
| 508 | [shaded] | 11 | 8 | 73 |

Figure 21K

| Glycan number | Glycan structure | Average RFU | StDev | % CV |
|---|---|---|---|---|
| 581 | Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-3Galb1-4GlcNAcb1-2Mana1-3)Mana1-4GlcNAcb1-4(Fuca1-6)GlcNAc-Sp19 | 10 | 1 | 12 |
| 421 | GlcNAcb1-2(GlcNAcb1-6)Mana1-6(GlcNAcb1-4(GlcNAcb1-2)Mana1-3)Manb1-4GlcNAcb1-4GlcNAc-Sp19 | 10 | 5 | 46 |
| 201 | GlcAa-Sp8 | 10 | 9 | 83 |
| 382 | Galb1-4GlcNAcb1-6(Galb1-3)GalNAca-Sp14 | 10 | 2 | 23 |
| 162 | Galb1-4GlcNAcb1-4(Fuca1-3)GlcNAc-Sp0 | 10 | 6 | 61 |
| 356 | KDNa2-3Galb1-4GlcNAcb1-3Galb1-4GlcNAc-Sp0 | 10 | 12 | 121 |
| 190 | GlcNAcb1-4GlcNAcb1-4(Fuca1-3)GlcNAc-Sp8 | 10 | 6 | 57 |
| 188 | GlcNAcb1-4Galb1-4GlcNAc-Sp8 | 10 | 9 | 92 |
| 491 | Neu5Aca2-3Galb1-8(GalNAcb1-6)GalNAca-Sp14 | 10 | 7 | 68 |
| 397 | GlcNAcb1-2Mana1-6(Galb1-4GlcNAcb1-2Mana1-3)Manb1-4GlcNAcb1-4GlcNAcb-Sp12 | 10 | 3 | 35 |
| 58 | Fuca1-2Galb1-3GalNAcb1-3Gala1-4Galb-Sp8 | 10 | 7 | 69 |
| 19 | Neu5Aca-Sp11 | 10 | 13 | 136 |
| 338 | GlcNAcb1-4Galb1-4GlcNAcb1-3Galb1-4GlcNAcb1-3Galb1-4GlcNAcb-Sp0 | 10 | 8 | 78 |
| 123 | Gala1-4Galb1-4GlcNAcb-Sp8 | 10 | 4 | 37 |
| 367 | Neu5Aca2-6GlcNAcb1-4GlcNAcb1-4GlcNAc-Sp21 | 10 | 8 | 86 |
| 77 | Fuca1-2Galb1-3GlcNAcb-Sp0 | 10 | 7 | 68 |
| 64 | Galb1-3(Galb1-4GlcNAcb1-6)GalNAca-Sp8 | 10 | 6 | 59 |
| 489 | Fuca1-2Galb1-4GlcNAcb1-2Mana-Sp0 | 10 | 10 | 104 |
| 194 | Galb1-6GalNAca-Sp8 | 9 | 6 | 63 |
| 202 | GlcAb-Sp8 | 9 | 1 | 14 |
| 114 | Gala1-3Galb1-3GlcNAcb-Sp0 | 9 | 3 | 37 |
| 72 | Galb1-3GlcNAcb-Sp0 | 9 | 4 | 41 |
| 279 | Neu5Aca2-6Galb1-4GlcNAcb-Sp8 | 9 | 6 | 62 |
| 433 | GlcNAcb1-6(GlcNAcb1-2)Mana1-6(GlcNAcb1-4(GlcNAcb1-2)Mana1-3)Manb1-4GlcNAcb1-4GlcNAc-Sp21 | 9 | 3 | 34 |
| 65 | Galb1-3GalNAcb1-3Gala-Sp8 | 9 | 1 | 15 |
| 393 | GalNAca1-3(Fuca1-2)Galb1-3GalNAcb1-3Gala1-4Galb1-4GlcNAcb-Sp14 | 9 | 15 | 161 |
| 598 | Galb1-3(Fuca1-4)GlcNAcb1-3Galb1-4GlcNAcb-Sp0 | 9 | 7 | 79 |
| 154 | Galb1-4(Fuca1-3)GlcNAcb1-4(Fuca1-3)GlcNAcb1-3Galb1-4GlcNAcb-Sp0 | 9 | 16 | 178 |
| 41 | 6P(6P)Mana-Sp8 | 9 | 12 | 131 |
| 402 | GalNAca1-3Galb1-3GalNAcb1-3Gala1-4Galb-Sp8 | 9 | 10 | 107 |
| 370 | GlcNAcb1-4GlcNAcb1-4GlcNAcb-Sp8 | 9 | 12 | 134 |
| 113 | Gala1-3Galb1-4(Fuca1-3)GlcNAcb-Sp0 | 9 | 10 | 110 |
| 15 | GalNAcb-Sp8 | 9 | 8 | 86 |
| 103 | Gala1-3Galb1-4GlcNAcb1-3Galb1-4GlcNAcb-Sp0 | 9 | 6 | 65 |

Figure 21L

| Glycan number | Glycan structure | Average RFU | StDev | % CV |
|---|---|---|---|---|
| | | 9 | 10 | 109 |
| 571 | Galb1-3GlcNAcb1-3Galb1-4GlcNAcb1-6(Galb1-3GlcNAcb1-3)Galb1-4GlcNAcb1-3Galb1-4GlcNAcb-Sp0 | 9 | 6 | 70 |
| 298 | Neu5Gca2-6Galb1-4GlcNAcb-Sp8 | 9 | 14 | 160 |
| 593 | GlcNAcb1-3Galb1-4GlcNAcb1-3SiaNAca-Sp14 | 9 | 7 | 77 |
| | | 9 | 10 | 118 |
| 48 | Neu5,9Ac-a-Sp8 | 9 | 7 | 85 |
| 357 | KDNa2-6GlcNa-Sp0 | 9 | 4 | 44 |
| 197 | Glca1-6Glca1-6Glcb-Sp8 | 8 | 9 | 108 |
| 575 | Galb1-4GlcNAcb1-3Galb1-4GlcNAcb1-2Mana1-3(Galb1-4GlcNAcb1-4(Fuca1- | 8 | 3 | 35 |
| 503 | 6)3KdnNAcb-Sp24 | 8 | 9 | 107 |
| | | 8 | 6 | 71 |
| 80 | Fuca1-4GlcNAcb-Sp8 | 8 | 5 | 56 |
| 533 | Fuca1-6(Galb1-3)GlcNAcb1-2 Mana-Sp0 | 8 | 10 | 127 |
| 50 | Mana1-6(Galb1-4GlcNAcb1-2Mana1-3)Mana1-4GlcNAca-Sp12 | 8 | 8 | 99 |
| 480 | Neu5Aca2-6Galb1-4GlcNAcb1-2Mana1-3)Mana1-4GlcNAcb1-4)GlcNAcb-Sp19 | 8 | 7 | 80 |
| 458 | Galb1-4GlcNAcb1-6(Galb1-4GlcNAcb1-3)Galb1-4)GlcNAcb-Sp8 | 8 | 3 | 40 |
| 284 | Neu5Aca2-3Galb1-4Galb-Sp8 | 8 | 3 | 35 |
| 226 | Neu5Aca2-3GalNAca-Sp8 | 8 | 6 | 78 |
| 449 | Fuca1-2Galb1-4GlcNAcb1-6(Fuca1-2Galb1-4GlcNAcb1-3)GalNAc-Sp14 | 8 | 4 | 54 |
| 513 | 3SGalNAcb1-4(6S)GlcNAc-Sp0 | 8 | 9 | 115 |
| 288 | Neu5Aca2-3Galb1-4GlcNAcb1-6(Galb1-3)GalNAca-Sp14 | 8 | 5 | 58 |
| 298 | Neu5Aca2-6(6S)Galb1-4(6S)GlcNAcb-Sp0 | 8 | 4 | 49 |
| | | 8 | 9 | 110 |
| | | 8 | 7 | 84 |
| | | 8 | 6 | 69 |
| 204 | GlcAb1-6Galb-Sp8 | 6 | 3 | 34 |
| 299 | Neu5Aca2-3Galb1-3(Fuca1-4)GlcNAcb-Sp8 | 8 | 6 | 74 |
| 211 | Mana1-2Mana1-6(Mana1-3)Mana1-6(Mana1-2Mana1-2Mana1-3)Mana-Sp12 | 8 | 6 | 73 |
| 94 | GalNAcb1-3GalNAca-Sp8 | 8 | 9 | 120 |
| 442 | GalNAcb1-6GalNAcb-Sp8 | 8 | 4 | 58 |
| 315 | Mana1-2Mana1-6(Mana1-3)Mana1-6(Mana1-2Mana1-3)Mana-Sp9 | 6 | 4 | 53 |
| 235 | Neu5Aca2-6(NeusAca2-3)GalNAca-Sp8 | 8 | 3 | 36 |
| 181 | Galb1-3GalNAcb-Sp8 | 8 | 4 | 49 |
| 419 | Galb1-4(Fuca1-3)GlcNAcb1-2Mana1-6(Galb1-4Fuca1-3)GlcNAcb1-2Mana1-3)Mana1-4GlcNAcb1-4(Fuca1-6)GlcNAcb-Sp22 | 7 | 1 | 17 |
| 505 | Galb1-3(Fuca1-2)Galb1-3GlcNAcb1-6GalNAc-Sp0 | 7 | 9 | 126 |
| 75 | Fuca1-2Galb1-4GlcNAcb-Sp0 | 7 | 15 | 198 |

Figure 21M

| Glycan number | Glycan structure | Average RFU | StDev | % CV |
|---|---|---|---|---|
| 468 | Gala1-3(Fuca1-2)Galb1-3GalNAcb-Sp8 | 7 | 11 | 154 |
| 551 | Galb1-3GlcNAcb1-4Galb1-4GlcNAcb1-2Mana1-6(GlcNAcb1-3Galb1-4GlcNAcb1-2Mana1-3)Manb1-4GlcNAcb1-4GlcNAc-Sp25 | 7 | 5 | 63 |
| 340 | GlcNAca1-4Galb1-3GlcNAcb-Sp0 | 7 | 3 | 39 |
| 366 | Neu5Aca2-6GlcNAcb1-4GlcNAcb-Sp0 | 7 | 9 | 127 |
| 414 | GalNAca1-3(Fuca1-2)Galb1-4GlcNAcb1-3GalNAca-Sp8 | 7 | 11 | 147 |
| 159 | Galb1-4GlcNAcb1-3GalNAca-Sp8 | 7 | 6 | 79 |
| | | 7 | 7 | 101 |
| 287 | Neu5Gca-Sp8 | 7 | 5 | 72 |
| 307 | GlcAb1-3GlcNAcb-Sp8 | 7 | 11 | 167 |
| 323 | Neu5Aca2-3Galb1-3GalNAca-Sp8 | 7 | 8 | 112 |
| 298 | (6P)Glcb-Sp10 | 7 | 7 | 110 |
| 450 | Gala1-3(Fuca1-2)Galb1-4GlcNAcb1-6(Gala1-3(Fuca1-2)Galb1-3)GalNAca-Sp14 | 7 | 8 | 117 |
| 279 | Neu5Aca2-6GalNAca-Sp0 | 7 | 3 | 53 |
| 454 | GalNAca1-3(Fuca1-2)Galb1-4GlcNAcb1-2Mana1-6(GalNAca1-3(Fuca1-2)Galb1-4GlcNAcb1-2Mana1-3)Manb1-4GlcNAcb1-4(Fuca1-6)GlcNAcb-Sp22 | 6 | 2 | 39 |
| | | 6 | 4 | 60 |
| 12 | Galb-Sp9 | 6 | 4 | 65 |
| 508 | Fuca1-2Galb1-3GlcNAcb1-6(Fuca1-4)Galb1-3GlcNAca-Sp14 | 6 | 2 | 40 |
| 170 | Galb1-4GlcNAcb-Sp23 | 6 | 8 | 128 |
| 520 | Neu5Aca2-6Galb1-4GlcNAcb1-3Gal-Sp21 | 6 | 5 | 81 |
| | | 6 | 8 | 133 |
| 389 | GlcNAcb1-2Mana1-6(GlcNAcb1-2Mana1-3)Manb1-4GlcNAcb1-4GlcNAcb-Sp21 | 6 | 18 | 316 |
| 167 | Galb1-4GlcNAcb1-6Galb1-3GalNAc-Sp0 | 6 | 1 | 17 |
| 562 | GalNAcb1-3GlcNAcb-Sp0 | 6 | 6 | 99 |
| 300 | Galb1-4GlcNAcb-Sp8 | 6 | 13 | 222 |
| 193 | GlcNAcb1-6GalNAca-Sp14 | 6 | 10 | 175 |
| 538 | Galb1-3GalNAcb1-3Gal-Sp21 | 6 | 8 | 138 |
| 17 | GlcNAcb-Sp8 | 6 | 6 | 111 |
| 604 | GlcNAcb1-6(Neu5Aca2-3Galb1-3)GalNAca-Sp14 | 6 | 7 | 132 |
| 81 | Fucb1-3GlcNAcb-Sp8 | 6 | 3 | 46 |
| 578 | GlcNAcb1-2Galb1-4GlcNAcb1-4(Fuca1-4)Galb1-3GlcNAcb1-2Mana1-6(Galb1-4GlcNAcb1-3Galb1-4GlcNAcb1-2Mana1-3)Manb1- | 6 | 12 | 224 |
| 528 | GalNAcb1-4Fuca1-4GlcNAcb-Sp24 | 6 | 5 | 96 |
| 389 | Galb1-3Galb1-3GlcNAcb1-3GalNAca-Sp0 | 6 | 9 | 160 |
| 508 | 4GlcNAcb1-4Fuca1-6)GlcNAc-Sp21 | 6 | 2 | 33 |

Figure 21N

| Glycan number | Glycan structure | Average RFU | StDev | % CV |
|---|---|---|---|---|
| 11 | Neu5Acb-Sp8 | 5 | 8 | 140 |
| 425 | Gala1-2Galb1-3GlcNAcb1-3GalNAc-Sp14 | 5 | 7 | 119 |
| 380 | Fuca1-2Galb1-3GalNAca1-3(Fuca1-2)Galb1-4GlcNAcb-Sp0 | 5 | 6 | 107 |
| 56 | Fuca1-2Galb1-3GlcNAcb1-3Galb1-4Glcb-Sp0 | 5 | 4 | 66 |
| 439 | Fuca1-2Galb1-3GlcNAcb1-3Galb1-4Glcb-Sp0 | 5 | 5 | 89 |
| 56 | Fuca1-2Galb1-3GlcNAcb1-3Galb1-4Glcb-Sp0 | 5 | 8 | 157 |
| 168 | Galb1-4GlcNAcb-Sp0 | 5 | 2 | 44 |
| 500 | Galb1-3GlcNAcb1-3Fuca-3Galb1-4Glc-Sp0 | 5 | 3 | 52 |
| 111 | Galb1-3GalNAca-Sp16 | 5 | 4 | 81 |
| 498 | Gala1-3Fuca1-2)Galb1-4GlcNAcb1-6GalNAca-Sp14 | 5 | 4 | 77 |
| 232 | GalNAcb1-4(Neu5Aca2-3)Galb1-4GlcNAcb-Sp8 | 5 | 3 | 62 |
| 500 | Fuca1-2Galb1-3GlcNAcb1-3Galb1-4Glcb-Sp0 | 5 | 12 | 225 |
| 192 | GlcNAcb1-6GalNAca-Sp8 | 5 | 3 | 59 |
| 561 | GlcNAcb1-3Galb1-4GlcNAcb1-6(GlcNAcb1-3)GalNAca-Sp8 | 5 | 5 | 101 |
| 293 | Galb1-4GlcNAcb1-3Galb1-3GlcNAc-Sp0 | 5 | 6 | 111 |
| 333 | Neu5Gcb2-6Galb1-4GlcNAc-Sp8 | 5 | 8 | 169 |
| 22 | 6s(3S)Galb1-4(6S)GlcNAcb-Sp0 | 5 | 10 | 207 |
| 68 | Fuca1-3Galb1-3GlcNAcb1-3Gala-Sp0 | 5 | 5 | 95 |
| 84 | Fuca1-2Galb1-3GlcNAcb1-3Galb1-4Glcb-Sp0 | 5 | 3 | 58 |
| 588 | Neu5Acb-Sp0 | 5 | 8 | 157 |
| 363 | Galb1-3Galb1-4GlcNAcb1-2Mana1-6(Galb1-3Galb1-4GlcNAcb1-2Mana1-3)Mana1-4GlcNAcb-Sp20 | 5 | 5 | 105 |
| 189 | Galb1-4GlcNAcb-Sp8 | 5 | 10 | 203 |
| 407 | Galb1-3GlcNAca1-6Galb1-4GlcNAc-Sp0 | 4 | 7 | 154 |
| 112 | Galb1-3GalNAcb-Sp8 | 4 | 6 | 134 |
| 504 | Fuca1-2Galb1-3GlcNAcb1-3Galb1-4Glcb-Sp0 | 4 | 4 | 102 |
| 180 | Galb1-4GlcNAcb1-3Fuca-3Galb1-4Glc-Sp0 | 4 | 11 | 248 |
| 107 | Gala1-3Fuca1-2)Galb-Sp8 | 4 | 5 | 119 |
| 217 | Mana1-4GlcNAcb-Sp8 | 4 | 4 | 97 |
| 166 | Galb1-4GlcNAcb1-6Galb1-3GlcNAca-Sp0 | 4 | 12 | 292 |
| 213 | Mana1-6(Mana1-3)Mana-Sp8 | 4 | 1 | 23 |
| 499 | Galb1-3Fuca1-2Galb1-4Glcb-Sp21 | 4 | 7 | 188 |
| 34 | Fuca1-2Galb1-3GlcNAcb1-3Galb1-4Glcb-Sp0 | 4 | 7 | 174 |
| 540 | GlcNAcb1-3Galb1-4GlcNAcb1-2Mana1-6(GlcNAcb1-2Mana1-3)Mana1-4GlcNAcb1-4GlcNAcb-Sp25 | 4 | 10 | 245 |
| 132 | Galb1-4GlcNAca1-6GalNAc-Sp14 | 4 | 7 | 169 |
| 82 | GalNAca1-3Fuca1-2)Galb1-4GlcNAcb-Sp0 | 4 | 2 | 64 |
| 183 | GlcNAcb1-3Galb1-4GlcNAcb-Sp8 | 4 | 9 | 236 |
| 422 | Fuca1-2Galb1-3GlcNAcb1-3GalNAc-Sp14 | 4 | 12 | 308 |

Figure 21O

| Glycan number | Glycan structure | Average RFU | StDev | % CV |
|---|---|---|---|---|
| 105 | Galα1-3Fucα1-2Galβ1-4GlcNAc-Sp0 | 4 | 11 | 281 |
| 499 | Galα1-3Galβ1-3GlcNAcβ1-6GalNAcα-Sp14 | 4 | 7 | 199 |
| 280 | Neu5Fcα2-3Galβ1-3Fucα1-4GlcNAc-Sp0 | 4 | 6 | 149 |
| 142 | Galβ1-3GalNAc-Sp8 | 4 | 7 | 176 |
| 305 | Galβ1-4GlcNAcβ1-6GalNAcα-Sp8 | 4 | 8 | 217 |
| 163 | Galβ1-4GlcNAcβ1-3Galβ1-4GlcNAc-Sp0 | 4 | 4 | 111 |
| 356 | (6S)GalNAcβ1-3Galβ1-4GlcNAc-Sp0 | 4 | 4 | 103 |
| 176 | GlcNAcβ1-6(GlcNAcβ1-3)GalNAcα-Sp8 | 4 | 6 | 135 |
| 515 | (3S)GalNAcβ1-4GlcNAc-Sp0 | 3 | 6 | 171 |
| 140 | Galβ1-3GalNAcα-Sp14 | 3 | 10 | 301 |
| 250 | Neu5Acα2-3Galβ1-3GlcNAc-Sp8 | 3 | 7 | 226 |
| 45 | (6S)Galβ1-4(6S)GlcNAc-Sp8 | 3 | 4 | 138 |
| 283 | Neu5Gcα2-3Galβ1-4GlcNAc-Sp0 | 3 | 1 | 46 |
| 108 | Galβ1-3Fucα1-2Galβ1-Sp18 | 3 | 13 | 426 |
| 214 | Manα1-2Manα1-2Manα1-6)Manα1-3)Manα-Sp0 | 3 | 7 | 239 |
| 435 | Galβ1-4GlcNAcβ1-2Manα1-6(GlcNAcβ1-4)(Galβ1-4GlcNAcβ1-2Manα1-3)Manβ1-4GlcNAc-Sp21 | 3 | 5 | 172 |
| 451 | GalNAcβ1-2(Fucα1-3)Galβ1-4(Fucα1-3)GlcNAc-Sp0 | 3 | 6 | 192 |
| 492 | (3S)GalNAcβ1-4GlcNAc-Sp8 | 3 | 2 | 86 |
| 83 | GalNAcα1-3Galβ1-3Fucα1-2(Galβ1-4)GlcNAc-Sp0 | 3 | 10 | 360 |
| 130 | Fucα1-4Galβ1-4GlcNAc-Sp0 | 3 | 7 | 278 |
| 161 | Galβ1-4GlcNAcβ1-4(Fucα1-3)GlcNAcβ1-3Galβ1-4(Fucα1-3)GlcNAc-Sp0 | 3 | 3 | 123 |
| 592 | Galβ1-4GlcNAcβ1-2 Manα1-6(Manα1-6(Galβ1-4)GlcNAcβ1-4(Fucα1-6)GlcNAc-Sp21 | 3 | 2 | 65 |
| | | 2 | 7 | 293 |
| 331 | Neu5Acα2-3Galβ1-3Fucα1-4)GlcNAcβ1-3Galβ1-3(Fucα1-4)GlcNAc-Sp0 | 2 | 2 | 108 |
| 23 | β(3S)Galβ1-4GlcNAcα-Sp10 | 2 | 5 | 232 |
| 310 | GlcNAcβ1-4GlcNAca-Sp0 | 2 | 6 | 307 |
| 479 | Neu5Acα2-3Galβ1-4GlcNAcβ1-6GalNAcα-Sp14 | 2 | 5 | 285 |
| 539 | GlcNAcβ1-3Galβ1-4GlcNAcβ1-2Manα1-6(GlcNAcβ1-3)Manβ1-4GlcNAcβ1-4GlcNAc-Sp12 | 2 | 9 | 475 |
| 175 | GlcNAcβ1-2GalNAcα-Sp8 | 2 | 8 | 447 |
| | | 2 | 7 | 417 |
| 594 | GlcNAcβ1-3Galβ1-4GlcNAcβ1-6(Galβ1-3)GalNAcα-Sp14 | 2 | 7 | 444 |
| 512 | (6S)GalNAcβ1-4GlcNAc-Sp8 | 2 | 5 | 305 |
| 397 | Galβ1-4GlcNAcβ1-6(Galβ1-4GlcNAcβ1-2)Manα1-6(Galβ1-4GlcNAcβ1-4)(Galβ1-4GlcNAcβ1-2)Manα1-3)Manβ1-4GlcNAc-Sp21 | 1 | 5 | 336 |
| | | 1 | 6 | 400 |
| 592 | Neu5Acα2-3Galβ1-4GlcNAcβ1-3GalNAca-Sp14 | 1 | 3 | 203 |

Figure 21P

| Glycan number | Glycan structure | Average RFU | StDev | % CV |
|---|---|---|---|---|
| 313 | Mana1-6Manb-Sp19 | 1 | 3 | 238 |
| 590 | Galb1-4GlcNAcb1-3Galb1-4GlcNAcb1-6(Galb1-4GlcNAca-Sp14 | 1 | 7 | 494 |
| 35 | (3S)Galb1-4(6S)GlcNAcb-Sp8 | 1 | 10 | 757 |
| 418 | GalNAca1-3(Fuca1-2)Galb1-4(Fuca1-3)GlcNAcb1-3GalNAc-Sp14 | 1 | 5 | 426 |
| 438 | Galb1-4GlcNAcb1-6(Galb1-4GlcNAcb1-2)Mana1-6(GlcNAcb1-4(Galb1-4GlcNAcb1-2)Mana1-3)Manb1-4GlcNAcb1-4GlcNAc-Sp21 | 1 | 8 | 626 |
|  |  | 1 | 12 | 1085 |
| 555 | Neu5Gca2-3Neu5Gca2-3Galb1-3GlcNAcb-Sp0 | 1 | 4 | 351 |
| 434 | Galb1-4GlcNAcb1-6(GlcNAcb1-2Mana1-3)Manb1-4GlcNAc-Sp21 | 1 | 4 | 363 |
| 230 | Neu5Aca2-3(6S)Galb1-4(Fuca1-3)GlcNAcb-Sp8 | 1 | 7 | 641 |
| 196 | Glca1-4Glca-Sp8 | 1 | 3 | 247 |
| 436 | Galb1-4GlcNAcb1-2Mana1-6(GlcNAcb1-4(Galb1-4GlcNAcb1-2)Mana1-3)Manb1-4GlcNAcb1-4GlcNAc-Sp21 | 1 | 5 | 463 |
| 305 | GalNAcb1-3GlcNAc-Sp8 | 1 | 3 | 341 |
| 70 | Fuca1-3GlcNAcb-Sp8 | 1 | 4 | 485 |
| 236 | G-ol-Sp8 | 1 | 14 | 1855 |
| 285 | Neu5Aca2-6GalNAca-Sp0 | 1 | 5 | 826 |
| 578 | GlcNAcb1-2Galb1-4GlcNAcb1-3Galb1-4GlcNAcb1-2Mana1-6(GlcNAcb1-3Galb1-4GlcNAcb1-4GlcNAcb1-2Mana1-3)Manb1-4GlcNAcb1- | 0 | 4 | 1076 |
| 21 | GlcNAcb1-6(GlcNAcb1-4)GlcNAcb1-3GlcNAc-Sp24 | 0 | 5 | 1299 |
| 502 | Neu5Aca2-6(Gal1NAcb1-4(6S)GlcNAcb-Sp8 | 0 | 5 | 1181 |
| 158 | Galb1-4Galb1-4Galb1-4(Fuca1-2)Galb1-4GlcNAcb-Sp8 | 0 | 17 | 21991 |
|  |  | 0 | 7 | -1761 |
| 580 | GlcNAcb1-2Galb1-4GlcNAcb1-3Galb1-4GlcNAcb1-2Mana1-6(GlcNAcb1-3Galb1-4GlcNAcb1-2Mana1-6(Fuca1-6)GlcNAcb-Sp19 | -1 | 5 | -824 |
| 403 | Galb1-4GlcNAcb1-3Galb1-4GlcNAcb1-6(Galb1-4GlcNAcb1-3)Manb1-3)Manb1-4GlcNAc-Sp24 | -1 | 4 | -424 |
| 517 | Galb1-4(6P)GlcNAcb-Sp0 | -1 | 6 | -643 |
| 597 | Neu5Aca2-6(Galb1-4GlcNAcb1-3Galb1-4GlcNAca-Sp14 | -2 | 11 | -1149 |
| 220 | Fuca1-2(6S)Galb1-4GlcNAc-Sp0 | -2 | 6 | -417 |
| 609 | Galb1-3Fuca-Sp10 | -2 | 3 | -174 |
| 440 | Galb1-6Galb-Sp10 | -2 | 6 | -295 |
|  |  | -2 | 11 | -541 |
| 309 | GlcNAcb1-4GlcNAcb-Sp10 | -2 | 4 | -181 |
| 312 | MurNAcb1-4GlcNAc-Sp10 | -2 | 4 | -176 |
| 131 | Galb1-4(6S)GalNAca-Sp8 | -2 | 4 | -190 |
| 526 | Neu5Aca2-3Galb1-3GlcNAcb1-2Mana-Sp0 | -3 | 11 | -513 |
|  |  | -3 | 7 | -286 |
|  |  | -3 | 3 | -113 |

Figure 21Q

| Glycan number | Glycan structure | Average RFU | StDev | % CV |
|---|---|---|---|---|
| 19 | Galb1-4GlcNAcb1-6(Galb1-4GlcNAcb1-3)GalNAca-Sp8 | -3 | 10 | -343 |
| 599 | Galb1-4GlcNAcb1-3Galb1-3GalNAca-Sp14 | -3 | 6 | -223 |
| 277 | Galb1-3(Fuca1-4)GlcNAcb1-3(Fuca1-4)GlcNAcb-Sp0 | -3 | 9 | -290 |
| 191 | GlcNAcb1-4GlcNAcb1-4GlcNAc-Sp8 | -3 | 2 | -67 |
| 420 | Fuca1-2Galb1-4GlcNAcb1-3Mana1-6(Fuca1-2Galb1-4GlcNAcb1-3Mana1-3)Manb1-4GlcNAcb1-4(Fuca1-6)GlcNAcb-Sp22 | -4 | 3 | -90 |
| 516 | (4S)GalNAcb-Sp10 | -4 | 21 | -510 |
| 182 | GlcNAcb1-3Galb1-4GlcNAcb-Sp0 | -4 | 12 | -275 |
| 133 | GlcNAcb1-6(Galb1-3)GalNAca-Sp8 | -4 | 3 | -65 |
| 432 | GlcNAcb1-2Mana1-6(GlcNAcb1-4)(GlcNAcb1-2Mana1-3)Manb1-4GlcNAcb1-4GlcNAcb-Sp20 | 5 | 5 | -90 |
| 369 | KDNa2-3Galb1-3GalNAca-Sp14 | 6 | 6 | -95 |
| 327 | Galb1-4(Fuca1-3)GlcNAcb1-2Mana1-6(Fuca1-2Galb1-4(Fuca1-3)GlcNAcb1-2Mana1-3)Manb1-4GlcNAcb-Sp21 | 6 | 9 | -140 |
| 139 | Galb1-3GalNAca-Sp6 | -7 | 5 | -76 |
| 245 | Neu5Aca2-3Galb-Sp8 | -7 | 38 | -562 |
| 311 | GlcNAcb1-4GlcNAcb-Sp12 | 7 | 4 | -51 |
| 337 | Neu5Aca2-3Galb1-4(Fuca1-3)GlcNAcb1-6(Neu5Aca2-3Galb1-3)GalNAca-Sp14 | -8 | 4 | -50 |
| 405 | Gala1-3Galb1-4GlcNAcb1-3Mana1-3Manb-Sp9 | -9 | 8 | -89 |
| 381 | Galb1-3GalNAca1-3(Fuca1-2)Galb1-4GlcNAc-Sp0 | -9 | 7 | -78 |
| 308 | Neu5Aca2-6Galb1-4GlcNAcb1-2Mana1-3)Manb1-4GlcNAcb-Sp12 | -9 | 10 | -104 |
| 128 | Galb1-3(Fuca1-4)GlcNAc-Sp0 | -9 | 9 | -90 |
| 365 | Fuca1-4(Galb1-3)GlcNAcb1-2Mana1-6(Fuca1-4(Galb1-3)GlcNAcb1-2Mana1-3)Manb1-4GlcNAcb1-4(Fuca1-6)GlcNAcb-Sp22 | -10 | 25 | -256 |
| 194 | GlcNAcb1-3Galb1-4GlcNAcb1-3GalNAca-Sp14 | -10 | 3 | -31 |
| 14 | Man5-Sp9 | -10 | 44 | -422 |
| 40 | (4S)Galb1-4GlcNAcb-Sp8 | -10 | 48 | -461 |
| 296 | 4S(3S)Galb1-4GlcNAcb-Sp0 | -11 | 26 | -246 |
| 297 | Mana1-2Mana1-2Mana1-3Manb-Sp9 | -12 | 25 | -215 |
| 96 | (6S)Galb1-4GlcNAcb-Sp0 | -12 | 6 | -50 |
| 195 | Gala1-4Glcb-Sp8 | -13 | 5 | -38 |
| 354 | Galb1-3GlcNAcb1-2Mana1-6(Galb1-3GlcNAcb1-2Mana1-3)Manb1-4GlcNAcb1-4GlcNAcb-Sp12 | -16 | 17 | -109 |
| 595 | GlcNAcb1-3Galb1-4GlcNAcb1-6(GlcNAcb1-3Galb1-4GlcNAcb1-3)GalNAca-Sp14 | 22 | 29 | 130 |
| 406 | Galb1-3GlcNAcb1-4Galb-Sp0 | 23 | 13 | 56 |
| 500 | Fuca1-2Galb1-3(6S)GlcNAcb-Sp0 | -23 | 4 | -17 |
| 321 | Neu5Aca2-8Neu5Acb-Sp17 | -25 | 29 | -117 |
| 62 | (signal) | -34 | 34 | -102 |
| 408 | GalNAca1-3Galb1-6Galb1-4Glcb-Sp8 | -34 | 32 | -93 |
| 379 | GalNAcb1-4GlcNAca1-2Mana1-6(GalNAcb1-4GlcNAcb1-2Mana1-3)Manb1-4GlcNAcb1-4GlcNAc-Sp12 | -37 | 15 | -43 |
| 218 | Mana1-6(Mana1-3)Mana1-6(Mana1-3)Manb1-4GlcNAcb1-4GlcNAcb-Sp0 | -37 | 18 | -50 |
| | | -40 | 36 | -90 |

| Glycan number | Glycan structure | Average RFU | StDev | % CV |
|---|---|---|---|---|
| 565 | Galb1-4GlcNAcb1-3Galb1-4GlcNAcb1-3Galb1-4GlcNAcb1-3Galb1-4GlcNAcb1-2Mana1-6(Galb1-4GlcNAcb1-3Galb1-3(Fuca1-2)Galb1-4GlcNAcb1-6(Gala1-3(Fuca1-2)Galb1-4GlcNAcb1-3)Galb1-4GlcNAcb1-2Mana1-3)Manb1-4GlcNAcb1-4(Fuca1-6)GlcNAc-Sp25 | 45 | 15 | 34 |
| 427 | Galb1-4GlcNAcb1-2Mana1-6(Galb1-4GlcNAcb1-2Mana1-3)Manb1-4GlcNAcb1-4(Fuca1-6)GlcNAc-Sp22 | 45 | 18 | 40 |
| 577 | 2Mana1-3)Manb1-4GlcNAcb1-4(Fuca1-6)GlcNAcb-Sp24 | 45 | 9 | 21 |
| 225 | GalNAcb1-4(Neu5Aca2-8Neu5Aca2-8Neu5Aca2-3)Galb1-4Glcb-Sp0 | 44 | 15 | 34 |
| 362 | GlcNAcb1-2Mana1-6(GlcNAcb1-2Mana1-3)Manb1-4GlcNAcb1-4(Fuca1-6)GlcNAc-Sp22 | 43 | 18 | 40 |
| 501 | Fuca1-2(6S)Galb1-3(6S)GlcNAcb-Sp8 | 43 | 9 | 21 |
| 485 | Galb1-4GlcNAcb1-6(Galb1-4GlcNAcb1-2Mana1-3)Mana1-4(Fuca1-6)GlcNAcb-Sp24 | 43 | 19 | 45 |
| 9 | Fuca-Sp8 | 42 | 45 | 107 |
| 550 | Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-2Mana1-3)Manb1-4GlcNAcb1-4GlcNAc-Sp25 | 41 | 24 | 58 |
| 291 | Galb1-4(Fuca1-3)(6S)Glcb-Sp0 | 41 | 17 | 41 |
| 809 | Neu5Aca2-6Galb1-4 GlcNAcb1-6(Neu5Aca2-8Galb1-4(Neu5Aca2-6)GlcNAcb1-2Mana1-3)Manb1-4GlcNAcb1-4GlcNAc-Sp12 | 40 | 12 | 31 |
| 426 | Galb1-3GlcNAcb1-6(Galb1-4GlcNAcb1-2Mana1-6)(Galb1-4GlcNAcb1-2Mana1-3)Manb1-4GlcNAcb1-4GlcNAc-Sp19 | 40 | 7 | 16 |
| 363 | Gala1-3Galb1-4GlcNAcb1-6(Galb1-4GlcNAcb1-2Mana1-3)Manb1-4GlcNAc-Sp0 | 39 | 3 | 7 |
| 194 | Gala1-3Fuca1-2)Galb1-4(Fuca1-3)GlcNAcb-Sp8 | 38 | 20 | 51 |
| 445 | Fuca1-2 Galb1-4 GlcNAcb1-2(Fuca1-2Galb1-4GlcNAcb1-4)Mana1-3)Manb1-4GlcNAcb1-4GlcNAc-Sp12 | 38 | 16 | 42 |
| 357 | KDNa2-6Galb1-4GlcNAc-Sp0 | 37 | 21 | 58 |
| 580 | GlcNAcb1-3Galb1-4GlcNAcb1-3Galb1-6(Galb1-3(GlcNAcb1-6)Galb1-4GlcNAcb1-3Galb1-4GlcNAcb1-3Galb1-4GlcNAcb1-2Mana1-6(GlcNAcb1-2Mana1-3)Manb1-4GlcNAcb1-4(Fuca1-6)GlcNAcb-Sp19 | 37 | 11 | 29 |
| 481 | Neu5Aca2-8Neu5Aca2-3(GlcNAcb1-6)Galb1-4(Fuca1-3)GlcNAc-Sp14 | 37 | 18 | 48 |
| 573 | Neu5Aca2-8Neu5Aca2-3Galb1-4(Neu5Aca2-3)Galb1-4Glc-Sp21 | 37 | 14 | 38 |
| 42 | (6S)(3S)Galb1-4Glcb-Sp0 | 36 | 23 | 65 |
| 598 | GlcNAcb1-3Galb1-4GlcNAcb1-3Galb1-4GlcNAcb1-3GlcNAca-Sp14 | 36 | 29 | 80 |
| 572 | Galb1-4GlcNAcb1-2Mana1-6(Mana1-3)Mana1-6(Mana1-3)Manb1-4GlcNAcb1-4GlcNAcb-Sp19 | 36 | 14 | 39 |
| 508 | Galb1-4GlcNAcb1-2Mana1-6(Galb1-4(Fuca1-3)GlcNAcb1-4(Gal b1-4GlcNAcb1-2)Mana1-3)Manb1-4GlcNAcb-Sp19 | 36 | 32 | 89 |
| 324 | Galb1-3GlcNAcb1-2Mana1-6(Galb1-3GlcNAcb1-2Mana1-3)Manb1-4GlcNAcb1-4GlcNAc-Sp21 | 35 | 21 | 58 |
| 364 | Galb1-4GlcNAcb1-2Mana1-6(Mana1-3)Manb1-4GlcNAcb1-4GlcNAc-Sp12 | 35 | 10 | 30 |
| 334 | GalNAcb1-3Gala1-4Galb1-4GlcNAcb-Sp0 | 35 | 18 | 50 |
| 349 | Galb1-4GlcNAcb1-2Mana1-6GlcNAcb1-4GlcNAc-Sp12 | 35 | 15 | 42 |
| 361 | Fuca1-2Galb1-4GlcNAcb1-2Mana1-3)Manb1-4GlcNAc-Sp12 | 34 | 16 | 47 |
| 574 | GlcNAcb1-3Galb1-4GlcNAcb1-3GlcNAcb1-2Mana1-3Manb1-4GlcNAcb1-4(Fuca1-6)GlcNAcb-Sp24 | 33 | 10 | 31 |
| 490 | Galb1-3(Fuca1-4)GlcNAcb1-6GalNAca-Sp14 | 33 | 24 | 73 |

Figure 22C

| Glycan number | Glycan structure | Average RFU | StDev | % CV |
|---|---|---|---|---|
| 159 | Galb1-4GlcNAcb1-3GalNAca-Sp8 | 33 | 50 | 153 |
| 453 | GalNAcb1-4Galb1-4Glcb-Sp0 | 33 | 11 | 35 |
| 584 | GlcNAcb1-3Galb1-4GlcNAcb1-3Galb1-4GlcNAcb1-3Galb1-4GlcNAcb1-3Galb1-4GlcNAcb1-3Galb1-4GlcNAcb-Sp0 | 32 | 9 | 30 |
| 253 | 3'Sialb1-4GlcNAcb1-3Galb1-4GlcNAcb1-3Galb1-4(Fuca1-3)GlcNAcb1-3Galb1-4(Fuca1-3)GlcNAcb-Sp0 | 32 | 13 | 41 |
| 431 | GlcNAcb1-2Mana1-3(GlcNAcb1-4)(GlcNAcb1-2Mana1-6)Mana1-4GlcNAcb-Sp21 | 32 | 11 | 35 |
| 24 | (3S)Galb1-4(Fuca1-3)(6S)Glc-Sp0 | 31 | 21 | 65 |
| 330 | Neu5Aca2-6Galb1-3(6S)Glcb1-3GalNAca-Sp8 | 31 | 22 | 71 |
| 571 | Galb1-3GlcNAcb1-3Galb1-4GlcNAcb1-3Galb1-4(Fuca1-3)GlcNAcb1-3Galb1-4GlcNAcb-Sp24 | 31 | 2 | 8 |
| 342 | 6'SGalb1-4Galb1-3GlcNAcb1-3Galb1-4GlcNAcb1-3Galb1-4GlcNAcb1-3Galb1-4(Fuca1-3)GlcNAcb1-3Mana1-4GlcNAcb1-2Mana1-4GlcNAcb1-8GlcNAcb-Sp0 | 31 | 18 | 61 |
| 4 | GalNAca-Sp8 | 31 | 14 | 47 |
| 305 | Fuca1-4(Galb1-3)GlcNAcb1-3Galb1-4(Fuca1-3)GlcNAcb-Sp0 | 30 | 20 | 64 |
| 123 | Galb1-4GlcNAcb-Sp8 | 30 | 15 | 50 |
| 144 | GlcNAcb1-3GalNAca2-3Galb1-4Glcb-Sp0 | 30 | 13 | 42 |
| 568 | GlcNAcb1-6(GlcNAcb1-2)Mana1-6(GlcNAcb1-4)(GlcNAcb1-2Mana1-3)Man a1-3(Mana1-4)GlcNAcb1-4GlcNAcb-Sp12 | 29 | 8 | 29 |
| 310 | GlcNAcb1-4GlcNAcb-Sp10 | 29 | 17 | 59 |
| 260 | Galb1-4(Fuca1-3)(6S)GlcNAcb-Sp0 | 28 | 9 | 31 |
| 403 | Galb1-3GlcNAcb1-3Mana1-6(Galb1-4GlcNAcb1-2Mana1-3)Manb1-4GlcNAcb1-4GlcNAcb-Sp19 | 28 | 9 | 30 |
| 153 | Galb1-4(Galb1-3)GlcNAcb1-3Galb1-4(Fuca1-3)GlcNAcb-Sp0 | 28 | 16 | 59 |
| 442 | GlcNAcb1-6GalNAca-Sp8 | 28 | 7 | 25 |
| 118 | Galab1-3Galb1-4Glcb-Sp8 | 28 | 10 | 38 |
| 605 | Neu5Aca2-8(Neu5Aca2-8)Neu5Aca2-3(GalNAcb1-4)Galb1-4GlcNAcb-Sp0 | 27 | 11 | 41 |
| 192 | (6S)GalNAcb-Sp8 | 27 | 11 | 40 |
| 325 | (6S)GlcNAcb1-4(6S)GlcNAcb-Sp0 | 27 | 14 | 54 |
| 260 | Fuca1-2Galb1-3GlcNAcb1-3(Fuca1-2Galb1-4GlcNAcb1-6)Galb1-4GlcNAcb1-3GlcNAcb-Sp22 | 27 | 6 | 23 |
| 261 | GlcoA-Sp8 | 27 | 6 | 24 |
| 333 | Galb1-4Galb1-4GlcNAcb-Sp8 | 27 | 17 | 65 |
| 366 | Galb1-4GlcNAcb1-2Mana1-6(Galb1-4GlcNAcb1-2Mana1-3)Manb1-4GlcNAcb1-4GlcNAcb-Sp21 | 27 | 9 | 34 |
| 109 | Galb1-4(Gala1-3)Galb1-4GlcNAcb-Sp0 | 27 | 11 | 42 |
| 287 | Neu5Gca-Sp8 | 26 | 11 | 44 |
| 351 | Mana1-6(Galb1-4GlcNAcb1-2Mana1-3)Manb1-4GlcNAcb1-4GlcNAcb-Sp12 | 26 | 14 | 53 |
| 244 | GlcNAcb1-4Galb1-3GalNAca-Sp14 | 26 | 15 | 58 |
| 446 | Galb1-4GlcNAcb1-2Mana-Sp0 | 25 | 14 | 54 |
| 251 | Neu5Aca2-3Galb1-4(6S)GlcNAcb-Sp8 | 25 | 15 | 61 |
| 103 | Galb1-3Fuca1-2Galb1-4Fuca1-3GlcNAcb-Sp8 | 25 | 14 | 55 |
| 188 | Galb1-4Galb1-4GlcNAcb-Sp8 | 25 | 9 | 37 |
| 254 | Neu5Aca2-3Galb1-4(Fuca1-3)GlcNAcb-Sp0 | 25 | 17 | 69 |

Figure 22D

| Glycan number | Glycan structure | Average RFU | StDev | % CV |
|---|---|---|---|---|
| 97 | GalNAcb1-4(Fuca1-3)GlcNAcb-Sp0 | 25 | 8 | 34 |
| 348 | Neu5Aca2-6Galb1-4GlcNAcb1-2Mana1-3Mana1-4GlcNAcb1-4GlcNAc-Sp12 | 24 | 9 | 38 |
| 45 | (6S)Galb1-4(6S)Glcb-Sp8 | 24 | 11 | 45 |
| 466 | Neu5Aca2-6Galb1-4GlcNAcb1-6(Neu5Aca2-6Galb1-4GlcNAcb1-2)Mana1-6(Neu5Aca2-6Galb1-4GlcNAcb1-4)(Neu5Aca2-6Galb1-4GlcNAcb1-2)Mana1-3)GlcNAcb1-4GlcNAc-Sp21 | 24 | 6 | 25 |
| 345 | Neu5Aca2-6Galb1-4GlcNAcb1-6(GlcNAcb1-2Mana1-3)Mana1-4GlcNAc-Sp12 | 23 | 5 | 23 |
| 121 | Gala1-4Galb1-4GlcNAcb-Sp8 | 23 | 11 | 46 |
| 227 | Neu5Aca2-8Neu5Aca2-8Neu5Aca2-3Galb1-4GlcNAcb-Sp0 | 23 | 12 | 51 |
| 563 | GalNAcb1-4GlcNAcb1-3Galb1-4GlcNAcb-Sp0 | 23 | 11 | 46 |
| 212 | Mana1-2Mana1-6(Mana1-2Mana1-3)Mana1-6(Mana1-2Mana1-2Mana1-3)Mana1-4GlcNAcb-Sp0 | 23 | 18 | 77 |
| 240 | Neu5Aca2-3Galb1-3(Fuca1-4)GlcNAcb1-3Galb1-4(Fuca1-3)GlcNAcb-Sp12 | 23 | 2 | 10 |
| 215 | Mana1-6(Mana1-3)Mana1-6(Mana1-3)Mana1-4GlcNAcb1-4GlcNAcb-Sp12 | 23 | 15 | 67 |
| 102 | Galb1-3Fuca1-2Galb1-3GlcNAcb-Sp8 | 23 | 19 | 83 |
| 533 | Fuca1-4(Galb1-3)GlcNAcb1-2 Mana-Sp0 | 23 | 20 | 87 |
| 167 | Galb1-4(3S)GlcNAcb1-6(Galb1-3)GalNAca-Sp14 | 23 | 9 | 42 |
| 455 | Galb1-3(Fuca1-2)Galb1-3GlcNAcb1-2Mana1-6(Gala1-3(Fuca1-2)Galb1-3GlcNAcb1-2Mana1-3)Mana1-4GlcNAcb1-4Fuca1-6)GlcNAcb-Sp22 | 23 | 20 | 91 |
| 471 | Neu5Aca2-3Galb1-4GlcNAcb1-6(Neu5Aca2-3Galb1-3)GalNAca-Sp14 | 22 | 12 | 52 |
| 156 | Galb1-4(6S)Glcb-Sp8 | 22 | 19 | 85 |
| 511 | (6S)(4S)GalNAcb1-4GlcNAcb-Sp0 | 22 | 5 | 25 |
| 206 | KDNa2-3Galb1-3GlcNAcb-Sp0 | 22 | 16 | 73 |
| 228 | GalNAca1-4(Neu5Aca2-8Neu5Aca2-3)Galb1-4Glcb-Sp0 | 22 | 12 | 55 |
| 194 | GlcNAcb1-6Galb1-4GlcNAcb1-2Man-Sp0 | 22 | 16 | 74 |
| 520 | Neu5Aca2-6Galb1-4Glcb-Sp10 | 22 | 6 | 29 |
| 440 | G-ol-Sp0 | 21 | 13 | 62 |
| 238 | Neu5Aca2-3Galb1-3(6S)GlcNAcb-Sp8 | 21 | 15 | 72 |
| 356 | KDNa2-3Galb1-4GlcNAcb1-6GalNAca-Sp14 | 21 | 12 | 54 |
| 479 | Neu5Aca2-3Galb1-4GlcNAcb1-6GalNAca-Sp14 | 21 | 16 | 73 |
| 378 | Neu5Aca2-3Gala1-3Galb1-4(Fuca1-3)GlcNAcb-Sp0 | 21 | 17 | 80 |
| 216 | Mana1-6(Mana1-3)Mana1-6(Mana1-3)Mana1-4GlcNAcb-Sp12 | 21 | 18 | 84 |
| 373 | GalNAca1-3(Fuca1-2)Galb1-4(Fuca1-3)GlcNAcb-Sp0 | 21 | 18 | 87 |
| 127 | Galb1-3(6S)GalNAcb1-3GalNAca-Sp8 | 21 | 13 | 61 |
| 200 | G-ol-Sp0 | 21 | 5 | 24 |
| 419 | Galb1-4(Fuca1-3)GlcNAcb1-2Mana1-6(Fuca1-3)GlcNAcb1-2Mana1-4)GlcNAcb1-4(Fuca1-3)GlcNAcb-Sp22 | 21 | 25 | 117 |
| 229 | Neu5Aca2-8Neu5Aca2-3Galb-Sp0 | 21 | 15 | 71 |
| 175 | GlcNAcb1-8GlcNAcb1-3GalNAca-Sp8 | 21 | 11 | 53 |

Figure 22E

| Glycan number | Glycan structure | Average RFU | StDev | % CV |
|---|---|---|---|---|
| 115 | Galα1-3Galβ1-4GlcNAcb-Sp8 | 21 | 5 | 25 |
| 64 | Fucα1-2Galβ1-3GalNAcb1-4(NeuSAca2-3)Galβ1-4Glcb-Sp9 | 21 | 13 | 62 |
| 333 | Neu5Aca2-6Galβ1-4GlcNAcb1-3Galβ1-4GlcNAcb1-3Galβ1-4Glcb-Sp0 | 21 | 10 | 47 |
| 275 | Neu5Aca2-8Neu5Aca-Sp0 | 21 | 9 | 42 |
| 436 | Galb1-4GlcNAcb1-2Mana1-6(GlcNAcb1-4)Galb1-4GlcNAcb1-2Mana1-3)Manb1-4GlcNAcb1-4GlcNAcb-Sp21 | 20 | 16 | 79 |
| 49 | (4S)Galb1-4GlcNAcb-Sp8 | 20 | 45 | 221 |
| 325 | Neu5Aca2-3Galb1-4GlcNAcb1-2Mana1-6(Neu5Aca2-3Galb1-4GlcNAcb1-2Mana1-3)Manb1-4GlcNAcb1-4GlcNAcb-Sp12 | 20 | 7 | 35 |
| 417 | Galα1-3Fucα1-2Galβ1-4(Fucα1-3)GlcNAc-Sp8 | 20 | 7 | 35 |
| 358 | KDNa2-3Galb1-4Glc-Sp0 | 20 | 6 | 31 |
| 311 | GlcNAcb1-4GlcNAcb-Sp12 | 20 | 13 | 65 |
| 456 | Neu5Aca2-6Galb1-4(Fuca1-2Galb1-4)GlcNAcb1-3)Galb1-4Glc-Sp21 | 20 | 6 | 31 |
| 28 | (3S)Galb1-3(Fuca1-4)GlcNAcb-Sp0 | 20 | 20 | 99 |
| 321 | Neu5Aca2-3Neu5Acb-Sp17 | 20 | 11 | 54 |
| 464 | Neu5Aca2-6Galb1-4GlcNAcb1-4Mana1-6(GlcNAcb1-4(Neu5Aca2-6Galb1-4GlcNAcb1-2Mana1-3)Manb1-4GlcNAcb1-4GlcNAcb1-2)Mana1-... | 20 | 8 | 39 |
| 412 | Neu5Aca2-3Galb1-3GalNAcb1-2Mana1-6Neu5Aca2-8Neu5Aca2-3)Galb1-4Glcb-Sp0 | 20 | 11 | 56 |
| 350 | Galb1-4GlcNAcb1-2Mana1-2Mana1-6Manb1-4GlcNAca-Sp12 | 19 | 16 | 85 |
| 294 | Neu5Gca2-3Galb1-3GlcNAc-Sp0 | 19 | 7 | 38 |
| 2 | Glca-Sp8 | 19 | 18 | 92 |
| 187 | GlcNAcb1-6(GlcNAcb1-4)GlcNAcb-Sp8 | 19 | 16 | 83 |
| 147 | Galb1-3GlcNAcb1-3Galb1-4GlcNAcb-Sp0 | 19 | 11 | 57 |
| 217 | Manb1-4GlcNAcb-Sp0 | 19 | 5 | 29 |
| 145 | Galb1-3GalNAcα1-4Galb1-4Glcb-Sp8 | 19 | 14 | 75 |
| 393 | GalNAcb1-4(Neu5Aca2-3)Galb1-4GlcNAcb1-3GalNAcα-Sp14 | 19 | 14 | 71 |
| 446 | Fucα1-2Galb1-4(Fucα1-3)GlcNAcα1-2Mana1-6(Fucα1-6)Galb1-4(Fucα1-3)GlcNAcb1-4)GlcNAcb1-2)Mana1-3)GlcNAcb-Sp12 | 19 | 10 | 53 |
| 599 | 3Manb1-4GlcNAcb1-4GlcNAcb-Sp12 | 19 | 4 | 21 |
| 117 | Galb1-4GlcNAcb1-3GalNAcα-Sp14 | 19 | 20 | 105 |
| 607 | Neu5Aca2-3Galb1-4GlcNAcb1-3Galb1-4GlcNAcb1-2Mana1-6(Neu5Aca2-3Galb1-4GlcNAcb1-3Galb1-... | 19 | 14 | 75 |
| 5 | GalNAca-Sp15 | 19 | 10 | 54 |
| 308 | Galb1-3GalNAcα1-6Galb1-4GlcNAcb1-2Mana1-6(GlcNAcb1-2Mana1-3)Manb1-4GlcNAcb-Sp12 | 19 | 13 | 70 |
| 581 | Galb1-4GlcNAcb1-3Galb1-3GlcNAcb1-3Galb1-3GlcNAcb1-3Galb1-4(Fuca1-4)GlcNAcb1-6)GlcNAcb1... | | | |
| | Sp19 | 19 | 5 | 26 |
| 256 | Neu5Aca2-3Galb1-4Fucα1-3)GlcNAcb1-3Gala-Sp0 | 19 | 15 | 78 |
| 249 | Neu5Aca2-3Galb1-3GlcNAcb-Sp0 | 18 | 13 | 68 |
| 1 | Gala-Sp8 | 18 | 8 | 45 |
| 478 | Neu5Aca2-3Galb1-4GlcNAcb1-2Mana-Sp0 | 18 | 4 | 21 |

Figure 22F

| Glycan number | Glycan structure | Average RFU | StDev | % CV |
|---|---|---|---|---|
| 370 | GalNAca1-3(Fuca1-2)Galb1-3(Fuca1-2)Galb1-4GlcNAcb1-3(Fuca1-2)Galb1-4(Fuca1-3)GlcNAcb1-2Mana1-3(GalNAca1-3(Fuca1-2)Galb1-4(Fuca1-3)GlcNAcb1-2Mana1-3)Manb1-4GlcNAcb1-4GlcNAcb- | 18 | 9 | 47 |
| 100 | Galb1-2Galb-Sp8 | 18 | 15 | 84 |
| 540 | GlcNAca1-3Galb1-4GlcNAcb1-2Mana1-6(GlcNAca1-3Galb1-4GlcNAcb1-2Mana1-3)Manb1-4GlcNAcb-Sp25 | 18 | 13 | 70 |
| 33 | (3S)Galb1-4(Fuca1-3)GlcNAcb-Sp0 | 18 | 11 | 58 |
| 568 | Galb1-4GlcNAcb1-3Galb1-4GlcNAcb1-3Galb1-4GlcNAcb1-2Mana1-6(Galb1-4GlcNAcb1-3Galb1-4GlcNAcb1-3Galb1-4GlcNAcb1-2Mana1-3)Manb1-4GlcNAcb1-4GlcNAcb-Sp25 | 18 | 12 | 67 |
| 542 | Galb1-4GlcNAcb1-3Galb1-4(Fuca1-3)GlcNAcb1-2Mana1-6(Galb1-4GlcNAcb1-2Mana1-3)Manb1-4GlcNAcb1-4GlcNAcb-Sp24 | 18 | 31 | 170 |
| 51 | Mana1-6(Mana1-3)Mana1-6(Mana1-3)Manb1-4GlcNAcb1-4GlcNAcb-Sp13 | 18 | 9 | 50 |
| 548 | Galb1-4GlcNAcb1-3Galb1-4GlcNAcb1-2Mana1-6(Galb1-4GlcNAcb1-3Galb1-4GlcNAcb1-2Mana1-3)Manb1-4GlcNAcb-Sp24 | 18 | 5 | 26 |
| 98 | 2Mana1-3)Manb1-4GlcNAcb-Sp25 | 18 | 4 | 22 |
| 132 | GalNAcb1-4GlcNAcb-Sp0 | 18 | 8 | 43 |
| 221 | Fuca1-2Galb1-4(6S)GalNAcb-Sp14 | 18 | 11 | 60 |
| 211 | Mana1-2Mana1-3Mana1-6(Mana1-3)Manb1-4GlcNAcb1-4GlcNAcb-Sp12 | 18 | 17 | 95 |
| 549 | GlcNAcb1-3Galb1-4GlcNAcb1-3Galb1-4GlcNAcb1-2Mana1-6(GlcNAcb1-3Galb1-4GlcNAcb1-2Mana1-3)Manb1-4GlcNAcb-Sp25 | 18 | 11 | 62 |
| 70 | Galb1-2Galb1-4(Fuca1-3)GlcNAcb1-3Galb1-4(Fuca1-3)GlcNAcb-Sp0 | 18 | 12 | 67 |
| 313 | Mana1-6Manb-Sp10 | 17 | 6 | 36 |
| 493 | Galb1-4GlcNAcb1-3(Neu5Aca2-6)GalNAca-Sp14 | 17 | 11 | 61 |
| 119 | Galb1-3Galb-Sp8 | 17 | 14 | 83 |
| 136 | Neu5Aca2-8(Galb1-3)GalNAca-Sp14 | 17 | 5 | 27 |
| 449 | Fuca1-2Galb1-4GlcNAcb1-6Fuca1-2Galb1-3GalNAca-Sp14 | 17 | 8 | 45 |
| 472 | Fuca1-2Galb1-4(Fuca1-3)GlcNAcb1-2Mana1-6(Fuca1-2Galb1-4(Fuca1-3)GlcNAcb1-2Mana1-3)Manb1-4GlcNAcb-Sp24 | 17 | 10 | 57 |
| 504 | (3S)Galb1-4(Fuca1-3)GlcNAcb-Sp8 | 17 | 9 | 53 |
| 83 | GalNAca1-3(Fuca1-2)Galb1-4(Fuca1-3)GlcNAcb-Sp0 | 17 | 20 | 119 |
| 207 | Mana1-2Mana1-3Manb-Sp0 | 17 | 7 | 41 |
| 301 | Neu5Aca2-6Galb1-4GlcNAcb1-2Mana1-6(Galb1-4GlcNAcb1-2Mana1-3)Manb1-4GlcNAcb-Sp12 | 17 | 11 | 66 |
| 165 | Galb1-4(Fuca1-3)Galb1-4GlcNAcb-Sp0 | 17 | 11 | 66 |
| 234 | Neu5Aca2-3Galb1-4(Neu5Aca2-3)Galb1-4GlcNAcb-Sp0 | 17 | 14 | 87 |
| 41 | (6P)Mana-Sp0 | 17 | 13 | 77 |
| 473 | Fuca1-2(3S)Galb1-3(Fuca1-4)GlcNAcb1-2Galb1-3(Fuca1-4)GlcNAcb1-2Mana1-3)Manb1-4GlcNAcb1-4(Fuca1-5)GlcNAcb1-4GlcNAc-Sp19 | 16 | 3 | 18 |
| 424 | GalNAca1-3(Fuca1-2)Galb1-3GalNAcb-Sp14 | 16 | 4 | 23 |

Figure 22G

| Glycan number | Glycan structure | Average RFU | StDev | % CV |
|---|---|---|---|---|
| 346 | Mana1-6(NeuSAca2-6(Galb1-4GlcNAcb1-2Mana1-3)Manb1-4GlcNAcb1-4GlcNAc-Sp12 | 16 | 16 | 100 |
| 138 | NeuSAca2-6(Galb1-3)GlcNAcb1-3Galb1-4GlcNAc-Sp10 | 16 | 12 | 71 |
| 388 | GlcNAcb1-2Mana1-6(GlcNAcb1-4)(GlcNAcb1-2Mana1-3)Mana1-4GlcNAc-Sp21 | 16 | 7 | 44 |
| 438 | Galb1-4GlcNAcb1-6(Galb1-4GlcNAcb1-2)Mana1-6(Galb1-4GlcNAcb1-4)(Galb1-4GlcNAcb1-2)Mana1-3)Manb1-4GlcNAcb1-4GlcNAc-Sp21 | 16 | 13 | 82 |
| 316 | Mana1-2Mana1-6(Mana1-2Mana1-3)Mana1-6(Mana1-2Mana1-2Mana1-3)Mana-Sp9 | 16 | 3 | 20 |
| 244 | NeuSAca2-6(NeuSAca2-3)Galb1-3)GalNAca-Sp14 | 16 | 5 | 32 |
| 526 | NeuSAca2-3Galb1-4GlcNAcb1-6(NeuSAca2-3Galb1-2Mana1-6)Galb1-4GlcNAcb1-2Mana1-3)Manb1-4GlcNAcb1-4GlcNAc-Sp12 | 16 | 5 | 31 |
| 483 | NeuSAca2-3(Galb1-4(GlcNAcb1-4)NeuSAca2-3Galb1-4(GlcNAc)b1-3)Mana1-3(Mana1-6)Manb1-4GlcNAcb1-4(Fuca1-6)GlcNAcb1-Sp24 | 16 | 5 | 28 |
| 71 | Fuca1-2Galb1-4(Fuca1-3)GlcNAcb-Sp8 | 16 | 11 | 69 |
| 20 | Galb1-4(3SGalNAca-Sp16 | 16 | 16 | 101 |
| 111 | Galb1-3GalNAca-Sp16 | 16 | 10 | 64 |
| 190 | GlcNAcb1-4Galb1-4GlcNAcb1-4Galb1-4GlcNAc-Sp0 | 16 | 20 | 127 |
| 22 | 8Su(3Su)Galb1-4(6Su)GlcNAc-Sp0 | 16 | 8 | 50 |
| 226 | GalNAcb1-4(NeuSAca2-8NeuSAca2-3)Galb1-4GlcNAc-Sp0 | 16 | 8 | 49 |
| 252 | NeuSAca2-3Galb1-4(Fuca1-3)6Su)Galb1-4Fuca-Sp14 | 16 | 9 | 58 |
| 378 | NeuSAca2-3Galb1-4GlcNAcb1-3Galb-Sp0 | 16 | 19 | 120 |
| 76 | Fuca1-2Galb1-4GlcNAcb-Sp0 | 16 | 9 | 58 |
| 243 | NeuSAca2-6(NeuSAca2-3Galb1-3)GalNAca-Sp8 | 16 | 6 | 40 |
| 393 | GalNAcb1-3(Fuca1-2)Galb1-3GalNAca-Sp14 | 15 | 28 | 181 |
| 450 | Galb1-3(Fuca1-2)Galb1-4(3&6-NAcb1-4GlcNAcb1-3)GalNAca-Sp14 | 15 | 13 | 82 |
| 179 | GlcNAcb1-3Galb-Sp8 | 15 | 10 | 68 |
| 535 | GlcNAcb1-3Galb1-4GlcNAcb1-6(GlcNAcb1-3)GalNAc-Sp0 | 15 | 10 | 65 |
| 36 | (3SU)Galb1-4GlcNAc-Sp0 | 15 | 15 | 101 |
| 543 | NeuSGca2-6(Galb1-4(GlcNAcb1-3)Galb1-4(NeuSAca2-3Galb1-4(GlcNAcb1-3)Galb1-2Mana1-3)(Galb1-4GlcNAcb1-2Mana1-3)Manb1-4GlcNAcb1-4GlcNAc-Sp0 | 15 | 10 | 64 |
| 270 | NeuSAca2-6Galb1-4GlcNAcb1-3Galb1-4(Fuca1-3)GlcNAcb1-4(Fuca1-3)GlcNAcb-Sp0 | 15 | 4 | 30 |
| 499 | Fuca1-2Galb1-6(Mana1-3)Mana-Sp9 | 15 | 8 | 55 |
| 213 | Mana1-6(Mana1-3)Manb1-4GlcNAc-Sp0 | 15 | 7 | 47 |
| 231 | GalNAcb1-4(NeuSAca2-3)Galb1-4GlcNAcb-Sp0 | 15 | 4 | 28 |
| 347 | Galb1-4(6Su)Galb1-2Mana1-3Manb1-4GlcNAcb1-4GlcNAc-Sp12 | 15 | 8 | 50 |
| 320 | NeuSAca2-6(Galb1-4(GlcNAcb1-6)Galb1-4GlcNAcb1-2Mana1-4GlcNAc-Sp0 | 15 | 6 | 42 |
| 285 | NeuSGca2-6Galb1-4GlcNAca-Sp0 | 15 | 17 | 116 |
| 84 | (3S)Galb1-4(Fuca1-3)GlcNAcb-Sp0 | 15 | 5 | 34 |
| 32 | (3S)Galb1-4(Fuca1-3)GlcNAc-Sp0 | 14 | 7 | 51 |
| 85 | GalNAcb1-3(Fuca1-2)Galb1-4GlcNAcb-Sp0 | 14 | 13 | 88 |
| 601 | NeuSAca2-6Galb1-4GlcNAcb1-3Galb1-4GlcNAcb1-6)Galb1-3GalNAca-Sp14 | 14 | 9 | 66 |
| 359 | (3S)Galb1-3GlcNAca-Sp0 | 14 | 6 | 42 |
| 32 | (3S)Galb1-4(Fuca1-3)GlcNAc-Sp0 | 14 | 20 | 144 |
| 85 | Galb1-6Glca1-6Galb1-6GlcNAcb-Sp10 | 14 | 7 | 48 |
| 469 | Glca1-6(GlcNAcb-Sp0) | 14 | 7 | 48 |
| 155 | Galb1-4(6Su)Galb-Sp0 | 14 | 9 | 64 |

Figure 22H

| Glycan number | Glycan structure | Average RFU | StDev | % CV |
|---|---|---|---|---|
| 15 | GalNAcb-Sp8 | 14 | 6 | 43 |
| 575 | Galb1-4GlcNAcb1-2Galb1-4GlcNAcb1-2Mana1-6)Galb1-4)Galb1-4GlcNAcb1-2Mana1-3)Galb1-4GlcNAcb1-2Mana1-3)Mana1-4)GlcNAcb1-4(Fuca1-6)GlcNAc-Sp24 | 14 | 4 | 31 |
| 184 | Galb1-4GlcNAcb1-3Galb1-4GlcNAcb-Sp0 | 14 | 11 | 76 |
| 261 | Neu5Aca2-3Galb1-4GlcNAcb1-4)Galb1-4)GlcNAcb-Sp0 | 14 | 23 | 165 |
| 135 | Neu5Aca2-6Galb1-3)GalNAca-Sp8 | 14 | 14 | 96 |
| 248 | Fuca1-2(6S)Galb1-4)Glcb-Sp0 | 14 | 17 | 122 |
| 354 | Galb1-3GlcNAcb1-2Mana1-6)Galb1-3GlcNAcb1-2Mana1-3)Mana1-4)GlcNAcb1-4(Fuca1-6)GlcNAcb-Sp22 | 14 | 6 | 45 |
| 328 | Neu5,9Ac2a2-3Galb1-4GlcNAcb-Sp0 | 14 | 10 | 70 |
| 273 | GlcNAcb1-6)GalNAca-Sp8 | 14 | 10 | 74 |
| 199 | Glcα1-4)Glcb-Sp8 | 14 | 8 | 59 |
| 263 | Neu5Aca2-3Galb1-4GlcNAcb-Sp0 | 14 | 7 | 49 |
| 408 | Galb1-3GlcNAcb1-6)Galb1-4GlcNAcb-Sp0 | 14 | 9 | 68 |
| 191 | Galb1-3)Fuca1-2)Galb1-3)GlcNAcb-Sp14 | 14 | 8 | 57 |
| 447 | Galb1-4)Fuca1-3)Y)GlcNAc1-6)GalNAca-Sp14 | 13 | 7 | 50 |
| 9 | Neu5Aca-Sp8 | 13 | 9 | 64 |
| 570 | (3S)Y)3)kcAb1-3)Galb1-4GlcNAcb1-2Mana-Sp0 | 13 | 13 | 100 |
| 247 | Neu5Aca2-3Galb1-3GlcNAcb1-3Galb1-4GlcNAcb-Sp0 | 13 | 10 | 72 |
| 91 | GalNAca1-3GalNAcb-Sp8 | 13 | 8 | 63 |
| 317 | Neu5Aca2-3Galb1-4GlcNAcb1-6)Neu5Aca2-3Galb1-3)GalNAca-Sp14 | 13 | 12 | 93 |
| 274 | Neu5Aca2-6Galb-Sp8 | 13 | 20 | 148 |
| 47 | (6S)GlcNAcb-Sp8 | 13 | 4 | 30 |
| 556 | Neu5Gca2-3Neu5Aca2-8)Galb1-4)GlcNAc-Sp0 | 13 | 15 | 114 |
| 160 | Galb1-4GlcNAcb1-3)GalNAc-Sp14 | 13 | 3 | 25 |
| 193 | GlcNAcb1-6)GalNAca-Sp14 | 13 | 6 | 48 |
| 277 | Galb1-3)Fuca1-4)GlcNAcb1-3Galb1-3)Fuca1-4)GlcNAcb-Sp0 | 13 | 10 | 75 |
| 259 | Neu5Aca2-3Galb1-4GlcNAcb-Sp0 | 13 | 8 | 63 |
| 294 | Neu5Aca2-3Galb1-3)GlcNAcb1-3Galb1-3GlcNAcb-Sp0 | 13 | 15 | 118 |
| 429 | Galb1-4)Fuca1-3)GlcNAcb1-3)Galb1-4)GalNAca1-3)Galb1-4Glc-Sp21 | 13 | 20 | 151 |
| 49 | Neu5,9Ac2a2-6Galb1-4)GlcNAc-Sp8 | 13 | 7 | 51 |
| 46 | Neu5Aca2-3)(6S)Galb1-4GlcNAc-Sp8 | 13 | 18 | 136 |
| 295 | Neu5Aca2-3Galb-Sp8 | 13 | 8 | 63 |
| 482 | Neu5Aca2-6Galb1-4GlcNAcb1-2Mana1-6)Neu5Aca2-6)Galb1-4)GlcNAcb1-2Mana1-3)Mana1-4)GlcNAcb1-4(Fuca1-6)GlcNAc-Sp24 | 13 | 11 | 83 |
| 495 | Galb1-3Galb1-4)GlcNAcb1-6)GalNAca-Sp14 | 13 | 9 | 73 |
| 273 | GalNAcb1-3)Fuca1-2)Galb1-3)GlcNAcb1-3)Galb1-4)Mana1-4)GalNAca1-2Mana1-6)Galb1-4)GlcNAcb1-4)GlcNAcb-Sp0 | 13 | 14 | 113 |
| 88 | Fuca1-2Galb1-3)GlcNAcb-Sp8 | 13 | 5 | 41 |

Figure 22I

| Glycan number | Glycan structure | Average RFU | StDev | % CV |
|---|---|---|---|---|
| 69 | Fuca1-2Galb1-4(Fuca1-3)GlcNAcb1-3Galb1-4(Fuca1-3)GlcNAcb-Sp0 | 13 | 5 | 40 |
| 25 | (3S)Galb1-4Glcb-Sp0 | 13 | 16 | 123 |
| 367 | Neu5Aca2-6GlcNAcb1-4GlcNAcb1-4GlcNAc-Sp21 | 13 | 8 | 62 |
| 402 | GalNAca1-3GalNAcb1-3Gala1-4Galb1-4Glcb-Sp0 | 13 | 7 | 57 |
| 510 | Galb1-3(6S)GlcNAcb-Sp8 | 13 | 5 | 40 |
| 79 | Fuca1-3GlcNAcb-Sp8 | 12 | 17 | 137 |
| 418 | GalNAca1-3(Fuca1-2)Galb1-4(Fuca1-3)GlcNAcb1-3GalNAc-Sp14 | 12 | 9 | 71 |
| 306 | GalNAcb1-3Galb-Sp8 | 12 | 8 | 67 |
| 126 | Galb1-3(Fuca1-4)GlcNAcb1-3Galb1-4(Fuca1-3)GlcNAcb-Sp0 | 12 | 17 | 140 |
| 616 | Galb1-3GalNAcb1-4(Neu5Aca2-8Neu5Aca2-3)Galb1-4Glcb-Sp21 | 12 | 7 | 56 |
| 37 | (3S)Galb1-4Glcb-Sp10 | 12 | 11 | 89 |
| 343 | GlcNAca1-4Galb1-4GlcNAcb1-3Galb1-4GlcNAcb-Sp0 | 12 | 8 | 67 |
| 46 | Neu5,9Ac-a-Sp8 | 12 | 6 | 51 |
| 462 | (3S)Galb1-4(Fuca1-3)GlcNAc-Sp0 | 12 | 10 | 83 |
| 512 | (6S)GalNAcb1-4(6S)GlcNAc-Sp0 | 12 | 8 | 69 |
| 557 | Neu5Aca2-3Neu5Aca2-3Galb1-4GlcNAc-Sp0 | 12 | 6 | 52 |
| 66 | Fuca1-2Galb1-3GlcNAcb1-3Galb1-4(Fuca1-3)GlcNAc-Sp10 | 12 | 3 | 22 |
| 382 | Galb1-4GlcNAcb1-3GalNAca1-3(Fuca1-2)Galb1-4GlcNAcb-Sp0 | 12 | 5 | 44 |
| 389 | Fuca1-2Galb1-3GalNAca1-3(Fuca1-2)Galb1-4Glcb-Sp0 | 12 | 6 | 52 |
| 380 | Galb1-3GalNAca1-3(Fuca1-2)Galb1-4Glc-Sp0 | 12 | 8 | 69 |
| 451 | GalNAca1-3GalNAcb1-3(Fuca1-2)Galb1-4(Fuca1-3)GlcNAcb-Sp14 | 12 | 10 | 87 |
| 18 | GlcN(Gc)b-Sp8 | 12 | 9 | 79 |
| 307 | GlcAb1-3GlcNAcb-Sp8 | 11 | 14 | 123 |
| 413 | Gala1-3(Fuca1-2)Galb1-4GlcNAcb1-3GalNAca-Sp14 | 11 | 3 | 29 |
| 388 | Galb1-4GlcNAcb1-2Mana1-6(GlcNAcb1-2Mana1-3)Manb1-4GlcNAcb1-4Glc-Sp12 | 11 | 4 | 39 |
| 537 | Gala1-3(Fuca1-2)Galb1-3GalNAca1-3Gala1-4Galb1-4Glc-Sp0 | 11 | 6 | 57 |
| 465 | Neu5Aca2-6Galb1-4GlcNAcb1-6(Neu5Aca2-6Galb1-2)Mana1-3(Neu5Aca2-6Galb1-4)GlcNAcb1-2Mana1-3)Manb1-4GlcNAcb1-4GlcNAca-Sp12 | 11 | 8 | 70 |
| 38 | (3S)Galb-Sp8 | 11 | 11 | 98 |
| 596 | Neu5Aca2-3Galb1-4GlcNAcb1-6(Neu5Aca1-4)GlcNAcb1-3Galb1-4GlcNAca-Sp14 | 11 | 14 | 130 |
| 470 | Glca1-4Glca1-4Glcb-Sp10 | 11 | 4 | 39 |
| 397 | GlcNAcb1-2Mana1-6(Gala1-3GalNAca1-2Mana1-3)Manb1-4GlcNAc-Sp12 | 11 | 7 | 68 |
| 143 | Galb1-3GalNAca1-3Gala1-4Galb1-4Glcb-Sp0 | 11 | 3 | 25 |
| 219 | (3S)Galb1-4(Fuca1-3)(6S)GlcNAcb-Sp0 | 11 | 7 | 62 |
| 87 | GalNAca1-3(Fuca1-2)Galb1-4Glcb-Sp0 | 11 | 4 | 34 |
| 494 | Fuca1-2Galb1-4GlcNAcb1-6GalNAca-Sp14 | 11 | 4 | 39 |

Figure 22J

| Glycan number | Glycan structure | Average RFU | StDev | % CV |
|---|---|---|---|---|
| 460 | NeuSAca2-3Galb1-4GlcNAcb1-4Manb1-6(NeuSAca2-3Galb1-4GlcNAcb1-4(NeuSAca2-3Galb1-4GlcNAcb1-2)Mana1-3)Manb1-4GlcNAcb1-4GlcNAcb1-2Mana1-Sp21 | 11 | 3 | 26 |
| 422 | Fuca1-2Galb1-3GlcNAcb1-4GlcNAc-Sp14 | 11 | 11 | 100 |
| 171 | Galb1-4Glcb-Sp0 | 11 | 2 | 15 |
| 604 | GlcNAcb1-6(NeuSAca2-3Galb1-3)GalNAca-Sp14 | 11 | 6 | 60 |
| 185 | GlcNAcb1-3Galb1-4Glcb-Sp0 | 11 | 8 | 71 |
| 129 | Galb1-3(Fuca1-4)GlcNAc-Sp8 | 11 | 14 | 128 |
| 196 | Galα1-4Gβa-Sp8 | 11 | 5 | 45 |
| 514 | GalNAcb1-4(6S)GlcNAc-Sp8 | 11 | 12 | 114 |
| 302 | Galb1-4GlcNAcb1-6(Galb1-4GlcNAcb1-3)Galb1-4GlcNAc-Sp0 | 11 | 9 | 81 |
| 553 | NeuSAca2-8NeuSAca2-3Galb1-4GlcNAc-Sp0 | 11 | 12 | 113 |
| 242 | NeuSAca2-3Galb1-3(6S)GalNAca-Sp8 | 11 | 7 | 67 |
| 296 | 4S(6S)Galb1-4GlcNAcb-Sp0 | 11 | 7 | 66 |
| 241 | NeuSAca2-3Galb1-4(Fuca1-3)GlcNAcb1-3)GlcNAcb-Sp0 | 11 | 4 | 42 |
| 60 | Fuca1-2Galb1-3(Fuca1-4)GlcNAc-Sp8 | 10 | 5 | 47 |
| 459 | NeuSAca2-3Galb1-4GlcNAcb1-2Mana1-6(GlcNAcb1-2Mana1-3)Manb1-4GlcNAcb1-4GlcNAcb-Sp21 | 10 | 7 | 63 |
| 199 | Glcb1-4Glcb-Sp0 | 10 | 6 | 59 |
| 31 | (3S)Galb1-3GlcNAcb-Sp8 | 10 | 6 | 61 |
| 322 | NeuSAca2-8NeuSAca2-8NeuSAc-Sp8 | 10 | 4 | 43 |
| 486 | NeuSAca2-3Galb1-4GlcNAcb1-2Mana1-6(NeuSAca2-3Galb1-4GlcNAcb1-2Mana1-3)Manb1-4GlcNAcb1-4GlcNAc-Sp21 | 10 | 3 | 26 |
| 554 | NeuSgca2-8NeuSAca2-3Galb1-4GlcNAc-Sp0 | 10 | 6 | 56 |
| 175 | GlcNAcb1-2Galb1-3GalNAca-Sp14 | 10 | 10 | 94 |
| 204 | GlcAb1-6Galb-Sp8 | 10 | 6 | 62 |
| 114 | Galb1-3GlcNAcb1-3Galb1-4GlcNAc-Sp0 | 10 | 5 | 48 |
| 567 | Galb1-3GlcNAcb1-6(GlcNAcb1-3)GalNAca-Sp14 | 10 | 6 | 62 |
| 432 | GlcNAcb1-2Mana1-6(GlcNAcb1-4)(GlcNAcb1-2Mana1-3)Manb1-4GlcNAcb1-4GlcNAc-Sp21 | 10 | 4 | 35 |
| 44 | (6S)Galb1-4GlcNAcb-Sp8 | 10 | 1 | 9 |
| 108 | Galb1-4GlcNAcb-Sp8 | 10 | 5 | 54 |
| 139 | Galb1-3GalNAca-Sp8 | 10 | 15 | 145 |
| 489 | Galα1-3Galb1-3GlcNAcb1-4GalNAca-Sp14 | 10 | 8 | 81 |
| 88 | GlcNAcb1-3Galb1-3GalNAc-Sp8 | 10 | 3 | 27 |
| 425 | Galα1-3Galb1-3GlcNAcb1-3GalNAca-Sp8 | 10 | 5 | 49 |
| 12 | Galb-Sp8 | 10 | 7 | 72 |
| 368 | Galb1-4(Fuca1-3)GlcNAcb1-6(Fuca1-2Galb1-3)GalNAca-Sp21 | 10 | 3 | 30 |
| 55 | NeuSAca2-6Galb1-4GlcNAcb1-4(NeuSAca2-6Galb1-4GlcNAcb-Sp12 | 10 | 8 | 84 |
| 130 | Fuca1-4Galb1-3GlcNAcb-Sp0 | 10 | 3 | 33 |

Figure 22K

| Glycan number | Glycan structure* | Average RFU | StDev | % CV |
|---|---|---|---|---|
| 461 | NeuSAca2-3Galb1-4GlcNAcb1-6(NeuSAca2-3Galb1-4GlcNAcb1-2Manb1-6(GlcNAcb1-4)(NeuSAca2-3Galb1-4GlcNAcb1-2Mana1- 3)Manb1-4GlcNAcb1-4GlcNAca-Sp21 | 10 | 13 | 131 |
| 381 | Galb1-3GlcNAcb1-3GalNAca-Sp14 | 9 | 10 | 109 |
| 504 | GlcNAcb1-3Galb1-4GlcNAcb1-6(Galb1-3)GalNAca-Sp8 | 9 | 6 | 60 |
| 184 | GlcNAcb1-3Galb1-4GlcNAcb1-3GalNAcb1-4GlcNAcb-Sp0 | 9 | 7 | 75 |
| 438 | Galb1-4Galb-Sp10 | 9 | 8 | 86 |
| 191 | GlcNAcb1-3Galb-Sp8 | 9 | 6 | 63 |
| 57 | NeuSAca2-6Galb1-4GlcNAcb1-2Mana1-6(NeuSAca2-6Galb1-4GlcNAcb1-2Mana1-3)Manb1-4GlcNAcb1-4GlcNAcb-Sp24 | 9 | 6 | 59 |
| 169 | Galb1-4GlcNAcb-Sp8 | 9 | 8 | 87 |
| 124 | Gala1-6Glcb-Sp8 | 9 | 10 | 108 |
| 595 | GlcNAcb1-3Galb1-4GlcNAcb1-6(GlcNAcb1-3)Galb1-4GlcNAca-Sp14 | 9 | 8 | 87 |
| 488 | Galb1-3GalNAcb1-4GalNAca-Sp8 | 9 | 4 | 42 |
| 29 | GlcNAcb1-3GalNAca-Sp8 | 9 | 9 | 96 |
| 280 | NeuSGca2-3Galb1-3(Fuca1-4)GlcNAcb-Sp0 | 9 | 9 | 101 |
| 16 | GlcNAca-Sp8 | 9 | 6 | 64 |
| 152 | Galb1-4(Fuca1-3)GlcNAca-Sp8 | 9 | 6 | 63 |
| 415 | GalNAca1-3GalNAcb1-3Gala1-4Galb1-4Glcb-Sp8 | 9 | 8 | 84 |
| 110 | Gala1-3GalNAca-Sp8 | 9 | 11 | 123 |
| 295 | NeuSAca2-3Galb1-4GlcNAcb1-6(Galb1-3)GalNAca-Sp8 | 9 | 4 | 41 |
| 94 | GalNAcb1-3GalNAca-Sp8 | 9 | 8 | 90 |
| 515 | (3S)GalNAcb1-4GlcNAc-Sp0 | 9 | 2 | 18 |
| 151 | Galb1-4(Fuca1-3)GlcNAcb-Sp0 | 9 | 7 | 77 |
| 340 | GlcNAcb1-3GlcNAcb-Sp8 | 9 | 5 | 59 |
| 172 | Galb1-4Glcb-Sp8 | 9 | 4 | 45 |
| 206 | KDNa2-3Galb1-4GlcNAcb-Sp0 | 9 | 8 | 87 |
| 93 | GalNAca1-4(Fuca1-2)Galb1-4GlcNAcb-Sp0 | 9 | 13 | 146 |
| 158 | Galb1-4GalNAca1-3(Fuca1-2)Galb1-4GlcNAcb-Sp8 | 9 | 3 | 37 |
| 27 | (3S)Galb1-4(6S)Glcb-Sp0 | 9 | 5 | 62 |
| 288 | NeuSAca2-3Galb1-4GlcNAcb1-6(Galb1-3)GalNAca-Sp14 | 9 | 5 | 58 |
| 98 | Fuca1-4GlcNAcb-Sp8 | 9 | 3 | 30 |
| 149 | Galb1-3GlcNAcb-Sp0 | 9 | 3 | 32 |
| 374 | Gala1-3(Fuca1-2)Galb1-4(Fuca1-3)GlcNAcb1-3Gala1-2)Galb1-3GlcNAcb1-3Fuca1-2)Mana1-2Mana1-3)GlcNAcb1-4GlcNAcb1-4GlcNAcb-Sp20 | 9 | 6 | 73 |
| 146 | Galb1-3Glcb-Sp8 | 9 | 5 | 53 |
| 257 | NeuSAca2-3Galb1-4(6S)Glcb-Sp0 | 8 | 2 | 20 |
| 208 | Mana1-2Mana1-6(Mana1-3)Mana-Sp9 | 8 | 11 | 132 |
| 65 | Fuca1-3Galb1-3GlcNAcb1-3Galb1-4Glcb-Sp8 | 8 | 3 | 35 |

Figure 22L

| Glycan number | Glycan structure | Average RFU | StDev | % CV |
|---|---|---|---|---|
| 441 | NeuSAca2-3Galb1-3GalNAcb1-4GlcNAcb1-3Galb-Sp8 | 8 | 3 | 37 |
| 203 | GlcAb1-3Galb-Sp8 | 8 | 5 | 54 |
| 276 | NeuSAca2-8NeuSAca2-8NeuSAca2-3Galb1-4Glcb-Sp0 | 8 | 8 | 99 |
| 134 | GlcNAcb1-6(Galb1-3)GalNAca-Sp14 | 8 | 2 | 28 |
| 236 | NeuSAca2-3GalNAca-Sp8 | 8 | 8 | 95 |
| 437 | Galb1-4GlcNAcb1-6(Galb1-4GlcNAcb1-2Mana1-6(GlcNAcb1-4)(GalNAcb1-4GlcNAcb1-2Mana1-3)Mana1-4GlcNAcb1-4GlcNAc-Sp21 | 8 | 4 | 52 |
| 411 | Galb1-3GalNAcb1-4(NeuSAca2-8NeuSAca2-3)Galb1-4Glcb-Sp0 | 8 | 7 | 81 |
| 508 | Galb1-3GalNAcb1-3Ga-Sp21 | 8 | 6 | 68 |
| 513 | (3S)GalNAcb1-4(3S)GlcNAc-Sp8 | 8 | 3 | 37 |
| 524 | Galb1-3GlcNAcb1-2Mana-Sp0 | 8 | 6 | 73 |
| 468 | Gala1-3Fuca1-2Galb1-3GalNAcb-Sp8 | 8 | 5 | 53 |
| 381 | Galb1-3GalNAca1-3Fuca1-2)Galb1-4GlcNAc-Sp0 | 8 | 7 | 84 |
| 407 | Galb1-3GlcNAca1-3(Fuca1-4)Galb1-4GlcNAc-Sp8 | 8 | 3 | 42 |
| 592 | GlcNAcb1-3Galb1-4GlcNAcb-Sp0 | 8 | 4 | 50 |
| 303 | GlcNAcb1-6(Galb1-3)GalNAcb1-3Galb1-4GlcNAc-Sp0 | 8 | 2 | 30 |
| 91 | Fucb1-3GlcNAcb-Sp8 | 8 | 3 | 32 |
| 58 | Fuca1-2Galb1-3GalNAcb1-3Gala-Sp9 | 8 | 5 | 69 |
| 355 | Galb1-3GalNAcb1-4Galb1-4GlcNAcb-Sp0 | 8 | 3 | 33 |
| 203 | GlcAb-Sp8 | 8 | 9 | 113 |
| 488 | NeuSAca2-6(Galb1-4GlcNAcb1-6)GalNAca-Sp14 | 8 | 10 | 130 |
| 174 | GlcNAcb1-6(Galb1-3)GalNAcb1-6GalNAca-Sp14 | 8 | 10 | 124 |
| 95 | GalNAcb1-3(Fuca1-2)Galb-Sp8 | 8 | 7 | 94 |
| 7 | Fuca-Sp9 | 8 | 4 | 45 |
| 408 | Fuca1-2Galb1-4GlcNAcb1-3GalNAca-Sp14 | 8 | 6 | 80 |
| 67 | Fuca1-2Galb1-3GlcNAcb-Sp0 | 8 | 5 | 65 |
| 34 | (3S)Galb1-4(6S)GlcNAcb-Sp0 | 8 | 3 | 41 |
| 481 | NeuSAca2-3Galb1-3GlcNAcb1-6GalNAca-Sp14 | 8 | 8 | 106 |
| 239 | GalNAca1-3(Fuca1-2)Galb-Sp8 | 8 | 6 | 81 |
| 281 | NeuSAca2-3Galb1-4GlcNAcb-Sp0 | 8 | 12 | 150 |
| 561 | GlcNAcb1-3Galb1-4GlcNAcb1-6(GlcNAcb1-3Galb1-3)GalNAca-Sp14 | 8 | 9 | 113 |
| 8 | Rhaa-Sp8 | 8 | 8 | 107 |
| 463 | NeuSAca2-6(Galb1-4GlcNAcb1-2Mana1-6(GlcNAcb1-4)(NeuSAca2-6Galb1-4GlcNAcb1-2Mana1-3)Mana1-4GlcNAcb1-4GlcNAc-Sp21 | 8 | 8 | 104 |
| 522 | Gala1-3Fuca1-2)Galb1-4GlcNAcb1-2Mana-Sp0 | 8 | 10 | 126 |
| 236 | NeuSAca2-3(6S)Galb1-4Fuca1-3)GlcNAc-Sp8 | 8 | 8 | 109 |
| 52 | GlcNAcb1-6(GlcNAcb1-2Mana1-3)Manb1-4GlcNAcb1-4GlcNAc-Sp12 | 8 | 3 | 38 |

| Glycan number | Glycan structure | Average RFU | StDev | % CV |
|---|---|---|---|---|
| 246 | Neu5Aca2-3Galb1-3GalNAcb1-3Gala1-4Galb1-4Glcb-Sp0 | 6 | 6 | 99 |
| 183 | GlcNAcb1-3Galb1-4GlcNAcb-Sp8 | 6 | 17 | 269 |
| 521 | Gala1-3Galb1-4GlcNAcb1-2Mana-Sp0 | 6 | 14 | 224 |
| 555 | Neu5Gca1-3Neu5Gca2-8Neu5Gca2-3Galb1-3GlcNAc-Sp0 | 6 | 2 | 37 |
| 150 | Galb1-3GlcNAcb1-4Glcb-Sp8 | 6 | 6 | 100 |
| 527 | Galb1-3Galb1-3GlcNAcb1-2Mana-Sp0 | 6 | 20 | 328 |
| 283 | Neu5Aca2-3Galb1-4GlcNAcb-Sp8 | 6 | 8 | 127 |
| 107 | Gala1-3Fuca1-2Galb-Sp8 | 6 | 3 | 48 |
| 21 | GlcNAcb1-6(GlcNAcb1-4)GlcNAcb1-3)GlcNAc-Sp8 | 6 | 5 | 81 |
| 180 | GlcNAcb1-3GalNAca-Sp14 | 6 | 9 | 160 |
| 148 | Galb1-3GlcNAcb1-3Galb1-4Glcb-Sp10 | 6 | 3 | 45 |
| 405 | Galb1-3GlcNAcb1-4GlcNAcb1-3)GalNAca-Sp14 | 6 | 3 | 51 |
| 592 | Neu5Aca2-3Galb1-3(Neu5Aca2-3Galb1-4)GlcNAcb1-3GalNAca-Sp14 | 6 | 9 | 151 |
| 89 | GalNAca1-3(Fuca1-2)Galb-Sp8 | 6 | 2 | 39 |
| 502 | Neu5Aca2-6GalNAcb1-4(6S)GlcNAcb-Sp8 | 6 | 10 | 183 |
| 318 | Neu5Aca2-3Galb1-4GlcNAcb1-2Mana1-6(Neu5Aca2-3Galb1-3Mana1-3)Manb1-4GlcNAcb1-4GlcNAcb-Sp12 | 6 | 3 | 61 |
| 108 | Gala1-3Fuca1-2)Galb-Sp18 | 6 | 3 | 51 |
| 408 | Galb1-3(Sia1-6)Galb1-4Glcb-Sp8 | 6 | 4 | 77 |
| 239 | Neu5Aca2-3Galb1-3Fuca1-4)GlcNAcb-Sp8 | 6 | 4 | 73 |
| 222 | Fuca1-2(6S)Galb1-4(6S)Glcb-Sp8 | 5 | 18 | 324 |
| 106 | Gala1-3(Fuca1-2)Galb1-4Glcb-Sp0 | 5 | 4 | 74 |
| 583 | GlcNAcb1-3GalNAcb1-4GlcNAcb1-3GalNAca-Sp14 | 5 | 2 | 38 |
| 56 | Neu5Aca2-6Galb1-4GlcNAcb1-2Mana1-6(Neu5Aca2-6Galb1-4GlcNAcb1-2Man-a1-3)Manb1-4GlcNAcb-Sp21 | 5 | 3 | 58 |
| 484 | Mana1-6(Mana1-3)Manb1-4GlcNAcb1-4(Fuca1-6)GlcNAc-Sp19 | 5 | 3 | 64 |
| 497 | Neu5Aca2-6Galb1-4GlcNAcb1-2Mana1-6(Neu5Aca2-6Galb1-4GlcNAcb1-3)Galb1-4Glc-Sp21 | 5 | 4 | 79 |
| 467 | Galb1-3Fuca1-2Galb1-3GalNAca-Sp8 | 5 | 4 | 79 |
| 430 | Fuca1-3(Galb1-4)GlcNAcb1-6Galb1-4GlcNAcb1-3Galb1-4Glc-Sp21 | 5 | 5 | 88 |
| 503 | GalNAca1-4Fuca1-3(6S)GlcNAcb-Sp8 | 5 | 5 | 88 |
| 516 | (4S)GalNAca-Sp10 | 5 | 2 | 46 |
| 53 | GlcNAcb1-2Mana1-6(GlcNAcb1-2Mana1-3)Manb1-4GlcNAcb-Sp0 | 5 | 8 | 151 |
| 163 | Galb1-4GlcNAcb1-3Galb1-4GlcNAcb-Sp0 | 5 | 3 | 59 |
| 293 | Galb1-4GlcNAcb1-3GlcNAcb-Sp0 | 5 | 3 | 95 |
| 519 | GalNAca1-3Galb1-2)Galb1-4GlcNAcb1-3SiaNAc-Sp14 | 5 | 10 | 201 |
| 13 | l3cb-Sp8 | 5 | 9 | 88 |
| 177 | GlcNAcb1-6(GalNAca1-3)Galb1-3GalNAca-Sp14 | 5 | 5 | 97 |
| 387 | GlcNAcb1-4GlcNAcb1-6(Galb1-4GlcNAcb1-2Mana1-6(Galb1-4GlcNAcb1-2Mana1-3)Manb1-4GlcNAcb1-4GlcNAcb-Sp21 | 5 | 9 | 171 |

Figure 22O

| Glycan number | Glycan structure | Average RFU | StDev | % CV |
|---|---|---|---|---|
| 383 | Galb1-4(Fuca1-3)GlcNAcb1-6(Galb1-3)GlcNAcb1-3)Galb1-4Glc-Sp21 | 5 | 4 | 87 |
| 399 | Neu5Aca2-3Galb1-3GlcNAcb1-3)Galb1-4GalNAca-Sp14 | 5 | 6 | 128 |
| 179 | GlcNAcb1-6(GlcNAcb1-3)GalNAca-Sp8 | 5 | 10 | 217 |
| 498 | Gala1-3(Fuca1-2)Galb1-3GlcNAcb1-6GalNAca-Sp14 | 5 | 6 | 125 |
| 210 | Mana1-6(Mana1-2Mana1-3)Mana1-6(Mana1-3)Manb1-4GlcNAcb1-4GlcNAc-Sp12 | 5 | 6 | 119 |
| 548 | GlcNAcb1-6(Galb1-3)GalNAca1-3(Fuca1-2)Galb1-4(Fuca1-3)GlcNAcb1-3)Galb1-4(Fuca1-3)GlcNAcb1-3)Galb1-4(Fuca1-3)GlcNAcb1-3)Galb1-4(Fuca1-3)GlcNAcb1-3)Galb1-4(Fuca1-3)GlcNAcb1-3)Galb1-4(Fuca1-3)GlcNAcb1-3)Galb1-4GlcNAcb1-3)Manb1-4GlcNAcb1-4GlcNAc-Sp25 | 5 | 7 | 144 |
| 315 | Mana1-2Mana1-6(Mana1-3)Mana1-6(Mana1-2Mana1-2Mana1-3)Mana-Sp9 | 5 | 8 | 179 |
| 414 | Galb1-3(Fuca1-2)Galb1-4GlcNAcb1-3GalNAca-Sp14 | 5 | 9 | 200 |
| 314 | Mana1-6(Mana1-2)Mana1-6)Manb1-3)Manb-Sp10 | 5 | 3 | 57 |
| 539 | GlcNAcb1-3Galb1-4GlcNAcb1-6(Galb1-3GlcNAcb1-2Mana1-3)Mana1-3)Manb1-4GlcNAcb1-4GlcNAc-Sp12 | 4 | 11 | 245 |
| 59 | Fuca1-3Galb1-3GlcNAcb1-3Galb1-4Glcb-Sp9 | 4 | 5 | 119 |
| 10 | Neu5Aca-Sp11 | 4 | 6 | 147 |
| 523 | Neu5Acb2-6Galb1-4GlcNAc-Sp8 | 4 | 6 | 136 |
| 90 | GalNAca1-3(Fuca1-2)Galb1-2)Galb-Sp18 | 4 | 4 | 86 |
| 580 | Gala1-4Galb1-4GlcNAcb1-6(Gala1-3Galb1-4GlcNAcb1-2Mana1-3)Mana1-3)Manb1-4GlcNAcb1-4GlcNAcb-Sp24 | 4 | 29 | 690 |
| 599 | Galb1-4GlcNAcb1-3Galb1-4GalNAca-Sp14 | 4 | 7 | 165 |
| 185 | Glca1-4Glcb-Sp8 | 4 | 9 | 206 |
| 603 | Neu5Aca2-3(Galb1-4GlcNAcb1-4)Mana1-6(Neu5Aca2-3Galb1-4GlcNAcb1-3Galb1-4GlcNAcb1-2Mana1-3)Manb1-4GlcNAcb1-4GlcNAc-Sp12 | 4 | 9 | 214 |
| 297 | Neu5Aca2-6Galb1-4(6S)GlcNAcb-Sp8 | 4 | 4 | 91 |
| 268 | Neu5Aca2-6Galb1-4GlcNAcb-Sp0 | 4 | 9 | 214 |
| 600 | Neu5Aca2-3Galb1-3(Fuca1-4)GlcNAcb1-6(Galb1-3)GalNAca-Sp14 | 4 | 5 | 136 |
| 19 | Galb1-4GlcNAcb1-6(Galb1-3)GalNAca-Sp8 | 4 | 4 | 103 |
| 62 | Fuca1-2Galb1-3GalNAca-Sp14 | 4 | 3 | 73 |
| 434 | GlcNAcb1-6(Galb1-3)Mana1-2Mana1-6(GlcNAcb1-4)(GlcNAcb1-2Mana1-3)Manb1-4GlcNAcb1-4GlcNAc-Sp21 | 4 | 5 | 136 |
| 157 | Galb1-4GlcNAcb1-3(Fuca1-2)Galb1-4Glcb-Sp0 | 4 | 3 | 81 |
| 131 | Galb1-4GlcNAca1-3GalNAcb-Sp8 | 4 | 4 | 110 |
| 272 | Neu5Aca2-6Galb1-4GlcNAcb-Sp9 | 4 | 6 | 160 |
| 298 | Neu5Gca2-6Galb1-4GlcNAcb-Sp8 | 4 | 6 | 167 |
| 435 | Galb1-4GlcNAcb1-2Mana1-6(Galb1-4GlcNAcb1-2Mana1-3)Manb1-4GlcNAcb1-4GlcNAc-Sp21 | 4 | 4 | 104 |
| 386 | Galb1-3GlcNAcb1-4(Fuca1-3)GlcNAcb1-6(Galb1-3GlcNAcb1-3)Galb1-4Glc-Sp21 | 4 | 7 | 188 |
| 433 | GlcNAcb1-6(Galb1-3)GalNAcb1-2Mana1-6(GlcNAcb1-4)(GlcNAcb1-2Mana1-3)Manb1-4GlcNAcb1-4GlcNAc-Sp21 | 4 | 6 | 162 |
| 17 | GlcNAcb-Sp0 | 3 | 5 | 154 |
| 173 | GlcNAcb1-3Galb1-4GlcNAcb-Sp8 | 3 | 6 | 167 |
| 154 | Galb1-4(Fuca1-3)Galb1-3Galb1-4(Fuca1-3)GlcNAcb-Sp0 | 3 | 6 | 174 |
| 265 | Neu5Aca2-6GalNAca-Sp8 | 3 | 10 | 297 |

Figure 22P

| Glycan number | Glycan structure | Average RFU | StDev | % CV |
|---|---|---|---|---|
| 276 | Neu5Acb2-6(Gaib1-4)GicNAcb-Sp8 | 3 | 5 | 158 |
| 218 | Neu5Aca2-3Galb1-3GicNAcb1-3Galb1-4(Fuca1-3)GicNAcb-Sp0 | 3 | 8 | 257 |
| 580 | Fuca1-2Galb1-3GalNAca1-3(Fuca1-2)Galb1-4GicNAcb-Sp0 | 3 | 2 | 80 |
| 443 | (6S)Galb1-3GicNAcb-Sp0 | 3 | 14 | 504 |
| 309 | GicNAcb1-3Man-Sp10 | 3 | 6 | 222 |
| 401 | Galb1-4Fuca1-3GicNAcb1-3Galb1-3GalNAca-Sp14 | 3 | 4 | 144 |
| 112 | Galb1-3GalNAcb-Sp8 | 3 | 4 | 152 |
| 191 | GicNAcb1-4GicNAcb1-4GicNAcb-Sp8 | 3 | 6 | 210 |
| 525 | Galb1-3(Fuca1-2)Galb1-3(Fuca1-4)GicNAcb-Sp14 | 3 | 4 | 142 |
| 589 | (3S)GicNAcb1-3Galb1-4GicNAcb1-3Galb1-4Glc-Sp0 | 3 | 6 | 245 |
| 566 | GicNAb1-3Galb1-3GalNAc-Sp14 | 2 | 5 | 204 |
| 73 | Fuca1-2Galb1-4GicNAcb1-4GicNAcb-Sp0 | 2 | 3 | 113 |
| 162 | Galb1-4GicNAcb1-4GicNAcb-Sp8 | 2 | 4 | 173 |
| 54 | Galb1-4GicNAcb1-2Mana1-6(Galb1-4GicNAcb-Sp12) | 2 | 6 | 253 |
| 329 | Neu5,9Ac2a2-3Galb1-3GicNAcb-Sp0 | 2 | 4 | 228 |
| 271 | Neu5Aca2-6(Galb1-3)GicNAcb1-3Galb1-4GicNAcb-Sp0 | 2 | 6 | 326 |
| 250 | Neu5Aca2-3Galb1-3-3GalNAcb1-4Galb-Sp8 | 2 | 6 | 340 |
| 197 | Glca1-6Glca1-6Glcb-Sp0 | 2 | 4 | 264 |
| 409 | Gala1-3(Fuca1-2)Galb1-4(Fuca1-3)Gicb-Sp21 | 2 | 3 | 137 |
| 50 | Mana1-6(Mana1-3)Manb1-4GicNAcb1-4GicNAc-Sp12 | 2 | 3 | 219 |
| 214 | Mana1-2Mana1-2Mana1-6Mana1-3Mana-Sp9 | 1 | 5 | 332 |
| 137 | Neu5Aca2-6(Galb1-3)GicNAcb1-2Mana-Sp8 | 1 | 6 | 303 |
| 526 | Neu5Aca2-3Galb1-3GicNAcb1-3Galb1-4GicNAcb-Sp0 | 1 | 6 | 495 |
| 529 | Neu5Aca2-3Galb1-3-3GalNAcb1-3(Fuca1-3)GicNAcb1-4Galb1-4Gicb-Sp0 | 1 | 3 | 235 |
| 562 | GalNAcb1-3GicNAcb-Sp0 | 1 | 7 | 657 |
| 273 | Neu5Aca2-6Galb1-4Glcb-Sp8 | 1 | 4 | 542 |
| 421 | GicNAcb1-2(6cNAcb1-6)Mana1-6(Mana1-3)Manb1-4GicNAcb1-4GicNAcb-Sp19 | 1 | 4 | 576 |
| 364 | Galb1-4GicNAcb1-6(Fuca1-4)Fuca1-4Galb1-3GicNAcb1-3Galb1-4Gic-Sp21 | 1 | 2 | 386 |
| 30 | (3S)Galb1-3GicNAcb-Sp0 | 1 | 8 | 1397 |
| 166 | Galb1-4GicNAcb1-6Galb1-3GalNAca-Sp8 | 0 | 2 | 502 |
| 292 | Galb1-4(Fuca1-3)GicNAcb1-3Galb1-3(Fuca1-4)GicNAcb1-4GicNAc-Sp8 | 0 | 7 | 2362 |
| 189 | GicNAcb1-4GicNAcb1-4GicNAcb1-4GicNAcb1-4GicNAcb1-4GicNAcb1-Sp0 | 0 | 6 | 1209 |
| 287 | (6S)Galb1-4(6S)GicNAcb-Sp8 | 0 | 4 | 2762 |
| 3 | Mana-Sp8 | 0 | 3 | 2170 |
| 232 | GalNAcb1-4Neu5Aca2-3Galb1-4GicNAcb-Sp8 | 0 | 4 | -7445 |
| 467 | Fuca1-2(6S)Galb1-3GicNAcb-Sp0 | 0 | 10 | -5710 |
| 120 | Gala1-4Galb1-4GicNAcb-Sp0 | 0 | 7 | -2298 |

Figure 22Q

| Glycan number | Glycan structure* | Average RFU | StDev | % CV |
|---|---|---|---|---|
| 591 | Neu5Aca2-3Galb1-3(Fuca1-4)GlcNAcb1-3Galb1-3(Fuca1-3)Galb1-4)GlcNAcb-Sp0 | 0 | 7 | -2070 |
| 609 | GlcNAcb1-3Fuca-Sp21 | 0 | 5 | -1390 |
| 43 | 6SKGalb1-4Glcb-Sp8 | -1 | 5 | -763 |
| 96 | GalNAcb1-3Galb1-4GlcNAcb1-4GlcNAcb-Sp0 | -1 | 8 | -1245 |
| 505 | Fuca1-2Galb1-3(Fuca1-3/Fuca1-4)Fuca1-3GalNAcb1-3GalNAca-Sp14 | -1 | 4 | -546 |
| 282 | Neu5Aca2-3Galb1-4(Fuca1-3)GlcNAca-Sp0 | -1 | 4 | -566 |
| 170 | Galb1-4/3GlcNAca-Sp23 | -1 | 4 | -427 |
| 597 | Neu5Aca2-6Galb1-4GlcNAcb1-3Galb1-4GlcNAcb1-3GalNAca-Sp14 | -1 | 3 | -362 |
| 410 | Galb1-4GlcNAcb1-6)Neu5Aca2-6Galb1-3GlcNAcb1-3)Fuca1-3/Galb-Sp21 | -1 | 10 | -970 |
| 23 | 6SKGalb1-4GlcNAcb-Sp0 | -1 | 9 | -738 |
| 385 | Galb1-4(Fuca1-3)GlcNAcb1-6(Fuca1-4(Fuca1-2Galb1-3)GlcNAcb1-3)Galb1-4Glc-Sp0 | -1 | 12 | -962 |
| 366 | Neu5Aca2-6GlcNAcb1-4GlcNAcb-Sp0 | -2 | 4 | -196 |
| 220 | Fuca1-2(6S)Galb1-4GlcNAcb-Sp0 | -2 | 12 | -540 |
| 390 | Galb1-3GlcNAcb1-4GlcNAcb-Sp0 | -2 | 3 | -131 |
| 602 | Neu5Aca2-3Galb1-4GlcNAcb1-3Galb1-3)Galb1-3)GalNAca-Sp14 | -3 | 7 | -249 |
| 532 | Galb1-4GlcNAcb1-2 Mana1-6(Galb1-4)GlcNAcb1-4)Galb1-4GlcNAcb1-2Mana1-3)Mana1-4)Glcb1-4)Fuca1-6)GlcNAc-Sp21 | -3 | 11 | -408 |
| 517 | Galb1-4(6F)GlcNAcb-Sp8 | -3 | 11 | -394 |
| 538 | GlcNAca2-2Fuca1-2 Mana1-6(GlcNAcb1-4 GlcNAcb1-3)Galb1-4)GlcNAcb1-3)GalNAca-Sp21 | -3 | 19 | -616 |
| 530 | GlcNAcb1-2 Mana1-6(GlcNAcb1-4)Galb1-4(Fuca1-3)GlcNAcb-Sp21 | -3 | 2 | -57 |
| 258 | Neu5Aca2-3Galb1-4GlcNAcb1-3)Galb1-4)GlcNAca-Sp0 | -3 | 6 | -195 |
| 132 | Gala1-4Galb1-4GlcNAcb-Sp0 | -4 | 17 | -478 |
| 26 | 4OS)Galb1-4(6S)Glcb-Sp8 | -4 | 8 | -185 |
| 534 | Neu5Aca2-3Galb1-4(Fuca1-3)GlcNAcb1-2Mana-Sp0 | -4 | 11 | -269 |
| 528 | GalNAcb1-4GlcNAcb1-3GalNAca-Sp0 | -4 | 6 | -139 |
| 61 | Fuca1-2Galb1-3GalNAca-Sp8 | -4 | 4 | -91 |
| 452 | Neu5Aca2-8Neu5Aca2-3Galb1-3GalNAcb1-4(Neu5Aca2-8Neu5Aca2-3Galb1-4)Glcb-Sp0 | -4 | 6 | -145 |
| 262 | Fuca1-2Galb1-4(6S)Glcb-Sp0 | -5 | 11 | -225 |
| 264 | Neu5Aca2-3Galb1-3Glcb-Sp0 | -5 | 3 | -49 |
| 133 | GlcNAca2-6Galb1-3GalNAca-Sp8 | -6 | 8 | -128 |
| 255 | Neu5Aca2-3Galb1-4(Fuca1-3)GlcNAcb-Sp0 | -6 | 8 | -134 |
| 105 | Gala1-3Fuca1-2Galb1-4GlcNAc-Sp0 | -7 | 3 | -46 |
| 289 | Galb1-3GlcNAcb1-3Glcb-Sp0 | -7 | 10 | -144 |
| 99 | GalNAcb1-4GlcNAcb-Sp0 | -9 | 5 | -49 |
| 304 | Galb1-4GlcNAcb1-8Galb1-4GlcNAcb-Sp0 | -10 | 7 | -69 |
| 125 | Galb1-2Galb-Sp8 | -10 | 8 | -74 |
| 280 | Neu5Aca2-3Galb1-4GlcNAcb-Sp8 | -14 | 9 | -64 |

COMPOSITIONS AND METHODS FOR DIAGNOSING, PREVENTING AND TREATING *SALMONELLA TYPHI* AND *SALMONELLA PARATYPHI* INFECTION

CROSS-REFERENCE TO RELATED APPLICATIONS

The present application is the U.S. national phase application filed under 35 U.S.C. § 371 claiming benefit to International Patent Application No. PCT/US14/38805, filed May 20, 2014, which claims priority to U.S. Provisional Application Ser. No. 61/825,375, filed May 20, 2013, all of which applications are hereby incorporated by reference in their entireties herein.

STATEMENT REGARDING FEDERALLY SPONSORED RESEARCH OR DEVELOPMENT

This invention was made with government support under grant number AI079022 awarded by the National Institute of Allergy and Infectious Diseases. The government has certain rights in the invention.

BACKGROUND OF THE INVENTION

*Salmonella enterica* serovar *Typhi* (*S. typhi*) and *paratyphi* (*S. paratyphi*), the causes of typhoid fever, results in more than 200,000 annual deaths (Parry et al., N. Engl. J. Med. 347:1770-1782; Crump et al., 2008, Antimicrob. Agents Chemother. 52:1278-1284; Raffatellu et al., 2008, J. Infect. Dev. Ctries. 2:260-266; Butler, 2011, Clin. Microbiol. Infect. 17:959-963; Crump and Mintz, 2010, Clin. Infect. Dis. 50:241-246). Unlike other Salmonella serovars, which typically cause self-limiting gastroenteritis, *S. typhi* and *S. paratyphi* cause a systemic, life-threatening disease (Parry et al., N. Engl. J. Med. 347:1770-1782). The genomes of *S. typhi* and *S. paratyphi* contain a dearth of unique virulence factors that are not found in non-typhoidal serovars, and the molecular bases for its unique virulence properties and clinical presentation are unknown (Sabbagh et al., 2010, FEMS Microbiol. Lett. 305:1-13; Parkhill et al., 2001, Nature 413:848-852).

One of the few *S. typhi*- and *S. paratyphi*-specific factors that has been shown to directly impact its interaction with host cells is an AB-type toxin dubbed typhoid toxin (Haghjoo and Galan, 2004, Proc. Natl. Acad. Sci. USA 101:4614-4619; Spano et al., 2008, Cell Host Microbe 3:30-38; Spano and Galan, 2008, Curr. Opin. Microbiol. 11:15-20). AB family toxins consists of enzymatically active A subunits that interfere with host functions, and B subunits that deliver the toxins to their target cells through receptor-mediated endocytosis (Beddoe et al., 2010, Trends Biochem. Sci. 35:411-418; Merritt and Hol, 1995, Curr. Opin. Struct. Biol. 5:165-171). Unlike typical AB toxins, typhoid toxin is composed of two A subunits, PltA and CdtB, which are homologs of the A subunits of the pertussis and cytolethal distending toxins, respectively (Spano et al., 2008, Cell Host Microbe 3:30-38). Its single B subunit, PltB, is a homolog of one of the components of the heteropentameric B subunit of pertussis toxin. Although the cellular targets of the ADP-ribosyl transferase activity of PltA have not yet been identified, CdtB is a deoxyribonuclease that is targeted to the nucleus where it inflicts DNA-damage and induces cell cycle arrest (Haghjoo and Galan, 2004, Proc. Natl. Acad. Sci. USA 101:4614-4619; Lara-Tejero and Galan, 2000, Science 290:354-357; Lara-Tejero and Galan, 2002, Trends in Microbiology 10:147-152).

This toxin is remarkable in that the activities of two powerful toxins seem to have been co-opted into a single toxin with unique biology. There are currently no effective vaccines to protect against typhoid fever, and in particular to protect young children, the most susceptible population, against typhoid fever. Moreover, there are currently no effective and specific diagnostic tools for typhoid fever, and multiple antibiotic resistant *S. Typhi* is rapidly emerging, with the prospects of typhoid fever being untreatable by antibiotics becoming a real threat (Butler, 2011, Clin. Microbiol. Infect. 17:959-963). Thus, there is a need in the art for compositions and methods for preventing, treating and diagnosing typhoid fever. The present invention addresses this unmet need.

SUMMARY

The invention described herein provides compositions and methods for preventing, treating and diagnosing infection by *Salmonella enterica* serovar *typhi* (*S. typhi*) and/or *S. paratyphi*, i.e., typhoid fever. In one embodiment, the invention is a vaccine having at least one polypeptide selected from the group consisting of PltA, or a PltA mutant, PltB, or a PltB mutant, and CdtB or a CdtB mutant. In some embodiments, the PltA mutant is PltA E133X, relative to SEQ ID NO: 8. In some embodiments, the PltA mutant is PltA E133A, relative to SEQ ID NO: 8. In some embodiments, the PltB mutant is PltB S35X, relative to SEQ ID NO: 9. In some embodiments, the PltB mutant is PltB S35A, relative to SEQ ID NO: 9. In some embodiments, the CdtB mutant is CdtB H160X, relative to SEQ ID NO: 7. In some embodiments, the CdtB mutant is CdtB H160Q, relative to SEQ ID NO: 7. In some embodiments, the CdtB mutant is CdtB R119X, relative to SEQ ID NO: 7. In some embodiments, the CdtB mutant is CdtB H259X, relative to SEQ ID NO: 7. In some embodiments, the CdtB mutant is CdtB ΔCys269, relative to SEQ ID NO: 7. In some embodiments, the CdtB mutant is CdtB C269X, relative to SEQ ID NO: 7. In some embodiments, the PltA mutant comprises any mutation in PltA that disrupts its enzymatic activity. In some embodiments, the CdtB mutant comprises any mutation in CdtB that disrupts its enzymatic activity.

In another embodiment, the invention is a method of immunizing a subject against *S. typhi*, the method including the step of administering to the subject a vaccine comprising at least a portion of at least one polypeptide selected from the group consisting of PltA, a PltA mutant, PltB, a PltB mutant, CdtB, a CdtB mutant, PltA E133X, relative to SEQ ID NO: 8, PltA E133A, relative to SEQ ID NO: 8, PltB S35X, relative to SEQ ID NO: 9, PltB S35A, relative to SEQ ID NO: 9, CdtB H160X, relative to SEQ ID NO: 7, CdtB H160Q, relative to SEQ ID NO: 7, CdtB R119X, relative to SEQ ID NO: 7, CdtB H259X, relative to SEQ ID NO: 7, CdtB ΔCys269, relative to SEQ ID NO: 7, and CdtB C269X, relative to SEQ ID NO: 7. In some embodiments, the subject is currently infected with *S. typhi* or *S. paratyphi* and the vaccine induces an immune response against *S. typhi* or *S. paratyphi*. In other embodiments, the subject is not currently infected with *S. typhi* or *S. paratyphi* and the vaccine induces an immune response against *S. typhi* or *S. paratyphi*.

In one embodiment, the invention is a method of treating a subject infected with *S. typhi*, the method including the step of administering to the subject a vaccine comprising at least a portion of at least one polypeptide selected from the group consisting of PltA, a PltA mutant, PltB, a PltB mutant, CdtB, a CdtB mutant, PltA E133X, relative to SEQ ID NO: 8, PltA E133A, relative to SEQ ID NO: 8, PltB S35X, relative to SEQ ID NO: 9, PltB S35A, relative to SEQ ID NO: 9, CdtB H160X, relative to SEQ ID NO: 7, CdtB H160Q, relative to SEQ ID NO: 7, CdtB R119X, relative to SEQ ID NO: 7, CdtB H259X, relative to SEQ ID NO: 7, CdtB ΔCys269, relative to SEQ ID NO: 7, and CdtB C269X, relative to SEQ ID NO: 7. In some embodiments, the subject is currently infected with *S. typhi* or *S. paratyphi* and the vaccine induces an immune response against *S. typhi* or *S. paratyphi*. In other embodiments, the subject is not currently infected with *S. typhi* or *S. paratyphi* and the vaccine induces an immune response against *S. typhi* or *S. paratyphi*. In some embodiments, the method of treating further comprises the step of administering an antibiotic to the subject.

In one embodiment, the invention is an isolated polypeptide selected from the group consisting of PltA E133X, PltA E133A, PltB S35X, PltB S35A, CdtB H160X, CdtB H160Q, CdtB R119X, CdtB H259X, CdtB ΔCys269, and CdtB C269X. In another embodiment, the invention is an amino acid sequence selected from the group consisting of PltA E133X, PltA E133A, PltB S35X, PltB S35A, CdtB H160X, CdtB H160Q, CdtB R119X, CdtB H259X, CdtB ΔCys269, and CdtB C269X. In one embodiment, the invention is an antibody the specifically binds to at least one selected from the group consisting of PltA E133X, PltA E133A, PltB S35X, PltB S35A, CdtB H160X, CdtB H160Q, CdtB R119X, CdtB H259X, CdtB ΔCys269, and CdtB C269X.

In another embodiment, the invention is a method of treating a subject infected with *S. typhi*, the method including the step of administering to the subject at least one antibody, wherein the at least one antibody specifically binds to at least one of PltA, PltA E133X, PltA E133A, PltB, PltB S35X, PltB S35A, CdtB, CdtB H160X, H160Q, CdtB R119X, CdtB H259X, CdtB C269X and CdtB ΔCys269. In some embodiments, the method of treating further comprises the step of administering an antibiotic to the subject.

In one embodiment, the invention is an inhibitor composition useful for treating or preventing *S. typhi* infection, wherein the inhibitor composition inhibits the interaction between the *S. typhi* toxin and the *S. typhi* toxin receptor. In one embodiment, the inhibitor composition specifically binds to the *S. typhi* toxin. In another embodiment, the inhibitor composition specifically binds to the *S. typhi* toxin receptor. In one embodiment, the *S. typhi* toxin receptor is a glycan. In various embodiments, the inhibitor composition is at least one selected from the group consisting of a chemical compound, a protein, a peptide, a peptidomemetic, an antibody, a ribozyme, a small molecule chemical compound, a glycan, an antisense nucleic acid molecule. In various embodiments, the inhibitor composition comprises at least one glycan listed in FIG. 20, 21 or 22. In some embodiments, the glycan is soluble. In another embodiment, the invention is a method of treating a subject infected with *S. typhi*, the method comprising administering to the subject an inhibitor composition. In some embodiments, the method of treating further comprises the step of administering an antibiotic to the subject.

In another embodiment, the invention is a method of diagnosing an *S. typhi* or *S. paratyphi* infection in a subject in need thereof, the method including the steps of determining the level of at least one of PltA, PltB, CdtB in a biological sample of the subject, comparing the level of the at least one of PltA, PltB, CdtB in the biological sample with level in a comparator control, and diagnosing the subject with an infection by *S. typhi* or *S. paratyphi* when the level of the at least one of PltA, PltB, CdtB in the biological sample is elevated when compared with the level in the comparator control. In some embodiments, the level of the at least one of PltA, PltB, CdtB in the biological sample is determined by measuring the level of at least one of PltA mRNA, PltB mRNA, CdtB mRNA in the biological sample. In other embodiments, the level of the at least one of PltA, PltB, CdtB in the biological sample is determined by measuring the level of at least one of PltA polypeptide, PltB polypeptide, CdtB polypeptide in the biological sample. In some embodiments, the comparator control is at least one selected from the group consisting of: a positive control, a negative control, a historical control, a historical norm, or the level of a reference molecule in the biological sample. In some embodiments, the method further comprises the step of administering a therapy to the subject to treat the infection.

In another embodiment, the invention is a method of diagnosing an *S. typhi* or *S. paratyphi* infection in a subject in need thereof, the method including the steps of determining the level of antibody that specifically binds to at least one of PltA, PltB, CdtB in a biological sample of the subject, comparing the level of antibody that specifically binds to the at least one of PltA, PltB, CdtB in the biological sample with level in a comparator control, and diagnosing the subject with an infection by *S. typhi* or *S. paratyphi* when the level of the antibody that specifically binds to at least one of PltA, PltB, CdtB in the biological sample is elevated when compared with the level in the comparator control. In some embodiments, the comparator control is at least one selected from the group consisting of: a positive control, a negative control, a historical control, a historical norm, or the level of a reference molecule in the biological sample. In some embodiments, the method further comprises the step of administering a therapy to the subject to treat the infection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprised of FIGS. 1A-1G, depicts how systemic administration of typhoid toxin causes symptoms observed during the acute phase of typhoid fever. FIG. 1A depicts an exemplary chromatographic profile of the typhoid toxin holotoxin used in the biological assays. The inset shows a Coomassie blue stained SDS-PAGE analysis of the peak fraction shown on the chromatogram. FIG. 1B depicts how typhoid toxin induces cell cycle arrest in cultured cells. Human intestinal epithelial Henle-407 cells were left untreated, or treated for 48 hrs with 0.02 nM of the purified typhoid toxin. The cell cycle profiles were then analyzed by flow cytometry. The insets show representative light microscope images of mock or typhoid toxin treated Henle-407 cells 48 hrs after treatment. FIG. 1C depicts how typhoid toxin induces cell cycle arrest in cultured cells. Averages of cell cycle profiles from at least 3 independent experiments. Bar represents average ± standard deviation. *, $P<0.001$, compared to the number of cells in G2M of the control untreated group. UT: untreated; TT: typhoid toxin treated. FIG. 1D depicts weight loss after treatment with different typhoid toxin preparations. The indicated typhoid toxin preparations were administered intravenously to groups of C57BL/6 and 5 days after treatment animals were weighed. Lines are the mean ± standard error of the mean and represent the weight relative to the values before treatment. *, P<0.0001. FIG. 1E depicts the survival of animals receiving different typhoid toxin preparations. n=3-5 animals per group. FIG. 1F depicts how typhoid toxin causes neutrophil depletion. Circulating white blood cells were counted in a hematology analyzer (*, P<0.05). FIG. 1G depicts how typhoid toxin causes neutrophil depletion. Alternatively, peripheral blood cells from animals that have received the indicated treatment were stained with an antibody directed to the neutrophil cell marker Grl and the number of stained cells was determined by flow cytometry. Numbers of neutrophils (vertical dashed line) were significantly reduced by typhoid toxin injection. The histograms shown are from ungated samples. Similar results were obtained in several independent repetitions of the experiment. RFI, relative fluorescence intensity.

FIG. 2, comprised of FIGS. 2A-2H, depicts how typhoid toxin recognizes terminally sialylated glycans on surface glycoproteins of target cells. FIG. 2A depicts affinity purification of typhoid toxin-interacting surface proteins. Henle-407 cell surface proteins were biotinylated, co-immunoprecipitated with purified typhoid toxin (TT), and analyzed by SDS-PAGE. FIG. 2B depicts affinity purification of typhoid toxin-interacting surface proteins. Henle-407 cell surface proteins were biotinylated, co-immunoprecipitated with purified typhoid toxin (TT), and analyzed by LC-MS/MS. The peptides from Podocalixin like protein 1 (PODXL) (indicated by an asterix in FIG. 2A) identified by LC-MS/MS are indicated in bold, the shaded sequence indicates the position of its transmembrane domain, and the underlined sequence its signal peptide. Note that a majority of identified peptides are from the C-terminal region because the heavy glycosylation of the N-terminus extracellular region of Podocalyxin interferes with the LC-MS/MS analysis. FIG. 2C depicts how PODXL depletion reduces toxin binding and toxicity. PODXL-depleted (by an specifically targeted siRNA) and control cells were treated with fluorescently-labeled typhoid toxin and toxin binding was evaluated by flow cytometry (* P=0.024 for three independent determinations). FIG. 2D depicts how PODXL depletion reduces toxin binding and toxicity. siRNA-depleted and control cells were treated with typhoid toxin and subjected to flow cytometric cell cycle analysis (to evaluate toxicity). FIG. 2E depicts how the removal of surface glycans reduces toxin binding. Henle-407 cells were treated with a mixture of glycosidases and the ability of treated and control cells to bind fluorescently-labeled toxin was subsequently evaluated by flow cytometry (*, P<0.001 from three independent experiments). FIG. 2F depicts how a mutant cell line lacking surface N-glycans is resistant to typhoid toxin. The N-acetylglucosaminyltransferase I-deficient (Lec1) and its parent (Pro5) cell lines were treated with typhoid toxin and toxicity was evaluated by flow cytometric cell cycle analysis. FIG. 2G depicts the averages of cell cycle profiles from several independent experiments exemplified in FIG. 2F. Bar represents average ± standard deviation of at least three independent determinations. , P<0.01, compared to the number of Pro5 cells in G2M. FIG. 2H depicts an exemplary glycan array analysis of typhoid toxin binding. Included in this array were 610 glycans and the highest and lowest points from each set of 6 replicates have been removed so the average RFU (relative fluorescence unit) is of 4 values. The X axis depicts the glycan numbers. The structure of the most relevant glycans is shown. The raw data are shown in FIGS. 20 and 21.

FIG. 3, comprised of FIGS. 3A-3E, depicts how the crystal structure of typhoid toxin depicts a unique architecture. FIG. 3A depicts two views of the overall structure of the typhoid holotoxin complex shown as a ribbon cartoon and related by 90° rotation about a vertical axis. CdtB, PltA and PltB are shown. FIG. 3B depicts a bottom view of the channel formed by the PltB pentamer, depicting the PltA C-terminal a-helix within it. FIG. 3C depicts the surface charge distribution of the predicted sugar-binding pockets of different B subunit homologs of the indicated $AB_5$ toxins (SubB for Subtilase and S2 for Pertussis toxins). A highly conserved serine residue critical for sugar binding is indicated within the sugar-binding pocket. The sugars N-glycolylneuraminic acid (within SubB) and N-acetylneuraminic acid (within typhoid and pertussis toxins) are shown. FIG. 3D depicts molecular modeling of N-acetylneuraminic acid within the typhoid and pertussis toxins binding pocket. Critical residues engaged in this interaction are shown. FIG. 3E depicts the atomic interface between CdtB and PltA. The inset shows a detailed view of a critical disulfide bond between PltA Cys214 and CdtB Cys269.

FIG. 4, comprised of FIGS. 4A-4I, depicts an exemplary structure-function analysis of typhoid toxin. FIGS. 4A-4D depicts how Ser35 on the predicted PltB glycan-binding site is critical for typhoid toxin binding and toxicity. FIG. 4A depicts how fluorescently labeled typhoid toxin containing PltBSer35A was tested for its binding to glycans. FIG. 4B depicts how fluorescently labeled typhoid toxin containing PltBSer35A was tested for its binding to cultured epithelial cells. (For FIGS. 4A and 4B, see FIG. 2 legend for details; raw data to generate panel A is shown in Table 1) (***, P<0.001 from at least three independent determinations). FIG. 4C depicts how the toxicity of fluorescently labeled typhoid toxin was assayed by flow cytometric cell cycle analysis of toxin-treated cultured epithelial cells. FIG. 4D depicts how the toxicity of fluorescently labeled typhoid toxin was assayed by systemic administration to C57BL/6 mice (n=3 to 5 mice). Equivalent results were observed in several independent experiments. FIGS. 4E-4I depict how the disulfide bond between PltA and CdtB is essential for typhoid toxin complex formation in vitro and toxicity in vivo. FIG. 4E depicts how the typhoid toxin complex was analyzed by ion exchange chromatography before and after treatment with DTT (L: loading control; M: molecular weight markers; F: chromatographic fraction). The different fractions were then analyzed by SDS-PAGE (shown in the inset) for the presence of the different components of typhoid toxin (i.e., PltB, CdtB, and PltA). Treatment with DTT resulted in the release of CdtB from the PltA/PltB complex. FIG. 4F depicts how CdtB ΔCys269 is not incorporated into the typhoid toxin complex. A typhoid toxin preparation obtained from a bacterial strain expressing CdtB ΔCys269 was analyzed by gel filtration chromatography and compared to wild-type toxin. While wild-type holotoxin eluted in fractions 13 and 14, toxin obtained from a bacterial strain encoding CdtB ΔCys269 eluted in fractions 14 and 15 due to the loss of its CdtB subunit. FIG. 4G depicts how Henle-407 cells infected with *S. typhi* strains were examined for toxicity by flow cytometric cell cycle analysis. FIG. 4H depicts how Henle-407 cells infected with *S. typhi* strains were fixed 24 hours after infection cells, stained with anti-FLAG antibody, and imaged in a fluorescence microscope. The puncta staining, which represent CdtB in typhoid toxin export carriers, are not observed in cells infected with the strain that expresses CdtB ΔCys269. FIG. 4I depicts the quantification of puncta staining The values shown represent averages of puncta intensities in infected cells. Bar represents average ± standard error means. At least 100 cells were examined. Scale bar:10 μm. FIG. 4J depicts how the critical cysteines that tether CdtB to PltA are absent in close homologs. ClustalW amino acid sequence comparison analyses of CdtB and PltA homologs. The CdtB homologs (and Genbank entry numbers) used in the alignment were from *Shigella boydii* (AAU88264.1), *Providencia alcalifaciens* (BAL72684.1), *Helicobacter hepaticus* (AAF19158.1), *Haemophilus ducreyi* (NP 873398.1), *E. coli* (BAH72965.1), *Campylobacter jejuni* (AAS01598.1), and *Aggregatibacter actinomycetemcomitans* (AAC70898.1). The PltA homolog used in the alignment was the highly related *S. typhimurium* DT104 ArtA (BAE20153.1). Conserved and unique cysteines are shown.

FIG. 5 is a graph depicting body temperature of typhoid toxin or buffer treated animals. Each dot represents a measurement of a single animal.

FIG. 6 is a series of graphs depicting how typhoid toxin is able to intoxicate a broad range of host cells. Various host cells were mock treated or treated with 0.02 nM of purified typhoid holotoxin for 24 hours (i.e., Raw, Jurkat, and Ramos cells) or for 48 hours (i.e., COS1, CHO, MDCK, and NIH3T3) and the cell cycle profiles of the treated cells determined by flow cytometric analysis. Equivalent results were obtained in several repetitions of this experiment.

FIG. 7 is a graph depicting podxl mRNA levels in control cells or cell expressing an siRNA targeted to podxl as measured by real-time PCR. Bar represents the average of the expression level ± standard deviation of three independent determinations.

FIG. 8, comprising FIGS. 8A-8B, depicts how typhoid toxin recognizes terminally sialylated glycans on CD45 in T, B, and macrophage cell lines. Cell surface proteins from Jurkat, Ramos, and THP1 cells were biotinylated, co-immunoprecipitated with purified typhoid toxin (TT), and analyzed by SDS-PAGE and LC-MS/MS. FIG. 8A is a photograph of a gel depicting Jurkat cells analyzed by SDS-PAGE. FIG. 8B is an image depicting the CD45 peptides identified by LCMS/MS. The CD45 peptides are indicated as underlined for Jurkat, shaded boxes for Ramos, and THP1 cells. The location of the signal peptide is indicated in italics.

FIG. 9 is a series of images depicting how a mutant cell line that lacks surface N-glycans is more resistant to typhoid toxin. The N-acetylglucosaminyltransferase I-deficient (Lec1) and its parent (Pro5) cell lines were treated with wild typhoid toxin and examined by light microscopy. Cell distention is observed in Pro5, but not in Lec1 toxin treated cells. Scale bar: 50 μm.

FIG. 10 is a graph depicting how a mutant cell line that lacks surface N-glycans can be intoxicated by typhoid toxin when administered at high concentrations. The N-acetylglucosaminyltransferase I-deficient (Lec1) and its parent (Pro5) cell lines were treated with increasing concentrations of typhoid toxin (as indicated) and toxicity was evaluated by flow cytometric cell cycle analysis 36 hours after treatment. Bar presents average ± standard deviation of at least three independent determinations. *, $P<0.05$, **$P<0.01$ compared to the number of cells in G2M of untreated (UT) group.

FIG. 11, comprised of FIGS. 11A-11C, depicts how typhoid toxin exhibits an $A_2B_5$ composition. FIG. 11A is a table depicting all the possible complexes compatible with the observed molecular weight of typhoid toxin (116 kDA as measured by SEC-LS analysis). FIG. 11B is a table depicting how complex 1 is the most likely for the observed extinction coefficient. FIG. 11C is a table depicting amino acid composition analysis of typhoid toxin. The purified typhoid holotoxin complex was resolved on a 15% SDS-PAGE gel, stained with coomassie brilliant blue, and the three individual bands were excised for quantitative amino acid analysis.

FIG. 12 is an illustration depicting structure alignment between typhoid toxin PltA and pertussis toxin 51. The conserved catalytic residue glutamic acid and disulfide bond are shown in inset.

FIG. 14 is an illustration depicting structure alignment of PltB homologs from the B subunits of Subtilase (SubB) and Pertussis (S2) toxins. A conserved serine essential for sugar binding is depicted in the inset showing the different structural elements surrounding this critical residue (a loop in PltB and S2, and a β-strand in SubB).

Figure 16:
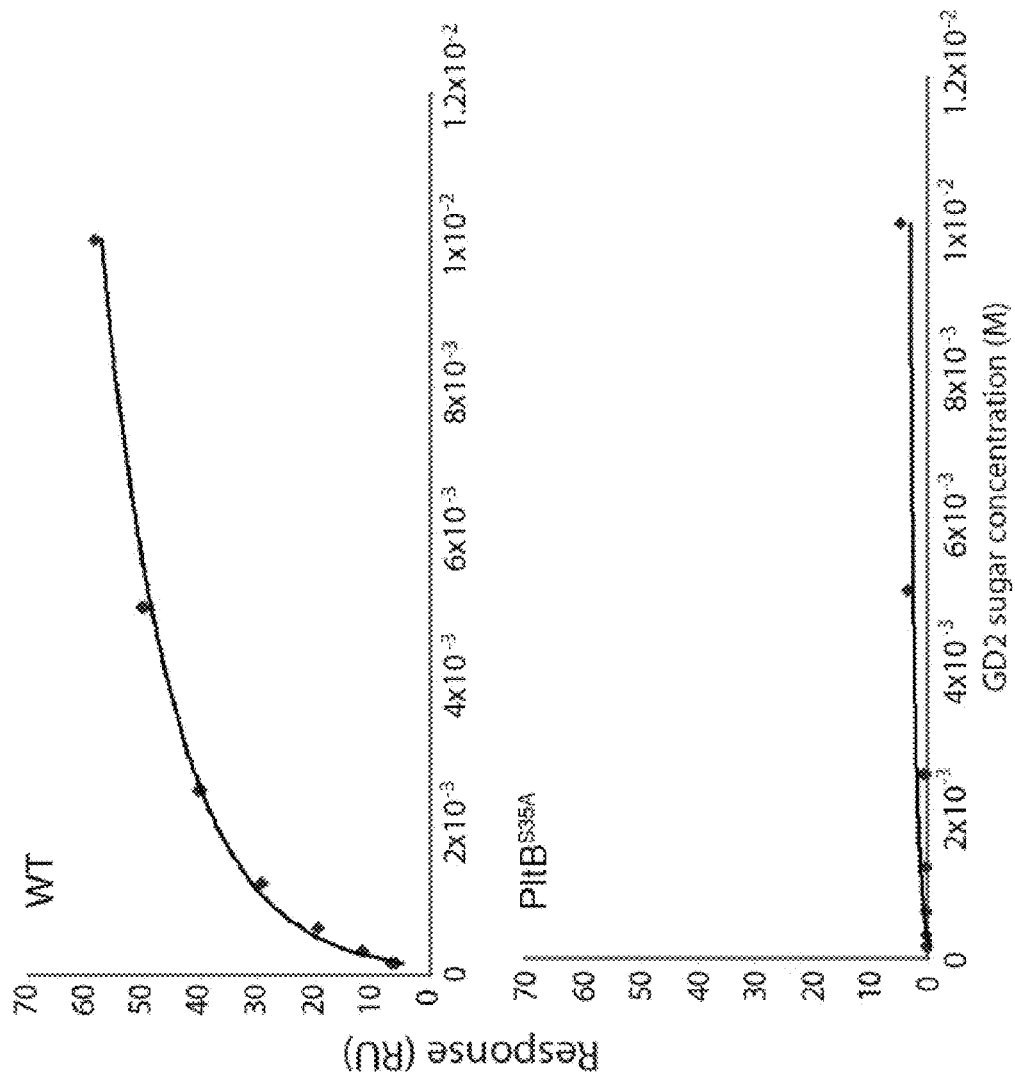

FIG. 16 is a series of graphs depicting how Ser35 is critical for typhoid toxin glycan binding. Surface plasmon resonance assay of the binding of wild type (WT) and PltBS35A typhoid toxin preparations to the GD2 glycan. Numbers on the y axis depict the relative response units (RU). Binding curves were generated by averaging the values several independent determinations. The observed Rmax suggests that ~50% of protein remains active when captured by an anti-flag antibody. Although not wishing to be bound by any particular theory, such Rmax values strongly suggest that, for wild type, on average there are 2.5 sugar molecules per PltB pentamer, assuming that each monomer is 100% active for binding.

Figure 17:
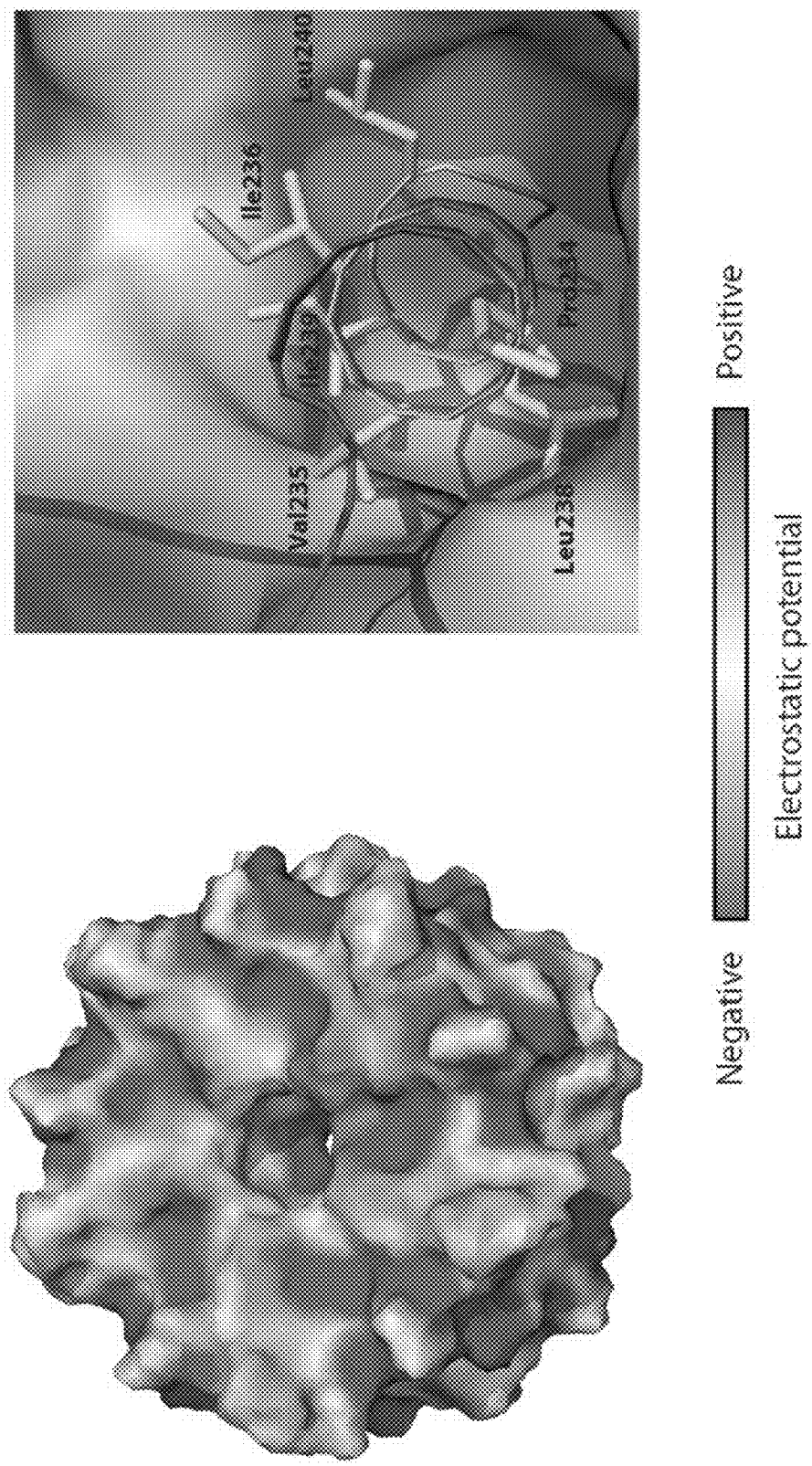

FIG. 17 is a series of illustrations depicting surface charge distribution of the PltB pentamer depicting its hydrophobic channel (left panel). The interaction of key PltA residue with the lumen of the PltB channel is shown in detail (right panel).

Figure 18:
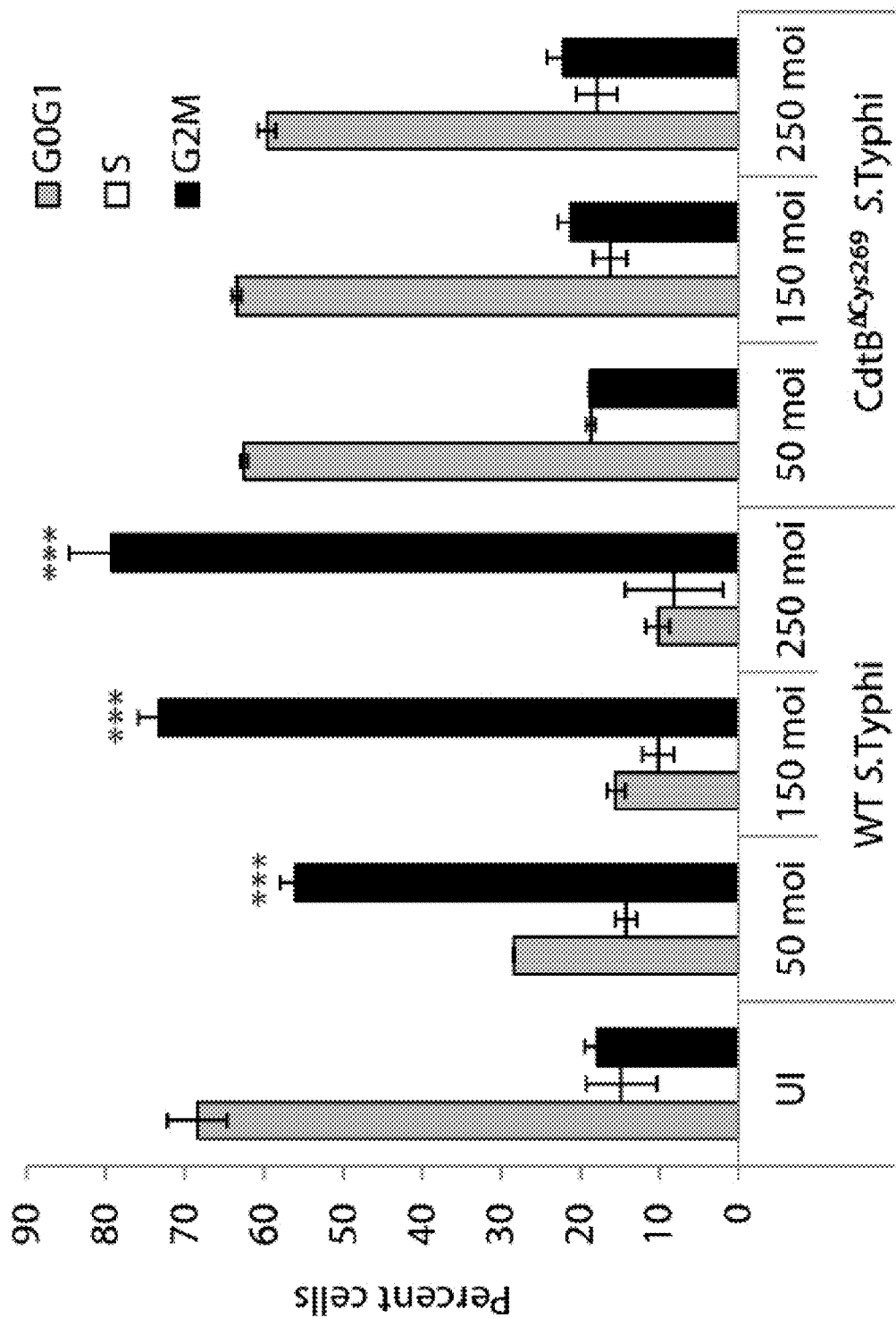

FIG. 18 is a graph depicting how an *S. typhi* CdtB ΔCys269 mutant does not intoxicate culture cells. Henle-407 cells were left uninfected or infected for 4 days with wild type *S. typhi* or a CdtB ΔCys269 mutant at various multiplicity of infections (moi) as indicated. Typhoid toxin mediated toxicity was evaluated by flow cytometric cell cycle analysis. Bar represents the average ± standard deviation. ***, $P<0.001$ compared to the number of cells in G2M in the uninfected (UI) group.

Figure 19:
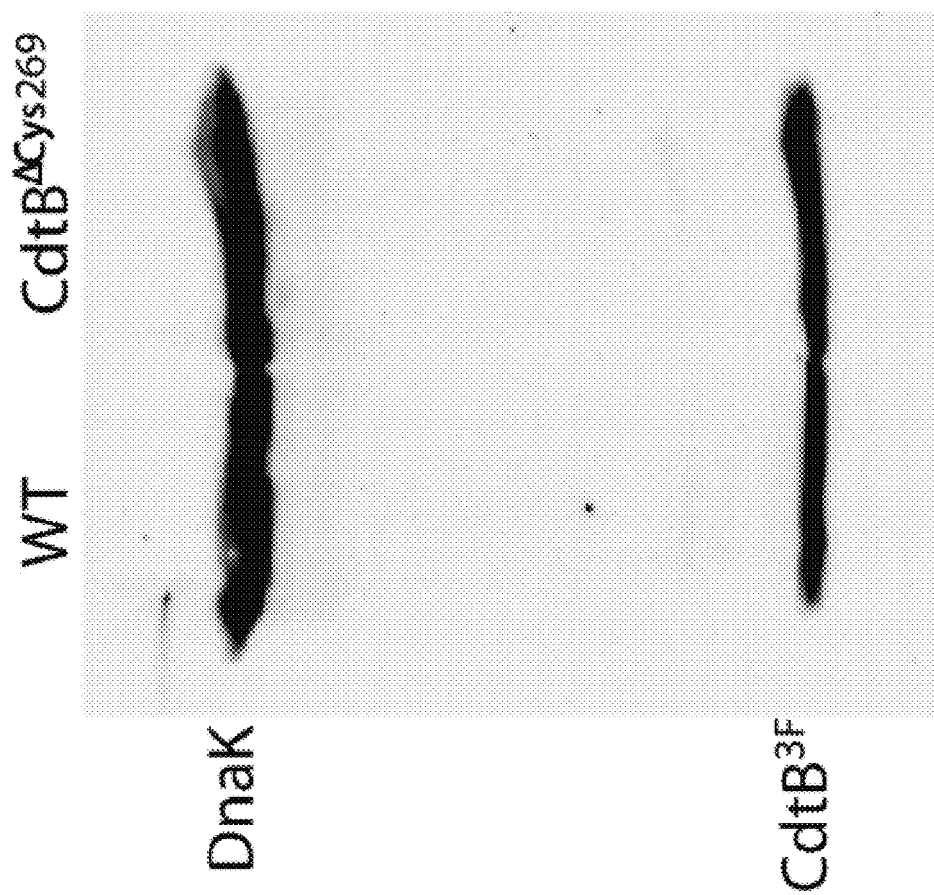

FIG. 19 is an image of a gel depicting expression of CdtB ΔCys269 in *S. typhi* infected culture epithelial cells. Henle-407 cells were infected with *S. typhi* strains expressing FLAG-epitope tag wild type CdtB or CdtB ΔCys269 and 24 hrs after infection, the levels of CdtB in cell lysates was investigated by western blot analysis. The bacterial protein DnaK was used as a loading control.

FIG. 20, comprised of FIGS. 20A-20C, is a series of tables depicting glycans showing typhoid toxin binding activity classified by their structural features.

Figure 21B:
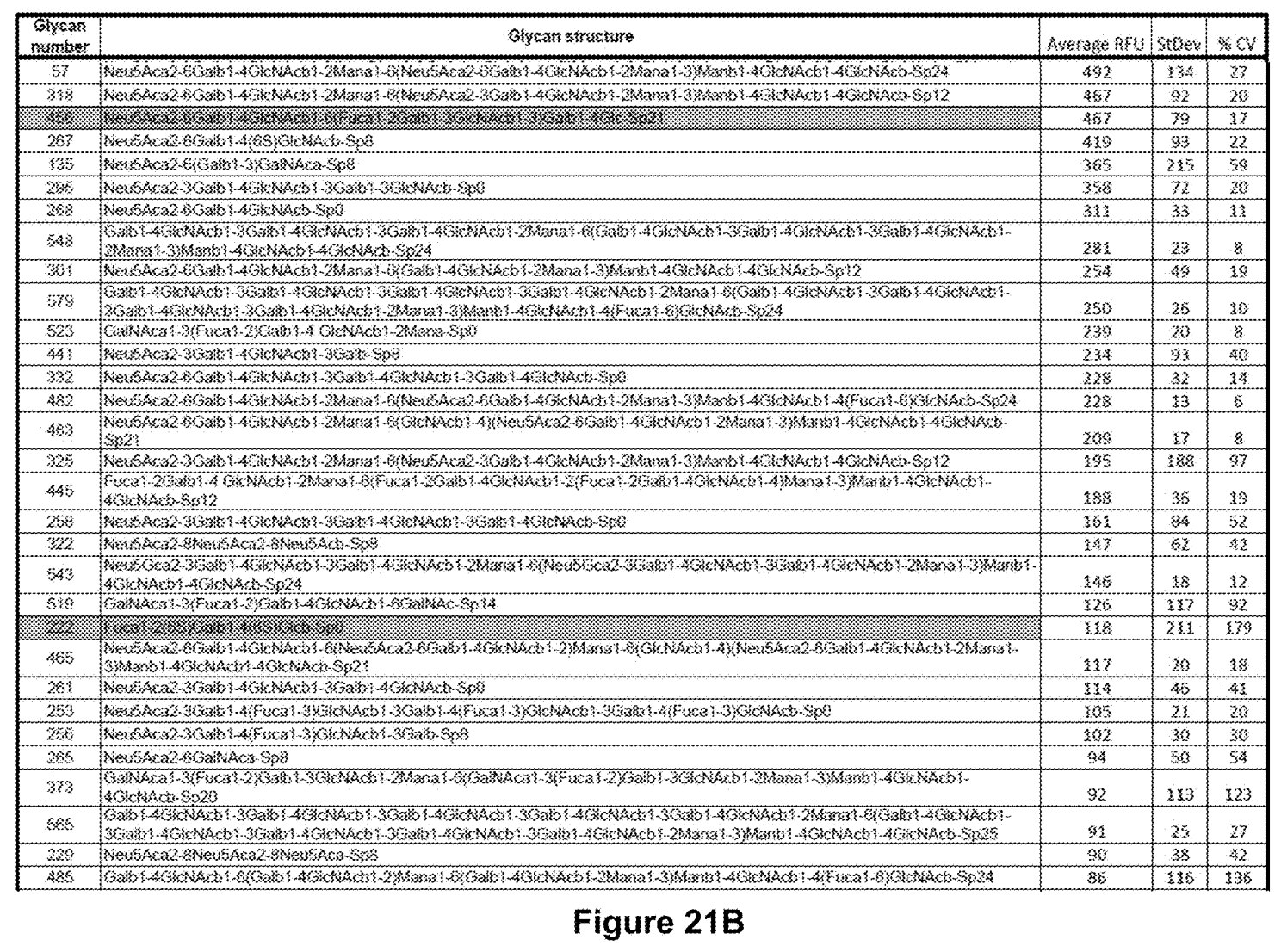

FIG. 21, comprised of FIGS. 21A-21R, is a series of tables depicting glycan array analysis for binding to typhoid toxin. The highlighted area in grey depicts glycans present in glycolipids. Average RFU indicates the average fluorescent unites from 4 independent determinations. STDv: standard deviation; % CV: variation coefficient.

Figure 22A:
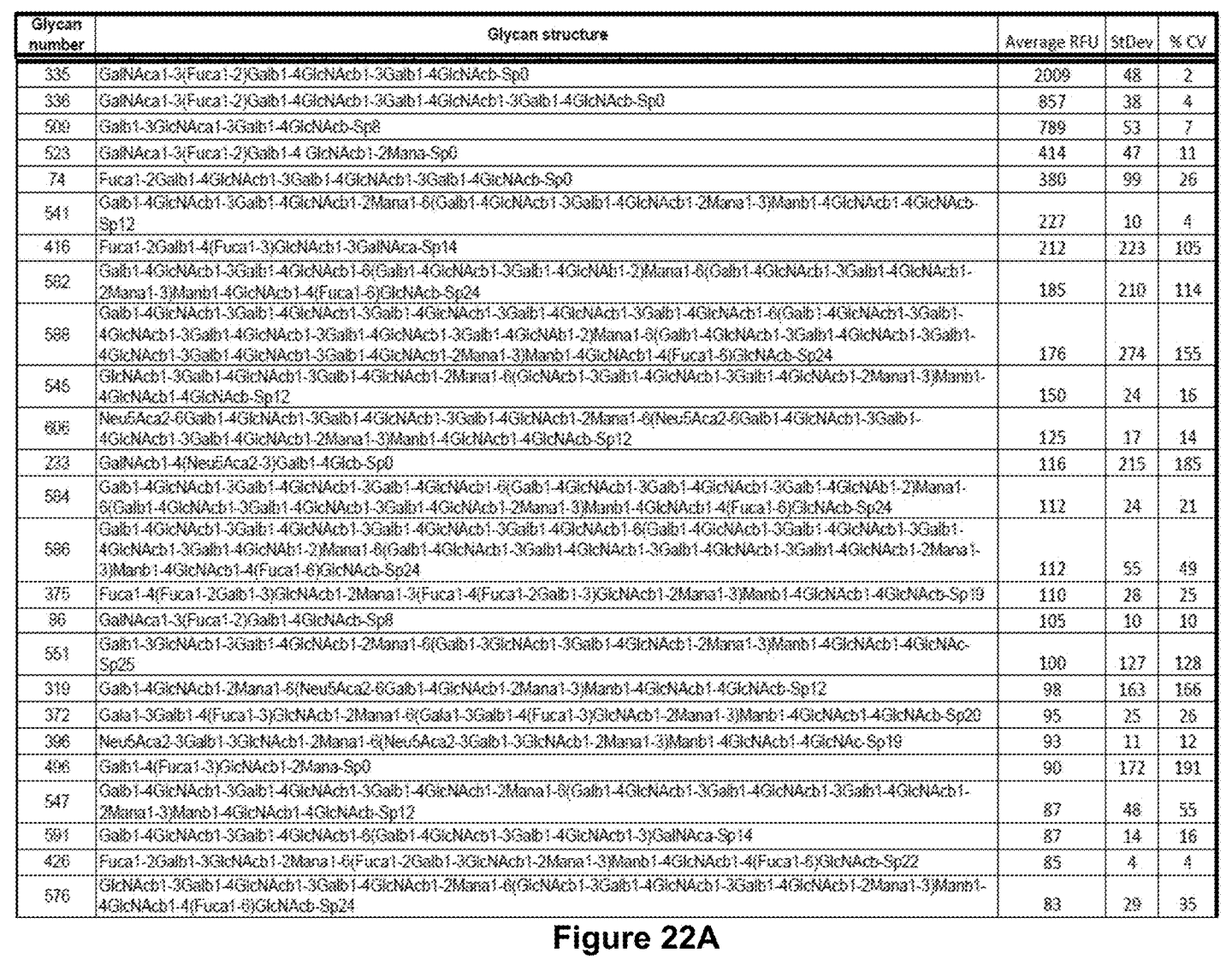
Figure 22B:
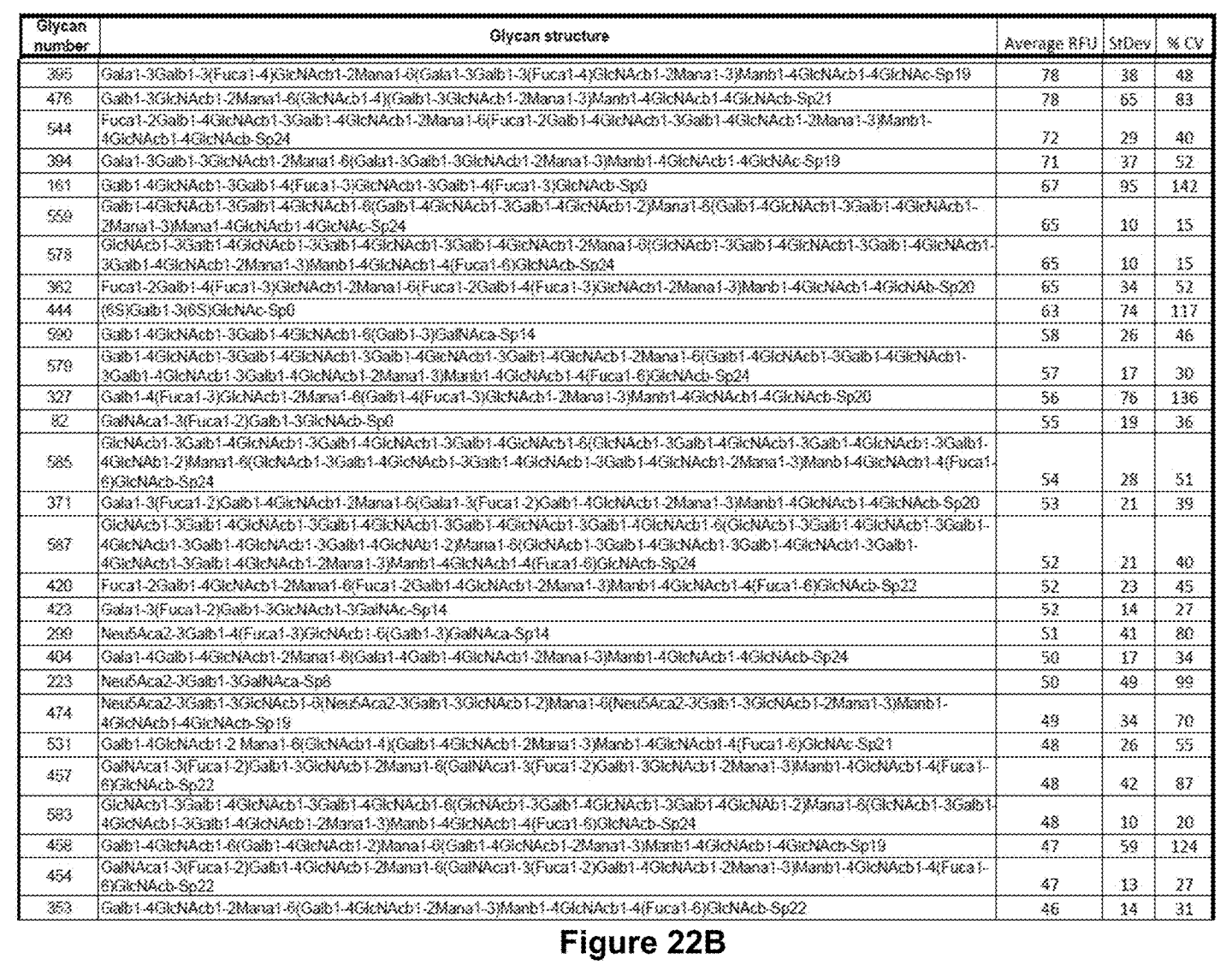
Figure 22N:
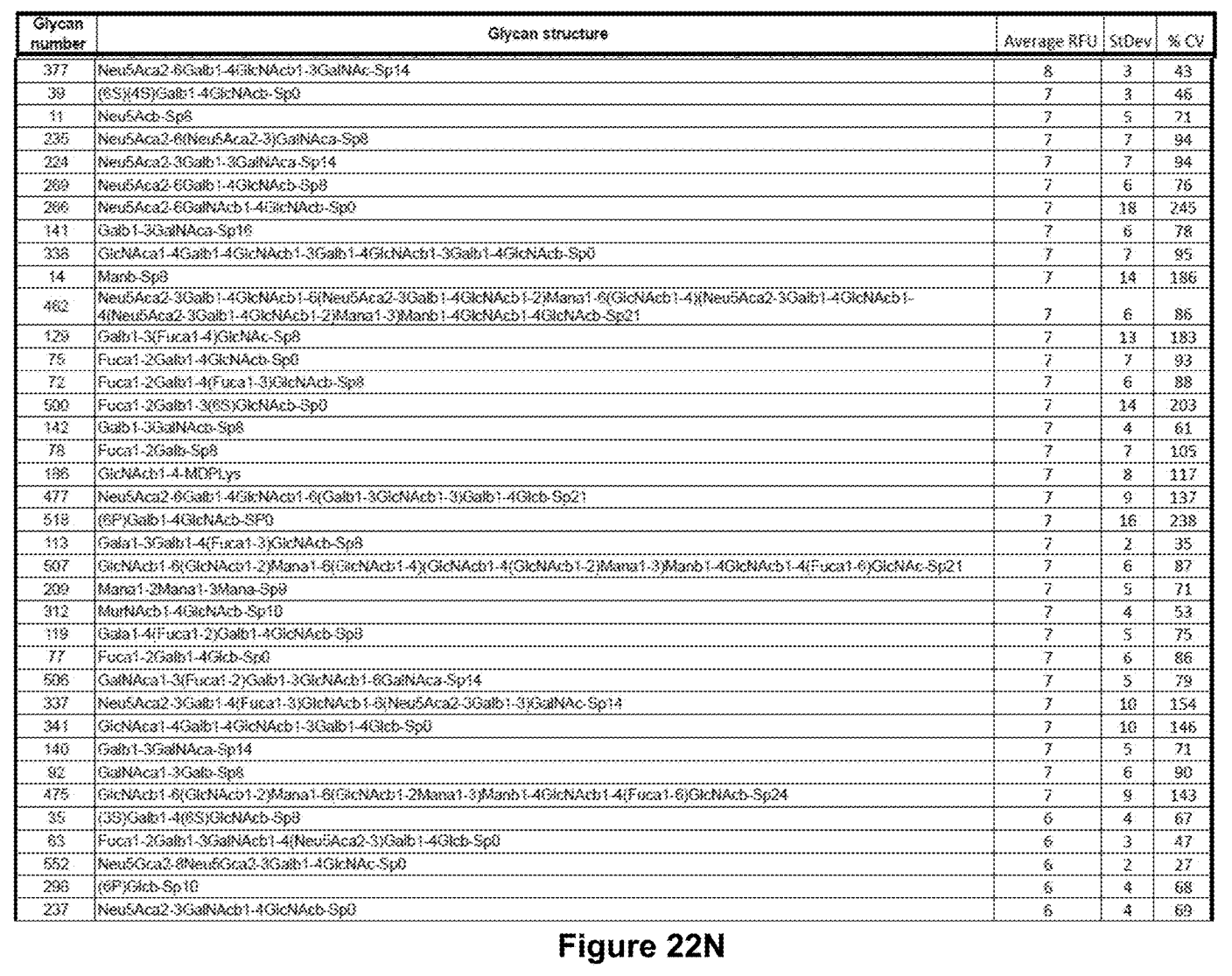

FIG. 22, comprised of FIGS. 22A-22R, is a series of tables depicting glycan array analysis for binding to the typhoid toxin Ser53A mutant. Average RFU indicates the average fluorescent unites from 4 independent determinations. STDv: standard deviation; % CV: variation coefficient.

Figure 23:
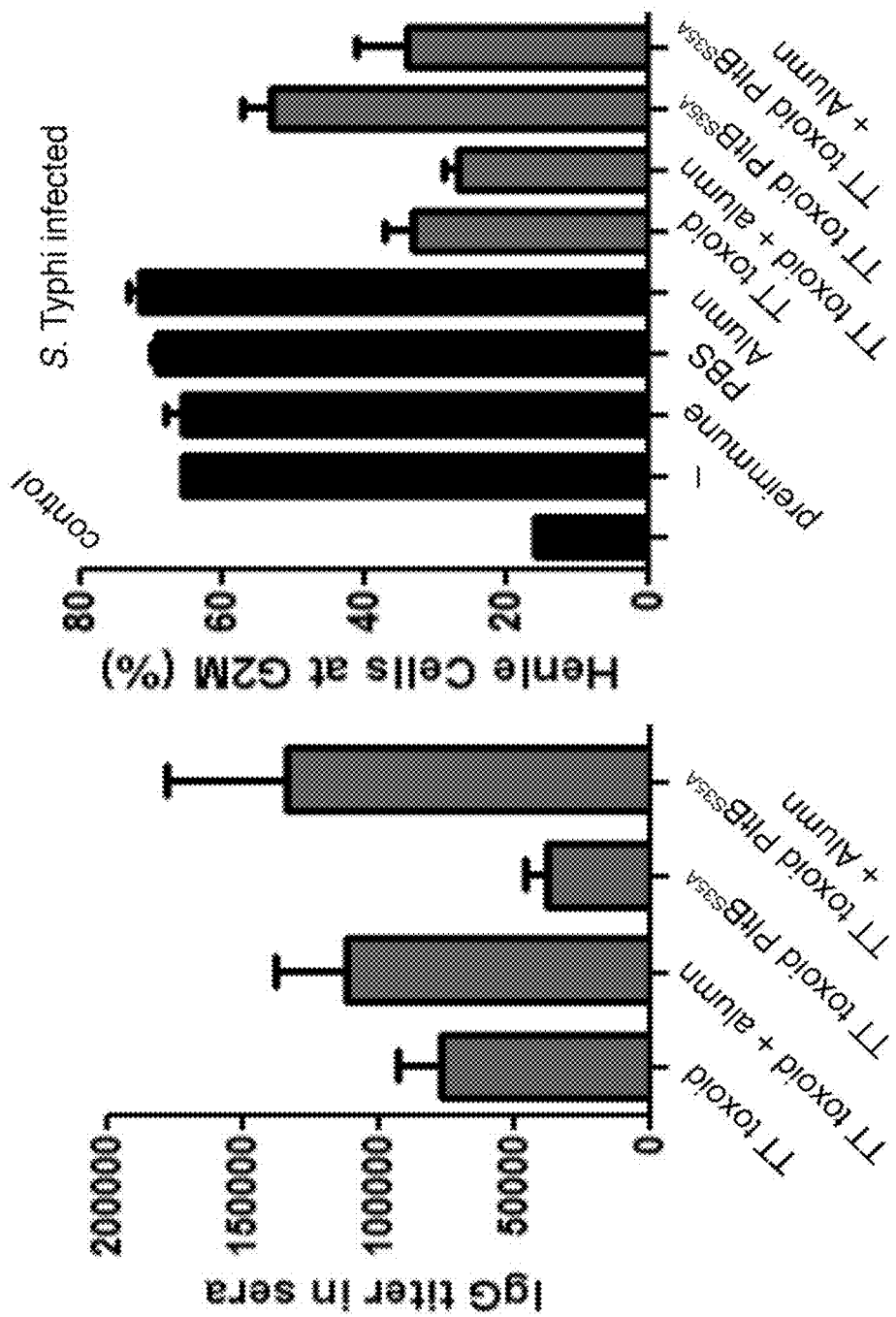

FIG. 23 depicts the results of experiments demonstrating that Typhoid toxin stimulates the production of neutralizing antibodies in mice. Mice (4 animals per group) were immunized with a typhoid toxin toxoid preparation, or a typhoid toxin preparation containing a glycan-binding deficient B subunit (PltBS35A), alone or in combination with an adjuvant (Alumn). Sera were collected from immunized animals 4 weeks after immunization and tested for levels of antibody by ELISA (left panel). In addition, the sera of immunized animals were tested for the presence of typhoid toxin neutralizing antibodies (left panel) as previously described (Spano et al., 2009, Cell Host Microbe 3:30-38). Briefly, cultured cells were infected with S. Typhi, left untreated (control) or treated with antibodies obtained from non-immunized animals (−), animals immunized with the indicated preparations. Forty-eight hours after infection, the DNA content of cells (to determine cell cycle stage) was determined by flow cytometry.

Figure 24:
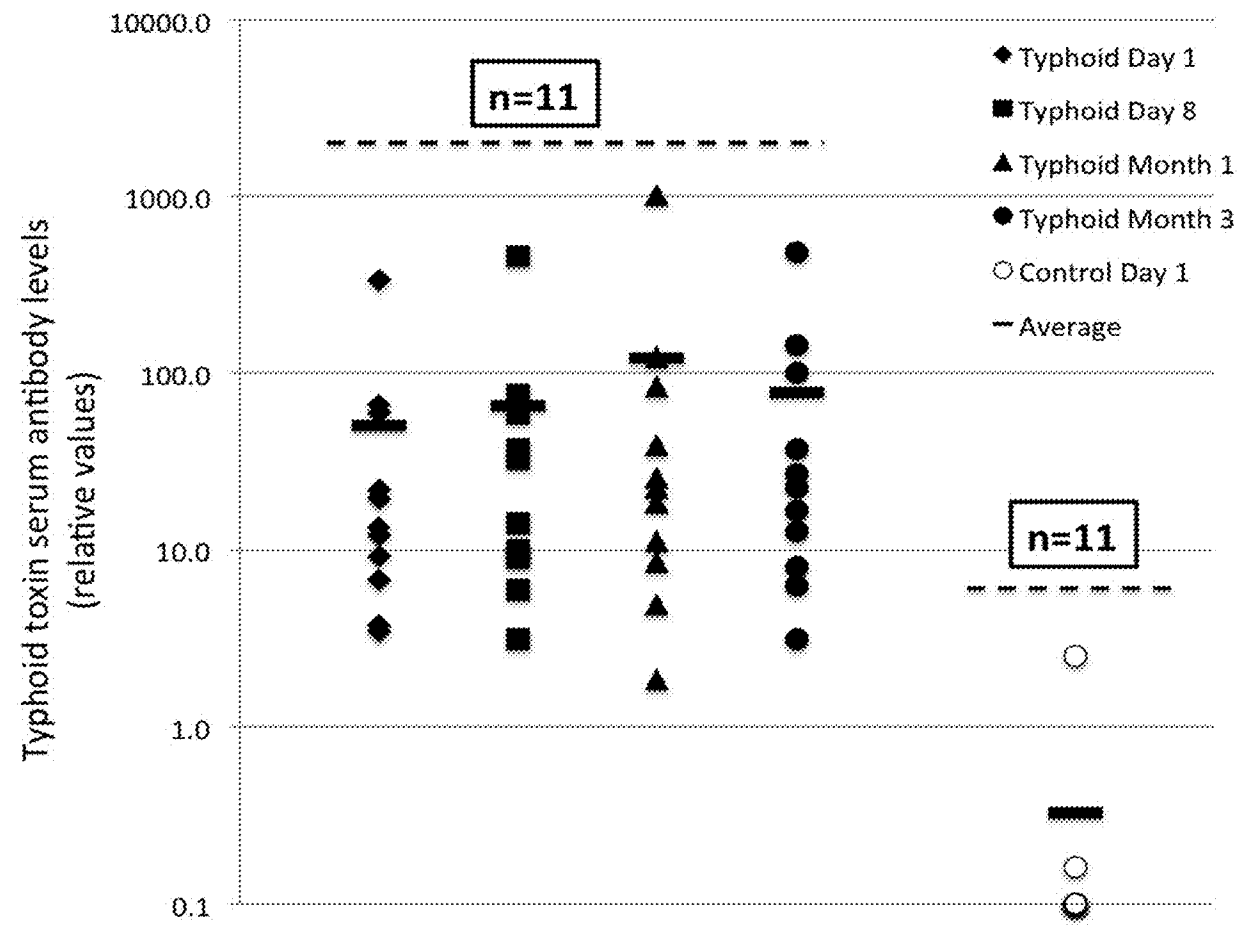

FIG. 24 depicts the results of experiments assessing anti-typhoid toxin serum antibody levels in a convalescent and a control population.

DETAILED DESCRIPTION

The present invention provides compositions and methods to prevent, treat and diagnose infection by *Salmonella enterica* serovar *typhi* (*S. typhi*) and/or *S. paratyphi*, i.e., typhoid fever. In one embodiment, the composition of the invention is a vaccine that induces the cell-mediated and/or humoral immunity directed against at least one *S. typhi* and/or *S. paratyphi* protein (e.g., PltA, PltB, CdtB, etc). In one embodiment, the composition comprises PltA, or a mutant thereof. In one embodiment, the composition comprises PltB, or a mutant thereof. In one embodiment, the composition comprises CdtB, or a mutant thereof.

In another embodiment, the composition of the invention comprises a nucleic acid sequence encoding PltA, or a mutant thereof. In another embodiment, the composition of the invention comprises a nucleic acid sequence encoding PltB, or a mutant thereof. In one embodiment, the composition of the invention comprises a nucleic acid sequence encoding CdtB, or a mutant thereof.

In one embodiment, the composition comprises an antibody that specifically binds to PltA, or a mutant thereof. In one embodiment, the composition comprises an antibody that specifically binds to PltB, or a mutant thereof. In one embodiment, the composition comprises an antibody that specifically binds to CdtB, or a mutant thereof.

The invention provides methods of inducing an immune response for preventing or treating infection by *S. typhi* or *S. paratyphi*. In one embodiment, the methods comprise administering at least one of PltA, PltB, CdtB, or mutants thereof, to a subject. In another embodiment, the methods comprise administering a nucleic acid encoding at least one of PltA, PltB, CdtB, or mutants thereof, to a subject.

In another embodiment, the methods comprise administering a nucleic acid encoding and expressing at least one of PltA, PltB, CdtB, or mutants thereof, to a bacterium. In some embodiments, the bacterium already comprises a nucleic that encodes, but does not express, PltA, PltB, CdtB, or mutants thereof. In other embodiments, the bacterium already comprises a nucleic that encodes, and does express, PltA, PltB, CdtB, or mutants thereof.

The invention also provides methods of treating infection by *S. typhi* or *S. paratyphi* in a subject in need thereof. In one embodiment, the method comprises administering to the subject at least one antibody that specifically binds to PltA, or a mutant thereof. In one embodiment, the method comprises administering to the subject at least one antibody that specifically binds to PltB, or a mutant thereof. In one embodiment, the method comprises administering to the subject at least one antibody that specifically binds to CdtB, or a mutant thereof. In one embodiment, the method comprises administering to the subject at least two antibodies that specifically bind to at least two of PltA, PltB and CdtB, or mutants thereof.

The invention also includes inhibitor compositions and methods for inhibiting with the interaction between the *S. typhi* or *S. paratyphi* toxin and the toxin's receptor.

The invention also provides methods of diagnosing infection by *S. typhi* or *S. paratyphi* in a subject by detecting the presence of, or measuring the level of, in the subject, at least one of PltA, PltB, CdtB, or antibodies that specifically bind to at least one of PltA, PltB, CdtB, or mutants thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from an individual to which it is later to be re-introduced into the same individual.

The term "agent" includes any substance, metabolite, molecule, element, compound, or a combination thereof. It includes, but is not limited to, e.g., protein, oligopeptide, small organic molecule, glycan, polysaccharide, polynucleotide, and the like. It can be a natural product, a synthetic compound, a chemical compound, or a combination of two or more substances. Unless otherwise specified, the terms "agent," "substance," and "compound" can be used interchangeably. Further, a "test agent" or "candidate agent" is generally a subject agent for use in an assay of the invention.

The term "binding" refers to a direct association between at least two molecules, due to, for example, covalent, electrostatic, hydrophobic, ionic and/or hydrogen-bond interactions.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

A "chimeric antibody" refers to a type of engineered antibody which contains a naturally-occurring variable region (light chain and heavy chains) derived from a donor antibody in association with light and heavy chain constant regions derived from an acceptor antibody.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap temporally with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared multiplied by 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

As used herein, an "inhibitory-effective amount" is an amount that results in a detectable (e.g., measurable) amount of inhibition of an activity. In some instance, the activity is its ability to bind with another component.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

"Parenteral" administration of an immunogenic composition includes, e.g., subcutaneous (s.c.), intravenous (i.v.), intramuscular (i.m.), or intradermal (i.d.) injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "X," the presence of a molecule containing epitope X (or free, unlabeled A), in a reaction containing labeled "X" and the antibody, will reduce the amount of labeled X bound to the antibody.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "therapeutic" as used herein means a treatment and/or prophylaxis. A therapeutic effect is obtained by suppression, diminution, remission, or eradication of a disease state.

The term "therapeutically effective amount" refers to the amount of the subject compound that will elicit the biological or clinical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

A term "toxoid" as used herein, refers to a bacterial toxin, the toxicity of which has been inactivated or suppressed, such as by introduction of a mutation, a chemical treatment, or a heat treatment, while other properties of the toxin, such as immunogenicity, are maintained in the toxoid. In some literature, toxoids are referred to as anatoxins.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the administration of at least one of PltA, PltB, CdtB, or mutants thereof, of S. typhi or and S. paratyphi to a subject to induce an immune response. Thus, the present invention provides a polypeptide or a combination of polypeptides, a polynucleotide or a combination of polynucleotides, which are useful in inducing an immune response, for the treatment or prevention of infection by S. typhi or S. paratyphi.

The invention provides an immunological composition comprising a polypeptide or combination of polypeptides derived from at least one of PltA, PltB, CdtB, or mutants thereof, useful in eliciting an immune response. The compositions comprising one or more polypeptides of the invention not only are useful as a prophylactic therapeutic agent for immunoprotection, but are also useful as a therapeutic agent for treatment of an ongoing condition associated with infection by S. typhi or S. paratyphi in a subject.

In one embodiment, the composition of the invention comprises a nucleic acid sequence encoding PltA, or a mutant thereof. In one embodiment, the PltA mutant is PltA E133X. In another embodiment, the PltA mutant is PltA E133A.

In another embodiment, the composition of the invention comprises a nucleic acid sequence encoding PltB, or a mutant thereof. In one embodiment, the PltB mutant is PltB S35X. In another embodiment, the PltB mutant is PltB S35A.

In one embodiment, the composition of the invention comprises a nucleic acid sequence encoding CdtB, or a mutant thereof In one embodiment, the CdtB mutant is CdtB H160X. In another embodiment, the CdtB mutant is CdtB H160Q. In one embodiment, the CdtB mutant is CdtB R119X. In one embodiment, the CdtB mutant is CdtB H259X. In one embodiment, the CdtB mutant is CdtB ΔCys269. In another embodiment, the CdtB mutant is CdtB C269X.

In one embodiment, the mutant PltA comprises any mutation in PltA that disrupts its enzymatic activity. In one embodiment, the mutant PltB comprises any mutation in PltB that disrupts its enzymatic activity. In one embodiment, the mutant CdtB comprises any mutation in CdtB that disrupts its enzymatic activity.

The skilled artisan will understand that the least one of PltA, PltB, CdtB, or mutants thereof, useful in eliciting an immune response, can each be used alone or in any combination for eliciting an immune response.

The present invention also provides methods of preventing, inhibiting, and treating infection by S. typhi or S. paratyphi in a subject in need thereof In one embodiment, the methods of the invention induce immunity against S. typhi or S. paratyphi in the subject, by generating an immune response in the subject directed to at least one polypeptide, such as PltA, PltB and CdtB. In one embodiment, the methods of the invention induce production of PltA-specific antibodies in the subject. In one embodiment, the methods of the invention induce production of PltB-specific antibodies in the subject. In one embodiment, the methods of the invention induce production of CdtB-specific antibodies in the subject.

In one embodiment, the methods of the invention prevent S. typhi or S. paratyphi related pathology in a subject in need thereof. In one embodiment, the methods of the invention comprise administering to the subject a composition comprising at least a portion of at least one of PltA, PltB, CdtB, or mutants thereof, to a subject. In another embodiment, the methods of the invention comprise administering to the subject a composition comprising a nucleic acid sequence encoding at least one of PltA, PltB, CdtB, or mutants thereof, to a subject. In various embodiments, the composition can be comprise a single subunit of $A_2B_5$, a combination of subunits of $A_2B_5$, or the entire $A_2B_5$, wherein at least one of the subunits is a mutant subunit.

In another embodiment, the methods of the invention comprise administering to the subject a bacterium or virus comprising a nucleic acid sequence encoding at least one of PltA, PltB, CdtB, or mutants thereof. In another embodiment, the methods of the invention comprise administering to the subject a bacterium or virus expressing at least a portion of at least one of PltA, PltB, CdtB, or mutants thereof. In another embodiment, the methods of the invention comprise administering to the subject a bacterium or virus comprising at least a portion of at least one of PltA, PltB, CdtB, or mutants thereof.

The invention also includes inhibitor compositions and methods for inhibiting with the interaction between the S. typhi or S. paratyphi toxin and the toxin's receptor.

The invention also provides methods of diagnosing infection by *S. typhi* or *S. paratyphi* in a subject by detecting the presence of, or measuring the level of, in the subject, at least one of PltA, PltB, CdtB, or mutants thereof, or antibodies that specifically bind to at least one of PltA, PltB, CdtB, or mutants thereof.

Compositions

The present invention provides compositions, including polypeptides, nucleotides, vectors, and vaccines, that when administered to a subject, elicit an immune response directed against *S. typhi* or *S. paratyphi*, including an immune response directed against at least one of PltA, PltB, CdtB, or mutants thereof. Further, when the compositions are administered to a subject, they elicit an immune response that serves to protect the inoculated subject against conditions associated with *S. typhi* or *S. paratyphi* infection.

In one embodiment, the present invention provides compositions that are useful as immunomodulatory agents, for example, in stimulating immune responses and in preventing *S. typhi* or *S. paratyphi* related pathology. In various embodiments, the immunomodulatory agents comprise at least one of PltA, PltB, CdtB, or mutants thereof. In one embodiment, the immune response is not detrimental to the host and therefore the compositions of the invention are useful as a vaccine. In one embodiment, the immunomodulatory agents are administered in combination with an adjuvant. In another embodiment, the immunomodulatory agents are administered in the absence of an adjuvant.

PltA, PltB, CdtB, or mutants thereof can be, used as immunostimulatory agents to induce the production of specific antibodies and protect against *S. typhi* or *S. paratyphi* induced pathology. Therefore, in one embodiment, the composition of the invention comprises a PltA polypeptide, or a mutant thereof. In one embodiment, the PltA mutant is PltA E133X. In another embodiment, the PltA mutant is PltA E133A. In another embodiment, the composition of the invention comprises a PltB polypeptide, or a mutant thereof. In one embodiment, the PltB mutant is PltB S35X. In another embodiment, the PltB mutant is PltB S35A. In another embodiment, the composition of the invention comprises a CdtB polypeptide, or a mutant thereof. In one embodiment, the CdtB mutant is CdtB H160X. In another embodiment, the CdtB mutant is CdtB H160Q. In one embodiment, the CdtB mutant is CdtB R119X. In another embodiment, the CdtB mutant is CdtB H259X. In one embodiment, the CdtB mutant is CdtB ΔCys269. In another embodiment, the CdtB mutant is CdtB C269X. The skilled artisan will understand that the least one of PltA, PltB, CdtB, or mutants thereof, useful in eliciting an immune response, can each be used alone or in any combination for eliciting an immune response.

The present invention also provides polynucleotides that encode the polypeptides described herein. Therefore, in one embodiment, the composition of the invention comprises a nucleic acid sequence encoding PltA, or a mutant thereof. In one embodiment, the PltA mutant is PltA E133X. In another embodiment, the PltA mutant is PltA E133A. In another embodiment, the composition of the invention comprises a nucleic acid sequence encoding PltB, or a mutant thereof. In one embodiment, the PltB mutant is PltB S35X. In another embodiment, the PltB mutant is PltB S35A. In one embodiment, the composition of the invention comprises a nucleic acid sequence encoding CdtB, or a mutant thereof. In one embodiment, the CdtB mutant is CdtB H160X. In another embodiment, the CdtB mutant is CdtB H160Q. In one embodiment, the CdtB mutant is CdtB R119X. In another embodiment, the CdtB mutant is CdtB H259X. In one embodiment, the CdtB mutant is CdtB ΔCys269. In another embodiment, the CdtB mutant is CdtB C269X. The skilled artisan will understand that the least one of PltA, PltB, CdtB, or mutants thereof, useful in eliciting an immune response, can each be used alone or in any combination for eliciting an immune response.

In various embodiments, the invention provides a polypeptide, or a fragment of a polypeptide, a homolog, a mutant, a variant, a derivative or a salt of a polypeptide as elsewhere described herein, wherein the immunogenic activity of the polypeptide or fragment thereof is retained.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

In one embodiment, the polypeptide or combination of polypeptides of the present invention are capable of generating a specific immune response. In another embodiment, the polypeptide or combination of polypeptides of the present invention are capable of generating specific antibodies.

Polypeptides of the present invention can be prepared using well known techniques. For example, the polypeptides can be prepared synthetically, using either recombinant DNA technology or chemical synthesis. Polypeptides of the present invention may be synthesized individually or as longer polypeptides composed of two or more polypeptides. The polypeptides of the present invention can be isolated, i.e., substantially free of other naturally occurring host cell proteins and fragments thereof.

The polypeptides of the present invention may contain modifications, such as glycosylation, aglycosylation, side chain oxidation, or phosphorylation; so long as the modifications do not destroy the immunologic activity of the polypeptides. Other modifications include incorporation of D-amino acids or other amino acid mimetics that can be used, for example, to increase the serum half-life of the polypeptides.

The polypeptides of the invention can be modified whereby the amino acid is substituted for a different amino acid in which the properties of the amino acid side-chain are conserved (a process known as conservative amino acid substitution).

Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note that the parenthetic letters indicate the one-letter codes of amino acids. As used herein, X stands for any amino acid.

The polypeptides of the invention can be prepared as a combination, which includes two or more of polypeptides of the invention, for use as a vaccine for prevention or treatment of *S. typhi* or *S. paratyphi* infection. The polypeptides may be in a cocktail or may be conjugated to each other using standard techniques. For example, the polypeptides can be expressed as a single polypeptide sequence. The polypeptides in the combination may be the same or different.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid encoding a polypeptide having substantial homology to the polypeptides disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass an RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

Vectors

The nucleic acids encoding the polypeptide or combinations of polypeptides of the invention of the invention can be incorporated into suitable vectors, including but not limited to, plasmids and retroviral vectors. Such vectors are well known in the art and are therefore not described in detail herein. In one embodiment, the invention includes a nucleic acid sequence encoding one or more polypeptides of the invention operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). The incorporation of a desired polynucleotide into a vector and the choice of vectors is well-known in the art as described in, for example, Sambrook et al. (2012), and in Ausubel et al. (1997).

The polynucleotide can be cloned into a number of types of vectors. However, the present invention should not be construed to be limited to any particular vector. Instead, the present invention should be construed to encompass a wide plethora of vectors which are readily available and/or well-known in the art. For example, the polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired nucleotide sequences of the invention, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 by upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 by apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or polypeptides. The promoter may be heterologous or endogenous.

One example of a constitutive promoter sequence is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter, where the promoter is active only in a desired tissue. Tissue-specific promoters are well known in the art and include, but are not limited to, the HER-2 promoter and the PSA associated promoter sequences.

In order to assess the expression of the nucleotide sequences encoding the polypeptide or combinations of polypeptides of the invention, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the expression vector is modified to increase the expression of the desired polypeptide. For example, the vector can undergo codon optimization to improve expression in a given mammal. For example, the vector can be codon-optimized for human expression. In another embodiment, the expression vector comprises an effective secretory leader. An exemplary leader is an IgE leader sequence. In another embodiment, the expression vector comprises a Kozak element to initiate translation. In another embodiment, the nucleic acid is removed of cis-acting sequence motifs/RNA secondary structures that would impede translation. Such modifications, and others, are known in the art for use in DNA vaccines (Kutzler et al, 2008, Nat. Rev. Gen. 9: 776-788; PCT App. No. PCT/US2007/000886; PCT App. No.; PCT/US2004/018962).

Vaccine

For an antigenic composition to be useful as a vaccine, the antigenic composition must induce an immune response to the antigen in a cell, tissue or subject (e.g., a human). Preferably, the vaccine induces a protective immune response in the subject. As used herein, an "immunological composition" may comprise, by way of examples, an antigen (e.g., a polypeptide), a nucleic acid encoding an antigen (e.g., an antigen expression vector), or a cell expressing or presenting an antigen. In particular embodiments the antigenic composition comprises or encodes all or part of any polypeptide antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" (also referred to as an immunogenic composition) refers to a substance that induces anti-*S. typhi* or *S. paratyphi* immunity or suppresses *S. typhi* or *S. paratyphi* upon inoculation into an animal. In various embodiments, the vaccine of the invention comprises at least one of PltA, PltB, CdtB, or mutants thereof, of *S. typhi* or and *S. paratyphi* to a subject to induce an immune response. In one embodiment, the vaccine is administered in combination with an adjuvant. In another embodiment, the vaccine is administered in the absence of an adjuvant.

A vaccine of the present invention may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment, the polypeptide vaccine of the invention includes, but is not limited to at least one polypeptide, or a fragment thereof, optionally mixed with adjuvant substances. In some embodiments, the polypeptide is introduced together with an antigen presenting cell (APC). The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen polypeptides. Presenting the polypeptide can be effected by loading the APC with a polynucleotide (e.g., DNA, RNA) encoding the polypeptide or loading the APC with the polypeptide itself.

Thus, the present invention also encompasses a method of inducing *S. typhi* or *S. paratyphi* immunity using one or more of polypeptides described herein. When a certain polypeptide or combination of polypeptides induces an *S. typhi* or *S. paratyphi* immune response upon inoculation into an animal, the polypeptide or combination of polypeptides are determined to have an immunity inducing effect. The induction of the *S. typhi* or *S. paratyphi* immunity by a polypeptide or combination of polypeptides can be detected by observing in vivo or in vitro the response of the immune system in the host against the polypeptide.

In another embodiment, the methods of the invention comprise administering to the subject a bacterium or virus comprising a nucleic acid sequence encoding at least one of PltA, PltB, CdtB, or mutants thereof. In another embodiment, the methods of the invention comprise administering to the subject a bacterium or virus expressing at least a portion of at least one of PltA, PltB, CdtB, or mutants thereof. In another embodiment, the methods of the invention comprise administering to the subject a bacterium or virus comprising at least a portion of at least one of PltA, PltB, CdtB, or mutants thereof.

For example, a method for detecting the induction of cytotoxic T lymphocytes is well known. A foreign substance that enters the living body is presented to T cells and B cells by the action of APCs. T cells that respond to the antigen presented by APC in an antigen-specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by a certain polypeptide or combination of polypeptides of the invention can be evaluated by presenting the polypeptide to a T cell by APC, and detecting the induction of CTL. Furthermore, APCs have the effect of activating CD4+T cells, CD8+T cells, macrophages, eosinophils and NK cells.

A method for evaluating the inducing action of CTL using dendritic cells (DCs) as APC is well known in the art. DC is a representative APC having the strongest CTL inducing action among APCs. In this method, the polypeptide or combination of polypeptides are initially contacted with DC and then this DC is contacted with T cells. Detection of T cells having cytotoxic effects against the cells of interest after the contact with DC shows that the polypeptide or combination of polypeptides have an activity of inducing the cytotoxic T cells. Furthermore, the induced immune response can be also examined by measuring IFN-gamma produced and released by CTL in the presence of antigen-presenting cells that carry immobilized polypeptide or combination of polypeptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The polypeptide, or combination of polypeptides, confirmed to possess CTL inducing activity by these methods are polypeptides having DC activation effect and subsequent CTL inducing activity. Therefore, a polypeptide or combination of polypeptides that induce CTL against toxin A and toxin B are useful as vaccines against *S. typhi* or *S. paratyphi* associated pathology. Furthermore, CTL that have acquired cytotoxicity due to presentation of the polypeptide or combination of polypeptides by APC can be also used as vaccines against *S. typhi* or *S. paratyphi* infection.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of *S. typhi* or *S. paratyphi* immunity by a polypeptide or combination of polypeptides can be further confirmed by observing the induction of antibody production against the specific toxins. For example, when antibodies against a polypeptide or combination of polypeptides are induced in a laboratory animal immunized with the polypeptide or combination of polypeptides, and when *S. typhi* or *S. paratyphi* associated pathology is suppressed by those antibodies, the polypeptide or combination of polypeptides are determined to induce anti-*S. typhi* or anti-*S. paratyphi* immunity.

*S. typhi* or *S. paratyphi* immunity can be induced by administering a vaccine of the invention, and the induction of *S. typhi* or *S. paratyphi* immunity enables treatment and prevention of pathologies associated with *S. typhi* or *S. paratyphi*. Thus, the invention provides a method for treating, or preventing infection by *S. typhi* or *S. paratyphi*. The therapeutic compounds or compositions of the invention may be administered prophylactically or therapeutically to subjects suffering from, or at risk of, or susceptible to, developing *S. typhi* or *S. paratyphi* infection. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The polypeptide or combination of polypeptides of the invention having immunological activity, or a polynucleotide or vector encoding such a polypeptide or combination of polypeptides, may optionally be combined with an adjuvant. An adjuvant refers to a compound that enhances the immune response against the polypeptide or combination of polypeptides when administered together (or successively) with the polypeptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering a composition comprising at least one polypeptide of the invention, and/or at least one polynucleotide encoding at least one polypeptide of the invention, to a subject. Administration of the composition can comprise, for example, intramuscular, intravenous, peritoneal, subcutaneous, intradermal, as well as topical administration.

The actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

These methods described herein are by no means all-inclusive, and further methods to suit the specific application will be apparent to the ordinary skilled artisan. Moreover, the effective amount of the compositions can be further approximated through analogy to compounds known to exert the desired effect.

Therapeutic Inhibitor Compositions and Methods

In various embodiments, the present invention includes inhibitor compositions for inhibiting with the interaction between the *S. typhi* or *S. paratyphi* toxin and the toxin's receptor. Inhibition of the interaction between the *S. typhi* or *S. paratyphi* toxin and the toxin's receptor can be assessed using a wide variety of methods, including those disclosed herein, as well as methods known in the art or to be developed in the future.

One skilled in the art, based upon the disclosure provided herein, would understand that the inhibitor compositions and methods of the invention are useful in treating preventing and infection by *S. typhi* and *S. paratyphi*.

The inhibitor compositions and methods of the invention that interfere with the interaction between the *S. typhi* or *S. paratyphi* toxin and the toxin's receptor include, but should not be construed as being limited to, a chemical compound, a protein, a peptide, a peptidomemetic, an antibody, a ribozyme, a small molecule chemical compound, a glycan, an antisense nucleic acid molecule (e.g., siRNA, miRNA, etc.), or combinations thereof. One of skill in the art would readily appreciate, based on the disclosure provided herein, that the inhibitor compositions of the invention include those that interfere with the interaction between the toxin and its receptor. In some embodiments, the inhibitor compositions bind to the toxin and interfere with the interaction between the toxin and its receptor. In other embodiments, the inhibitor compositions bind to the toxin's receptor and interfere with the interaction between the toxin and its receptor.

In various embodiments, the treatment of *S. typhi* or *S. paratyphi* infection in a subject is accomplished through passive antibody therapy (i.e., the transfer of antibodies to the *S. typhi* or *S. paratyphi* infected subject). In various embodiments, the inhibitor compositions and methods of the invention that interfere with the interaction between the *S. typhi* or *S. paratyphi* toxin and the toxin's receptor are used in combination with an antibiotic therapy. When used in combination, the antibiotic therapy can be administered before, during or after the administration of the inhibitor compositions of the invention.

In some embodiments, the receptor for the *S. typhi* or *S. paratyphi* toxin is a glycan. In one embodiment, the glycan is an N-linked glycan such as, by way of non-limiting examples, a sialylated tri- or bi-antennary glycan with one or all of the branches terminally sialylated. In another embodiment, the glycan is a non-sialylated tri- or bi-antennary glycan. In another embodiment, the glycan is a ganglioside. In another embodiment, the glycan is a glycan found on O-glycans. In various embodiments, the glycan is any one or more of the glycans listed in FIGS. 20, 21 and 22.

Further, one of skill in the art would, when equipped with this disclosure and the methods exemplified herein, appreciate that an inhibitor composition includes such inhibitors as discovered in the future, as can be identified by well-known criteria in the art of pharmacology, such as the physiological results of inhibition of the toxin as described in detail herein and/or as known in the art. Therefore, the present invention is not limited in any way to any particular inhibitor composition as exemplified or disclosed herein; rather, the invention encompasses those inhibitor compositions that would be understood by the routineer to be useful as are known in the art and as are discovered in the future.

Further methods of identifying and producing inhibitor compositions are well known to those of ordinary skill in the art, including, but not limited, obtaining an inhibitor from a naturally occurring source (i.e., *Streptomyces* sp., *Pseudomonas* sp., *Stylotella aurantium*). Alternatively, an inhibitor can be synthesized chemically. Further, the routineer would appreciate, based upon the teachings provided herein, that an inhibitor composition can be obtained from a recombinant organism. Compositions and methods for chemically synthesizing inhibitors and for obtaining them from natural sources are well known in the art and are described in the art.

One of skill in the art will appreciate that an inhibitor can be administered as a small molecule chemical, a protein, an antibody, a glycan, a nucleic acid construct encoding a protein, an antisense nucleic acid, a nucleic acid construct encoding an antisense nucleic acid, or combinations thereof. In one embodiment, the inhibitor composition of the invention that interferes with the interaction between the *S. typhi* or *S. paratyphi* toxin and the toxin's receptor is a soluble form of at least a fragment of at least one glycan that is a receptor for the *S. typhi* or *S. paratyphi* toxin. In various embodiments, the soluble form of at least a fragment of at least one glycan is a soluble form of at least a fragment of at least one glycan listed in FIGS. 20, 21 and 22.

Numerous vectors and other compositions and methods are well known for administering a protein or a nucleic acid construct encoding a protein to cells or tissues. Therefore, the invention includes a method of administering a protein or a nucleic acid encoding a protein that is an inhibitor. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will appreciate that inhibitors of the invention can be administered singly or in any combination. Further, inhibitors can be administered singly or in any combination in a temporal sense, in that they may be administered concurrently, or before, and/or after each other.

In various embodiments, any of the inhibitors of the invention described herein can be administered alone or in combination with other inhibitors of other molecules associated with *S. typhi* or *S. paratyphi* infection.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing infection in a subject, in that an inhibitor composition, as discussed previously elsewhere herein, can be administered to a subject prior to the onset of the infection.

The invention encompasses administration of an inhibitor to practice the methods of the invention; the skilled artisan would understand, based on the disclosure provided herein, how to formulate and administer the appropriate inhibitor to a subject. Indeed, the successful administration of the inhibitor has been reduced to practice herein. However, the present invention is not limited to any particular method of administration or treatment regimen.

Pharmaceutical Compositions

The present invention includes the treatment of a *S. typhi* or *S. paratyphi* infection in a subject by the administration of a therapeutic composition of the invention to a subject in need thereof. In one embodiment, the therapeutic composition of the invention is an inhibitor composition. In one embodiment, the therapeutic composition of the invention for the treatment of *S. typhi* or *S. paratyphi* infection is at least one antibody that specifically binds to at least one of PltA, PltB, CdtB, or mutants thereof. In various embodiments, the treatment of *S. typhi* or *S. paratyphi* infection in a subject is accomplished through passive antibody therapy (i.e., the transfer of antibodies to the *S. typhi* or *S. paratyphi* infected subject).

Administration of the therapeutic composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

When the compositions of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the compositions of the invention can be prepared by procedures known in the art using well known and readily available ingredients. The compositions of the invention can also be formulated as solutions appropriate for parenteral administration, for instance by intramuscular, subcutaneous or intravenous routes.

Thus, the composition may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

These methods described herein are by no means all-inclusive, and further methods to suit the specific application will be apparent to the ordinary skilled artisan. Moreover, the effective amount of the compositions can be further approximated through analogy to compounds known to exert the desired effect.

Methods of Diagnosis

In other embodiments, the invention is a method of determining whether a subject is, or has been, infected with *S. typhi* or *S. paratyphi*. In some embodiments, the method comprises detecting or measuring the level of typhoid toxin in the subject. In various embodiments, the method comprises detecting or measuring the level of at least one of PltA, CdtB and PltB in the subject. In some embodiments, the method comprises detecting or measuring the level of antibodies that specifically bind to the typhoid toxin in the subject. In various embodiments, the method comprises detecting or measuring the level of at least one antibody that specifically binds to PltA, CdtB or PltB in the subject.

In one embodiment, the invention is a method of determining whether a subject is infected with *S. typhi* or *S. paratyphi*, comprising the step of detecting or measuring the level of typhoid toxin in a biological sample of the subject. In various embodiments, the method comprises detecting or measuring the level of typhoid toxin by detecting or measuring the level of at least one of PltA, CdtB and PltB in the biological sample of the subject. In various embodiments, to determine whether the level of typhoid toxin is elevated in a biological sample of the subject, the level of typhoid toxin is compared with the level of at least one comparator control, such as a positive control, a negative control, a historical control, a historical norm, or the level of another reference molecule in the biological sample. The results of the diagnostic assay can be used alone, or in combination with other information from the subject, or other information from the biological sample obtained from the subject.

In one embodiment, the invention is a method of determining whether a subject is, or has been, infected with *S. typhi* or *S. paratyphi*, comprising the step of detecting or measuring the level of antibodies that specifically bind to the typhoid toxin in a biological sample of the subject. In various embodiments, the method comprises detecting or measuring the level of antibodies that specifically bind to typhoid toxin by detecting or measuring the level of at least one antibody that specifically binds to PltA, CdtB, or PltB in the biological sample of the subject. In various embodiments, to determine whether the level of antibodies that specifically bind to typhoid toxin is elevated in a biological sample of the subject, the level of antibodies that specifically bind to typhoid toxin is compared with the level of at least one comparator control, such as a positive control, a negative control, a historical control, a historical norm, or the level of another reference molecule in the biological sample. The results of the diagnostic assay can be used alone, or in combination with other information from the subject, or other information from the biological sample obtained from the subject.

In various embodiments of the methods of the invention, the level of antibody that specifically binds to typhoid toxin is determined to be elevated when the level of antibody that specifically binds to typhoid toxin is increased by at least 1%, at least 5%, at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator control.

In various embodiments, the biological sample is a sample containing a polypeptide or nucleic acid of at least one of PltA, CdtB, PltB, an antibody the specifically binds to PltA, an antibody the specifically binds to CdtB, or an antibody the specifically binds to PltB. The biological sample can be a sample from any source which contains a polypeptide or a nucleic acid, such as a bodily fluid or a tissue, or a combination thereof. A biological sample can be obtained by appropriate methods, such as, by way of examples, blood draw, fluid draw, or biopsy. A biological sample can be used as the test sample; alternatively, a biological sample can be processed to enhance access to the polypeptides or nucleic acids, or copies of the nucleic acids, and the processed biological sample can then be used as a test sample.

In various embodiments of the invention, methods of detecting or measuring the level of at least one of PltA, CdtB, PltB, an antibody the specifically binds to PltA, an antibody the specifically binds to CdtB, or an antibody the specifically binds to PltB levels in a biological sample obtained from a patient include, but are not limited to, an immunochromatography assay, an immunodot assay, a Luminex assay, an ELISA assay, an ELISPOT assay, a protein microarray assay, a ligand-receptor binding assay, displacement of a ligand from a receptor assay, displacement of a ligand from a shared receptor assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bio-analytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In various embodiments of the invention, methods of detecting or measuring the level of at least one of PltA, CdtB, PltB, an antibody the specifically binds to PltA, an antibody the specifically binds to CdtB, or an antibody the specifically binds to PltB levels in a biological sample obtained from a patient include, but are not limited to, quantitative hybridization methods, such as Southern analysis, Northern analysis, or in situ hybridizations, (see Current Protocols in Molecular Biology, Ausubel, F. et al., eds., John Wiley & Sons, including all supplements). A "nucleic acid probe," as used herein, can be a DNA probe or an RNA probe. The probe can be, for example, a gene, a gene fragment (e.g., one or more exons), a vector comprising the gene, a probe or primer, etc. For representative examples of use of nucleic acid probes, see, for example, U.S. Pat. Nos. 5,288,611 and 4,851,330. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA or cDNA. The hybridization sample is maintained under conditions which are sufficient to allow specific hybridization of the nucleic acid probe to mRNA or cDNA. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe having a mRNA or cDNA in the test sample, the level of the mRNA or cDNA in the sample can be assessed. More than one nucleic acid probe can also be used concurrently in this method. Specific hybridization of any one of the nucleic acid probes is indicative of the presence of the mRNA or cDNA of interest, as described herein.

Alternatively, a peptide nucleic acid (PNA) probe can be used instead of a nucleic acid probe in the quantitative hybridization methods described herein. PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a target nucleic acid sequence. Hybridization of the PNA probe to a nucleic acid sequence is used to determine the level of the target nucleic acid in the biological sample.

In another embodiment, arrays of oligonucleotide probes that are complementary to target nucleic acid sequences in the biological sample obtained from a subject can be used to determine the level of typhoid toxin in the biological sample of a subject. The array of oligonucleotide probes can be used to determine the level of typhoid toxin, or at least one of PltA, CdtB, PltB, alone, or the level of typhoid toxin, or at least one of PltA, CdtB, PltB, in relation to the level of one or more other nucleic acids in the biological sample. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and its level is quantified. Hybridization and quantification are generally carried out by methods described herein and also in, e.g., published PCT Application Nos. WO 92/10092 and WO 95/11995, and U.S. Pat. No. 5,424,186. In brief, a target nucleic acid sequence is amplified by well-known amplification techniques, e.g., PCR. Typically, this involves the use of primer sequences that are complementary to the target nucleic acid. Asymmetric PCR techniques may also be used. Amplified target, generally incorporating a label, is then hybridized with the array under appropriate conditions. Upon completion of hybridization and washing of the array, the array is scanned to determine the quantity of hybridized nucleic acid. The hybridization data obtained from the scan is typically in the form of fluorescence intensities as a function of quantity, or relative quantity, of the target nucleic acid in the biological sample. The target nucleic acid can be hybridized to the array in combination with one or more comparator controls (e.g., positive control, negative control, quantity control, etc.) to improve quantification of the target nucleic acid in the sample.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of 32P, 33P, 35S or 3H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the cells using known techniques. Nucleic acid herein refers to RNA, including mRNA, and DNA, including cDNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a biological sample, including a biological fluid and fresh or fixed tissue sample.

There are many methods known in the art for the detection and quantification of specific nucleic acid sequences and new methods are continually reported. A great majority of the known specific nucleic acid detection and quantification methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids in a biological sample known in the art are the hybridization methods as exemplified by U.S. Pat. No. 6,159,693 and No. 6,270,974, and related patents. To briefly summarize one of those methods, a nucleic acid probe of at least 10 nucleotides, preferably at least 15 nucleotides, more preferably at least 25 nucleotides, having a sequence complementary to a nucleic acid of interest is hybridized in a sample, subjected to depolymerizing conditions, and the sample is treated with an ATP/luciferase system, which will luminesce if the nucleic sequence is present. In quantitative Southern blotting, the level of the nucleic acid of interest can be compared with the level of a second nucleic acid of interest, and/or to one or more comparator control nucleic acids (e.g., positive control, negative control, quantity control, etc.).

Many methods useful for the detection and quantification of nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed elsewhere herein. Most preferably the detection of the duplex is done using at least one primer directed to the nucleic acid of interest. In yet another embodiment of PCR, the detection of the hybridized duplex comprises electrophoretic gel separation followed by dye-based visualization.

Typical hybridization and washing stringency conditions depend in part on the size (i.e., number of nucleotides in length) of the oligonucleotide probe, the base composition and monovalent and divalent cation concentrations (Ausubel et al., 1994, eds Current Protocols in Molecular Biology).

In a preferred embodiment, the process for determining the quantitative and qualitative profile of the nucleic acid of interest according to the present invention is characterized in that the amplifications are real-time amplifications performed using a labeled probe, preferably a labeled hydrolysis-probe, capable of specifically hybridizing in stringent conditions with a segment of the nucleic acid of interest. The labeled probe is capable of emitting a detectable signal every time each amplification cycle occurs, allowing the signal obtained for each cycle to be measured.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In one aspect, the invention includes a primer that is complementary to a nucleic acid of interest, and more particularly the primer includes 12 or more contiguous nucleotides substantially complementary to the nucleic acid of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence In another aspect, the length of the primer can vary in length, preferably about 15 to 28 nucleotides in length (e.g., 16, 17, 18, 19, 20, 21, 22, 23, 24, 25, 26, or 27 nucleotides in length).

EXPERIMENTAL EXAMPLE

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Conferring Virulence: Structure and Function of the Chimeric $A_2B_5$ Typhoid Toxin The results described herein demonstrate that the systemic administration of typhoid toxin, a unique virulence factor of S. typhi, reproduces many of the acute symptoms of typhoid fever. Specific carbohydrate moieties on specific surface glycoproteins that serve as receptors for typhoid toxin were identified. These carbohydrate moieties provide the broad cell target specificity of typhoid toxin. The atomic structure of typhoid toxin was identified, which shows an unprecedented $A_2B_5$ organization with two covalently-linked A subunits non-covalently-associated to a pentameric B subunit. The structure provides insight into the toxin's receptor-binding specificity and delivery mechanisms. The structure also demonstrates how the activities of two powerful toxins have been co-opted into a single, unique toxin that can induce many of the symptoms characteristic of typhoid fever. These findings are useful for the life-saving therapeutics against typhoid fever.

The materials and methods employed in these experiments are now described.

Bacterial Strains, Mammalian Cells, and Growth Conditions

The wild-type *Salmonella enterica* serovar *Typhi* strain ISP2825 has been described previously (Galan and Curtiss, 1991, Infect. Immun. 59:2901-2908). A derivative of this strain encoding a FLAG-epitope tagged CdtB has been previously described (Spano et al., 2008, Cell Host Microbe 3:30-38). Other *S. typhi* mutant strains were constructed by allelic exchange using previously described methods (Kaniga et al., 1994, Mol. Microbiol. 13:555-568). Site directed mutations and epitope tagging was carried out following standard recombinant DNA procedures.

For all infection experiments, *S. typhi* strains were grown at 37° C. in 2 ml LB broth containing 0.3 M NaCl to an OD600 of ~0.9 after inoculation from overnight cultures at a dilution of 1:50. Cultured cells and culture medium used in these studies were as follows:

Henle-407 (human intestinal epithelial cells): DMEM+10% BCS;

Jurkat (human T lymphocytes): RPMI1640+10% FBS;

Ramos (human B lymphocytes): RPMI1640+10% FBS;

THP1 (human monocytic cells): RPMI1640+10% FBS+0.05 mM β-mercaptoethanol;

Raw (mouse monocytes/macrophages): DMEM+10% FBS;

NIH3T3 (mouse embryonic fibroblasts): DMEM+10% BCS;

COS1 (monkey kidney fibroblasts): DMEM+10% BCS;

CHO (Chinese hamster ovary epithelial cells): Ham's F12+10% FBS;

MDCK (canine kidney epithelial cells): MEM+10% FBS;

Lec-1 (N-acetylglucosaminyltransferase I mutant) and parent cell Pro-5: alpha MEM with ribonucleosides and deoxyribonucleosides+10% FBS.

All mammalian cells were cultured at 37° C. under an atmosphere of 5% $CO_2$.

Typhoid Toxin Expression and Purification

PltB, PltA, and CdtB (wild type or mutant alleles, and 3× FLAG or 6× His tagged at the carboxy terminus of CdtB, as indicated) were cloned as a single operon in either a low copy plasmid derived from pWSK129 (Wang and Kushner, 1001, Gene 100:195-199), or in pET28a+ (Novagen). *E. coli* strains carrying the different plasmids were grown to an OD600 of 0.6-0.7 at 37° C., expression of typhoid toxin was subsequently induced by the addition of 0.5 mM IPTG, and induced cultures were incubated overnight at 30° C. Bacterial cells were pelleted by centrifugation, and bacterial cells were resuspended in a buffer containing 200 mM Tris-HCl (pH 7.5), 20% sucrose, 1 mM EDTA, 2 mg/ml lysozyme, and 1× protease inhibitors (2 ml per each gram of wet cell pellet weight), incubated for 5 min at RT, mixed with $dH_2O$ (3 ml per each gram of wet cell pellet weight) by inversion, and incubated for additional 10 min on ice. A crude periplasmic protein fraction was obtained by centrifugation at 4,000×g for 15 min at RT, and used as a source of typhoid toxin for affinity chromatography purification using M2 Flag affinity gel (Sigma). The periplasmic fraction containing typhoid holotoxin was incubated for 3 hrs at 4° C. with M2 agarose beads packed on a 10 ml column (Bio-rad), washed with ~20 bed volume of PBS, and eluted twice with PBS containing 3× Flag peptide (Sigma; 150 ng/μl). Partially purified holotoxin was applied on a superdex 200 size-exclusion chromatography (Tris-HCl buffer, 15-50 mM, in a pH range of 7.6-8.0 supplemented with 150 mM NaCl) to complete its purification.

His-epitope-tagged typhoid toxin was purified as follows. *E. coli* cultures were resuspended in a buffer containing 15 mM Tris-HCl, pH8.0, 150 mM NaCl, 2 mg/ml lysozyme, 10 μg/ml DNase, and 1× protease inhibitor cocktail, lysed by passing them through a French press three times, pelleted, and affinity-purified using a Nickel-resin (Qiagen) according to the vendor's recommendation. The eluates were diluted in 20 mM MES, pH6.0 buffer and loaded onto a Hitrap ion-exchange column. Fractions from the ion-exchange chromatography were monitored on SDS-PAGE, concentrated, and further purified by using a superdex 200 column. Final fractions were examined for purity on a 15% SDS-PAGE.

Mammalian Cell Intoxication Assay

Cell cycle arrest after typhoid toxin intoxication was examined by flow cytometry using previously described methods (Spano et al., 2008, Cell Host Microbe 3:30-38). Briefly, after treatment with 3× FLAG-tagged typhoid toxin or bacterial infection for different times (as indicated), cells were trypsinized, harvested, washed, and fixed overnight at −20° C. in ~70% ethanol/PBS. Fixed cells were washed with PBS and resuspended in 500 μl of PBS containing 50 μg/m1propidium iodide (PI), 0.1 mg/ml RNase A, and 0.05% Triton X-100. After incubation for 40 min at 37° C., cells were washed with PBS, resuspended in 500 μl PBS, filtered, and analyzed by a flow cytometry. DNA contents of cells were determined using Flowjo (Treestar).

Light-Scattering Size Exclusion Chromatography and Amino Acid Composition Analysis Light-Scattering Size Exclusion Chromatography (SEC-LS) and amino acid composition analysis were carried out at the Keck Biotechnology Resource Laboratory at the Yale University School of Medicine. For SEC-LS analysis, the toxin was purified in 50 mM Hepes buffer containing 150 mM NaCl and run on a Superdex 200 column equipped with a light scattering detector using a same Hepes buffer. For amino acid composition analysis, typhoid toxin was resolved on a 15% SDS-PAGE gel, stained with Coomassie brilliant blue, and the three individual bands were excised and used for amino acid composition analysis.

Mouse Intoxication Experiments

All animal experiments were conducted according to protocols approved by an Institutional Animal Care and Use Committee. Groups of C57BL/6 mice were intravenously injected with 100 μl solutions containing either TBS buffer alone or 10 μg of each of the purified holotoxin preparations (endotoxin free). His-tagged wild type, PltA catalytic mutant (PltA E133A), CdtB catalytic mutant (CdtB H160Q), double catalytic mutant (PltA E133A CdtB H160Q), and PltB S35A mutant holotoxins were purified as described elsewhere herein. Changes in behavior, weight, and temperature of the toxin-injected mice as well as their survival were closely monitored during the duration of the experiment.

Peripheral Blood Leukocyte Preparation, Immunostaining, and Flow Cytometry Analysis Peripheral blood samples of typhoid toxin treated and control mice were collected into heparinized tubes, incubated with 1 ml ACK lysis buffer (BioWhittaker) (to remove red blood cells), incubated for 5 min on ice, washed with 2 ml PBS, and centrifuged to collect peripheral blood leukocytes (PBLs). After a repetition of the red blood cell removal step, PBLs were used for immunostaining as described elsewhere herein. After washing, the cells were immediately incubated for 30 min on ice with 100 µl of anti-mouse Ly-6G (Gr-1) antibody conjugated with FITC (eBioscience). The cells were then washed with 2 ml FACS buffer (PBS, 0.16% BSA), resuspended in 100 µl FACS fixation buffer (PBS, 1% paraformaldehyde, 1% FCS), and used for flow cytometric analyses on a FACSCalibur flow cytometer (BD Biosciences). Alternatively, blood samples collected by heart puncture 4 days after toxin treatment were analyzed in a Hemavet 950FS hematology analyszer (Drew Scientific).

Identification of Typhoid Toxin Interacting, Biotin-Labeled Host Cell Surface Proteins Cultured cells (Henle, Jurkat, Ramos, or THP1 at ~50% confluency) were washed with PBS, treated with PBS containing ~100 µg/ml of Sulfo-NHS-SS-Biotin (Thermo) for 30 min at RT, and subsequently washed 3 times with 50 mM Tris-HCl pH8.0/150 mM NaCl buffer to quench and to remove extra biotin reagent. After additional washings (3 times with PBS), cells were resuspended in a lysis buffer containing 50 mM Tris-HCl, pH7.4, 150 mM NaCl, 1% NP-40, and 1× protease inhibitor, incubated for 20 min on ice, and homogenized by passing a 26-G needle ~20 times.

After removal of cellular debris by centrifugation, the supernatants were mixed with 10 µg purified FLAG-tagged typhoid toxin and incubated for 3 hrs at 4° C. Anti-FLAG antibody-containing agarose beads were added, incubated for additional 1 hr at 4° C., washed 5 times with PBS, SDS-PAGE sample buffer was added, boiled, and run on SDS-PAGE. The gels were transferred to nitrocellulose membranes, blocked with TBS containing 5% BSA, incubated overnight at 4° C. with Streptavidin-HRP (1:5000) in TBS/1% BSA, washed with TBST, and developed with ECL substrates (Pierce).

To identify the typhoid toxin-interacting proteins by LC-MS/MS, equivalently obtained samples were run in parallel, stained with Coomassie blue, and gel regions corresponding to the molecular weight of typhoid-toxin interacting proteins identified by western blot analysis were excised and processed for LC-MS/MS using previously described methods (Liu et al., 2012, PLoS pathogens 8:e1002562). Briefly, gel slices were destained in destaining buffer (50 mM $NH_4HCO_3$, 50% Acetonitrile (ACN)), and dehydrated with ACN. Disulfide bonds were reduced by incubating the samples with $NH_4HCO_3$ containing 10 mM DTT and alkylated by incubating them with 55 mM 2-iodoacetamide in 100 mM $H_4HCO_3$ buffer for 20 min at RT. Gel pieces were dehydrated, trypsin-digested overnight, extracted, run on an LTQ-Velos Mass Spectrometer, and spectra analyzed with Mascot (Matrixscience). As negative controls, equivalently processed samples obtained with two irrelevant baits (GST-3× Flag and InvC-3× Flag) were used.

Oregon Green 488 Typhoid Toxin Labeling

Purified wild type and PltBS35A mutant typhoid toxin preparations were fluorescently labeled with Oregon Green (OG)-488 dye (Invitrogen) according to the vendor's recommendation. OG-488 dye has a succinimidyl ester moiety that reacts with primary amines of proteins to form stable dye-protein conjugates. Purified toxin preparations (1 mg/ml) were incubated with reactive dye in 500 µl of 100 mM bicarbonate buffer for 1 hr at RT, and applied to a size exclusion chromatography column provided by the vendor to separate the dye-protein conjugates from free dye. Degree of labeling was determined by measuring the absorbance of the conjugate solution at 280 nm and 496 mm, which yielded comparable toxin labeling for both toxin preparations (4.4:1 and 4.36:1 dye/holotoxin ratios for wild type and PltB S35A mutant toxin, respectively). A predicted extinction coefficient of 191,400 $M^{-1} cm^{-1}$ was used to calculate the dye/toxin ratio.

Typhoid Toxin Binding Assay

Cells were harvested by trypsinization, washed with HBSS, resuspended in 100 µl HBSS containing 0.2 µg of Oregon Green-488 (Invitrogen)-labeled purified wild type or mutant toxin preparations. Cells were incubated in the presence of the labeled toxin preparations for 30 min at room temperature, washed with PBS, resuspended in 100 µl PBS containing 1% paraformaldehyde, and analyzed by flow cytometry. When indicated, Henle-407 cells were treated for 2 hrs with 10 µl deglycosidase mix (NEB) in 2 ml HBSS prior to processing for toxin-binding assays as described elsewhere herein.

Generation of PODXL-Depleted Cell Lines

RNA interference vector pSUPER-H1 (Oligoengine) was used to generate a plasmid expressing an shRNA construct targeted to podxl. Oligos including a target region for podx

```
                                    (SEQ ID NO: 1)
5'-GATCCCCGGACAAATGGGATGAACTATTCAAGAGATAGTTCA
TCCCATTTGTCCTTTTTC
and (SEQ ID NO: 2)
5'-TCGAGAAAAAGGACAAATGGGATGAACTATCTCTTGAATAGT
TCATCCCATTTGTCCGGG
``` were annealed to form double-stranded DNA and cloned into the BglII and HindIII sites of pSUPER-H1 vector. Henle-407 cells were transfected with this plasmid using Lipofectamine 2000 (Invitrogen) and puromycin-resistant stable-transfected cell lines were screened for PODXL expression by real time-PCR using a podx1-specific primer set. The primer sequences were as follows:

```
            (sense; SEQ ID NO: 3)
            5'-ACCGGGGACTACAACCCTG
            and (antisense; SEQ ID NO: 4)
            5'-TGTGGTGTTAGGTTTAGCTGTG
            for podxl and (sense; SEQ ID NO: 5)
            5'-GATTACTGCTCTGGCTCCTAGC
            and (antisense; SEQ ID NO: 6)
            5'-GACTCATCGTACTCCTGCTTGC
            for β-actin.
```

Glycan Array Analysis

OG488-labeled wild type and PltB S35A mutant holotoxins were diluted to 180 µg/ml or 20 µg/ml and an aliquot (70 µl) was applied to separate microarray slides (version 5.1) at the Consortium for Functional Glycomics Protein-Glycan Interaction Core, at Emory University. The data are reported as average relative fluorescence units of four of six replicates (after removal of the highest and lowest values) for each glycan represented on the array. Glycans showing typhoid toxin binding activity (listed in FIG. 20) were selected considering a cut off value that was larger or equal to than 1% of the values obtained with the glycan showing the highest binding activity. Glycans showing a variation coefficient higher than 30% were eliminated from this group. In addition some specific glycans were eliminated from the group because they are physiologically irrelevant (glycan #509) or showed non-specific binding (glycans #335, 336, 523).

Surface Plasmon Resonance

Surface plasmon resonance analysis was carried out at the Keck Biotechnology Resource Laboratory at the Yale University School of Medicine using a BiaCore biosensor. Briefly, 50 µg/ml anti-M2 Flag antibody was immobilized on the surface of a chip by amine coupling. Purified wild type or PltB S35A (both FLAG tagged on the C-terminus of CdtB) mutant toxin preparations were applied to the chip followed by application of Ganglisoside GD2 glycan (Elicityl) at various concentrations.

Crystallization

The purification of 6× His-tagged typhoid toxin used for crystallization is described elsewhere herein. Initial spare matrix crystallization trials of full-length holotoxin protein preparations (2 mg/ml) were carried out at the Yale University School of Medicine Structural Biology Core facility. After crystal optimization trials, full length typhoid toxin (4.5 mg/ml) crystals grew in ~3 weeks at room temperature using the hanging-drop vapour-diffusion method in a mix of 1 µl of protein with 1 µl of reservoir solution consisting of 1.6 M sodium formate and 0.1 M sodium acetate, pH 4.5.

X-Ray Data Collection and Structure Determination

X-ray data were collected to 2.4A at the wavelength of 1.5418 Å on a Rigaku Homelab system at the Yale University Chemical and Biophysical Instrumentation Center (CBIC). Data were integrated and scaled using the HKL-2000 package using previously described methods (Otwinowski and Minor, 1997, Methods Enzymol. 276:307-326). Further processing was performed with programs from the CCP4 suite using previously described methods (Project, 1994, Acta Crystallogr. D 50:760-763). The holotoxin structure was determined by molecular replacement using PHASER8 with the atomic coordinates of Chain B of H. ducreyi CDT (PDB ID, 15R4; Nesié et al., 2004, Nature 429:429-433), Chain A of pertussis toxin (PDB ID, 1PRT; Stein et al., 1994, Nat. Struct. Biol. 1:591-596) and Subtilase cytotoxin B-subunit (PDB ID, 3DWP; Byres et al., 2008, Nature 456:2126-2132) as the initial search model. The atomic coordinates have been deposited in the RCSB Protein Data Bank (entry number 4KSL).

To complete the model, manual building was carried out in COOT using previously described methods (Emsley and Cowtan, 2004, Acta Crystallogr. D 60:2126-2132). Figures were prepared using PyMol using previously described methods (Delano, 2002, The PyMOL Molecular Graphics System; www.pymol.org). The structure refinement was done by PHENIX using previously described methods (Adams et al., 2010, Acta Crystallogr. D 66:213-221). The data collection and refinement statistics are summarized in FIG. 21.

Molecular Docking

Molecular docking of Neu5Ac onto PltB was carried out with AutoDock Vina using previously described methods (Trott and Olson, 2010, J. Computational Chem. 31:455-461). Based on the available structural and functional information on pertussis and subtilase toxins as well as functional data indicating the importance of PltB Ser35 in sugar binding (FIG. 4), the binding of Neu5Ac was modeled onto a pocket surrounding PltB Ser35 and consider several amino acid residues (Tyr33, Tyr34, Ser35 and Lys59) as flexible. The calculation yielded 20 possible models, of which the one with the highest ranking was selected as the most likely.

Fluorescence Microscopy

Fluorescence microscopy analysis of typhoid toxin in S. typhi infected cells was carried out using previously described methods (Spano et al., 2008, Cell Host Microbe 3:30-38). Briefly, Henle-407 cells were seeded on coverslips placed within 24-well plates and cultured overnight. Cultured cells were infected with different strains of S. typhi expressing FLAG-epitope tagged typhoid toxin with a multiplicity of infection of 20 for 1 hr. Infected cells were washed, treated for 1 hr with 100 µg/ml gentamicin to kill extracellular bacteria, washed again, and incubated for 24 hr in a cell culture medium containing 10 µg/ml gentamicin. Infected cells were washed with PBS, fixed with 4% paraformaldehyde for 10 min at RT, washed, and incubated for 30 min at RT with PBS containing 50 mM $NH_4Cl$, 0.2% Triton X-100 and 3% BSA.

Cells were then incubated for 30 min at RT with a primary antibody mixture of mouse anti-Flag M2 (Sigma; 1:4000) and rabbit anti-S. typhi (Difco; 1:4000) in PBS containing 3% BSA, washed, incubated for 30 min at RT with a secondary antibody mixture of Alexa-488 anti-mouse (1:2000) and Alexa-594 anti-rabbit (1:2000) in PBS containing 3% BSA. Cells were washed, stained with DAPI (1:10,000), washed again, mounted, and viewed using a 100× objective on a fluorescence microscope (Nikon TE2000). Puncta intensities of images were analyzed using ImageJ software using methods previously described (Spano et al., 2011, Proc. Natl. Acad. Sci. USA 108:18418-18432).

Statistics

The two-tailed student T-test was performed to determine the statistical significance of experimental changes from control values. A p value of less than 0.05 was considered significant.

Sequences

CdtB; NP_456275.1

(SEQ ID NO: 7)
MKKPVFFLLTMIICSYISFACANISDYKVMTWNLQGSSASTESKWNV

NVRQLLSGTAGVDILMVQEAGAVPTSAVPTGRHIQPFGVGIPIDEYT

WNLGTTSRQDIRYIYHSAIDVGARRVNLAIVSRQRADNVYVLRPTTV

ASRPVIGIGLGNDVFLTAHALASGGPDAAAIVRVTINFFRQPQMRHL

SWFLAGDFNRSPDRLENDLMTEHLERVVAVLAPTEPTQIGGGILDYG

VIVDRAPYSQRVEALRNPQLASDHYPVAFLARSC

PltA; NP_456278

(SEQ ID NO: 8)
MKKLIFLTLSIVSFNNYAVDFVYRVDSTPPDVIFRDGFSLLGYNRNF

QQFISGRSCSGGSSDSRYIATTSSVNQTYAIARAYYSRSTFKGNLYR

YQIRADNNFYSLLPSITYLETQGGHFNAYEKTMMRLQREYVSTLSIL

PENIQKAVALVYDSATGLVKDGVSTMNASYLGLSTTSNPGVIPFLPE

PQTYTQQRIDAFGPLISSCFSIGSVCHSRGQRADVYNMSFYDARPV

IELILSK

PltB; NP_456279.1

(SEQ ID NO: 9)
MYMSKYVPVYTLLILIYSFNASAEWTGDNTNAYYSDEVISELHVGQI

DTSPYFCIKTVKANGSGTPVVACAVSKQSIWAPSFKELLDQARYFYS

TGQSVRIHVQKNIWTYPLFVNTFSANALVGLSSCSATQCFGPK

The results of the experiments are now described.

$A_2B_5$ Organization of Typhoid Toxin

Figure 1:
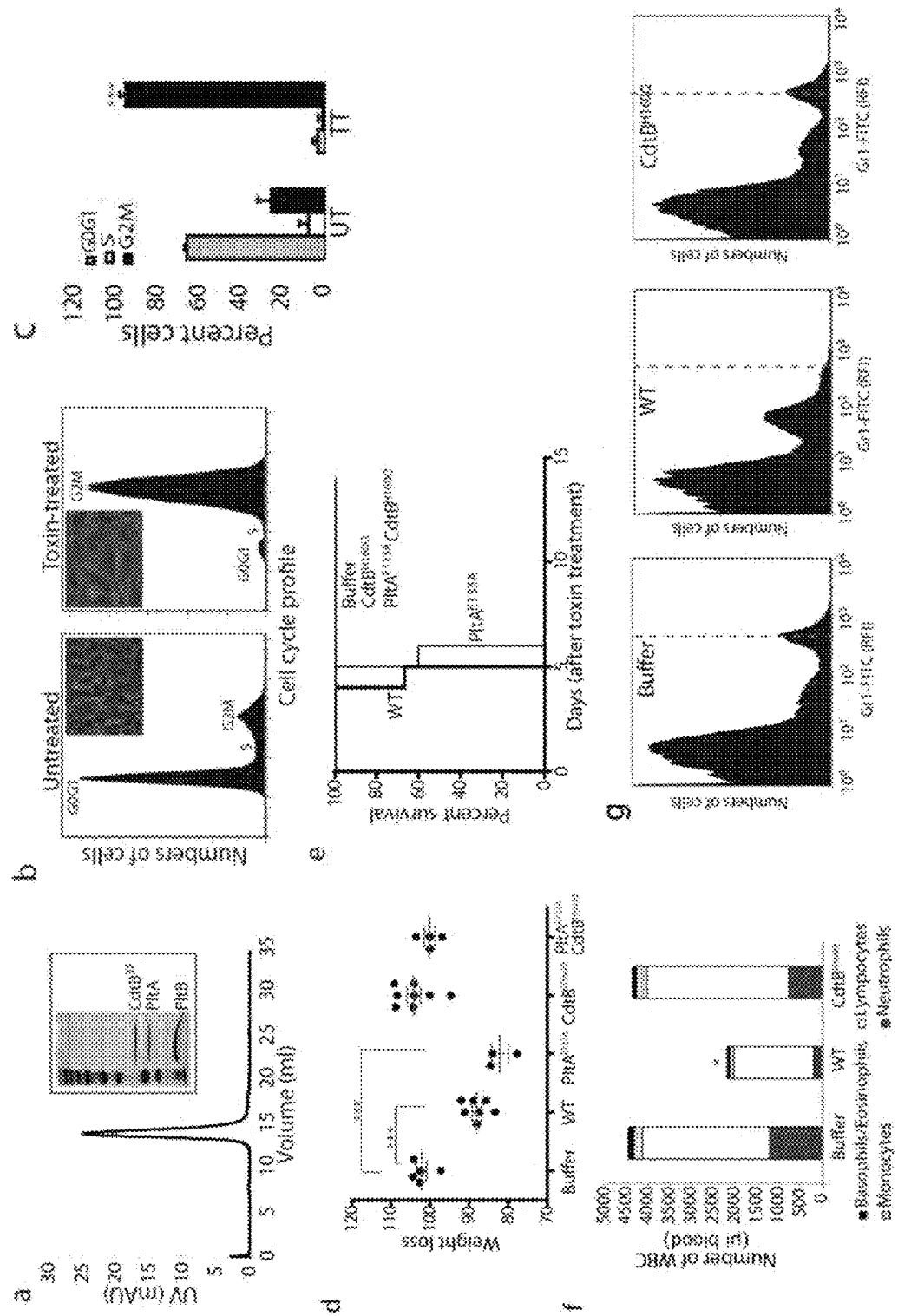
Figure 5:
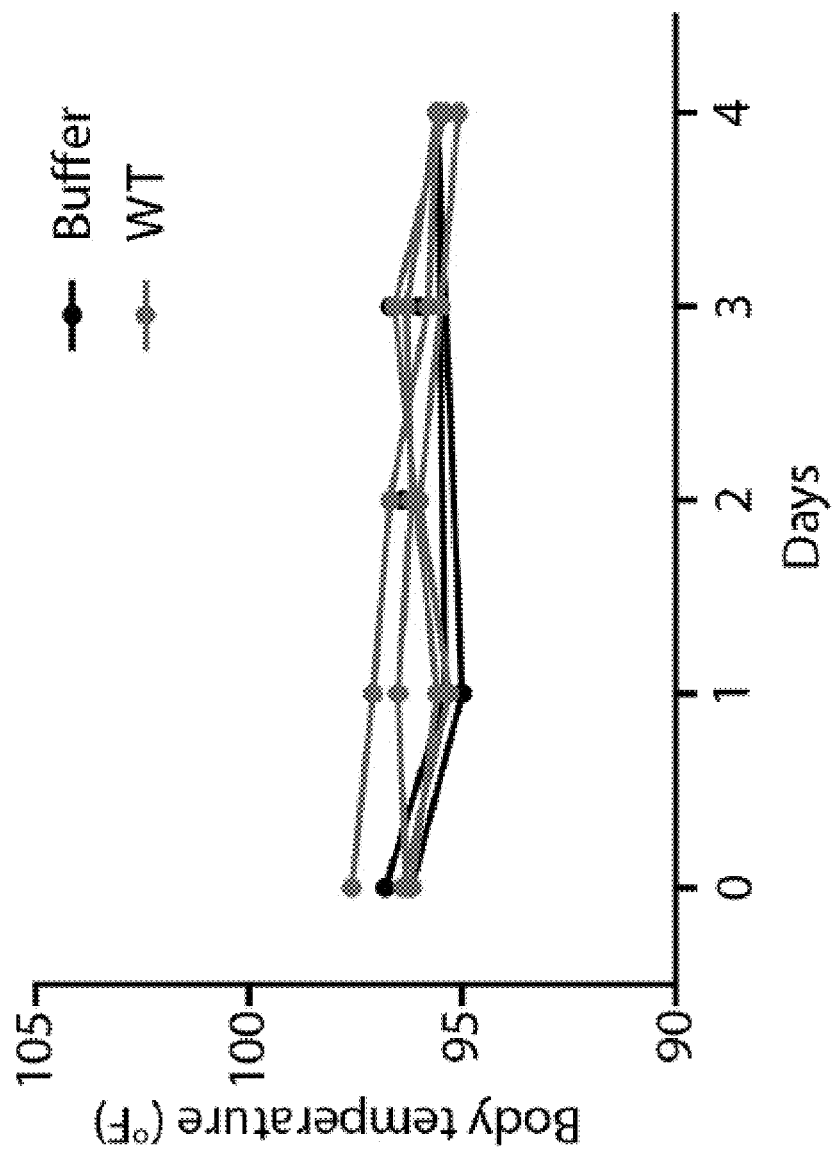
Figure 6:
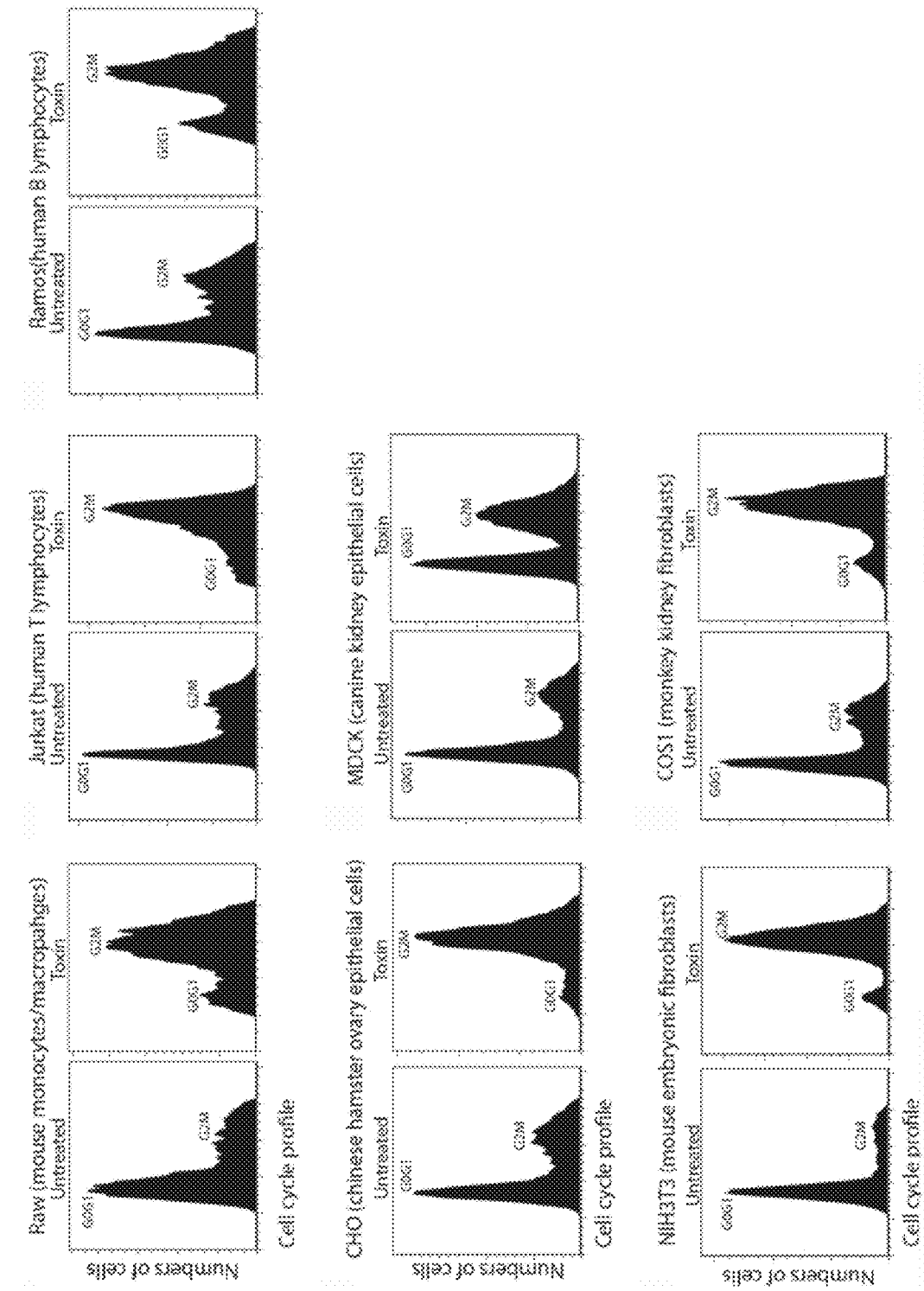

To examine the potential role of typhoid toxin in the acute phase of typhoid fever, a protocol to obtain a highly purified preparation of active holotoxin was developed (FIGS. 1A-1C). It was observed that systemic administration of typhoid toxin into mice caused many of the symptoms observed during the acute phase of typhoid fever. Despite the lack of fever (FIG. 5), the mice appeared lethargic showing clear signs of stupor and malaise. Furthermore, the mice lost weight (FIG. 1D) and eventually died (FIG. 1E). The toxin-injected animals also showed a significant reduction in the number of circulating immune cells, resulting in the almost complete depletion of circulating neutrophils (FIGS. 1F-1G), a phenotype often observed during the acute phase of typhoid fever. Consistent with this observation, typhoid toxin was able to intoxicate a broad range of cells in vitro, including several epithelial and immune cells (FIG. 6). Although symptoms were observed in animals inoculated with a toxin carrying a catalytic mutant of PltA (FIG. 1D), no detectable symptoms were observed when animals were inoculated with equally purified preparations of typhoid toxin carrying a catalytic mutant of its CdtB subunit (FIGS. 1D-1G). Although not wishing to be bound by any particular theory, when taken together, these results indicate that typhoid toxin, through its CdtB subunit, may contribute to the acute symptomatology observed during typhoid fever.

Figures 2A, 2B, 2C, 2D, 2E:
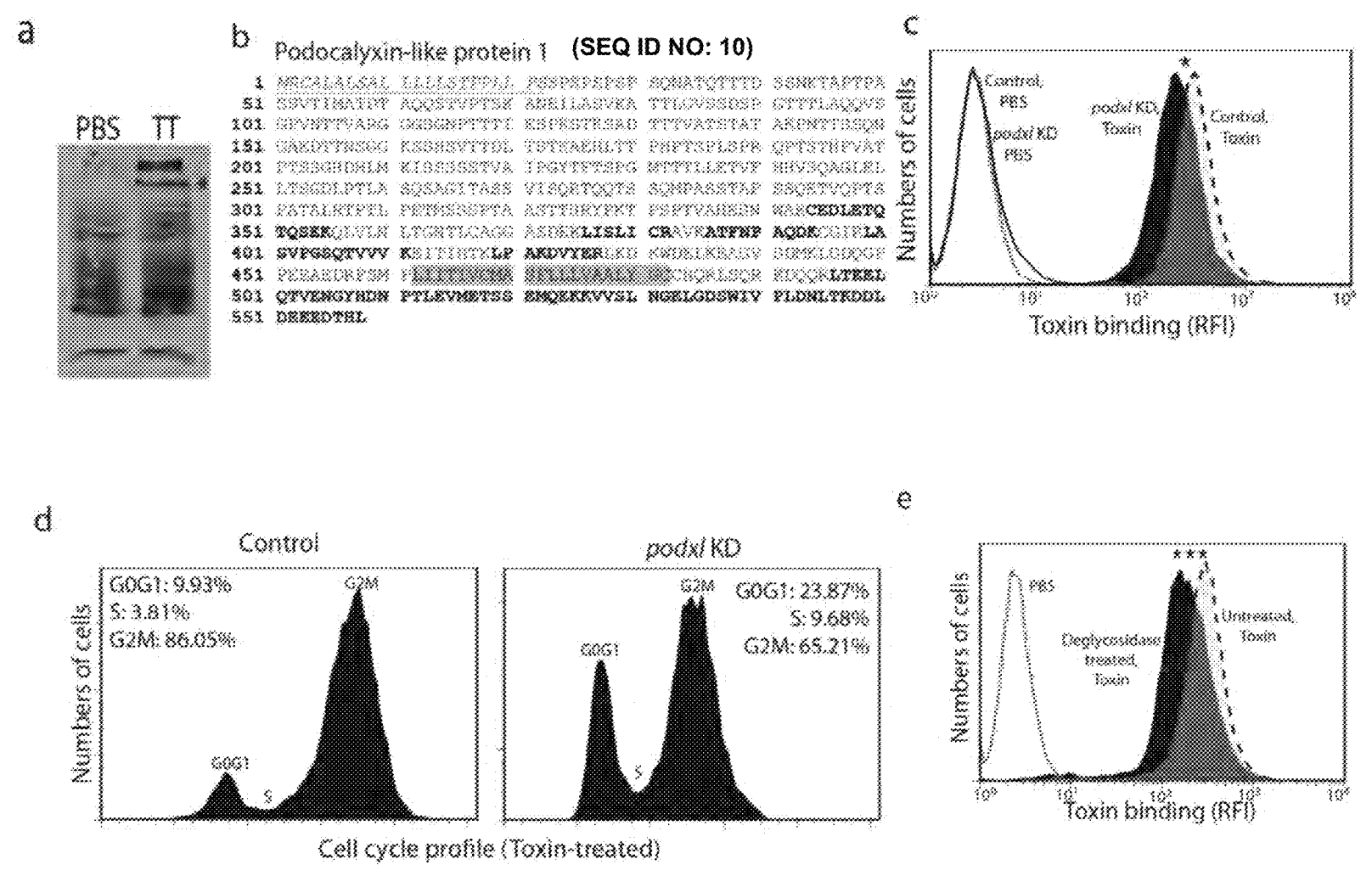
Figure 7:
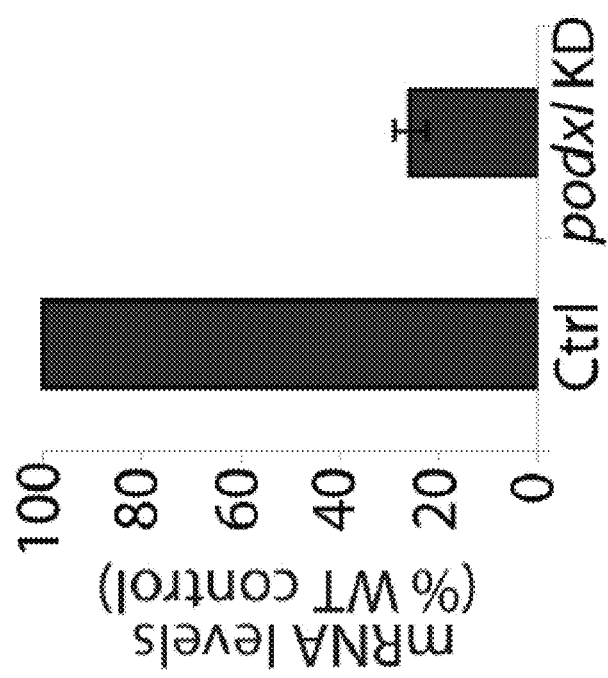

To gain further insight into the mechanism of action of typhoid toxin, its cellular receptor or receptors were identified. A highly purified biologically active typhoid toxin preparation was used to affinity purify biotin-labeled host cell surface interacting proteins. It was observed by LC-MS/MS analyses of interacting proteins that in human Henle-407 epithelial cells, typhoid toxin interacts with Podocalyxin-like protein 1 (PODXL) (FIGS. 2A-2B). PODXL is a member of the CD34 sialomucin protein family, which localizes to the apical side of epithelial cells and is also expressed in vascular endothelial cells (Ue et al., 2007, Mol. Biol. Cell. 18:1710-1722). Consistent with its potential role as a toxin receptor, shRNA-mediated depletion of PODXL resulted in a significant reduction in toxin binding (FIG. 2C and FIG. 7) and toxin-mediated cell cycle arrest (FIG. 2D).

Because it was observed that in addition to the intoxication of epithelial cells, typhoid toxin is capable of intoxicating a broad range of cells (FIG. 6), the interaction of typhoid toxin with surface proteins of other cell lines was examined by affinity purification and LC-MS/MS analyses. It was found that in macrophages, as well as in T and B cells, typhoid toxin interacts with receptor tyrosine phosphatase C, also known as CD45 (FIG. 8), which is ubiquitously expressed in hematopoietic cells other than erythrocytes and platelets (Hermiston et al., 2009, Immunol. Rev. 228:288-311). Although not wishing to be bound by any particular theory, these results suggest that typhoid toxin may engage different receptors in different cells.

Figures 2F, 2G:
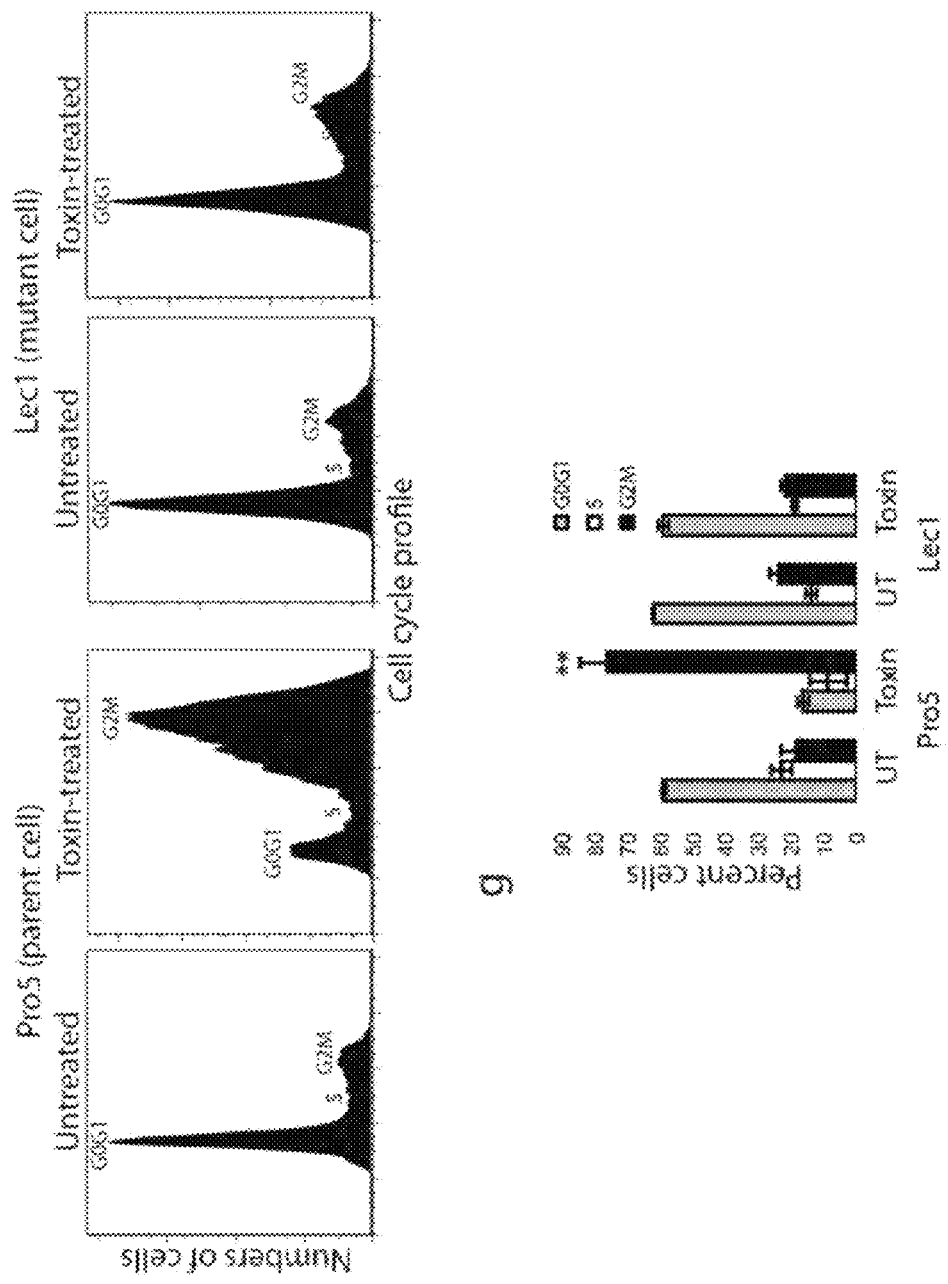
Figure 9:
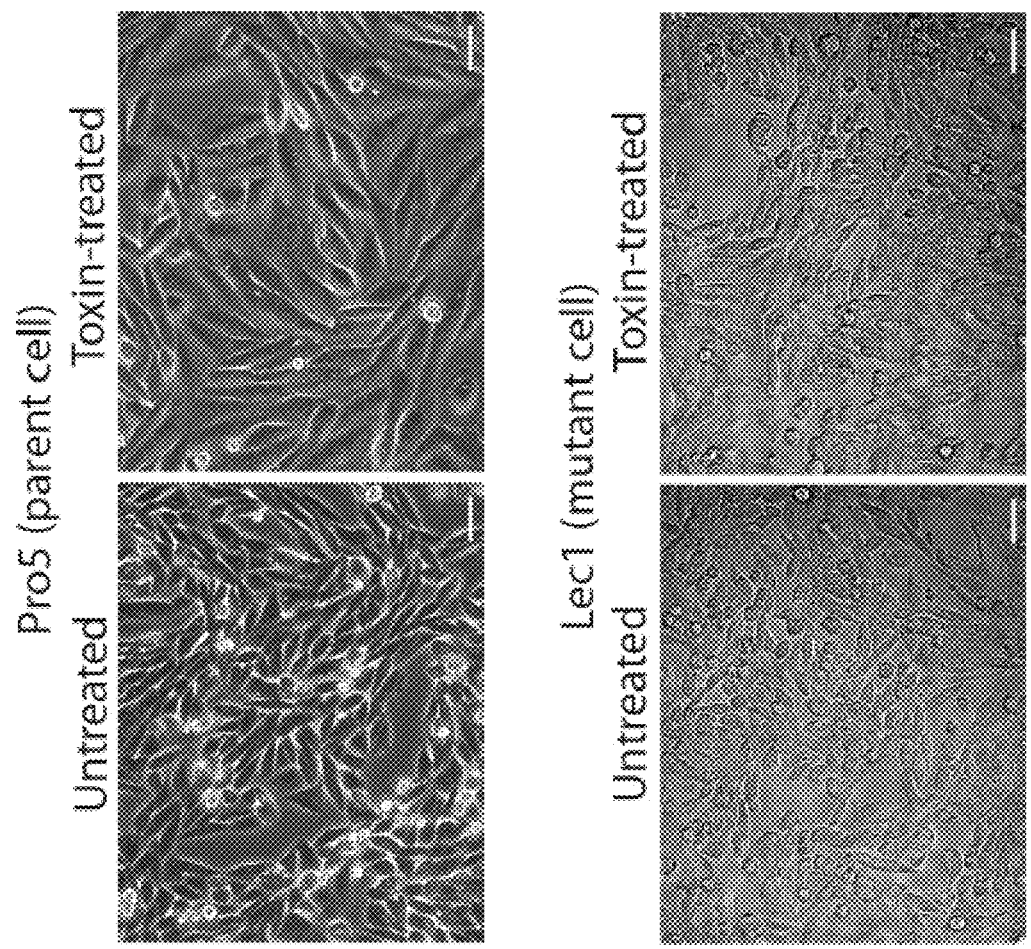

The identified typhoid toxin-interacting proteins, however, are all heavily glycosylated. It was hypothesized that typhoid toxin may interact with these different surface proteins through common carbohydrate moieties. This hypothesis was tested by examining typhoid toxin binding to cells that had been pre-treated with a mixture of glycosidases. It was observed that removal of surface glycans significantly reduced typhoid toxin binding (FIG. 2E). Furthermore, a cell line lacking all complex and hybrid N-glycans on glycoproteins due to a mutation in N-acetylglucosaminyltransferase I (Kumar et al., 1990, Proc. Natl. Acad. Sci. USA 87:9948-9952; Stanley et al., 1975, Proc. Natl. Acad. Sci. USA 3323-3327) was more resistant to typhoid toxin than its parent wild type cell line (FIGS. 2F, 2G, and FIG. 9). Although not wishing to be bound by any particular theory, these results indicate that a sugar moiety(s) on surface glycoproteins serves as a receptor for typhoid toxin.

Figure 2H:
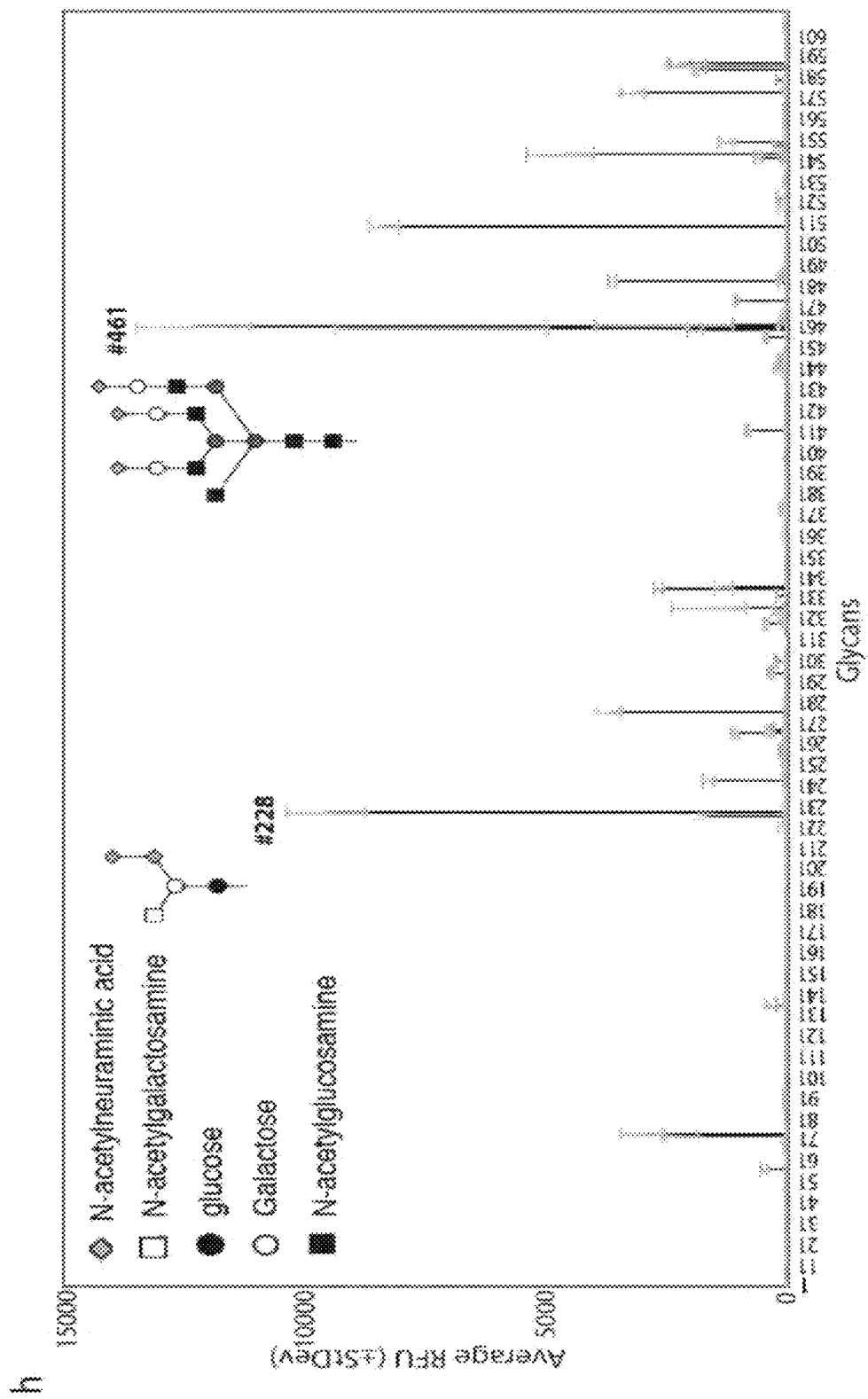

The nature of the glycan moiety on host cells that is recognized by typhoid toxin was identified. 610 glycans arrayed on a solid surface (Song et al., 2011, Nat. Methods 8:2085-2090) were probed for binding to biologically active, highly purified, fluorescently labeled typhoid toxin. This analysis revealed a complex binding pattern involving 4 main glycan groups (FIGS. 2H, 20, and 21). The first group, which is most commonly present in complex N-linked glycans, is represented by sialylated tri- or bi-antennary glycans (e. g. glycans #461, #483, and #482) with one or all of the branches terminally sialyated (note: glycan numbers correspond to the nomenclature used by the Consortium for Functional Glycomics, www.functionalglycomics.org). This group includes glycans with both Neu5Acα2-3 (e. g. #483) and Neu5Acα2-6 (e. g. #482) terminal linkages. However, although not wishing to be bound by any particular theory, typhoid toxin likely binds preferentially to Neu5Acα2-3 terminal linkages since glycan #483 showed stronger binding than glycan #482, which only differ in their terminal linkages (FIGS. 2H, 20, and 21). Furthermore, although not wishing to be bound by any particular theory, typhoid toxin likely preferentially binds tri-antennary over bi-antennary compounds, since glycan #461 exhibited the highest binding affinity. In addition, although not wishing to be bound by any particular theory, the toxin may also bind preferentially the type 2-N-acetyllactosamine unit (Galβ1-4GlcNAc), present in glycan #461, over type 1-N-acetyllactosamine unit (Galβ1-3GlcNAc), present in the very similar tri-antennary N-glycan #474, which showed lower binding affinity (FIGS. 2H, 20, and 21).

The second group consists of non-sialylated tri- or bi-antennary glycans also commonly found in complex N-linked glycans. Overall this group exhibited lower binding affinity than sialylated glycans. Although not wishing to be bound by any particular theory, this result suggests a preference of typhoid toxin for the terminal sialic acid modification.

Figure 10:
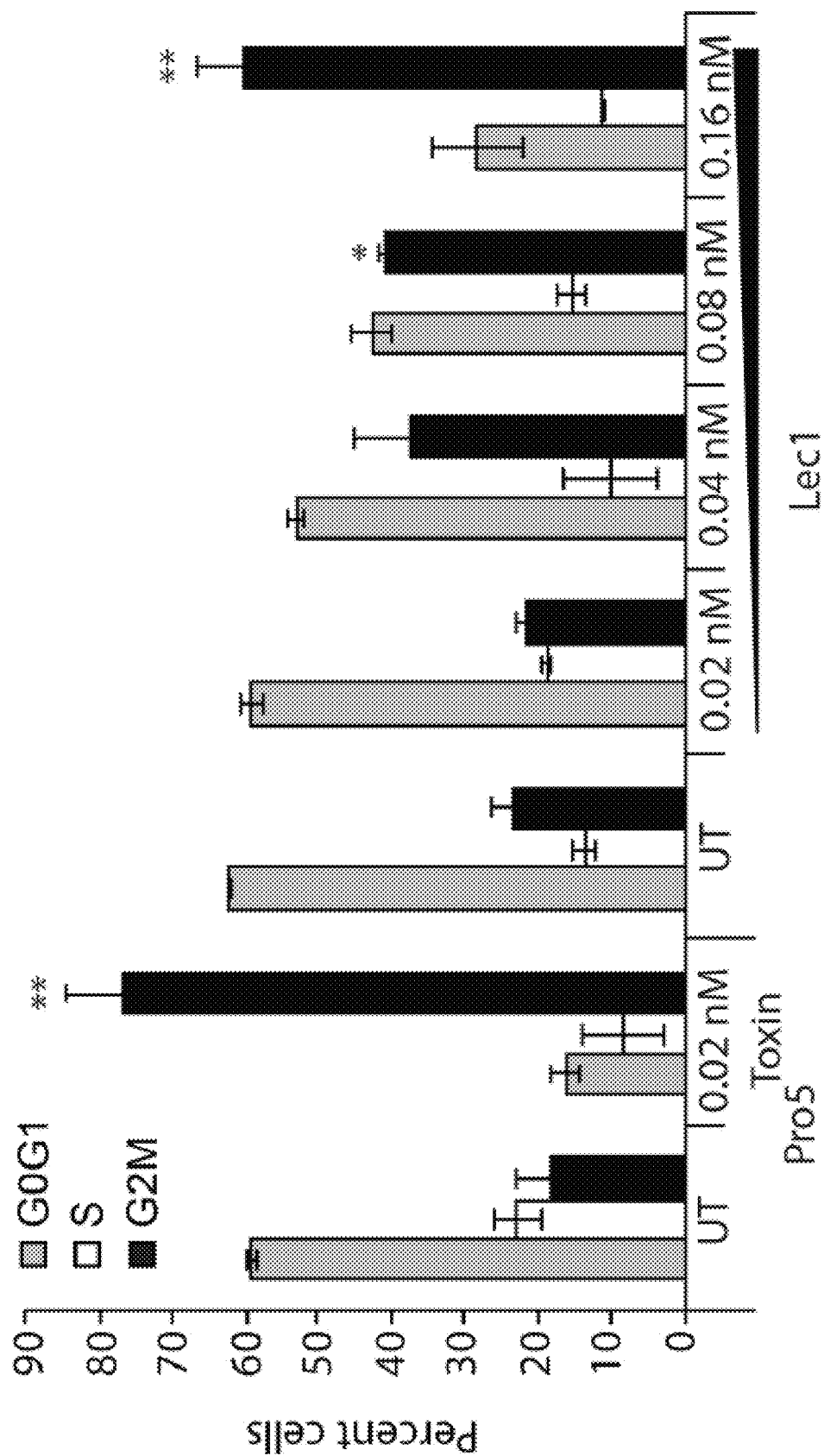

The third group consists of glycans commonly found in glycolipids, mostly as gangliosides. Six glycans were identified within this group (out of 75 present in the array) that showed toxin binding with various affinities. Although not wishing to be bound by any particular theory, the Neu5Acα 2-8 Neu5Ac disialoside group, present in ganglioside GD2 gangliosides (Yu et al., 2011, J. Oleo Sci. 60:537-544), (glycan #228), is likely preferred by the toxin since ganglioside GM3 (glycan #263) containing Neu5Ac monosialoside did not show toxin binding. Although not wishing to be bound by any particular theory, these results suggest that in certain cells, typhoid toxin may also be able to use glycolipids as a receptor. Consistent with this hypothesis, typhoid toxin was able to intoxicate an N-acetylglucosaminyltransferase I-deficient cell line although only when applied at high concentrations (FIG. 10).

The fourth group is defined by glycans commonly found on O-glycans. Among them is glycan #243, which shares the canonical structure of mucin type O-GalNAcylated glycan. Other glycans in this group share the canonical structure of O-GlcNAcylated glycans. The significance of this group for toxin-binding in vivo is unclear since they bind with low affinity and, unlike the other groups of glycans, they are mostly found within the nucleus and not on surface glycoproteins (Stein et al., 1994, Nature Struc. Biol. 1:591-596). Overall, typhoid toxin exhibits broad-binding specificity similar to that observed for pertussis toxin (Millen et al., 2010, Biochemistry 49:5954-5967), which also targets a large variety of cells, but significantly different from the much narrower specificity exhibited by other AB5 toxins, such as subtilase cytotoxin, which specifically recognizes glycans terminating in N-glycolylneuraminic acid (Neu5Gc) (Byres et al., 2008, Nature 456:648-652). However, unlike pertussis toxin, in which each of the heteromeric B subunits contributes diversity to the binding specificity (Millen et al., 2010, Biochemistry 49:5954-5967), typhoid toxin achieves this broad binding specificity with a single polypeptide, PltB, which forms its homomeric B subunit. Taken together, these results support the hypothesis that typhoid toxin can use as receptors a broad range of glycans preferentially on surface glycoproteins but also, although less efficiently, on surface glycolipids, providing a mechanistic explanation for its broad cell target specificity.

To uncover the organization of typhoid toxin, its crystal structure was solved to 2.4 Å resolution. The structure showed a complex of 5 PltB molecules and one molecule each of PltA and CdtB (FIG. 3A and Table 1), which is consistent with the stoichiometry observed by size exclusion chromatography combined with dynamic light scattering and quantitative amino acid composition analysis (FIG. 11).

TABLE 1

Statistics of Data Collection and Refinement

| Data | typhoid toxin |
|---|---|
| Integrate package | HKL2000 |
| Space Group | C222$_1$ |
| Unit Cell | 78.386, 261.076, 109.896 |
| (a, b, c in Å, β in degrees) | 90, 90, 90 |
| Wavelength (Å) | 1.5418 |
| Resolution (Å) | 31.91-2.393 (2.479-2.393) |
| R$_{merge}$ (%) | 9.7 (72.4) |
| I/sigma | 12.81 (2.62) |
| Completeness (%) | 97.14 (93.03) |
| No. of reflections | 284503 |
| No. of unique reflections | 43611 |
| Redundancy | 6.5 (5.8) |
| Wilson B factor (Å) | 41.49 |
| R/R$_{free}$ (%) | 0.2121 (0.3119)/0.2536 (0.3386) |
| No. of atoms | |
| Overall | 8526 |
| Macromolecules | 8102 |
| Glycerol | 48 |
| Water | 376 |
| Average B value (Å) | |
| Overall | 48.70 |
| Macromolecules | 49.00 |
| Solvent | 42.50 |
| R.m.s. deviations | |
| Bond (Å) | 0.004 |
| Angle (°) | 0.86 |
| Ramachandran plot statistics (%) | |
| Most favorable | 89.9 |
| Additionally allowed | 9.0 |
| Generously allowed | 1.1 |
| Disallowed | 0.0 |

Values in parentheses are for the highest resolution shell.

Figure 3A:
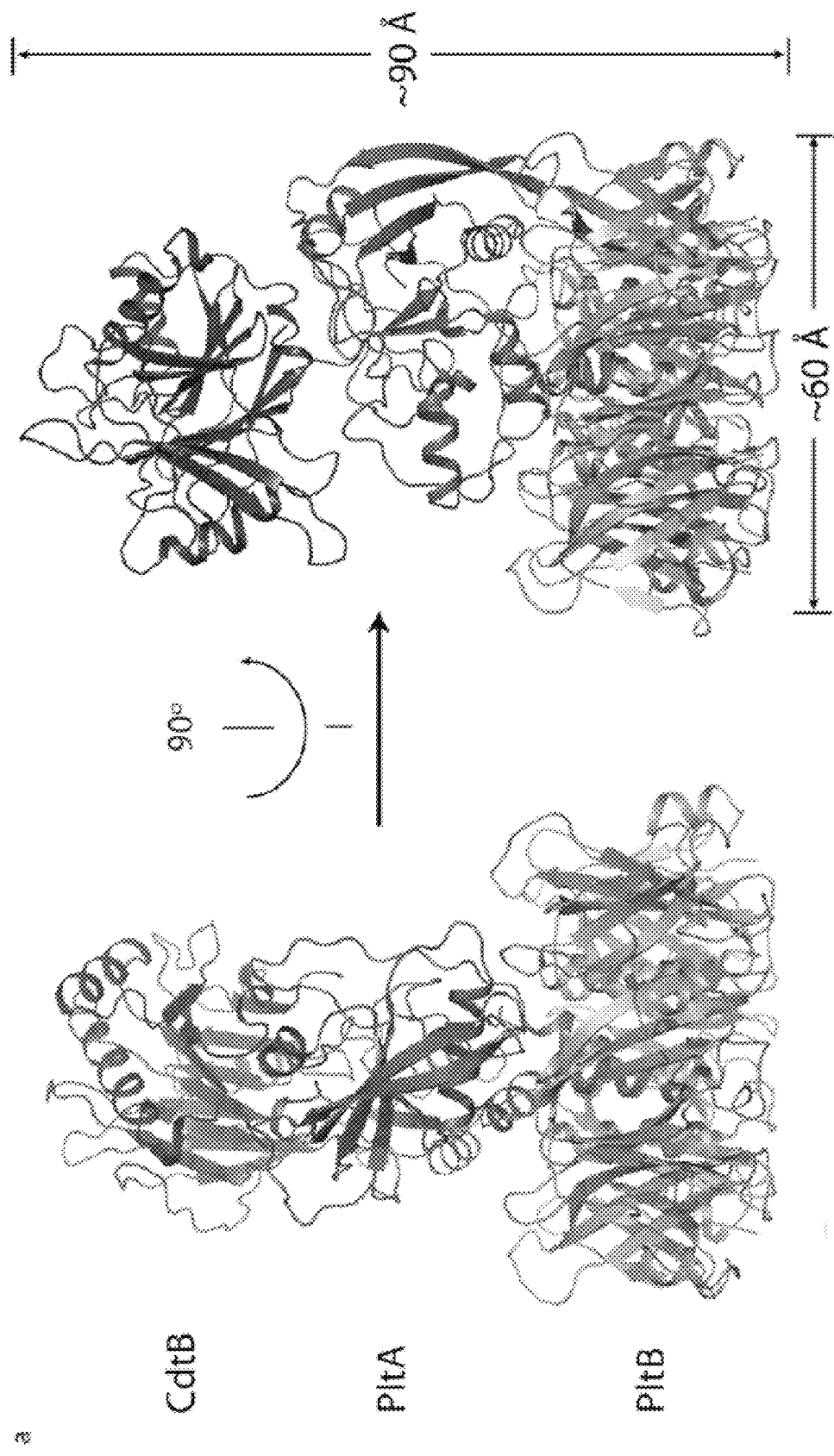
Figures 3B, 3C, 3D, 3E:
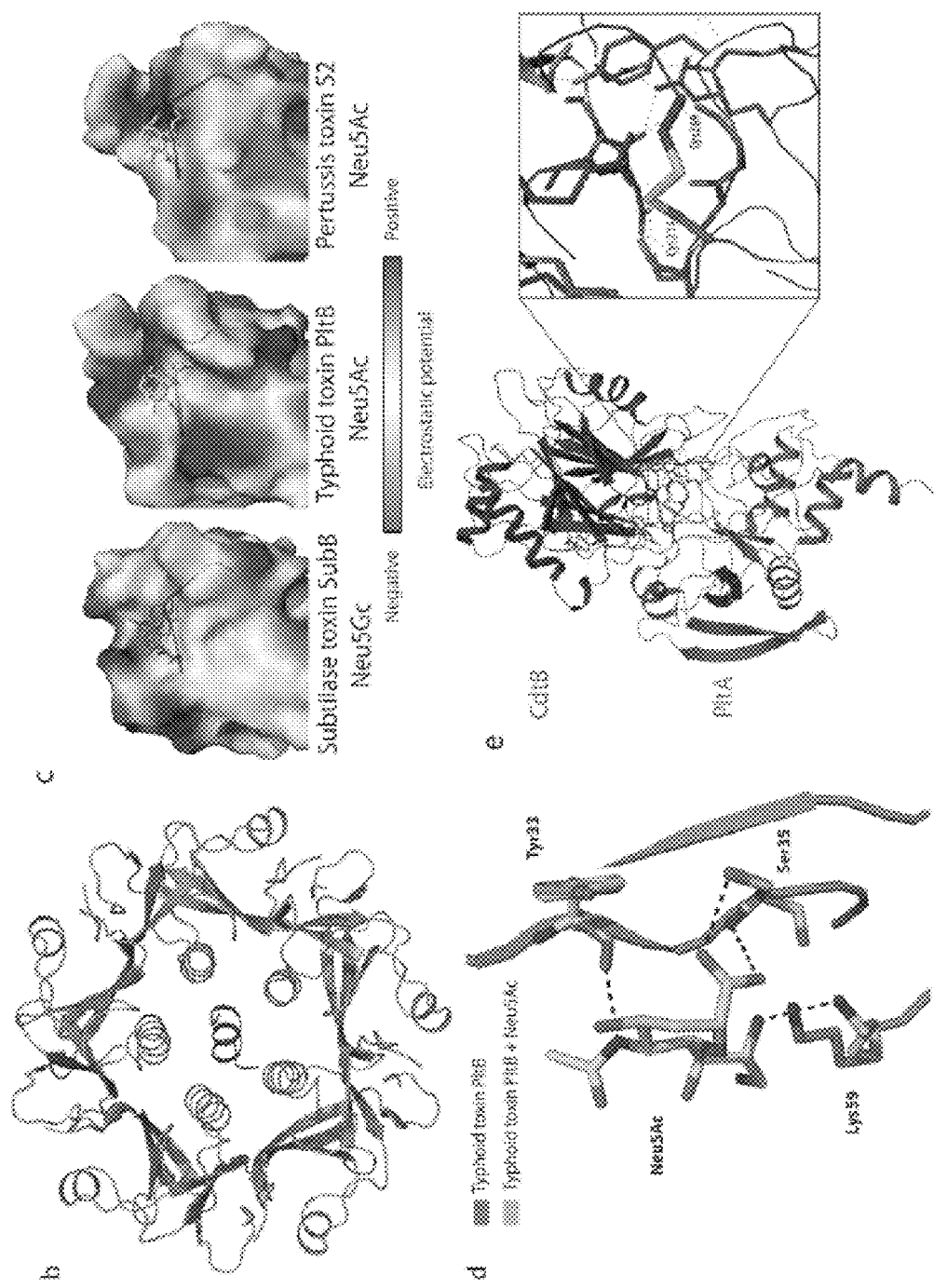

These results indicate an unprecedented A$_2$B$_5$ organization for typhoid toxin, which is in contrast to other known AB$_5$ toxins that have only one A subunit (Beddoe et al., 2010, Trends Biochem. Sci. 35:411-418; Merrit and Hol, 1995, Curr. Opin. Struct. Biol. 5:165-171). The pyramid shaped complex has a height of ~90 Å and a maximum width of ~60 Å (FIG. 3A), with CdtB located at the vertex, connected by PltA to a pentameric disc at the base of the pyramid made of 5 monomers of PltB (FIGS. 3A-3B). The tandem linear arrangement of the enzymatic subunits PltA and CdtB dictates that there are no interactions between CdtB and PltB. As predicted by the amino acid sequence similarities, the PltA and CdtB subunits exhibit a very similar structure to the pertussis toxin S1 (and other ADP ribosyl transferases; Stein et al., 1994, Structure 2:45-57) and to the CdtB subunit of Cytolethal distending toxin (Nesié et al., 2004, Nature 429:429-433).

Figure 12:
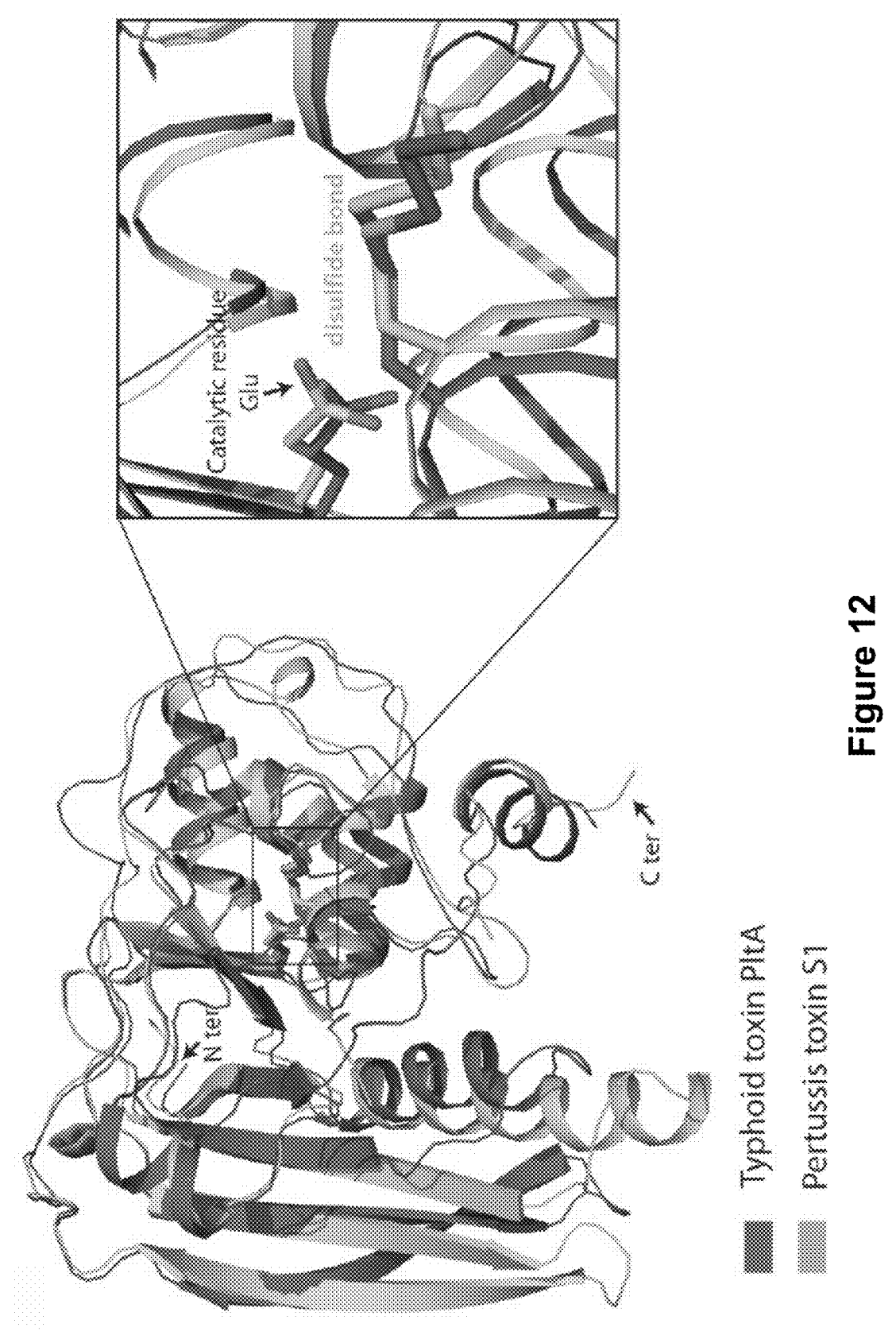
Figure 13:
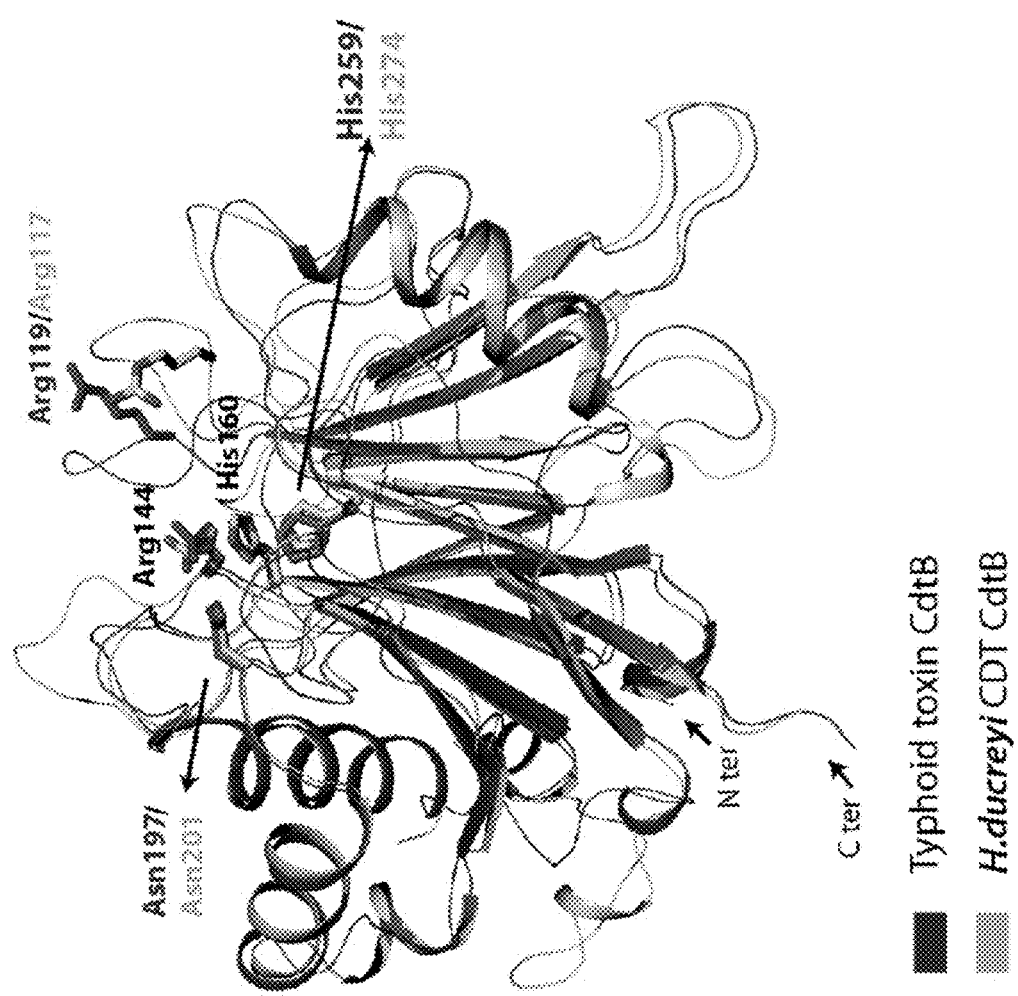
FIG. 13 is an illustration depicting structure alignment between CdtB from typhoid toxin and from H. ducreyi CDT. The conserved catalytic (His160 and His 274) and DNA-contact (Arg117, Arg144, and Asn201) are shown.

PltA aligns very well to the pertussis toxin S1 domain with a root-mean-squared deviation (rmsd) of 2.168 Å over 140 Cα atoms (with 31% sequence identity) (FIG. 12). The positions of the conserved catalytic residues (Glu133 in typhoid toxin and Glu129 in pertussis toxin S1), as well as the disulfide bonds (Cys56-Cys207 in typhoid toxin and Cys41-Cys201 in pertussis toxin S1) overlap almost completely (FIG. 12). The latter indicates that, similarly to the pertussis toxin S1 subunit (Stein et al., 1994, Structure 2:45-57; Locht et al., 2011, FEBS J. 278:4668-4682), PltA would have to be reduced to allow the access of NAD and its putative substrates to the active site, and consequently, a reducing activating step must be necessary prior to contacting its host cell target(s). Typhoid toxin CdtB aligns very well to the Haemophilus ducreyi CdtB with an rmsd of 0.947 Å over 206 Cα atoms (with 52% sequence identity) (FIG. 13). The positions of the conserved catalytic residues in Typhoid toxin's CdtB overlap almost completely with those of its homolog in H. ducreyi.

Similar to the B subunits of other AB$_5$ toxins (Beddoe et al., 2010, Trends Biochem Sci. 35:411-418; Byres et al., 2008, Nature 456:648-652), the PltB oligomer is arranged as a pentamer with a central channel that is lined by 5 helixes (FIG. 3B). As predicted from its amino acid sequence similarity and consistent with the data presented above, the PltB protomer shows a typical oligosaccharide-binding fold on the side of the pentamer (FIGS. 3C and 14), a location similar to that of toxins that preferentially bind glycoproteins but different from those that preferentially bind glycolipids, which have the sugar-binding pockets on the membrane-proximal face of the toxin (Beddoe et al., 2010, Trends Biochem Sci. 35:411-418). Therefore, these findings are consistent with the observation that typhoid toxin preferentially binds glycans present on surface glycoproteins over those present on glycolipids (FIGS. 20 and 21).

Figure 14:
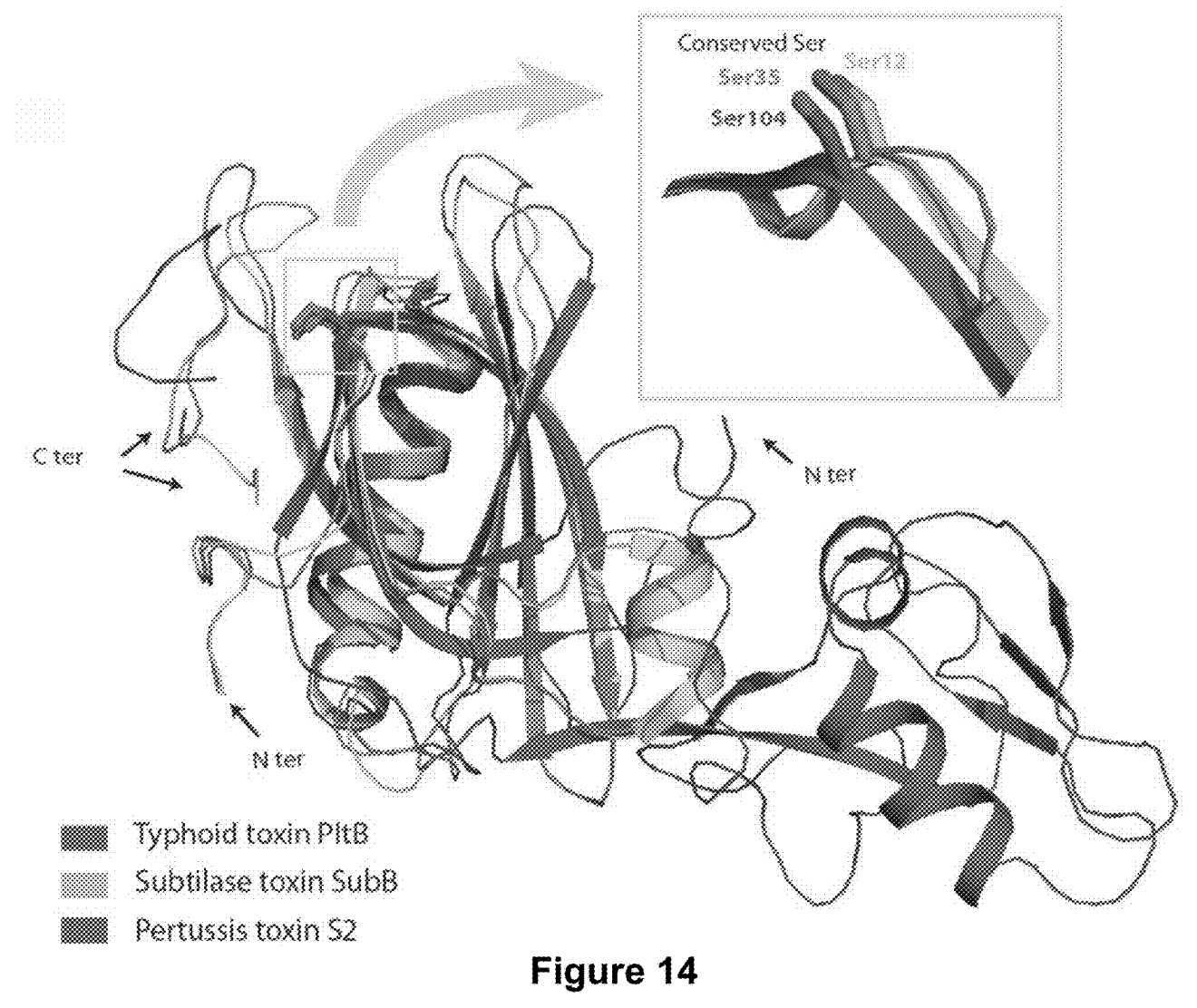

The monomer of typhoid holotoxin PltB aligns very well with SubB, the subtilase cytotoxin B subunit, with an rmsd of ~0.5 Å over 97 Cα atoms (with 50% sequence identity) (FIG. 14). Of note, the positions of the conserved putative sugar-binding residue Ser35 overlap very well, although in SubB Ser35 is located within a β-strand while in PltB is placed within a loop (FIGS. 3C and 14). The predicted sugar-binding pocket in PltB is not as deep and appears more extended than in SubB, which also differs in surface charge distribution (FIG. 3C). Although not wishing to be bound by any particular theory, these differences may account for the significantly different binding specificities exhibited by these two toxins (Byres et al., 2008, Nature 456:648-652). PltB was also compared to the pertussis toxin S2 B subunit (Stein et al., 1994, Nat. Struct. Biol. 1:591-596). Although their overall amino sequence similarity is low, the structures can be aligned very well around their sugar-binding domains with an rmsd of 1.752 Å over 80 Cα atoms (FIG. 14).

Figure 15:
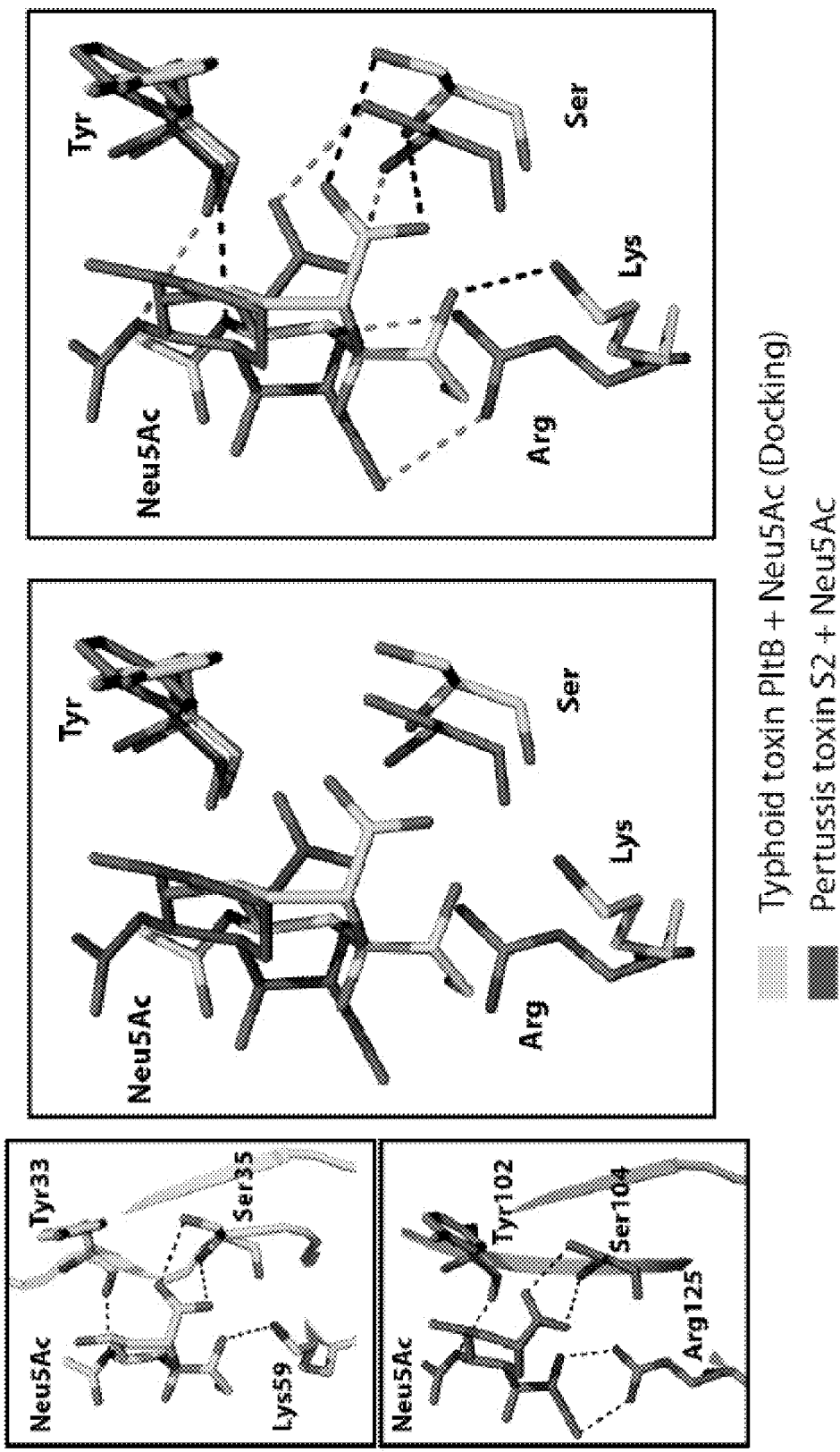
FIG. 15 is a series of images depicting conserved sugar-binding residues in typhoid toxin PltB and pertussis toxin S2. The position of the sugar ligand N-acetylneuraminic acid (Neu5Ac) relative to key residues of pertussis toxin S2 (from the crystal structure) and PltB (from molecular docking) is depicted.

Residues in pertussis toxin S2 involved in sugar binding (Tyr102, Ser104, Arg125) are well conserved in PltB (Tyr33, Ser35, Lys59) (FIG. 3D), and the charge distribution and architecture of the sugar-binding pockets are similar (FIG. 3C). This is consistent with the observation that, despite overall less conservation, these two B subunits share sugar-binding specificity. For example, several of the glycans that bind typhoid toxin possess an Neu5Ac moiety at their terminal end, a determinant that also binds pertussis toxin (Millen et al., 2010, Biochemistry 49:5954-5967). Structural modeling of Neu5Ac bound to PltB predicts almost identical interaction to those observed in the atomic structure of pertussis toxin bound to Neu5Ac (FIGS. 3C-3D and FIG. 15).

Figures 4A, 4B, 4C, 4D:
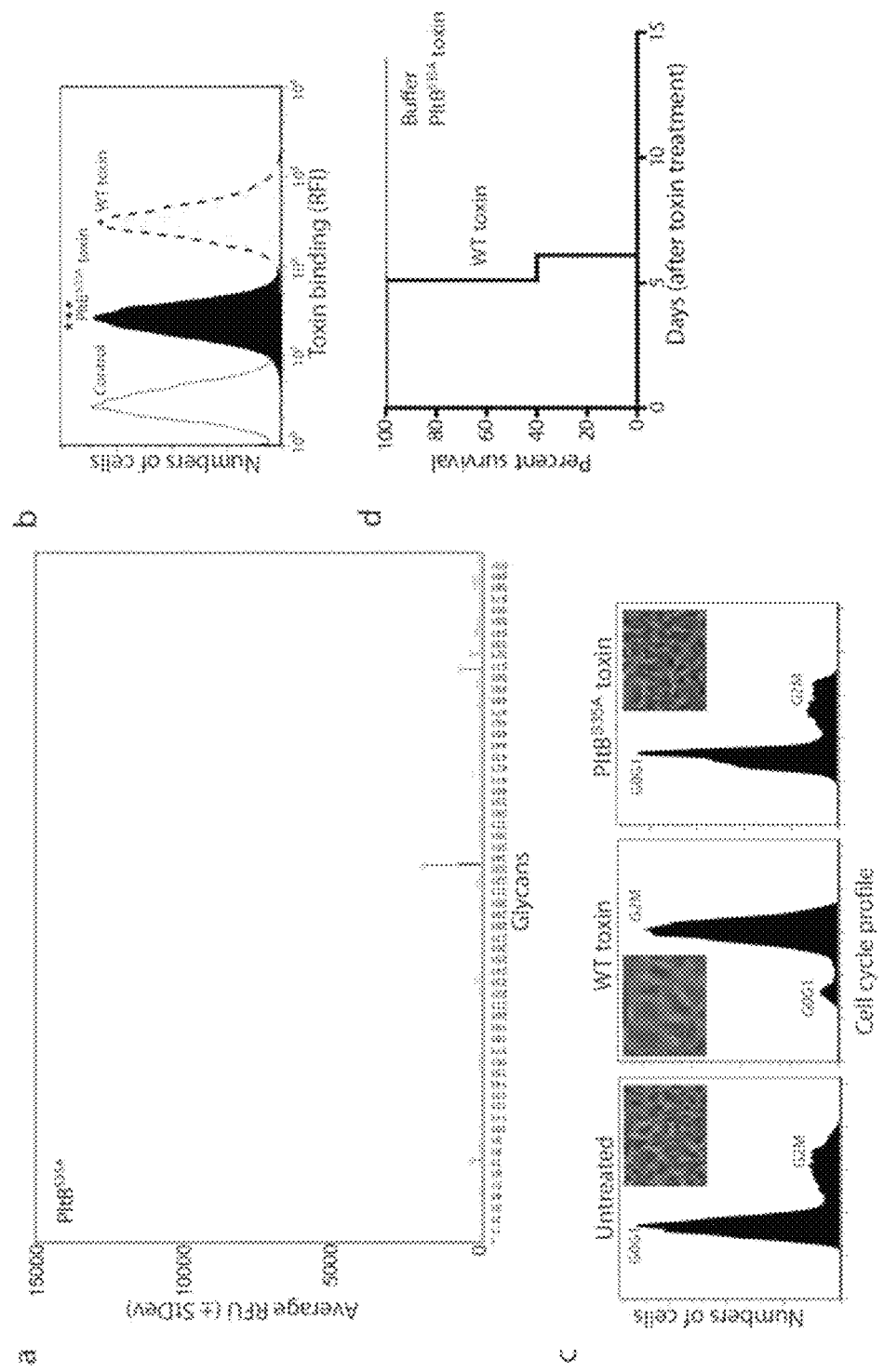

Consistent with the structural predictions, a mutation in the sugar-binding pocket of PltB (PltB Ser35A) abrogated the ability of typhoid toxin to bind glycans in glycoarray (FIGS. 4A and 22) and surface plasmon resonance assays (FIG. 16), and the ability of the toxin to bind (FIG. 4B) and intoxicate (FIG. 4C) cultured cells or to cause symptoms when systemically applied to mice (FIG. 4D). These results are also consistent with the explanation that there is a single carbohydrate-binding domain in typhoid toxin since the mutant abrogated binding to all carbohydrates. Surface plasmon resonance assays also indicated that on average at least for the glycan tested (GD2), each PltB pentamer binds 2.5 sugar molecules with an affinity of ~1.2 mM (FIG. 16). However, the glycoarray analysis predicts that the binding affinity is likely to be higher for other more complex glycans.

The interaction of PltA with the PltB oligomer occurs largely through its carboxy terminus, which buries 1,657 Å$^2$ and has a ΔiG of −17.7 kcal/mol. A critical element in this interaction is a short helix at the carboxyterminal end of PltA, which inserts into the hydrophobic lumen of the PltB channel (FIGS. 3B and 17) and stabilizes the complex by critical interactions mediated by Pro234, Val235, Ile236, Leu238, Ile239, and Leu240 in PltA.

Figures 4E, 4F, 4G:
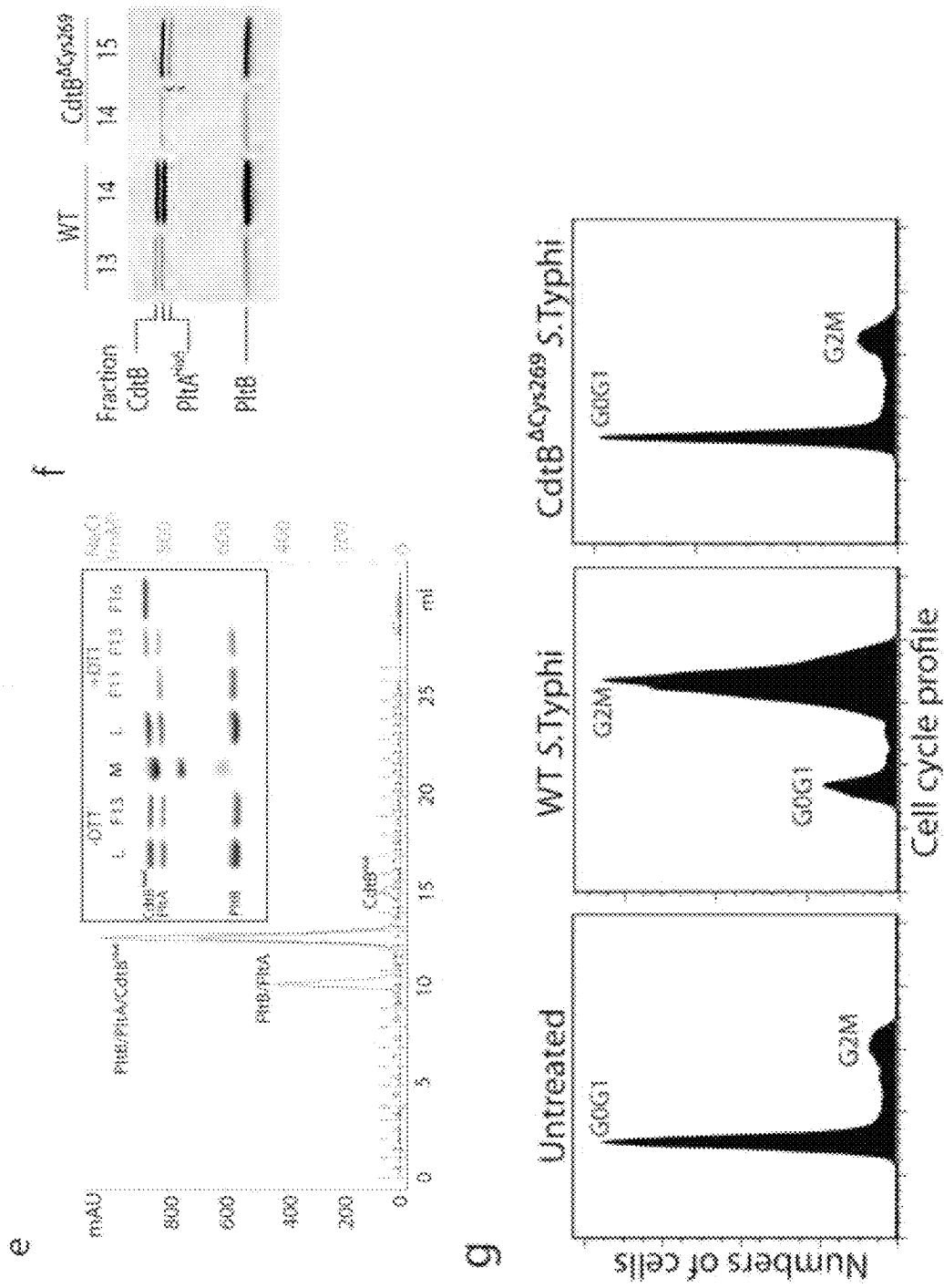

The most salient feature of the interface between PltA and CdtB is a disulfide bond between Cys214 of PltA and Cys269 of CdtB (FIG. 3E). The rest of the interface between the two A subunits is unremarkable, burying only 950 Å$^2$ with a ΔiG of only −5.2 kcal/mol. Although not wishing to be bound by any particular theory, this observation suggests that the disulfide bound is essential for the integrity of the holotoxin. Consistent with this hypothesis, subjecting the typhoid toxin to reducing conditions resulted in the dissociation of CdtB from the PltA-PltB complex (FIG. 4E). Furthermore, introduction of a mutation in Cys269 of CdtB destabilized the holotoxin complex in vitro (FIG. 4F), and resulted in a loss of CdtB-dependent toxicity in S. typhi-infected cells (FIGS. 4G and 18). This mutation also prevented the assembly of CdtB into its vesicle carrier intermediates that can be visualized as fluorescent puncta in S. typhi-infected cells (FIGS. 4H-4I), despite the fact that the mutant was expressed at equivalent levels to those of wild type (FIG. 19). These results support the hypothesis that the CdtB Cys269/PltACys214 disulfide bond is critical for the assembly of typhoid toxin holotoxin in the periplasm of the bacteria.

Figures 4H, 4I, 4J:
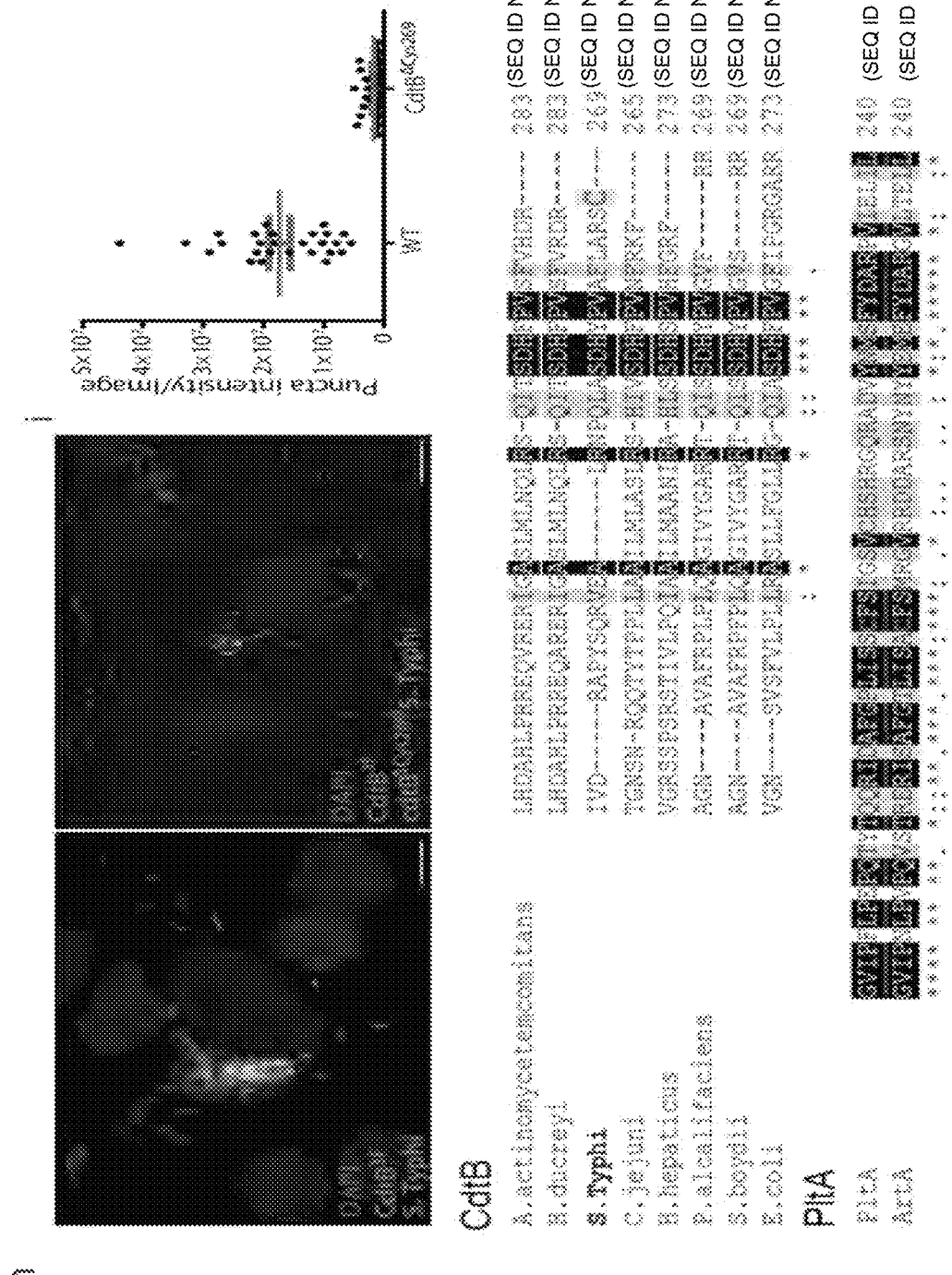

Even though the sequence conservation between typhoid toxin's CdtB and that of its cytolethal distending toxin homologs is very high, the Cys269 is unique to Typhoid toxin's CdtB (FIG. 4J). Likewise, although all close homologs of PltA including ArtA, a closely related mono ADP ribosyl transferase from S. typhimurium (Saitoh et al., 2005, Microbiology 151:3089-3096), have only two Cys that form an intramolecular disulfide bond, PltA is unique in that it has a third Cys (Cys214) to pair with S. typhi's CdtB (FIG. 4J). Therefore typhoid toxin's CdtB has been specifically adapted for its tethering to the PltA/PltB complex by the evolution of uniquely positioned Cys residues in both PltA and CdtB. The covalent linkage of CdtB to the PltA/PltB complex by a disulfide bond thus ensures that CdtB and PltA are simultaneously delivered to the same target cell. Furthermore, this arrangement would ensure that, after endocytosis and retrograde transport to its place of translocation (most likely the endoplasmic reticulum), PltA and CdtB would be freed from one another upon reduction of the disulfide bond by local reductases, thus allowing them to become competent for translocation to the cytosol and delivery to their place of action.

These results provide unique insight into typhoid toxin, a critical virulence factor of S. typhi, revealing unprecedented features for a bacterial exotoxin and providing significant information on the pathogenesis of typhoid fever. The potential implication of typhoid toxin in the development of symptoms during the acute, life threatening phase of typhoid fever, combined with its unique architecture, can be useful for the development of novel, potentially life-saving therapeutic interventions against this disease.

Immune Response to Typhoid Toxin

To test the ability of typhoid toxin to stimulate the production of neutralizing antibodies, mice were immunized with a purified preparation of inactivated typhoid toxin ("toxoid"). The typhoid toxin toxoid was generated by introducing mutations in the catalytic sites of its two enzymatic subunits, PltA (PltAE133A) and CdtB (CdtBH160Q). Animals immunized with the toxin mounted a strong immune response to the toxin generating toxin neutralizing antibodies (FIG. 23). Importantly, antibody responses were generated even in the absence of an immunological adjuvant, suggesting that the toxin itself may have adjuvant activity. In contrast, animals inoculated with an otherwise identical typhoid toxin toxoid preparation but carrying a mutation in the glycan-binding site of its PltB "B" subunit (PltBS35A) was only able to stimulate an immune response when administered with an immunological adjuvant (e.g., Alumn). Although not wishing to be bound by any particular theory, these results are consistent with the explanation that Typhoid toxin has immune adjuvant activity and that such activity is dependent on the toxin's ability to bind glycans since a glycan-defective mutant did not stimulate a strong immune response in the absence of an adjuvant (FIG. 23). These observations have profound implications for the potential design of a typhoid fever vaccine. Current vaccines against typhoid fever are composed of the so called Vi antigen, a surface polysaccharide of *Salmonella Typhi*. To render it sufficiently immunogenic, the polysaccharide is conjugated to a protein carrier. In addition, an immunological adjuvant is required to stimulate immune responses to the polysaccharide-protein conjugate. The results described herein support the conclusion that a Typhoid toxin toxoid could serve as 1) a potent immunogen to stimulate anti-toxin immunity; 2) a protein carrier (to stimulate immune responses to polysaccharide antigens such as, by way of non-limiting example, the Vi antigen); and 3) as an immunological adjuvant to stimulate an immune response.

As shown herein, patients convalescent of typhoid fever mount a strong serum immune response to typhoid toxin. Due to the lack of specific symptomatology diagnosing typhoid fever remains a challenge (Bhutta, 2006, BMJ 333:78-82; Parry et al., 2011, Expert Rev Anti Infect Ther 9:711-725). A positive blood culture test remains the gold standard, but since the bacterial load in the blood is so low, this test is often negative even in positive cases of typhoid fever. Thus, there is an urgent need for a practical, rapid test to diagnose typhoid fever. Although there are a number of serological tests such as the Widal test, their specificity and sensitivity are extremely poor. Typhoid toxin is an ideal antigen to diagnose typhoid fever since it is the only antigen known that is specific for the only two *Salmonella enterica* serovars that can cause typhoid fever: *Salmonella Typhi* and *Salmonella Paratyphi*. Patients convalescent of typhoid fever had a high serum antibody levels against typhoid toxin. Importantly, antibody levels were high upon admission to the Hospital, and remain high for several weeks (FIG. 24). In contrast, control patients with no history of typhoid fever had no serum antibodies to the toxin. These results indicate that typhoid toxin can provide the bases for the development of a diagnostic test for typhoid fever.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunological composition comprising
   a.) a mutant Pertussin-like toxin A (PltA) polypeptide comprising the mutation E133A within SEQ ID NO: 8,
   b.) a mutant Cytolethal distending toxin B (CdtB) polypeptide comprising the mutation H160Q within SEQ ID NO: 7 and
   c.) a Pertussin-like toxin B (PltB) polypeptide.

2. A method of inducing an immune response in a subject, the method comprising administering a therapeutically effective amount of the immunological composition of claim 1 to the subject.

3. The method of claim 2, wherein the polypeptide comprises at least one additional mutation that disrupts its enzymatic activity.

4. The method of claim 2, wherein the immunological composition comprises a bacterium.

5. The method of claim 2, further comprising administering an antibiotic to the subject.

6. The immunological composition of claim 1 wherein the-PltB polypeptide comprises a mutant PltB polypeptide comprising the mutation S35A within SEQ ID NO: 9.

* * * * *

SEQUENCE LISTING

```
<160> NUMBER OF SEQ ID NOS: 21

<210> SEQ ID NO 1
<211> LENGTH: 60
<212> TYPE: DNA
<213> ORGANISM: Artificial Sequence
<220> FEATURE:
<223> OTHER INFORMATION: chemically synthesized

<400> SEQUENCE: 1
gatccccgga caaatgggat gaactattca agagatagtt catcccattt gtccttttc          60

<210> SEQ ID NO 2
<211> LENGTH: 60
<212> TYPE: DNA
<213> ORGANISM: Artificial Sequence
<220> FEATURE:
<223> OTHER INFORMATION: chemically synthesized

<400> SEQUENCE: 2
tcgagaaaaa ggacaaatgg gatgaactat ctcttgaata gttcatccca tttgtccggg          60

<210> SEQ ID NO 3
<211> LENGTH: 19
<212> TYPE: DNA
<213> ORGANISM: Artificial Sequence
<220> FEATURE:
<223> OTHER INFORMATION: chemically synthesized

<400> SEQUENCE: 3
accggggact acaaccctg                                                       19

<210> SEQ ID NO 4
<211> LENGTH: 22
<212> TYPE: DNA
<213> ORGANISM: Artificial Sequence
<220> FEATURE:
<223> OTHER INFORMATION: chemically synthesized

<400> SEQUENCE: 4
tgtggtgtta ggtttagctg tg                                                   22

<210> SEQ ID NO 5
<211> LENGTH: 22
<212> TYPE: DNA
<213> ORGANISM: Artificial Sequence
<220> FEATURE:
<223> OTHER INFORMATION: chemically synthesized

<400> SEQUENCE: 5
gattactgct ctggctccta gc                                                   22
```

-continued

<210> SEQ ID NO 6
<211> LENGTH: 22
<212> TYPE: DNA
<213> ORGANISM: Artificial Sequence
<220> FEATURE:
<223> OTHER INFORMATION: chemically synthesized

<400> SEQUENCE: 6
gactcatcgt actcctgctt gc        22

<210> SEQ ID NO 7
<211> LENGTH: 269
<212> TYPE: PRT
<213> ORGANISM: Salmonella typhi

<400> SEQUENCE: 7

Met Lys Lys Pro Val Phe Phe Leu Leu Thr Met Ile Ile Cys Ser Tyr
1               5                   10                  15

Ile Ser Phe Ala Cys Ala Asn Ile Ser Asp Tyr Lys Val Met Thr Trp
            20                  25                  30

Asn Leu Gln Gly Ser Ser Ala Ser Thr Glu Ser Lys Trp Asn Val Asn
        35                  40                  45

Val Arg Gln Leu Leu Ser Gly Thr Ala Gly Val Asp Ile Leu Met Val
    50                  55                  60

Gln Glu Ala Gly Ala Val Pro Thr Ser Ala Val Pro Thr Gly Arg His
65                  70                  75                  80

Ile Gln Pro Phe Gly Val Gly Ile Pro Ile Asp Glu Tyr Thr Trp Asn
                85                  90                  95

Leu Gly Thr Thr Ser Arg Gln Asp Ile Arg Tyr Ile Tyr His Ser Ala
            100                 105                 110

Ile Asp Val Gly Ala Arg Arg Val Asn Leu Ala Ile Val Ser Arg Gln
        115                 120                 125

Arg Ala Asp Asn Val Tyr Val Leu Arg Pro Thr Thr Val Ala Ser Arg
    130                 135                 140

Pro Val Ile Gly Ile Gly Leu Gly Asn Asp Val Phe Leu Thr Ala His
145                 150                 155                 160

Ala Leu Ala Ser Gly Gly Pro Asp Ala Ala Ile Val Arg Val Thr
                165                 170                 175

Ile Asn Phe Phe Arg Gln Pro Gln Met Arg His Leu Ser Trp Phe Leu
            180                 185                 190

Ala Gly Asp Phe Asn Arg Ser Pro Asp Arg Leu Glu Asn Asp Leu Met
        195                 200                 205

Thr Glu His Leu Glu Arg Val Val Ala Val Leu Ala Pro Thr Glu Pro
    210                 215                 220

Thr Gln Ile Gly Gly Ile Leu Asp Tyr Gly Val Ile Val Asp Arg
225                 230                 235                 240

Ala Pro Tyr Ser Gln Arg Val Glu Ala Leu Arg Asn Pro Gln Leu Ala
                245                 250                 255

Ser Asp His Tyr Pro Val Ala Phe Leu Ala Arg Ser Cys
            260                 265

<210> SEQ ID NO 8
<211> LENGTH: 242
<212> TYPE: PRT
<213> ORGANISM: Salmonella typhi

<400> SEQUENCE: 8

Met Lys Lys Leu Ile Phe Leu Thr Leu Ser Ile Val Ser Phe Asn Asn

-continued

```
1               5                   10                  15
Tyr Ala Val Asp Phe Val Tyr Arg Val Asp Ser Thr Pro Pro Asp Val
                20                  25                  30

Ile Phe Arg Asp Gly Phe Ser Leu Leu Gly Tyr Asn Arg Asn Phe Gln
                35                  40                  45

Gln Phe Ile Ser Gly Arg Ser Cys Ser Gly Gly Ser Ser Asp Ser Arg
                50                  55                  60

Tyr Ile Ala Thr Thr Ser Ser Val Asn Gln Thr Tyr Ala Ile Ala Arg
 65                 70                  75                  80

Ala Tyr Tyr Ser Arg Ser Thr Phe Lys Gly Asn Leu Tyr Arg Tyr Gln
                85                  90                  95

Ile Arg Ala Asp Asn Asn Phe Tyr Ser Leu Leu Pro Ser Ile Thr Tyr
                100                 105                 110

Leu Glu Thr Gln Gly Gly His Phe Asn Ala Tyr Glu Lys Thr Met Met
                115                 120                 125

Arg Leu Gln Arg Glu Tyr Val Ser Thr Leu Ser Ile Leu Pro Glu Asn
                130                 135                 140

Ile Gln Lys Ala Val Ala Leu Val Tyr Asp Ser Ala Thr Gly Leu Val
145                 150                 155                 160

Lys Asp Gly Val Ser Thr Met Asn Ala Ser Tyr Leu Gly Leu Ser Thr
                165                 170                 175

Thr Ser Asn Pro Gly Val Ile Pro Phe Leu Pro Glu Pro Gln Thr Tyr
                180                 185                 190

Thr Gln Gln Arg Ile Asp Ala Phe Gly Pro Leu Ile Ser Ser Cys Phe
                195                 200                 205

Ser Ile Gly Ser Val Cys His Ser His Arg Gly Gln Arg Ala Asp Val
                210                 215                 220

Tyr Asn Met Ser Phe Tyr Asp Ala Arg Pro Val Ile Glu Leu Ile Leu
225                 230                 235                 240

Ser Lys
```

<210> SEQ ID NO 9
<211> LENGTH: 137
<212> TYPE: PRT
<213> ORGANISM: Salmonella typhi

<400> SEQUENCE: 9

```
Met Tyr Met Ser Lys Tyr Val Pro Val Tyr Thr Leu Leu Ile Leu Ile
 1               5                  10                  15

Tyr Ser Phe Asn Ala Ser Ala Glu Trp Thr Gly Asp Asn Thr Asn Ala
                20                  25                  30

Tyr Tyr Ser Asp Glu Val Ile Ser Glu Leu His Val Gly Gln Ile Asp
                35                  40                  45

Thr Ser Pro Tyr Phe Cys Ile Lys Thr Val Lys Ala Asn Gly Ser Gly
                50                  55                  60

Thr Pro Val Val Ala Cys Ala Val Ser Lys Ser Ile Trp Ala Pro
 65                 70                  75                  80

Ser Phe Lys Glu Leu Leu Asp Gln Ala Arg Tyr Phe Tyr Ser Thr Gly
                85                  90                  95

Gln Ser Val Arg Ile His Val Gln Lys Asn Ile Trp Thr Tyr Pro Leu
                100                 105                 110

Phe Val Asn Thr Phe Ser Ala Asn Ala Leu Val Gly Leu Ser Ser Cys
                115                 120                 125

Ser Ala Thr Gln Cys Phe Gly Pro Lys
```

```
        130                 135
```

<210> SEQ ID NO 10
<211> LENGTH: 558
<212> TYPE: PRT
<213> ORGANISM: Homo sapiens

<400> SEQUENCE: 10

```
Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Gln
            20                  25                  30

Asn Ala Thr Gln Thr Thr Thr Asp Ser Ser Asn Lys Thr Ala Pro Thr
                35                  40                  45

Pro Ala Ser Ser Val Thr Ile Met Ala Thr Asp Thr Ala Gln Gln Ser
            50                  55                  60

Thr Val Pro Thr Ser Lys Ala Asn Glu Ile Leu Ala Ser Val Lys Ala
65                  70                  75                  80

Thr Thr Leu Gly Val Ser Ser Asp Ser Pro Gly Thr Thr Leu Ala
                    85                  90                  95

Gln Gln Val Ser Gly Pro Val Asn Thr Thr Val Ala Arg Gly Gly Gly
                100                 105                 110

Ser Gly Asn Pro Thr Thr Thr Ile Glu Ser Pro Lys Ser Thr Lys Ser
                115                 120                 125

Ala Asp Thr Thr Thr Val Ala Thr Ser Thr Ala Thr Ala Lys Pro Asn
                130                 135                 140

Thr Thr Ser Ser Gln Asn Gly Ala Glu Asp Thr Asn Ser Gly Gly
145                 150                 155                 160

Lys Ser Ser His Ser Val Thr Thr Asp Leu Thr Ser Thr Lys Ala Glu
                165                 170                 175

His Leu Thr Thr Pro His Pro Thr Ser Pro Leu Ser Pro Arg Gln Pro
                180                 185                 190

Thr Ser Thr His Pro Val Ala Thr Pro Thr Ser Ser Gly His Asp His
                195                 200                 205

Leu Met Lys Ile Ser Ser Ser Ser Thr Val Ala Ile Pro Gly Tyr
        210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
                245                 250                 255

Pro Thr Leu Ala Ser Gln Ser Ala Gly Ile Thr Ala Ser Ser Val Ile
                260                 265                 270

Ser Gln Arg Thr Gln Gln Thr Ser Ser Gln Met Pro Ala Ser Ser Thr
                275                 280                 285

Ala Pro Ser Ser Gln Glu Thr Val Gln Pro Thr Ser Pro Ala Thr Ala
        290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
                325                 330                 335

His Glu Ser Asn Trp Ala Lys Cys Glu Asp Leu Glu Thr Gln Thr Gln
                340                 345                 350

Ser Glu Lys Gln Leu Val Leu Asn Leu Thr Gly Asn Thr Leu Cys Ala
        355                 360                 365
```

```
Gly Gly Ala Ser Asp Glu Lys Leu Ile Ser Leu Ile Cys Arg Ala Val
370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
            405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
            435                 440                 445

Gly Pro Pro Glu Glu Ala Glu Asp Arg Phe Ser Met Pro Leu Ile Ile
450                 455                 460

Thr Ile Val Cys Met Ala Ser Phe Leu Leu Val Ala Ala Leu Tyr
465                 470                 475                 480

Gly Cys Cys His Gln Arg Leu Ser Gln Arg Lys Asp Gln Arg Leu
                485                 490                 495

Thr Glu Glu Leu Gln Thr Val Glu Asn Gly Tyr His Asp Asn Pro Thr
                500                 505                 510

Leu Glu Val Met Glu Thr Ser Ser Glu Met Gln Glu Lys Lys Val Val
                515                 520                 525

Ser Leu Asn Gly Glu Leu Gly Asp Ser Trp Ile Val Pro Leu Asp Asn
530                 535                 540

Leu Thr Lys Asp Asp Leu Asp Glu Glu Asp Thr His Leu
545                 550                 555

<210> SEQ ID NO 11
<211> LENGTH: 42
<212> TYPE: PRT
<213> ORGANISM: Aggregatibacter actinomycetemcomitans

<400> SEQUENCE: 11

Leu Gly Asp Ala His Leu Pro Arg Arg Glu Gln Val Arg Glu Arg Ile
1               5                   10                  15

Gly Ala Ser Leu Met Leu Asn Gln Leu Arg Ser Gln Ile Thr Ser Asp
            20                  25                  30

His Phe Pro Val Ser Phe Val His Asp Arg
        35                  40

<210> SEQ ID NO 12
<211> LENGTH: 42
<212> TYPE: PRT
<213> ORGANISM: Haemophilus ducreyi

<400> SEQUENCE: 12

Leu His Asp Ala His Leu Pro Arg Arg Glu Gln Ala Arg Glu Arg Ile
1               5                   10                  15

Gly Ala Ser Leu Met Leu Asn Gln Leu Arg Ser Gln Ile Thr Ser Asp
            20                  25                  30

His Phe Pro Val Ser Phe Val Arg Asp Arg
        35                  40

<210> SEQ ID NO 13
<211> LENGTH: 33
<212> TYPE: PRT
<213> ORGANISM: Salmonella typhi

<400> SEQUENCE: 13

Ile Val Asp Arg Ala Pro Tyr Ser Gln Arg Val Glu Ala Leu Arg Asn
```

```
                1               5                  10                  15
Pro Gln Leu Ala Ser Asp His Tyr Pro Val Ala Phe Leu Ala Arg Ser
                 20                  25                  30

Cys

<210> SEQ ID NO 14
<211> LENGTH: 40
<212> TYPE: PRT
<213> ORGANISM: Campylobacter jejuni

<400> SEQUENCE: 14

Thr Gly Asn Ser Asn Arg Gln Gln Thr Tyr Thr Pro Pro Leu Leu Ala
1               5                   10                  15

Ala Ile Leu Met Leu Ala Ser Leu Arg Ser His Ile Val Ser Asp His
                 20                  25                  30

Phe Pro Val Asn Phe Arg Lys Phe
                 35                  40

<210> SEQ ID NO 15
<211> LENGTH: 41
<212> TYPE: PRT
<213> ORGANISM: Helicobacter hepaticus

<400> SEQUENCE: 15

Val Gly Arg Ser Ser Pro Ser Arg Ser Thr Ile Val Leu Pro Gln Ile
1               5                   10                  15

Ala Ala Ile Leu Met Ala Ala Asn Ile Arg Ala His Leu Ser Ser Asp
                 20                  25                  30

His Ser Pro Val His Phe Gly Arg Phe
                 35                  40

<210> SEQ ID NO 16
<211> LENGTH: 37
<212> TYPE: PRT
<213> ORGANISM: Providencia alcalifaciens

<400> SEQUENCE: 16

Ala Gly Asn Ala Val Ala Phe Arg Pro Leu Pro Leu Gln Ala Gly Ile
1               5                   10                  15

Val Tyr Gly Ala Arg Arg Thr Gln Ile Ser Ser Asp His Tyr Pro Val
                 20                  25                  30

Gly Val Phe Arg Arg
                 35

<210> SEQ ID NO 17
<211> LENGTH: 37
<212> TYPE: PRT
<213> ORGANISM: Shigella boydii

<400> SEQUENCE: 17

Ala Gly Asn Ala Val Ala Phe Arg Pro Phe Pro Leu Gln Ala Gly Ile
1               5                   10                  15

Val Tyr Gly Ala Arg Arg Thr Gln Ile Ser Ser Asp His Tyr Pro Val
                 20                  25                  30

Gly Val Ser Arg Arg
                 35

<210> SEQ ID NO 18
<211> LENGTH: 42
<212> TYPE: PRT
```

<213> ORGANISM: Escherichia coli

<400> SEQUENCE: 18

Val Gly Asn Ser Val Ser Phe Val Leu Pro Leu Leu Arg Ala Ser Leu
1               5                   10                  15

Leu Phe Gly Leu Leu Arg Gly Gln Ile Ala Ser Asp His Phe Pro Val
            20                  25                  30

Gly Phe Ile Pro Gly Arg Gly Ala Arg Arg
        35                  40

<210> SEQ ID NO 19
<211> LENGTH: 60
<212> TYPE: PRT
<213> ORGANISM: Salmonella typhi

<400> SEQUENCE: 19

Gly Val Ile Pro Phe Leu Pro Glu Pro Gln Thr Tyr Thr Gln Gln Arg
1               5                   10                  15

Ile Asp Ala Phe Gly Pro Leu Ile Ser Ser Cys Phe Ser Ile Gly Ser
            20                  25                  30

Val Cys His Ser His Arg Gly Gln Arg Ala Asp Val Tyr Asn Met Ser
        35                  40                  45

Phe Tyr Asp Ala Arg Pro Val Ile Glu Leu Ile Leu
    50                  55                  60

<210> SEQ ID NO 20
<211> LENGTH: 60
<212> TYPE: PRT
<213> ORGANISM: Salmonella typhimurium

<400> SEQUENCE: 20

Gly Val Ile Pro Asn Leu Pro Val Pro Gln Val Ser Thr Arg Glu Arg
1               5                   10                  15

Ile Ser Ala Phe Gly Thr Leu Ile Ser Ala Cys Phe Ser Met Arg Gly
            20                  25                  30

Val Arg Arg Asp Asp Ala Arg Ser Asn Tyr Asn Tyr Tyr Glu Met Glu
        35                  40                  45

Phe Tyr Asp Ala Arg Gly Val Leu Thr Glu Leu Leu
    50                  55                  60

<210> SEQ ID NO 21
<211> LENGTH: 1304
<212> TYPE: PRT
<213> ORGANISM: Homo sapiens

<400> SEQUENCE: 21

Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30

Leu Thr Thr Ala Lys Met Pro Ser Val Pro Leu Ser Ser Asp Pro Leu
        35                  40                  45

Pro Thr His Thr Thr Ala Phe Ser Pro Ala Ser Thr Phe Glu Arg Glu
    50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
                85                  90                  95

```
Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
        115                 120                 125

Ala Ala Asn Ala Lys Leu Asn Pro Thr Pro Gly Ser Asn Ala Ile Ser
    130                 135                 140

Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
                165                 170                 175

Ala Leu Pro Ala Arg Thr Ser Asn Thr Thr Ile Thr Ala Asn Thr Ser
            180                 185                 190

Asp Ala Tyr Leu Asn Ala Ser Glu Thr Thr Thr Leu Ser Pro Ser Gly
        195                 200                 205

Ser Ala Val Ile Ser Thr Thr Thr Ile Ala Thr Thr Pro Ser Lys Pro
    210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
                245                 250                 255

Glu Cys Gly Asn Asn Thr Cys Thr Asn Asn Glu Val His Asn Leu Thr
            260                 265                 270

Glu Cys Lys Asn Ala Ser Val Ser Ile Ser His Asn Ser Cys Thr Ala
        275                 280                 285

Pro Asp Lys Thr Leu Ile Leu Asp Val Pro Pro Gly Val Glu Lys Phe
    290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
                325                 330                 335

Thr Tyr Arg Phe Gln Cys Gly Asn Met Ile Phe Asp Asn Lys Glu Ile
            340                 345                 350

Lys Leu Glu Asn Leu Glu Pro Glu His Glu Tyr Lys Cys Asp Ser Glu
        355                 360                 365

Ile Leu Tyr Asn Asn His Lys Phe Thr Asn Ala Ser Lys Ile Ile Lys
    370                 375                 380

Thr Asp Phe Gly Ser Pro Gly Glu Pro Gln Ile Ile Phe Cys Arg Ser
385                 390                 395                 400

Glu Ala Ala His Gln Gly Val Ile Thr Trp Asn Pro Pro Gln Arg Ser
                405                 410                 415

Phe His Asn Phe Thr Leu Cys Tyr Ile Lys Glu Thr Glu Lys Asp Cys
            420                 425                 430

Leu Asn Leu Asp Lys Asn Leu Ile Lys Tyr Asp Leu Gln Asn Leu Lys
        435                 440                 445

Pro Tyr Thr Lys Tyr Val Leu Ser Leu His Ala Tyr Ile Ile Ala Lys
    450                 455                 460

Val Gln Arg Asn Gly Ser Ala Ala Met Cys His Phe Thr Thr Lys Ser
465                 470                 475                 480

Ala Pro Pro Ser Gln Val Trp Asn Met Thr Val Ser Met Thr Ser Asp
                485                 490                 495

Asn Ser Met His Val Lys Cys Arg Pro Pro Arg Asp Arg Asn Gly Pro
            500                 505                 510

His Glu Arg Tyr His Leu Glu Val Glu Ala Gly Asn Thr Leu Val Arg
```

```
                515                 520                 525
Asn Glu Ser His Lys Asn Cys Asp Phe Arg Val Lys Asp Leu Gln Tyr
    530                 535                 540

Ser Thr Asp Tyr Thr Phe Lys Ala Tyr Phe His Asn Gly Asp Tyr Pro
545                 550                 555                 560

Gly Glu Pro Phe Ile Leu His His Ser Thr Ser Tyr Asn Ser Lys Ala
                565                 570                 575

Leu Ile Ala Phe Leu Ala Phe Leu Ile Val Thr Ser Ile Ala Leu
            580                 585                 590

Leu Val Val Leu Tyr Lys Ile Tyr Asp Leu His Lys Lys Arg Ser Cys
                595                 600                 605

Asn Leu Asp Glu Gln Gln Glu Leu Val Glu Arg Asp Asp Glu Lys Gln
    610                 615                 620

Leu Met Asn Val Glu Pro Ile His Ala Asp Ile Leu Leu Glu Thr Tyr
625                 630                 635                 640

Lys Arg Lys Ile Ala Asp Glu Gly Arg Leu Phe Leu Ala Glu Phe Gln
                645                 650                 655

Ser Ile Pro Arg Val Phe Ser Lys Phe Pro Ile Lys Glu Ala Arg Lys
            660                 665                 670

Pro Phe Asn Gln Asn Lys Asn Arg Tyr Val Asp Ile Leu Pro Tyr Asp
        675                 680                 685

Tyr Asn Arg Val Glu Leu Ser Glu Ile Asn Gly Asp Ala Gly Ser Asn
690                 695                 700

Tyr Ile Asn Ala Ser Tyr Ile Asp Gly Phe Lys Glu Pro Arg Lys Tyr
705                 710                 715                 720

Ile Ala Ala Gln Gly Pro Arg Asp Glu Thr Val Asp Asp Phe Trp Arg
                725                 730                 735

Met Ile Trp Glu Gln Lys Ala Thr Val Ile Val Met Val Thr Arg Cys
            740                 745                 750

Glu Glu Gly Asn Arg Asn Lys Cys Ala Glu Tyr Trp Pro Ser Met Glu
            755                 760                 765

Glu Gly Thr Arg Ala Phe Gly Asp Val Val Lys Ile Asn Gln His
    770                 775                 780

Lys Arg Cys Pro Asp Tyr Ile Ile Gln Lys Leu Asn Ile Val Asn Lys
785                 790                 795                 800

Lys Glu Lys Ala Thr Gly Arg Glu Val Thr His Ile Gln Phe Thr Ser
                805                 810                 815

Trp Pro Asp His Gly Val Pro Glu Asp Pro His Leu Leu Lys Leu
            820                 825                 830

Arg Arg Arg Val Asn Ala Phe Ser Asn Phe Ser Gly Pro Ile Val
    835                 840                 845

Val His Cys Ser Ala Gly Val Gly Arg Thr Gly Thr Tyr Ile Gly Ile
    850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
                885                 890                 895

Glu Ala Gln Tyr Ile Leu Ile His Gln Ala Leu Val Glu Tyr Asn Gln
            900                 905                 910

Phe Gly Glu Thr Glu Val Asn Leu Ser Glu Leu His Pro Tyr Leu His
        915                 920                 925

Asn Met Lys Lys Arg Asp Pro Pro Ser Glu Pro Ser Pro Leu Glu Ala
    930                 935                 940
```

```
Glu Phe Gln Arg Leu Pro Ser Tyr Arg Ser Trp Arg Thr Gln His Ile
945                 950                 955                 960

Gly Asn Gln Glu Glu Asn Lys Ser Lys Asn Arg Asn Ser Asn Val Ile
                965                 970                 975

Pro Tyr Asp Tyr Asn Arg Val Pro Leu Lys His Glu Leu Glu Met Ser
            980                 985                 990

Lys Glu Ser Glu His Asp Ser Asp  Glu Ser Ser Asp Asp  Asp Ser Asp
        995                 1000                1005

Ser Glu  Glu Pro Ser Lys Tyr  Ile Asn Ala Ser Phe  Ile Met Ser
    1010                1015                1020

Tyr Trp Lys Pro Glu Val Met  Ile Ala Ala Gln Gly  Pro Leu Lys
    1025                1030                1035

Glu Thr Ile Gly Asp Phe Trp  Gln Met Ile Phe Gln  Arg Lys Val
    1040                1045                1050

Lys Val Ile Val Met Leu Thr  Glu Leu Lys His Gly  Asp Gln Glu
    1055                1060                1065

Ile Cys Ala Gln Tyr Trp Gly  Glu Gly Lys Gln Thr  Tyr Gly Asp
    1070                1075                1080

Ile Glu Val Asp Leu Lys Asp  Thr Asp Lys Ser Ser  Thr Tyr Thr
    1085                1090                1095

Leu Arg Val Phe Glu Leu Arg  His Ser Lys Arg Lys  Asp Ser Arg
    1100                1105                1110

Thr Val Tyr Gln Tyr Gln Tyr  Thr Asn Trp Ser Val  Glu Gln Leu
    1115                1120                1125

Pro Ala Glu Pro Lys Glu Leu  Ile Ser Met Ile Gln  Val Val Lys
    1130                1135                1140

Gln Lys Leu Pro Gln Lys Asn  Ser Ser Glu Gly Asn  Lys His His
    1145                1150                1155

Lys Ser Thr Pro Leu Leu Ile  His Cys Arg Asp Gly  Ser Gln Gln
    1160                1165                1170

Thr Gly Ile Phe Cys Ala Leu  Leu Asn Leu Leu Glu  Ser Ala Glu
    1175                1180                1185

Thr Glu Glu Val Val Asp Ile  Phe Gln Val Val Lys  Ala Leu Arg
    1190                1195                1200

Lys Ala Arg Pro Gly Met Val  Ser Thr Phe Glu Gln  Tyr Gln Phe
    1205                1210                1215

Leu Tyr Asp Val Ile Ala Ser  Thr Tyr Pro Ala Gln  Asn Gly Gln
    1220                1225                1230

Val Lys Lys Asn Asn His Gln  Glu Asp Lys Ile Glu  Phe Asp Asn
    1235                1240                1245

Glu Val Asp Lys Val Lys Gln  Asp Ala Asn Cys Val  Asn Pro Leu
    1250                1255                1260

Gly Ala Pro Glu Lys Leu Pro  Glu Ala Lys Glu Gln  Ala Glu Gly
    1265                1270                1275

Ser Glu Pro Thr Ser Gly Thr  Glu Gly Pro Glu His  Ser Val Asn
    1280                1285                1290

Gly Pro Ala Ser Pro Ala Leu  Asn Gln Gly Ser
    1295                1300
```

UNITED STATES PATENT AND TRADEMARK OFFICE
CERTIFICATE OF CORRECTION

PATENT NO. : 10,335,477 B2
APPLICATION NO. : 14/892237
DATED : July 2, 2019
INVENTOR(S) : Jorge E. Galan et al.

It is certified that error appears in the above-identified patent and that said Letters Patent is hereby corrected as shown below:

In the Specification

Please amend Column 1, Lines 18-24 as follows:
-- STATEMENT REGARDING FEDERALLY SPONSORED RESEARCH OR DEVELOPMENT
This invention was made with government support under AI079022 awarded by the National Institutes of Health. The government has certain rights in the invention. --

Signed and Sealed this
Eighth Day of September, 2020

Andrei Iancu
*Director of the United States Patent and Trademark Office*